(12) United States Patent
Krishnan et al.

(10) Patent No.: US 11,779,660 B2
(45) Date of Patent: Oct. 10, 2023

(54) VIRAL VECTORS FOR CANCER THERAPY

(71) Applicant: Krystal Biotech, Inc., Pittsburgh, PA (US)

(72) Inventors: Suma Krishnan, Pittsburgh, PA (US); Trevor Parry, San Diego, CA (US); Dana Michelle Previte, Sewickley, PA (US); Mary Jane Duermeyer, Glenshaw, PA (US)

(73) Assignee: Krystal Biotech, Inc., Pittsburgh, PA (US)

( * ) Notice: Subject to any disclaimer, the term of this patent is extended or adjusted under 35 U.S.C. 154(b) by 13 days.

(21) Appl. No.: 17/711,947

(22) Filed: Apr. 1, 2022

(65) Prior Publication Data

US 2022/0323613 A1 Oct. 13, 2022

Related U.S. Application Data

(60) Provisional application No. 63/170,103, filed on Apr. 2, 2021.

(51) Int. Cl.

| | | |
|---|---|---|
| *A61K 35/763* | (2015.01) | |
| *A61K 48/00* | (2006.01) | |
| *A61K 38/19* | (2006.01) | |
| *A61P 35/00* | (2006.01) | |
| *C12N 7/00* | (2006.01) | |
| *C12N 15/24* | (2006.01) | |
| *A61K 38/20* | (2006.01) | |
| *C12N 15/86* | (2006.01) | |

(52) U.S. Cl.
CPC ........ *A61K 48/0066* (2013.01); *A61K 38/193* (2013.01); *A61K 38/208* (2013.01); *A61K 38/2013* (2013.01); *A61P 35/00* (2018.01); *C12N 7/00* (2013.01); *C12N 15/86* (2013.01); *C12N 2710/16622* (2013.01); *C12N 2710/16633* (2013.01); *C12N 2710/16643* (2013.01); *C12N 2710/16662* (2013.01); *C12N 2710/16671* (2013.01)

(58) Field of Classification Search
None
See application file for complete search history.

(56) References Cited

U.S. PATENT DOCUMENTS

| | | | |
|---|---|---|---|
| 5,658,724 A | 8/1997 | Deluca et al. | |
| 5,672,344 A | 9/1997 | Kelley et al. | |
| 5,753,234 A | 5/1998 | Lee et al. | |
| 5,998,174 A | 12/1999 | Glorioso et al. | |
| 6,106,826 A | 8/2000 | Brandt et al. | |
| 6,719,982 B1 | 4/2004 | Coffin et al. | |
| 6,846,670 B2 | 1/2005 | Schwartz et al. | |
| 6,887,490 B1 | 5/2005 | Jahoda et al. | |
| 7,081,483 B2 | 7/2006 | Cahiko | |
| 7,531,167 B2 | 5/2009 | Glorioso et al. | |
| 9,314,505 B2 | 4/2016 | Wise et al. | |
| 9,877,990 B2 | 1/2018 | Krishnan et al. | |
| 10,155,016 B2 | 12/2018 | Krishnan et al. | |
| 10,174,341 B2 | 1/2019 | Glorioso et al. | |
| 10,441,614 B2 | 10/2019 | Krishnan et al. | |
| 10,525,090 B2 | 1/2020 | Krishnan et al. | |
| 10,786,438 B2 | 9/2020 | Krishnan et al. | |
| 10,829,529 B2 | 11/2020 | Parry et al. | |
| 11,185,564 B2 | 11/2021 | Krishnan et al. | |
| 2003/0082142 A1 | 5/2003 | Coffin et al. | |
| 2004/0253606 A1 | 12/2004 | Aziz et al. | |
| 2006/0246139 A1 | 11/2006 | Miyaji et al. | |
| 2007/0066552 A1 | 3/2007 | Clarke et al. | |
| 2007/0092575 A1 | 4/2007 | Balaban et al. | |
| 2007/0148074 A1 | 6/2007 | Sadoqi et al. | |
| 2008/0260851 A1 | 10/2008 | Somasundaran et al. | |
| 2008/0299182 A1 | 12/2008 | Zhang | |
| 2009/0136917 A1* | 5/2009 | Szalay ................... | A61K 38/45 435/235.1 |
| 2010/0081707 A1 | 4/2010 | Ali et al. | |
| 2011/0212530 A1 | 9/2011 | Baltimore et al. | |
| 2013/0280224 A1* | 10/2013 | Monsonego ............ | A61P 25/16 514/17.7 |
| 2013/0295076 A1 | 11/2013 | Kolattukudy et al. | |
| 2013/0331547 A1 | 12/2013 | Hall et al. | |
| 2014/0256798 A1 | 9/2014 | Osborn et al. | |

(Continued)

FOREIGN PATENT DOCUMENTS

| | | |
|---|---|---|
| CN | 102 212 559 | 4/2014 |
| EP | 3211000 | 8/2017 |

(Continued)

OTHER PUBLICATIONS

Conry et al., Talimogene laherparepvec: First in class oncolytic virotherapy, Human Vaccines & Immunotherapeutics 2018, vol. 14, No. 4, 839-846.*
Goins et al., Engineering HSV-1 Vectors for Gene Therapy, Herpes Simplex Virus: Methods and Protocols, Methods in Molecular Biology, Ed: Diefenbach, 2014, pp. 63-79.*
Wei et al., Pharmacokinetics of combined gene therapy expressing constitutive human GM-CSF and hyperthermia-regulated human IL-12, Journal of Experimental & Clinical Cancer Research, 2013, pp. 1-7.*
Aldawsari et al., "Progress in Topical siRNA Delivery Approaches for Skin Disorders," Curr Pharm Des. (2015) 21(31): 4594-4605.
Andtbacka et al., "Talimogene Laherparepvec Improves Durable Response Rate in Patients With Advanced Melanoma," J Clin Oncol. (2015) 33(25): 2780-2788.

(Continued)

*Primary Examiner* — Maria Marvich
(74) *Attorney, Agent, or Firm* — MORRISON & FOERSTER LLP

(57) ABSTRACT

The present disclosure provides recombinant nucleic acids comprising one or more polynucleotides encoding an immunomodulatory polypeptide (e.g., a pro-inflammatory cytokine such as a human IL-2 or IL-12 polypeptide); viruses comprising the recombinant nucleic acids; compositions and formulations comprising the recombinant nucleic acids and/or viruses; methods of their use (e.g., for the treatment of cancer, such as lung cancer); and articles of manufacture or kits thereof.

32 Claims, 26 Drawing Sheets

Specification includes a Sequence Listing.

(56) References Cited

U.S. PATENT DOCUMENTS

| | | |
|---|---|---|
| 2014/0288155 A1 | 9/2014 | Hovnanian et al. |
| 2014/0341877 A1 | 11/2014 | Kolattukudy |
| 2015/0038556 A1 | 2/2015 | Heartlein et al. |
| 2015/0352191 A1 | 12/2015 | South et al. |
| 2016/0153000 A1 | 6/2016 | Glorioso et al. |
| 2016/0250267 A1 | 9/2016 | Uchida et al. |
| 2016/0324934 A1 | 11/2016 | Angel et al. |
| 2017/0096684 A1 | 4/2017 | Alton et al. |
| 2017/0290866 A1 | 10/2017 | Krishnan et al. |
| 2017/0319693 A1 | 11/2017 | Koizumi et al. |
| 2018/0353614 A1 | 12/2018 | Peters |
| 2019/0160122 A1 | 5/2019 | Krishnan et al. |
| 2019/0276845 A1 | 9/2019 | Glorioso et al. |
| 2020/0009203 A1* | 1/2020 | Sobol ................. C07K 16/2818 |
| 2020/0061209 A1 | 2/2020 | Bennett et al. |
| 2020/0093874 A1 | 3/2020 | Agarwal et al. |
| 2020/0101123 A1 | 4/2020 | Krishnan et al. |
| 2020/0197456 A1 | 6/2020 | Krishnan et al. |
| 2020/0199618 A1 | 6/2020 | Krisky et al. |
| 2021/0040172 A1 | 2/2021 | Cascio et al. |
| 2021/0045988 A1 | 2/2021 | Krishnan et al. |
| 2021/0087245 A1 | 3/2021 | Parry et al. |
| 2021/0189427 A1 | 6/2021 | Krishnan et al. |
| 2021/0261649 A1 | 8/2021 | Parry et al. |
| 2021/0395775 A1 | 12/2021 | Parry et al. |
| 2022/0016191 A1* | 1/2022 | Weiss ..................... C12N 15/86 |
| 2022/0273737 A1 | 9/2022 | Krishnan et al. |
| 2023/0149486 A1 | 5/2023 | Krishnan |

FOREIGN PATENT DOCUMENTS

| | | |
|---|---|---|
| EP | 3377637 | 9/2018 |
| EP | 3640327 | 4/2020 |
| WO | WO 1999/007394 A1 | 2/1999 |
| WO | WO 1999/064094 | 12/1999 |
| WO | WO 2000/040734 | 7/2000 |
| WO | WO 2005/092374 | 10/2005 |
| WO | WO 2005092374 * | 10/2005 |
| WO | WO 2013/121202 | 8/2013 |
| WO | WO 2015/009952 | 1/2015 |
| WO | WO 2015/117021 | 8/2015 |
| WO | WO 2016/191684 A1 | 12/2016 |
| WO | WO 2017/165806 | 9/2017 |
| WO | WO 2017/165813 | 9/2017 |
| WO | WO 2017/176336 | 10/2017 |
| WO | WO 2017/189754 | 11/2017 |
| WO | WO 2021/046131 | 3/2021 |
| WO | WO 2022165340 * | 8/2022 |

OTHER PUBLICATIONS

Armstrong, M. "Krystal gets more skin in the epidermolysis bullosa game." Vantage. Mar. 5, 2019.

Armstrong, M. "Krystal gets a flying start in epidermolysis bullosa gene therapy" Vantage. Oct. 17, 2018.

Arndt et al., "Inhaled granulocyte-macrophage colony stimulating factor for first pulmonary recurrence of osteosarcoma: Effects on disease-free survival and immunomodulation. A report from the Children's Oncology Group," Clinical Cancer Research. (2010) 16: 4024-4030.

Arndt et al., "Common musculoskeletal tumors of childhood and adolescence," Mayo Clinic proceedings. (2012) 87: 475-87.

Assier et al. "NK cells and polymorphonuclear neutrophils are both critical for IL-2-induced pulmonary vascular leak syndrome," Journal of immunology. (2004) 172:7661-7668.

Bastian et al., "Herpes simplex virus type 1 immediate-early protein ICP22 is required for VICE domain formation during productive viral infection." J Viral. Mar. 2010;84(5):2384-94. doi: 10.1128/JVI.01686-09. Epub Dec. 23, 2009.

Baxevanis et al., "Granulocyte-macrophage colony-stimulating factor improves immunological parameters in patients with refractory solid tumours receiving second-line chemotherapy: correlation with clinical responses," European Journal of Cancer. (1997) 33(8): 1202-1208.

Becher et al., "GM-CSF: From Growth Factor to Central Mediator of Tissue Inflammation," Immunity. (2016) 45: 963-973.

Berkers et al., "Rectal Organoids Enable Personalized Treatment of Cystic Fibrosis," Cell Rep (2019) 26(7): 1701-1708.e3.

Birket et al., "Development of an airway mucus defect in the cystic fibrosis rat," JCI Insight (2018) 3(1): e97199.

Bowen et al., Comparison of Herpes Simplex Virus 1 Strains Circulating in Finland Demonstrates the Uncoupling of Whole-Genome Relatedness and Phenotypic Outcomes of Viral Infection, J Virol. (2019) 93(8):e01824-18.

Brehm et al., "Immunogenicity of herpes simplex virus type 1 mutants containing deletions in one or more alpha-genes: ICP4, ICP27, ICP22, and ICP0," Virology (1999) 256(2): 258-69.

Burton et al., "Gene delivery using herpes simplex virus vectors." DNA Cell Biol. Dec. 2002;21(12):915-936.

Carew et al., "A novel approach to cancer therapy using an oncolytic herpes virus to package amplicons containing cytokine genes," Mol Ther. (2001) 4(3): 250-6. doi: 10.1006/mthe.2001.0448. PMID: 11545616.

Carvalho et al., "The function and performance of aqueous devices for inhalation therapy," Journal of Pharmacy and Pharmacology. (2016) 68: 556-578.

Chamorro et al., "Gene Editing for the Efficient Correction of a Recurrent COL7A1 Mutation in Recessive Dystrophic Epidermolysis Bullosa Keratinocytes", Molecular Therapy—Nucleic Acids, vol. 5, 2016, pp. 1-13.

Christiano AM. Collagen, type VII, alpha 1 (epidermolysis bullosa, dystrophic, dominant and recessive) [Homo sapiens]. NCBI Reference Sequence: NP_000085.1. Dep. Mar. 19, 1999.

Clancy et al., "Personalized Medicine in Cystic Fibrosis: Dawning of a New Era," Am J Respir Crit Care Med (2012) 186(7): 593-597.

Clancy et al., "CFTR Modulator Theratyping: Current Status, Gaps and Future Directions," J Cyst Fibros (2019) 18(1): 22-34.

Clinicaltrials.gov. NCT03536143: Topical Bercolagene Telserpavec (KB103) Gene Therapy to Restore Functional Collagen VII for the Treatment of Dystrophic Epidermolysis Bullosa (GEM-1). May 24, 2018.

Clinicaltrials.gov. NCT04047732: Topical KB105 Gene Therapy for the Treatment of TGM1-deficient Autosonnal Recessive Congenital Ichthyosis (ARCI). Aug. 7, 2019.

Clinicaltrials.gov. NCT04214002: The Natural History of Wounds in Patients with Dystrophic Epidermolysis Bullosa (DEB). Dec. 30, 2019.

Collawn et al., "CFTR and Lung Homeostasis," Am J Physiol Lung Cell Mol Physiol (2014) 307(12): L917-923.

Cooney et al., "Cystic Fibrosis Gene Therapy: Looking Back, Looking Forward," Genes (Basel) (2018) 9(11): 538.

Cutting, G. "Cystic Fibrosis Genetics: From Molecular Understanding to Clinical Application," Nat Rev Genet (2015) 16(1): 45-56.

Dekkers et al., "A Functional CFTR Assay Using Primary Cystic Fibrosis Intestinal Organoids," Nat Med (2013) 19(7): 939-945.

Deluca et al., "Isolation and Characterization of Deletion Mutants of Herpes Simplex Virus Type 1 in the Gene Encoding Immediate-Early Regulatory Protein ICP4", Journal of Virology, (1985) 56(2): 558-570.

Derichs et al., "Hyperviscous Airway Periciliary and Mucous Liquid Layers in Cystic Fibrosis Measured by Confocal Fluorescence Photobleaching," FASEB J (2011) 25(7): 2325-2332.

Dingwell et al., "The Herpes Simplex Virus gE-gI Complex Facilitates Cell-to-Cell Spread and Binds to Components of Cell Junctions," J Virol. (1998) 72(11): 8933-8942.

Eming SA, Krieg T, Davidson JM. Gene therapy and wound healing. Clin Dermatol. Jan.-Feb. 2007;25(1):79-92.

Eming et al., "Gene transfer in tissue repair: status, challenges and future directions," Exp Opin Biol Ther (2004) 4(9):1373-1386.

Estrada-Veras et al., "Palliative Care for Patients With Cystic Fibrosis #265," J Palliat Med (2013) 16(4): 446-447.

Fath et al., "Multiparameter RNA and codon optimization: a standardized tool to assess and enhance autologous mammalian gene expression," PLOS One. (2011) 6(3): e17596.

(56) References Cited

OTHER PUBLICATIONS

Fink et al., "Gene therapy for pain: Results of a Phase I clinical trial," Ann Neurol (2011) 70(2):207-212.
Gallotta et al., "Inhaled TLR9 Agonist Renders Lung Tumors Permissive to PD-1 Blockade by Promoting Optimal CD4+ and CD8+ T-cell Interplay" Cancer Res. (2018) 78(17):4943-4956. doi: 10.1158/0008-5472.CAN-18-0729. Epub Jun. 26, 2018. PMID: 29945961.
Gardenhire et al. A Guide to Aerosol Delivery Devices for Respiratory Therapists, 4th Edition, American Association for Respiratory Care, 2017.
Geller et al., "An efficient deletion mutant packaging system for defective herpes simplex virus vectors: potential applications to human gene therapy and neuronal physiology," Proc Natl Acad Sci U S A. (1990) 87(22): 8950-8954.
Georgiadis et al., "Lentiviral Engineered Fibroblasts Expressing Codon-Optimized COL7A1 Restore Anchoring Fibrils in RDEB", Journal of Investigative Dermatology, (2016) 136: 284-292.
Ghimessy et al., "KRAS Mutations Predict Response and Outcome in Advanced Lung Adenocarcinoma Patients Receiving First-Line Bevacizumab and Platinum-Based Chemotherapy," Cancers. (2019) 11(10):1514. doi: 10.3390/cancers11101514. PMID: 31600989; PMCID: PMC6827133.
Ghouse et al., "Oncolytic Herpes Simplex Virus Encoding IL12 Controls Triple-Negative Breast Cancer Growth and Metastasis," Front Oncol. (2020) 10: 384. doi: 10.3389/fonc.2020.00384. PMID: 32266155; PMCID: PMC7105799.
Gill et al., "Delivery of Genes Into the CF Airway," Thorax (2014) 69(10): 962-964.
Glorioso JC. "Herpes simplex viral vectors: late bloomers with big potential." Hum Gene Ther. (2014) 25(2): 83-91.
Goins et al. "Engineering HSV-1 Vectors for Gene Therapy," Methods Mol Biol (2014) 1144: 63-79.
Goldsmith et al., "Infected cell protein (ICP)47 enhances herpes simplex virus neurovirulence by blocking the CD8+ T cell response," J Exp Med. (1998) 187(3): 341-348.
Gorell et al., "Gene therapy for skin diseases," Cold Spring Harb Perspect Med (2014) 4:a015149.
Goto et al., "Fibroblasts Show More Potential as Target Cells than Keratinocytes in COL7A1 Gene Therapy of Dystrophic Epidermolysis Bullosa", Journal of Investigative Dermatology, (2006) 126: 766-772.
Grant, Kyle, "Production and Purification of Highly Replication Defective Hsv-1 Based Gene Therapy Vectors", Doctoral Dissertation, University of Pittsburgh, 2008, 137 pages.
Grisez et al., "Highly metastatic K7M2 cell line: A novel murine model capable of in vivo imaging via luciferase vector transfection," Journal of Orthopaedic Research. (2018) 36: 2296-2304.
Guma et al., "Natural killer cell therapy and aerosol interleukin-2 for the treatment of osteosarcoma lung metastasis," Pediatric Blood Cancer (2014) 61(4): 618.
Gurevich et al. 759 "Successful in vivo COL7A1 gene delivery and correction of recessive dystrophic epidermolysis bullosa (RDEB) skin using an off the shelf HSV-1 vector (KB103)." J Invest Derm. vol. 138, Iss. 5 Supp. May 2018, p. S129. Available online Apr. 19, 2018.
Heikkinen et al., "Diremerization of human lysyl hydroxylase 3 (LH3) is mediated by the amino acids 541 547," Matrix Biology (2010) 30(1):27-33.
Hennig et al., "HEK293-based production platform for y-retroviral (self-inactivating) vectors: application for safe and efficient transfer of COL7A1 cDNA". Hum Gene Ther Clin Dev. Dec. 2014;25(4):218-28.
Herve et al., "VEGF neutralizing aerosol therapy in primary pulmonary adenocarcinoma with K-ras activating-mutations," MAbs. (2014); 6(6):1638-48. doi: 10.4161/mabs.34454. PMID: 25484066; PMCID: PMC4623465.
Hill et al., "Herpes simplex virus turns off the TAP to evade host immunity," Nature. (1995) 375(6530): 411-415.
Hyde et al., "Repeat Administration of DNA/liposomes to the Nasal Epithelium of Patients With Cystic Fibrosis," Gene Ther (2000) 7(13): 1156-1165.
IMLYGIC Prescribing Information, revised 2021.
Isakoff et al., Osteosarcoma: Current Treatment and a Collaborative Pathway to Success. Journal of clinical oncology : official journal of the American Society of Clinical Oncology. (2015) 33(27): 3029-35.
Jia et al., "Aerosol Gene Therapy with PEI:IL-12 Eradicates Osteosarcoma Lung Metastases1," Clin. Cancer Res. (2003) 9: 3462-3468.
Jia et al., "Eradication of osteosarcoma lung metastases following intranasal interleukin-12 gene therapy using a nonviral polyethylenimine vector," Cancer Gene Therapy. (2002) 9; 260-266.
Jiang et al., "Role of IL-2 in cancer immunotherapy," OncoImmunology. (2016) 5(6) e1163462.
Jorgovanovic et al., "Roles of IFN-γ in tumor progression and regression: A review," Biomarker Research. (2020) 8:49.
Kaste et al., "Metastases detected at the time of diagnosis of primary pediatric extremity osteosarcoma at diagnosis: imaging features," Cancer. (1999) 86(8); 1602-8.
Kell et al., "Preclinical development of the TLR9 agonist DV281 as an inhaled aerosolized immunotherapeutic for lung cancer: Pharmacological profile in mice, non-human primates, and human primary cells," Int Immunopharmacol. (2019) 66:296-308.
Kerem et al., "Identification of the Cystic Fibrosis Gene: Genetic Analysis," Science (1989) 245(4922): 1073-1080.
Kim et al., "Microneedles for Drug and Vaccine Delivery", Advanced Drug Delivery Reviews, vol. 64, 2012, pp. 1547-1568.
Kim et al., "Barriers to Inhaled Gene Therapy of Obstructive Lung Diseases: A Review," J Control Release (2016) 240: 465-488.
Knowles et al., "A Controlled Study of Adenoviral-Vector-Mediated Gene Transfer in the Nasal Epithelium of Patients With Cystic Fibrosis," N Engl J Med (1995) 333(13): 823-831.
Kohlhapp et al., Molecular Pathways: Mechanism of Action for Talimogene Laherparepvec, a New Oncolytic Virus Immunotherapy, Clinical Cancer Research (2015) 22(5):1048-1054.
Kopecki et al., "Commentary: New advances in the development of therapies for treating inherited skin fragility disorders," Wound Practice and Research (2015) 23(4): 184, Dec. 5, 2015.
Krisky et al., "Deletion of multiple immediate-early genes from herpes simplex virus reduces cytotoxicity and permits long-term gene expression in neurons," Gene Ther. (1998) 5(12):1593-603.
Krisky et al., "Development of herpes simplex virus replication-defective multigene vectors for combination gene therapy applications," Gene Ther (1998) 5(110):1517-1530.
Lachmann, R. "Herpes simplex virus-based vectors," Int J Exp Pathol. (2004) 85(4): 177-190.
Lasek et al., "Interleukin 12: still a promising candidate for tumor immunotherapy?" Cancer immunol Immunother. (2014) 63: 419-35.
Laurent et al., "Cetuxiimab administered through pulmonary route in a mice model of lung tumor," European Respiratory Society Annual Congress 2013, Abstract 401.
Leonard et al., "Effects of single-dose interleukin-12 exposure on interleukin-12 associated toxicity and interferon-γ production," Blood. (1997) 90(7): 2541-2548.
Lewin et al., "Gene therapy for autosomal dominant disorders of keratin," J Investig Dermatol Symp Proc. (2005) 10(1): 47-61.
Liou et al., "Year-to-year Changes in Lung Function in Individuals With Cystic Fibrosis," J Cyst Fibros (2010) 9(4): 250-256.
Liu et al., "An inhalable nanoparticulate STING agonist synergizes with radiotherapy to confer long-term control of lung metastases," Nat Commun. (2019) 10(1):5108. doi: 10.1038/s41467-019-13094-5. PMID: 31704921; PMCID: PMC6841721.
Lommatzsch et al., "The Combination of Tezacaftor and Ivacaftor in the Treatment of Patients With Cystic Fibrosis: Clinical Evidence and Future Prospects in Cystic Fibrosis Therapy," Ther Adv Respir Dis (2019) 13: 1-13. https://doi.org/10.1177/1753466619844424.
Lu et al., "Topical Application of Viral Vectors for Epidermal Gene Transfer", J Invest Dermatol. (1997) 108(5): 803-808.

(56) References Cited

OTHER PUBLICATIONS

Ma et al., "Efficacy of Herpes Simplex Virus Vector Encoding V the Human Preproenkephalin Gene for Treatment of Facial Pain in Mice," J aral Facial Pain Headachce (2016) 30(1):42-50.
Marconi et al., "HSV as a Vector in Vaccine Development and Gene Therapy." In: Madame Curie Bioscience Database [Internet]. Austin (TX): Landes Bioscience; 2000-2013. 30 pages.
Marconi et al., "Replication-defective herpes simplex virus vectors for gene transfer in vivo," Proc Natl Acad Sci USA (1996) 93:11319-11320.
Marx et al. Intranasal Drug Administration—An Attractive Delivery Route for Some Drugs, 2015.
Mayr et al., "Gene Therapy for the COL7A1 Gene", Chapter 23, Intech, 2013, pp. 561-589.
Miezeiewski et al., "Role of adherens junction proteins in differential herpes simplex virus type 2 infectivity in communication-competent and -deficient cell lines," Intervirology. (2012) 55(6): 465-474.
Mirabello et al., "International osteosarcoma incidence patterns in children and adolescents, middle ages and elderly persons," Int J Cancer. (2009) 125(1): 229-234.
Misaghi et al., "Osteosarcoma: a comprehensive review," SICOT-J. (2018) 4, 12.
Miyagawa et al., "Herpes simplex viral-vector design for efficient transfuction of nonneuronal cells without cytotoxcity," Proc Natl Acad Sci USA (2015) 112(13):E1632-E1641.
Miyagawa et al., "Deletion of the Virion Host Shut-off Gene Enhances Neuronal-Selective Transgene Expression from an HSV Vector Lacking Functional IE Genes," Mol Ther Methods Clin Dev. (2017) 6: 79-90.
Morales-Nebreda et al., "Intratracheal administration of influenza virus is superior to intranasal administration as a model of acute lung injury," Journal of Virological Methods. (2014) 209: 116-120.
Ng et al., "Fibroblast-Derived Dermal Matrix Drives Development of Aggressive Cutaneous Squamous Cell Carcinoma in Patients with Recessive Dystrophic Epidermolysis Bullosa", Cancer Research, vol. 72, No. 14, Jul. 15, 2012, pp. 3522-3534.
Nguyen et al., "Oncolytic Virus Encoding a Master Pro-Inflammatory Cytokine Interleukin 12 in Cancer Immunotherapy," Cells. (2020) 9(2):400. doi: 10.3390/cells9020400. PMID: 32050597; PMCID: PMC7072539.
Nguyen et al., "Localized Interleukin-12 for Cancer Immunotherapy," Frontiers in Immunology. (2020) 11: 575597.
Ortiz-Urda et al., "Injection of Genetically Engineered Fibroblasts Corrects Regenerated Human Epidermolysis Bullosa Skin Tissue", The Journal of Clinical Investigation, vol. 111, No. 2, Jan. 2003, pp. 251-255.
Parker et al., "Engineered herpes simplex virus expressing IL-12 in the treatment of experimental murine brain tumors," Proc Natl Acad Sci USA. (2000) 97(5): 2208-13. doi: 10.1073/pnas.040557897. PMID: 10681459; PMCID: PMC15779.
Patil et al., "Pulmonary Drug Delivery Strategies: A Concise, Systematic Review," Lung India (2012) 29(1): 44-49.
Peace et al., "Toxicity and therapeutic efficacy of high-dose interleukin 2. In vivo infusion of antibody to NK-1.1 attenuates toxicity without compromising efficacy against murine leukemia," J. Exp. Med. (1989) 169: 161.
Periphagen, Krystal Biotech Inc., Answer and Counterclaim in *PeriphaGen* v. *Krystal Biotech*, Filed Jun. 6, 2020 in the Western District of Pennsylvania (60 pgs).
Rahn et al., "Invasion of Herpes Simplex Virus Type 1 into Murine Epidermis: An Ex Vivo Infection Study," J Invest Dermatol. (2015) 135(12): 3009-3016.
Salam A. "Krystal's KB103 splits experts' thoughts on potential for HSV-1 risk in dystrophic epidermolysis bullosa patients, but final Phase I/II efficacy assured." Nov. 7, 2018. Biopharm Insight.
Salameh et al., "Early events in herpes simplex virus lifecycle with implications for an infection of lifetime," Open Virol J. (2012) 6:1-6.

Salmon-Ehr et al., "Implication of Interleukin-4 in Wound Healing", Laboratory Investigation, vol. 80, No. 8, Aug. 2000, pp. 1337-1343.
Samaniego et al., "Persistence and Expression of the Herpes Simplex Virus Genome in the Absence of Immediate-Early Proteins", Journal of Virology, (1998) 72(4); 3307-3320.
Samaniego et al., "The herpes simplex virus immediate-early protein ICP0 affects transcription from the viral genome and infected-cell survival in the absence of ICP4 and ICP27," J Virol. (1997) 71(6): 4614-4625.
Sankar et al., "A novel role for keratin 17 in coordinating oncogenic transformation and cellular adhersion in eqing sarcoma," Molecular and Cellular Biology (2013) 33(22):4448-4460.
Sapalidis et al., Inhaled Immunotherapy Administration for Lung Cancer; Efficient? Certainly Possible? J Cancer. (2018) 9(6):1121-1126. doi: 10.7150/jca.24397. PMID: 29581792; PMCID: PMC5868180.
Shen et al., "Herpes simplex virus 1 (HSV-1) for cancer treatment," Cancer Gene Therapy (2006) 13: 975-992.
Silva et al., "Herpes Virus Amplicon Vectors", Viruses, vol. 1, 2009, pp. 594-629.
Siprashvili et al., "Long-term type VII collagen restoration to human epidermolysis bullosa skin tissue," Hum Gene Ther. Oct. 2010;21(10):1299-310.
Stow et al., Isolation and characterization of a herpes simplex virus type 1 mutant containing a deletion within the gene encoding the immediate early polypeptide Vmw110. J Gen Viral. Dec. 1986;67 ( Pt 12):2571-85.
Sufiawati et al., "HIV-associated disruption of tight and adherens junctions of oral epithelial cells facilitates HSV-1 infection and spread," PLOS One. (2014) 9(2): e88803.
Sufiawati et al., "HIV-induced matrix metalloproteinase-9 activation through mitogen-activated protein kinase signalling promotes HSV-1 cell-to-cell spread in oral epithelial cells," J Gen Virol. (2018) 99(7): 937-947.
Theopold et al., "A novel replication-defective HSV-1 vector for regulatable gene delivery to wounds," Journal of the American College of Surgeons (2004) 199(3):57-58.
Uitto et al., "Progress toward Treatment and Cure of Epidermolysis Bullosa: Summary of the DEBRA International Research Symposium EB2015", Journal of Investigative Dermatology, vol. 136, 2016, pp. 352-358.
Vauthier et al., "Poly(alkylcyanoacrylates) as biodegradable materials for biomedical applications," Adv Drug Del Rev. (2003) 55: 519-48.
Wang et al., "Comparative Effectiveness of Antinociceptive Gene Therapies in Animal Models of Diabetic Neuropathic Pain", Gene Therapy, vol. 20, 2013, pp. 742-750.
Watanabe et al., "Properties of a Herpes Simplex Virus Multiple Immediate-early Gene-Deleted Recombinant as a Vaccine Vector", Virology, vol. 357, 2007, pp. 186-198.
Watt et al., "Lysyl Hydroxylase 3 Localizes to Epidermal Basement Membrane and is Reduced in Patients with Recessive Dystrophic Epidermolysis Bullosa", Plos One, (2015) 10(9): e0137639.
Weiss et al., "The Role of Interleukin 10 in the Pathogenesis and Potential Treatment of Skin Diseases", Journal of the American Academy of Dermatology, vol. 50, No. 5, May 2004, pp. 657-675.
White et al., "Evaluation and optimization of the administration of a selectively replicating herpes simplex viral vector to the brain by convection-enhanced delivery," Cancer Gene Ther. May 2011;18(5):358-69. doi: 10.1038/ cgt.2011 .2. Epub Mar. 4, 2011.
Wolfe et al., "Engineering Herpes Simplex Viral Vectors for Therapeutic Gene Transfer", Chapter 6, Gene and Cell Therapy, 2004, pp. 103-129.
Woodley et al., "Normal and Gene-Corrected Dystrophic Epidermolysis Bullosa Fibroblasts Alone Can Produce Type VII Collagen at the Basement Membrane Zone", The Journal of Investigative Dermatology, vol. 121, No. 5, Nov. 2003, pp. 1021-1028.
Woodley, et al., "Intradermal Injection of Lentiviral Vectors Corrects Regenerated Human Dystrophic Epidermolysis Bullosa Skin Tissue in Vivo", Molecular Therapy, vol. 10, No. 2, Aug. 2004, pp. 318-326.

(56) References Cited

OTHER PUBLICATIONS

Wu et al., "Prolonged gene expression and cell survival after infection by a herpes simplex virus mutant defective in the immediate-early genes encoding ICP4, ICP27, and ICP22," J Virol. (1996) 70(9): 6358-6369.
Yu et al., Evaluation of effectiveness of granulocyte-macrophage colony-stimulating factor therapy to cancer patients after chemotherapy: a meta-analysis. Oncotarget. (2018) 9(46): 28226-28239. doi: 10.18632/oncotarget.24890. PMID: 29963274; PMCID: PMC6021338.
Zhao et al., "Osteosarcoma: a review of current and future therapeutic approaches," BioMed Eng Online. (2021) 20: 24.
Watts et al., "Current therapies and technological advances in aqueous aerosol drug delivery," Drug Dev Ind Pharm. (2008) 34(9): 913-22.
Di et al., "Phase I study protocol for ex vivo lentiviral gene therapy for the inherited skin disease, Netherton syndrome," Hum Gene Ther Clin Dev. (2013) 24(4):182-190.
Goins et al. "Generation of replication-competent and -defective HSV vectors," Cold Spring Harb Protoc. May 1, 2011;2011(5): 512; pdb.prot5615.
Krystal Biotech, Inc. "Krystal Biotech Announces Settlement with PeriphaGen, Inc." Mar. 15, 2022, https://ir.krystalbio.com/node/8481/pdf. (Year: 2022).
McGowan et al., "Keratin 17 null mice exhibit age- and strain-dependent alopecia," Genes & Dev (2002) 16:1412-1422.
Acland et al., "Gene therapy restores vision in a canine model of childhood blindness," Nat Genet. (2001) 28(1):92-5.
Ali et al., "Gene therapy for inherited retinal degeneration," Br J Ophthalmol. (1997) 81(9):795-801.
Boehmer et al., "Herpes Virus Replication," IUBMB Life (2003) 55(1):13-22.
Choate et al., "Transglutaminase 1 delivery to lamellar ichthyosis keratinocytes," Human Gene Therapy (1996) 7:2247-2253.
Farasat et al., "Novel transglutaminase-1 mutations and genotype-phenotype investigations of 104 patients with autosomal recessive congenital ichthyosis in the USA," J Med Genet (2009) 46(2):103-111.
Fraefel et al., "In vivo gene transfer to the rat retina using herpes simplex virus type 1 (HSV-1)-based amplicon vectors," Gene Ther. (2005) 12(16):1283-8.
Liu et al., "Herpes simplex virus mediated gene transfer to primate ocular tissues," Exp Eye Res. (1999) 69(4):385-95.
Messmer et al., "Ocular manifestations of keratitis-ichthyosis-deafness (KID) syndrome," Ophthalmology. (2005) 112(2):e1-6.
Peek et al., "Herpes simplex virus infection of the human eye induces a compartmentalized virus-specific B cell response," J Infect Dis. (2002) 186(11):1539-46.
Pepose et al., "Herpes simplex viral vectors for therapeutic gene delivery to ocular tissues. Recent breakthroughs in the molecular genetics of ocular diseases," Invest Ophthalmol Vis Sci. (1994) 35(6):2662-6.
Spencer et al., "HSV-1 vector-delivered FGF2 to the retina is neuroprotective but does not preserve functional responses," Mol Ther. (2001) 3(5 Pt 1):746-56.
Wang et al., "Updates on Gene Therapy for Diabetic Retinopathy," Curr Diab Rep. (2020) 20(7):22.
Onsorio et al., "Recombinant Herpes Simplex Virus Type 1 (HSV-1) Codelivering Interleukin-12p35 as a Molecular Adjuvant Enhances the Protective Immune Response against Ocular HSV-1 Challenge," J Virol (2005) 79(6):3297-3308

\* cited by examiner

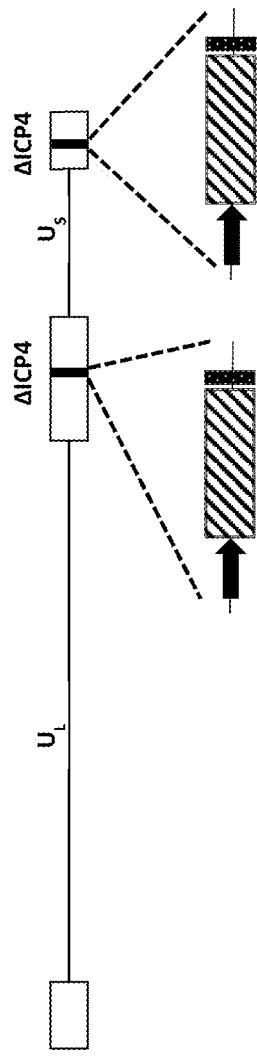
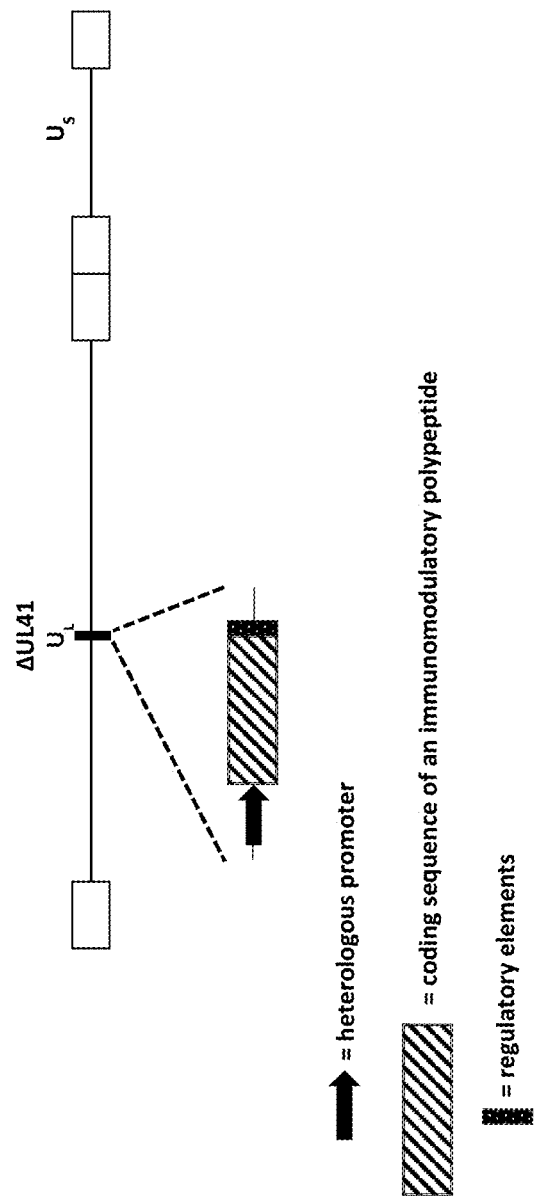
FIG. 1G
FIG. 1H human PBMC
24 hrs murine splenocytes
24 hrs

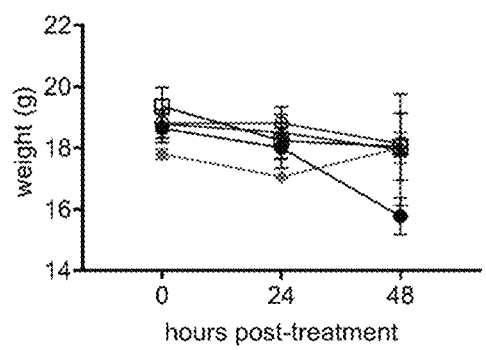
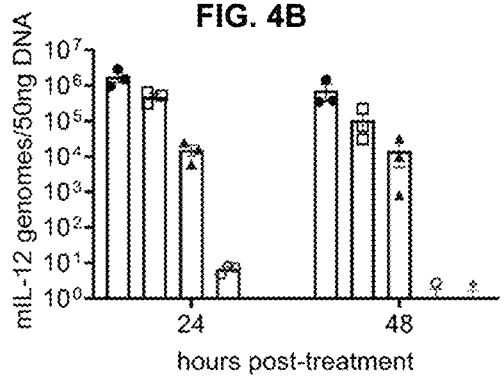
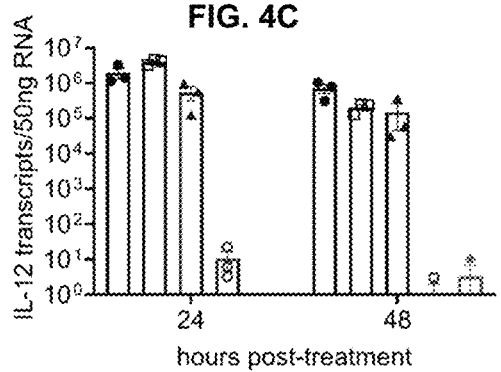

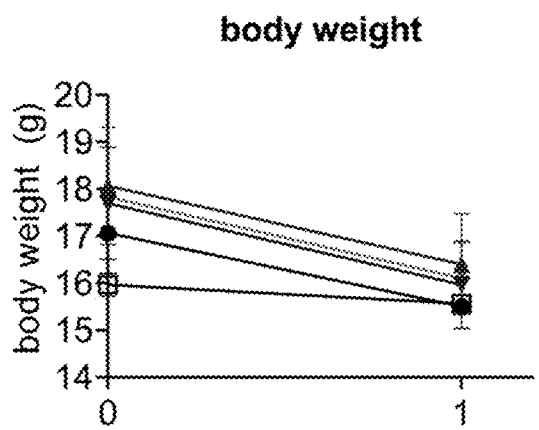
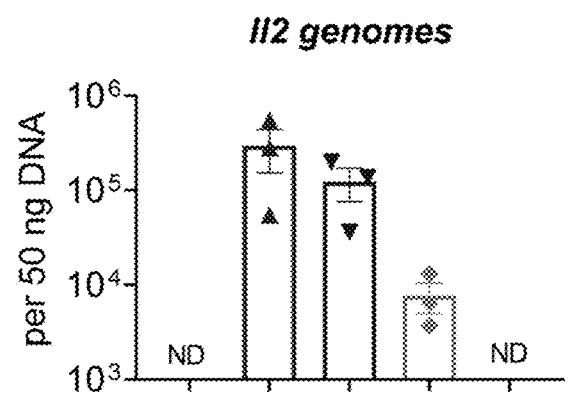
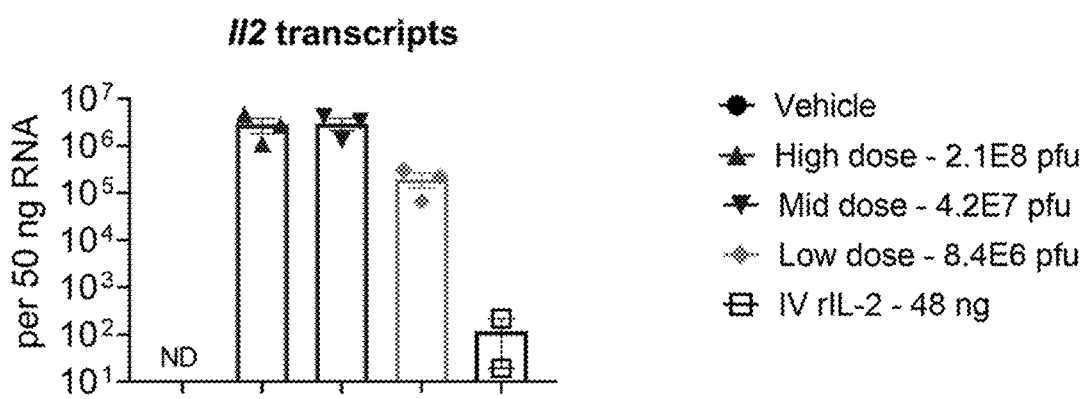
FIG. 5A body weight
FIG. 5B *Il2* genomes
FIG. 5C *Il2* transcripts serum

BALF lysate body weight

*Gmcsf* genomes

*Gmcsf transcripts*

- ● Vehicle
- ☐ High dose - 4.88E8 pfu
- ▲ Mid dose - 9.75E7 pfu
- ▽ Low dose - 1.95E7 pfu
- ◆ rGM-CSF - 0.6 μg

- ● Vehicle
- □ High dose - 4.88E8 pfu
- ▲ Mid dose - 9.75E7 pfu
- ▽ Low dose - 1.95E7 pfu
- ◆ rGM-CSF - 0.6 μg serum

BALF lung homogenates

BALF

BALF body weight

BALF - IL-12

BALF - GM-CSF

SEQUENCE LISTING

```
<160> NUMBER OF SEQ ID NOS: 85

<210> SEQ ID NO 1
<211> LENGTH: 271
<212> TYPE: PRT
<213> ORGANISM: Homo sapiens

<400> SEQUENCE: 1
```

Met Ala Lys Val Pro Asp Met Phe Glu Asp Leu Lys Asn Cys Tyr Ser
1               5                   10                  15

Glu Asn Glu Glu Asp Ser Ser Ser Ile Asp His Leu Ser Leu Asn Gln
                20                  25                  30

Lys Ser Phe Tyr His Val Ser Tyr Gly Pro Leu His Glu Gly Cys Met
            35                  40                  45

Asp Gln Ser Val Ser Leu Ser Ile Ser Glu Thr Ser Lys Thr Ser Lys
        50                  55                  60

Leu Thr Phe Lys Glu Ser Met Val Val Ala Thr Asn Gly Lys Val
65                  70                  75                  80

Leu Lys Lys Arg Arg Leu Ser Leu Ser Gln Ser Ile Thr Asp Asp Asp
                85                  90                  95

Leu Glu Ala Ile Ala Asn Asp Ser Glu Glu Ile Ile Lys Pro Arg
                100                 105                 110

```
Ser Ala Pro Phe Ser Phe Leu Ser Asn Val Lys Tyr Asn Phe Met Arg
        115                 120                 125

Ile Ile Lys Tyr Glu Phe Ile Leu Asn Asp Ala Leu Asn Gln Ser Ile
        130                 135                 140

Ile Arg Ala Asn Asp Gln Tyr Leu Thr Ala Ala Leu His Asn Leu
145                 150                 155                 160

Asp Glu Ala Val Lys Phe Asp Met Gly Ala Tyr Lys Ser Ser Lys Asp
                165                 170                 175

Asp Ala Lys Ile Thr Val Ile Leu Arg Ile Ser Lys Thr Gln Leu Tyr
                180                 185                 190

Val Thr Ala Gln Asp Glu Asp Gln Pro Val Leu Leu Lys Glu Met Pro
            195                 200                 205

Glu Ile Pro Lys Thr Ile Thr Gly Ser Glu Thr Asn Leu Leu Phe Phe
        210                 215                 220

Trp Glu Thr His Gly Thr Lys Asn Tyr Phe Thr Ser Val Ala His Pro
225                 230                 235                 240

Asn Leu Phe Ile Ala Thr Lys Gln Asp Tyr Trp Val Cys Leu Ala Gly
                245                 250                 255

Gly Pro Pro Ser Ile Thr Asp Phe Gln Ile Leu Glu Asn Gln Ala
            260                 265                 270

<210> SEQ ID NO 2
<211> LENGTH: 269
<212> TYPE: PRT
<213> ORGANISM: Homo sapiens

<400> SEQUENCE: 2

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
            100                 105                 110

Tyr Val His Asp Ala Pro Val Arg Ser Leu Asn Cys Thr Leu Arg Asp
        115                 120                 125

Ser Gln Gln Lys Ser Leu Val Met Ser Gly Pro Tyr Glu Leu Lys Ala
        130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
        195                 200                 205

Lys Lys Met Glu Lys Arg Phe Val Phe Asn Lys Ile Glu Ile Asn Asn
```

```
            210                 215                 220
Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
                260                 265
```

```
<210> SEQ ID NO 3
<211> LENGTH: 153
<212> TYPE: PRT
<213> ORGANISM: Homo sapiens

<400> SEQUENCE: 3

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
            130                 135                 140

Cys Gln Ser Ile Ile Ser Thr Leu Thr
145                 150
```

```
<210> SEQ ID NO 4
<211> LENGTH: 177
<212> TYPE: PRT
<213> ORGANISM: Homo sapiens

<400> SEQUENCE: 4

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
                20                  25                  30

Asp Gly Lys Gln Tyr Glu Ser Val Leu Met Val Ser Ile Asp Gln Leu
            35                  40                  45

Leu Asp Ser Met Lys Glu Ile Gly Ser Asn Cys Leu Asn Asn Glu Phe
50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
```

```
            115                 120                 125
Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 5
<211> LENGTH: 219
<212> TYPE: PRT
<213> ORGANISM: Homo sapiens

<400> SEQUENCE: 5

Met Cys Pro Ala Arg Ser Leu Leu Leu Val Ala Thr Leu Val Leu Leu
1               5                   10                  15

Asp His Leu Ser Leu Ala Arg Asn Leu Pro Val Ala Thr Pro Asp Pro
            20                  25                  30

Gly Met Phe Pro Cys Leu His His Ser Gln Asn Leu Leu Arg Ala Val
        35                  40                  45

Ser Asn Met Leu Gln Lys Ala Arg Gln Thr Leu Glu Phe Tyr Pro Cys
50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
        115                 120                 125

Glu Asp Leu Lys Met Tyr Gln Val Glu Phe Lys Thr Met Asn Ala Lys
    130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asp Arg Val Met Ser Tyr Leu Asn Ala Ser
    210                 215

<210> SEQ ID NO 6
<211> LENGTH: 328
<212> TYPE: PRT
<213> ORGANISM: Homo sapiens

<400> SEQUENCE: 6

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45
```

Thr Cys Asp Thr Pro Glu Glu Asp Gly Ile Thr Trp Thr Leu Asp Gln
            50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                    85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 7
<211> LENGTH: 146
<212> TYPE: PRT
<213> ORGANISM: Homo sapiens

<400> SEQUENCE: 7

Met His Pro Leu Leu Asn Pro Leu Leu Leu Ala Leu Gly Leu Met Ala
1               5                   10                  15

Leu Leu Leu Thr Thr Val Ile Ala Leu Thr Cys Leu Gly Gly Phe Ala
            20                  25                  30

Ser Pro Gly Pro Val Pro Pro Ser Thr Ala Leu Arg Glu Leu Ile Glu
        35                  40                  45

Glu Leu Val Asn Ile Thr Gln Asn Gln Lys Ala Pro Leu Cys Asn Gly
    50                  55                  60

Ser Met Val Trp Ser Ile Asn Leu Thr Ala Gly Met Tyr Cys Ala Ala
65                  70                  75                  80

Leu Glu Ser Leu Ile Asn Val Ser Gly Cys Ser Ala Ile Glu Lys Thr

```
                85                  90                  95
Gln Arg Met Leu Ser Gly Phe Cys Pro His Lys Val Ser Ala Gly Gln
            100                 105                 110

Phe Ser Ser Leu His Val Arg Asp Thr Lys Ile Glu Val Ala Gln Phe
            115                 120                 125

Val Lys Asp Leu Leu Leu His Leu Lys Lys Leu Phe Arg Glu Gly Arg
    130                 135                 140

Phe Asn
145

<210> SEQ ID NO 8
<211> LENGTH: 162
<212> TYPE: PRT
<213> ORGANISM: Homo sapiens

<400> SEQUENCE: 8

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
        50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 9
<211> LENGTH: 155
<212> TYPE: PRT
<213> ORGANISM: Homo sapiens

<400> SEQUENCE: 9

Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
                20                  25                  30

Cys Pro Asn Ser Glu Asp Lys Asn Phe Pro Arg Thr Val Met Val Asn
            35                  40                  45

Leu Asn Ile His Asn Arg Asn Thr Asn Thr Asn Pro Lys Arg Ser Ser
        50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95
```

```
Leu Gly Cys Ile Asn Ala Asp Gly Asn Val Asp Tyr His Met Asn Ser
                100                 105                 110

Val Pro Ile Gln Gln Glu Ile Leu Val Leu Arg Arg Glu Pro Pro His
            115                 120                 125

Cys Pro Asn Ser Phe Arg Leu Glu Lys Ile Leu Val Ser Val Gly Cys
        130                 135                 140

Thr Cys Val Thr Pro Ile Val His His Val Ala
145                 150                 155

<210> SEQ ID NO 10
<211> LENGTH: 193
<212> TYPE: PRT
<213> ORGANISM: Homo sapiens

<400> SEQUENCE: 10

Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
            20                  25                  30

Leu Glu Ser Asp Tyr Phe Gly Lys Leu Glu Ser Lys Leu Ser Val Ile
        35                  40                  45

Arg Asn Leu Asn Asp Gln Val Leu Phe Ile Asp Gln Gly Asn Arg Pro
    50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
            100                 105                 110

Glu Asn Lys Ile Ile Ser Phe Lys Glu Met Asn Pro Pro Asp Asn Ile
        115                 120                 125

Lys Asp Thr Lys Ser Asp Ile Ile Phe Phe Gln Arg Ser Val Pro Gly
    130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp

<210> SEQ ID NO 11
<211> LENGTH: 200
<212> TYPE: PRT
<213> ORGANISM: Homo sapiens

<400> SEQUENCE: 11

Met Lys Leu Asp Met Thr Gly Asp Cys Thr Pro Val Leu Val Leu Met
1               5                   10                  15

Ala Ala Val Leu Thr Val Thr Gly Ala Val Pro Val Ala Arg Leu His
            20                  25                  30

Gly Ala Leu Pro Asp Ala Arg Gly Cys His Ile Ala Gln Phe Lys Ser
        35                  40                  45

Leu Ser Pro Gln Glu Leu Gln Ala Phe Lys Arg Ala Lys Asp Ala Leu
    50                  55                  60
```

Glu Glu Ser Leu Leu Leu Lys Asp Cys Arg Cys His Ser Arg Leu Phe
65                  70                  75                  80

Pro Arg Thr Trp Asp Leu Arg Gln Leu Gln Val Arg Glu Arg Pro Met
            85                  90                  95

Ala Leu Glu Ala Glu Leu Ala Leu Thr Leu Lys Val Leu Glu Ala Thr
        100                 105                 110

Ala Asp Thr Asp Pro Ala Leu Val Asp Val Leu Asp Gln Pro Leu His
    115                 120                 125

Thr Leu His His Ile Leu Ser Gln Phe Arg Ala Cys Ile Gln Pro Gln
130                 135                 140

Pro Thr Ala Gly Pro Arg Thr Gly Arg Leu His His Trp Leu Tyr
145                 150                 155                 160

Arg Leu Gln Glu Ala Pro Lys Lys Glu Ser Pro Gly Cys Leu Glu Ala
                165                 170                 175

Ser Val Thr Phe Asn Leu Phe Arg Leu Leu Thr Arg Asp Leu Asn Cys
            180                 185                 190

Val Ala Ser Gly Asp Leu Cys Val
            195                 200

<210> SEQ ID NO 12
<211> LENGTH: 196
<212> TYPE: PRT
<213> ORGANISM: Homo sapiens

<400> SEQUENCE: 12

Met Thr Gly Asp Cys Met Pro Val Leu Val Leu Met Ala Ala Val Leu
1               5                   10                  15

Thr Val Thr Gly Ala Val Pro Val Ala Arg Leu Arg Gly Ala Leu Pro
            20                  25                  30

Asp Ala Arg Gly Cys His Ile Ala Gln Phe Lys Ser Leu Ser Pro Gln
        35                  40                  45

Glu Leu Gln Ala Phe Lys Arg Ala Lys Asp Ala Leu Glu Glu Ser Leu
    50                  55                  60

Leu Leu Lys Asp Cys Lys Cys Arg Ser Arg Leu Phe Pro Arg Thr Trp
65                  70                  75                  80

Asp Leu Arg Gln Leu Gln Val Arg Glu Arg Pro Val Ala Leu Glu Ala
                85                  90                  95

Glu Leu Ala Leu Thr Leu Lys Val Leu Glu Ala Thr Ala Asp Thr Asp
            100                 105                 110

Pro Ala Leu Gly Asp Val Leu Asp Gln Pro Leu His Thr Leu His His
        115                 120                 125

Ile Leu Ser Gln Leu Arg Ala Cys Ile Gln Pro Gln Pro Thr Ala Gly
    130                 135                 140

Pro Arg Thr Arg Gly Arg Leu His His Trp Leu His Arg Leu Gln Glu
145                 150                 155                 160

Ala Pro Lys Lys Glu Ser Pro Gly Cys Leu Glu Ala Ser Val Thr Phe
                165                 170                 175

Asn Leu Phe Arg Leu Leu Thr Arg Asp Leu Asn Cys Val Ala Ser Gly
            180                 185                 190

Asp Leu Cys Val
            195

<210> SEQ ID NO 13
<211> LENGTH: 234
<212> TYPE: PRT
<213> ORGANISM: Homo sapiens

<400> SEQUENCE: 13

```
Met Cys Phe Pro Lys Val Leu Ser Asp Asp Met Lys Lys Leu Lys Ala
1               5                   10                  15

Arg Met Val Met Leu Leu Pro Thr Ser Ala Gln Gly Leu Gly Ala Trp
            20                  25                  30

Val Ser Ala Cys Asp Thr Glu Asp Thr Val Gly His Leu Gly Pro Trp
        35                  40                  45

Arg Asp Lys Asp Pro Ala Leu Trp Cys Gln Leu Cys Leu Ser Ser Gln
    50                  55                  60

His Gln Ala Ile Glu Arg Phe Tyr Asp Lys Met Gln Asn Ala Glu Ser
65                  70                  75                  80

Gly Arg Gly Gln Val Met Ser Ser Leu Ala Glu Leu Glu Asp Asp Phe
                85                  90                  95

Lys Glu Gly Tyr Leu Glu Thr Val Ala Ala Tyr Tyr Glu Glu Gln His
            100                 105                 110

Pro Glu Leu Thr Pro Leu Leu Glu Lys Glu Arg Asp Gly Leu Arg Cys
        115                 120                 125

Arg Gly Asn Arg Ser Pro Val Pro Asp Val Glu Asp Pro Ala Thr Glu
    130                 135                 140

Glu Pro Gly Glu Ser Phe Cys Asp Lys Val Met Arg Trp Phe Gln Ala
145                 150                 155                 160

Met Leu Gln Arg Leu Gln Thr Trp Trp His Gly Val Leu Ala Trp Val
                165                 170                 175

Lys Glu Lys Val Val Ala Leu Val His Ala Val Gln Ala Leu Trp Lys
            180                 185                 190

Gln Phe Gln Ser Phe Cys Cys Ser Leu Ser Glu Leu Phe Met Ser Ser
        195                 200                 205

Phe Gln Ser Tyr Gly Ala Pro Arg Gly Asp Lys Glu Glu Leu Thr Pro
    210                 215                 220

Gln Lys Cys Ser Glu Pro Gln Ser Ser Lys
225                 230
```

<210> SEQ ID NO 14
<211> LENGTH: 270
<212> TYPE: PRT
<213> ORGANISM: Homo sapiens

<400> SEQUENCE: 14

```
Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr
        115                 120                 125
```

Tyr Asn Asp Gln Ser Ile Thr Phe Ala Leu Glu Asp Glu Ser Tyr Glu
            130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
            180                 185                 190

Trp Leu His Ala Asn Asn Lys Glu His Ser Val Glu Leu His Lys Cys
            195                 200                 205

Glu Lys Pro Leu Pro Asp Gln Ala Phe Phe Val Leu His Asn Met His
210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
                245                 250                 255

Asn Leu Cys Thr Glu Asn Ile Leu Phe Lys Leu Ser Glu Thr
            260                 265                 270

<210> SEQ ID NO 15
<211> LENGTH: 242
<212> TYPE: PRT
<213> ORGANISM: Homo sapiens

<400> SEQUENCE: 15

Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
            20                  25                  30

Glu Glu Cys Thr Val Thr Gly Phe Leu Arg Asp Lys Leu Gln Tyr Arg
        35                  40                  45

Ser Arg Leu Gln Tyr Met Lys His Tyr Phe Pro Ile Asn Tyr Lys Ile
    50                  55                  60

Ser Val Pro Tyr Glu Gly Val Phe Arg Ile Ala Asn Val Thr Arg Leu
65                  70                  75                  80

Gln Arg Ala Gln Val Ser Glu Arg Glu Leu Arg Tyr Leu Trp Val Leu
                85                  90                  95

Val Ser Leu Ser Ala Thr Glu Ser Val Gln Asp Val Leu Leu Glu Gly
            100                 105                 110

His Pro Ser Trp Lys Tyr Leu Gln Glu Val Glu Thr Leu Leu Leu Asn
        115                 120                 125

Val Gln Gln Gly Leu Thr Asp Val Glu Val Ser Pro Lys Val Glu Ser
    130                 135                 140

Val Leu Ser Leu Leu Asn Ala Pro Gly Pro Asn Leu Lys Leu Val Arg
145                 150                 155                 160

Pro Lys Ala Leu Leu Asp Asn Cys Phe Arg Val Met Glu Leu Leu Tyr
                165                 170                 175

Cys Ser Cys Cys Lys Gln Ser Ser Val Leu Asn Trp Gln Asp Cys Glu
            180                 185                 190

Val Pro Ser Pro Gln Ser Cys Pro Glu Pro Ser Leu Gln Tyr Ala
        195                 200                 205

Ala Thr Gln Leu Tyr Pro Pro Pro Trp Ser Pro Ser Ser Pro
210                 215                 220

His Ser Thr Gly Ser Val Arg Pro Val Arg Ala Gln Gly Glu Gly Leu

-continued

```
                225                 230                 235                 240
Leu Pro

<210> SEQ ID NO 16
<211> LENGTH: 233
<212> TYPE: PRT
<213> ORGANISM: Homo sapiens

<400> SEQUENCE: 16

Met Ser Thr Glu Ser Met Ile Arg Asp Val Glu Leu Ala Glu Glu Ala
1               5                  10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
        50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
                100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
        130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
                180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
        210                 215                 220

Gln Val Tyr Phe Gly Ile Ile Ala Leu
225                 230

<210> SEQ ID NO 17
<211> LENGTH: 166
<212> TYPE: PRT
<213> ORGANISM: Homo sapiens

<400> SEQUENCE: 17

Met Lys Tyr Thr Ser Tyr Ile Leu Ala Phe Gln Leu Cys Ile Val Leu
1               5                  10                  15

Gly Ser Leu Gly Cys Tyr Cys Gln Asp Pro Tyr Val Lys Glu Ala Glu
                20                  25                  30

Asn Leu Lys Lys Tyr Phe Asn Ala Gly His Ser Asp Val Ala Asp Asn
            35                  40                  45

Gly Thr Leu Phe Leu Gly Ile Leu Lys Asn Trp Lys Glu Glu Ser Asp
        50                  55                  60

Arg Lys Ile Met Gln Ser Gln Ile Val Ser Phe Tyr Phe Lys Leu Phe
65                  70                  75                  80
```

```
Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 18
<211> LENGTH: 207
<212> TYPE: PRT
<213> ORGANISM: Homo sapiens

<400> SEQUENCE: 18

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
    130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro
        195                 200                 205

<210> SEQ ID NO 19
<211> LENGTH: 144
<212> TYPE: PRT
<213> ORGANISM: Homo sapiens

<400> SEQUENCE: 19

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30
```

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
 50                  55                  60

Asp Leu Gln Glu Pro Thr Cys Leu Gln Thr Arg Leu Glu Leu Tyr Lys
 65                  70                  75                  80

Gln Gly Leu Arg Gly Ser Leu Thr Lys Leu Lys Gly Pro Leu Thr Met
                 85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
            115                 120                 125

Asp Phe Leu Leu Val Ile Pro Phe Asp Cys Trp Glu Pro Val Gln Glu
            130                 135                 140

<210> SEQ ID NO 20
<211> LENGTH: 107
<212> TYPE: PRT
<213> ORGANISM: Homo sapiens

<400> SEQUENCE: 20

Met Ala Arg Ala Ala Leu Ser Ala Ala Pro Ser Asn Pro Arg Leu Leu
 1               5                  10                  15

Arg Val Ala Leu Leu Leu Leu Leu Val Ala Ala Gly Arg Arg Ala
                 20                  25                  30

Ala Gly Ala Ser Val Ala Thr Glu Leu Arg Cys Gln Cys Leu Gln Thr
            35                  40                  45

Leu Gln Gly Ile His Pro Lys Asn Ile Gln Ser Val Asn Val Lys Ser
 50                  55                  60

Pro Gly Pro His Cys Ala Gln Thr Glu Val Ile Ala Thr Leu Lys Asn
 65                  70                  75                  80

Gly Arg Lys Ala Cys Leu Asn Pro Ala Ser Pro Ile Val Lys Lys Ile
                 85                  90                  95

Ile Glu Lys Met Leu Asn Ser Asp Lys Ser Asn
            100                 105

<210> SEQ ID NO 21
<211> LENGTH: 107
<212> TYPE: PRT
<213> ORGANISM: Homo sapiens

<400> SEQUENCE: 21

Met Ala Arg Ala Thr Leu Ser Ala Ala Pro Ser Asn Pro Arg Leu Leu
 1               5                  10                  15

Arg Val Ala Leu Leu Leu Leu Leu Val Ala Ala Ser Arg Arg Ala
                 20                  25                  30

Ala Gly Ala Pro Leu Ala Thr Glu Leu Arg Cys Gln Cys Leu Gln Thr
            35                  40                  45

Leu Gln Gly Ile His Leu Lys Asn Ile Gln Ser Val Lys Val Lys Ser
 50                  55                  60

Pro Gly Pro His Cys Ala Gln Thr Glu Val Ile Ala Thr Leu Lys Asn
 65                  70                  75                  80

Gly Gln Lys Ala Cys Leu Asn Pro Ala Ser Pro Met Val Lys Lys Ile
                 85                  90                  95

Ile Glu Lys Met Leu Lys Asn Gly Lys Ser Asn
            100                 105

```
<210> SEQ ID NO 22
<211> LENGTH: 99
<212> TYPE: PRT
<213> ORGANISM: Homo sapiens

<400> SEQUENCE: 22

Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
        35                  40                  45

Ile Lys Glu Leu Arg Val Ile Glu Ser Gly Pro His Cys Ala Asn Thr
50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Glu Lys Phe Leu Lys Arg Ala
                85                  90                  95

Glu Asn Ser

<210> SEQ ID NO 23
<211> LENGTH: 125
<212> TYPE: PRT
<213> ORGANISM: Homo sapiens

<400> SEQUENCE: 23

Met Lys Lys Ser Gly Val Leu Phe Leu Leu Gly Ile Ile Leu Leu Val
1               5                   10                  15

Leu Ile Gly Val Gln Gly Thr Pro Val Val Arg Lys Gly Arg Cys Ser
            20                  25                  30

Cys Ile Ser Thr Asn Gln Gly Thr Ile His Leu Gln Ser Leu Lys Asp
        35                  40                  45

Leu Lys Gln Phe Ala Pro Ser Pro Ser Cys Glu Lys Ile Glu Ile Ile
50                  55                  60

Ala Thr Leu Lys Asn Gly Val Gln Thr Cys Leu Asn Pro Asp Ser Ala
65                  70                  75                  80

Asp Val Lys Glu Leu Ile Lys Lys Trp Glu Lys Gln Val Ser Gln Lys
                85                  90                  95

Lys Lys Gln Lys Asn Gly Lys Lys His Gln Lys Lys Lys Val Leu Lys
            100                 105                 110

Val Arg Lys Ser Gln Arg Ser Arg Gln Lys Lys Thr Thr
            115                 120                 125

<210> SEQ ID NO 24
<211> LENGTH: 94
<212> TYPE: PRT
<213> ORGANISM: Homo sapiens

<400> SEQUENCE: 24

Met Ser Val Lys Gly Met Ala Ile Ala Leu Ala Val Ile Leu Cys Ala
1               5                   10                  15

Thr Val Val Gln Gly Phe Pro Met Phe Lys Arg Gly Arg Cys Leu Cys
            20                  25                  30

Ile Gly Pro Gly Val Lys Ala Val Lys Val Ala Asp Ile Glu Lys Ala
        35                  40                  45

Ser Ile Met Tyr Pro Ser Asn Asn Cys Asp Lys Ile Glu Val Ile Ile
```

Thr Leu Lys Glu Asn Lys Gly Gln Arg Cys Leu Asn Pro Lys Ser Lys
65                  70                  75                  80

Gln Ala Arg Leu Ile Ile Lys Lys Val Glu Arg Lys Asn Phe
                85                  90

<210> SEQ ID NO 25
<211> LENGTH: 254
<212> TYPE: PRT
<213> ORGANISM: Homo sapiens

<400> SEQUENCE: 25

Met Gly Arg Asp Leu Arg Pro Gly Ser Arg Val Leu Leu Leu Leu Leu
1               5                   10                  15

Leu Leu Leu Leu Val Tyr Leu Thr Gln Pro Gly Asn Gly Asn Glu Gly
                20                  25                  30

Ser Val Thr Gly Ser Cys Tyr Cys Gly Lys Arg Ile Ser Ser Asp Ser
            35                  40                  45

Pro Pro Ser Val Gln Phe Met Asn Arg Leu Arg Lys His Leu Arg Ala
    50                  55                  60

Tyr His Arg Cys Leu Tyr Tyr Thr Arg Phe Gln Leu Leu Ser Trp Ser
65                  70                  75                  80

Val Cys Gly Gly Asn Lys Asp Pro Trp Val Gln Glu Leu Met Ser Cys
                85                  90                  95

Leu Asp Leu Lys Glu Cys Gly His Ala Tyr Ser Gly Ile Val Ala His
            100                 105                 110

Gln Lys His Leu Leu Pro Thr Ser Pro Pro Ile Ser Gln Ala Ser Glu
        115                 120                 125

Gly Ala Ser Ser Asp Ile His Thr Pro Ala Gln Met Leu Leu Ser Thr
    130                 135                 140

Leu Gln Ser Thr Gln Arg Pro Thr Leu Pro Val Gly Ser Leu Ser Ser
145                 150                 155                 160

Asp Lys Glu Leu Thr Arg Pro Asn Glu Thr Thr Ile His Thr Ala Gly
                165                 170                 175

His Ser Leu Ala Ala Gly Pro Glu Ala Gly Glu Asn Gln Lys Gln Pro
            180                 185                 190

Glu Lys Asn Ala Gly Pro Thr Ala Arg Thr Ser Ala Thr Val Pro Val
        195                 200                 205

Leu Cys Leu Leu Ala Ile Ile Phe Ile Leu Thr Ala Ala Leu Ser Tyr
    210                 215                 220

Val Leu Cys Lys Arg Arg Arg Gly Gln Ser Pro Gln Ser Ser Pro Asp
225                 230                 235                 240

Leu Pro Val His Tyr Ile Pro Val Ala Pro Asp Ser Asn Thr
                245                 250

<210> SEQ ID NO 26
<211> LENGTH: 99
<212> TYPE: PRT
<213> ORGANISM: Homo sapiens

<400> SEQUENCE: 26

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu

```
                35                  40                  45
Ala Ser Tyr Arg Arg Ile Thr Ser Ser Lys Cys Pro Lys Glu Ala Val
 50                  55                  60

Ile Phe Lys Thr Ile Val Ala Lys Glu Ile Cys Ala Asp Pro Lys Gln
 65                  70                  75                  80

Lys Trp Val Gln Asp Ser Met Asp His Leu Asp Lys Gln Thr Gln Thr
                 85                  90                  95

Pro Lys Thr

<210> SEQ ID NO 27
<211> LENGTH: 92
<212> TYPE: PRT
<213> ORGANISM: Homo sapiens

<400> SEQUENCE: 27

Met Gln Val Ser Thr Ala Ala Leu Ala Val Leu Leu Cys Thr Met Ala
 1               5                  10                  15

Leu Cys Asn Gln Phe Ser Ala Ser Leu Ala Ala Asp Thr Pro Thr Ala
                20                  25                  30

Cys Cys Phe Ser Tyr Thr Ser Arg Gln Ile Pro Gln Asn Phe Ile Ala
                35                  40                  45

Asp Tyr Phe Glu Thr Ser Ser Gln Cys Ser Lys Pro Gly Val Ile Phe
 50                  55                  60

Leu Thr Lys Arg Ser Arg Gln Val Cys Ala Asp Pro Ser Glu Glu Trp
 65                  70                  75                  80

Val Gln Lys Tyr Val Ser Asp Leu Glu Leu Ser Ala
                85                  90

<210> SEQ ID NO 28
<211> LENGTH: 92
<212> TYPE: PRT
<213> ORGANISM: Homo sapiens

<400> SEQUENCE: 28

Met Lys Leu Cys Val Thr Val Leu Ser Leu Leu Met Leu Val Ala Ala
 1               5                  10                  15

Phe Cys Ser Pro Ala Leu Ser Ala Pro Met Gly Ser Asp Pro Pro Thr
                20                  25                  30

Ala Cys Cys Phe Ser Tyr Thr Ala Arg Lys Leu Pro Arg Asn Phe Val
                35                  40                  45

Val Asp Tyr Tyr Glu Thr Ser Ser Leu Cys Ser Gln Pro Ala Val Val
 50                  55                  60

Phe Gln Thr Lys Arg Ser Lys Gln Val Cys Ala Asp Pro Ser Glu Ser
 65                  70                  75                  80

Trp Val Gln Glu Tyr Val Tyr Asp Leu Glu Leu Asn
                85                  90

<210> SEQ ID NO 29
<211> LENGTH: 91
<212> TYPE: PRT
<213> ORGANISM: Homo sapiens

<400> SEQUENCE: 29

Met Lys Val Ser Ala Ala Ala Leu Ala Val Ile Leu Ile Ala Thr Ala
 1               5                  10                  15

Leu Cys Ala Pro Ala Ser Ala Ser Pro Tyr Ser Ser Asp Thr Thr Pro
                20                  25                  30
```

```
Cys Cys Phe Ala Tyr Ile Ala Arg Pro Leu Pro Arg Ala His Ile Lys
            35                  40                  45

Glu Tyr Phe Tyr Thr Ser Gly Lys Cys Ser Asn Pro Ala Val Val Phe
 50                  55                  60

Val Thr Arg Lys Asn Arg Gln Val Cys Ala Asn Pro Glu Lys Lys Trp
 65                  70                  75                  80

Val Arg Glu Tyr Ile Asn Ser Leu Glu Met Ser
                85                  90

<210> SEQ ID NO 30
<211> LENGTH: 97
<212> TYPE: PRT
<213> ORGANISM: Homo sapiens

<400> SEQUENCE: 30

Met Lys Val Ser Ala Ala Leu Leu Trp Leu Leu Leu Ile Ala Ala Ala
 1               5                  10                  15

Phe Ser Pro Gln Gly Leu Ala Gly Pro Ala Ser Val Pro Thr Thr Cys
                20                  25                  30

Cys Phe Asn Leu Ala Asn Arg Lys Ile Pro Leu Gln Arg Leu Glu Ser
            35                  40                  45

Tyr Arg Arg Ile Thr Ser Gly Lys Cys Pro Gln Lys Ala Val Ile Phe
 50                  55                  60

Lys Thr Lys Leu Ala Lys Asp Ile Cys Ala Asp Pro Lys Lys Lys Trp
 65                  70                  75                  80

Val Gln Asp Ser Met Lys Tyr Leu Asp Gln Lys Ser Pro Thr Pro Lys
                85                  90                  95

Pro

<210> SEQ ID NO 31
<211> LENGTH: 816
<212> TYPE: DNA
<213> ORGANISM: Homo sapiens

<400> SEQUENCE: 31
atggccaaag ttccagacat gtttgaagac ctgaagaact gttacagtga aaatgaagaa    60
gacagttcct ccattgatca tctgtctctg aatcagaaat ccttctatca tgtaagctat   120
ggcccactcc atgaaggctg catggatcaa tctgtgtctc tgagtatctc tgaaacctct   180
aaaacatcca agcttacctt caaggagagc atggtggtag tagcaaccaa cgggaaggtt   240
ctgaagaaga cacggttgag tttaagccaa tccatcactg atgatgacct ggaggccatc   300
gccaatgact cagaggaaga aatcatcaag cctaggtcag cacctttag cttcctgagc   360 aatgtgaaat acaactttat gaggatcatc aaatacgaat tcatcctgaa tgacgccctc   420
aatcaaagta taattcgagc caatgatcag tacctcacgg ctgctgcatt acataatctg   480
gatgaagcag tgaaatttga catgggtgct tataagtcat caaggatgac tgctaaaatt   540
accgtgattc taagaatctc aaaaactcaa ttgtatgtga ctgcccaaga tgaagaccaa   600
ccagtgctgc tgaaggagat gcctgagata cccaaaacca tcacaggtag tgagaccaac   660
ctcctcttct tctgggaaac tcacggcact aagaactatt tcacatcagt tgcccatcca   720
aacttgttta ttgccacaaa gcaagactac tgggtgtgct tggcagggg gccaccctct   780 atcactgact tcagatact ggaaaaccag gcgtag                              816

<210> SEQ ID NO 32
<211> LENGTH: 810
```

<212> TYPE: DNA
<213> ORGANISM: Homo sapiens

<400> SEQUENCE: 32

```
atggcagaag tacctgagct cgccagtgaa atgatggctt attacagtgg caatgaggat      60
gacttgttct ttgaagctga tggccctaaa cagatgaagt gctccttcca ggacctggac     120
ctctgccctc tggatggcgg catccagcta cgaatctccg accaccacta cagcaagggc     180
ttcaggcagg ccgcgtcagt tgttgtggcc atggacaagc tgaggaagat gctggttccc     240
tgcccacaga ccttccagga gaatgacctg agcaccttct ttcccttcat ctttgaagaa     300
gaacctatct tcttcgacac atgggataac gaggcttatg tgcacgatgc acctgtacga     360
tcactgaact gcacgctccg ggactcacag caaaaaagct ggtgatgtc tggtccatat      420
gaactgaaag ctctccacct ccagggacag gatatggagc aacaagtggt gttctccatg     480
tcctttgtac aaggagaaga agtaatgac aaaatacctg tggccttggg cctcaaggaa      540
aagaatctgt acctgtcctg cgtgttgaaa gatgataagc ccactctaca gctggagagt     600
gtagatccca aaaattaccc aaagaagaag atggaaaagc gatttgtctt caacaagata     660
gaaatcaata acaagctgga atttgagtct gcccagttcc ccaactggta catcagcacc     720
tctcaagcag aaaacatgcc cgtcttcctg ggagggacca aaggcggcca ggatataact     780
gacttcacca tgcaatttgt gtcttcctaa                                      810
```

<210> SEQ ID NO 33
<211> LENGTH: 462
<212> TYPE: DNA
<213> ORGANISM: Homo sapiens

<400> SEQUENCE: 33

```
atgtacagga tgcaactcct gtcttgcatt gcactaagtc ttgcacttgt cacaaacagt      60
gcacctactt caagttctac aaagaaaaca cagctacaac tggagcattt actgctggat     120
ttacagatga ttttgaatgg aattaataat tacaagaatc ccaaactcac caggatgctc     180
acatttaagt tttacatgcc caagaaggcc acagaactga acatcttca gtgtctagaa      240
gaagaactca aacctctgga ggaagtgcta aatttagctc aaagcaaaaa ctttcactta     300
agacccaggg acttaatcag caatatcaac gtaatagttc tggaactaaa gggatctgaa     360
acaacattca tgtgtgaata tgctgatgag acagcaacca ttgtagaatt tctgaacaga     420
tggattacct tttgtcaaag catcatctca acactgactt ga                       462
```

<210> SEQ ID NO 34
<211> LENGTH: 534
<212> TYPE: DNA
<213> ORGANISM: Homo sapiens

<400> SEQUENCE: 34

```
atgttccatg tttcttttag gtatatcttt ggacttcctc ccctgatcct tgttctgttg      60
ccagtagcat catctgattg tgatattgaa ggtaaagatg gcaaacaata tgagagtgtt     120
ctaatggtca gcatcgatca attattggac agcatgaaag aaattggtag caattgcctg     180
aataatgaat ttaacttttt taaaagacat atctgtgatg ctaataagga aggtatgttt     240
ttattccgtg ctgctcgcaa gttgaggcaa tttcttaaaa tgaatagcac tggtgatttt     300
gatctccact tattaaaagt ttcagaaggc acaacaatac tgttgaactg cactggccag     360
gttaaaggaa gaaaaccagc tgccctgggt gaagcccaac caacaaagag tttggaagaa     420
```

| | |
|---|---|
| aataaatctt taaaggaaca gaaaaaactg aatgacttgt gtttcctaaa gagactatta | 480 |
| caagagataa aaacttgttg gaataaaatt ttgatgggca ctaaagaaca ctga | 534 |

<210> SEQ ID NO 35
<211> LENGTH: 762
<212> TYPE: DNA
<213> ORGANISM: Homo sapiens

<400> SEQUENCE: 35

| | |
|---|---|
| atgtggcccc ctgggtcagc ctcccagcca ccgccctcac ctgccgcggc cacaggtctg | 60 |
| catccagcgg ctcgccctgt gtccctgcag tgccggctca gcatgtgtcc agcgcgcagc | 120 |
| ctcctccttg tggctaccct ggtcctcctg gaccacctca gtttggccag aaacctcccc | 180 |
| gtggccactc cagacccagg aatgttccca tgccttcacc actcccaaaa cctgctgagg | 240 |
| gccgtcagca acatgctcca gaaggccaga caaactctag aattttaccc ttgcacttct | 300 |
| gaagagattg atcatgaaga tatcacaaaa gataaaacca gcacagtgga ggcctgttta | 360 |
| ccattggaat taaccaagaa tgagagttgc ctaaattcca gagagacctc tttcataact | 420 |
| aatgggagtt gcctggcctc cagaaagacc tcttttatga tggccctgtg ccttagtagt | 480 |
| atttatgaag acttgaagat gtaccaggtg gagttcaaga ccatgaatgc aaagcttctg | 540 |
| atggatccta agaggcagat cttttctaga taaaacatgc tggcagttat tgatgagctg | 600 |
| atgcaggccc tgaatttcaa cagtgagact gtgccacaaa aatcctccct tgaagaaccg | 660 |
| gatttttata aaactaaaat caagctctgc atacttcttc atgctttcag aattcgggca | 720 |
| gtgactattg atagagtgat gagctatctg aatgcttcct aa | 762 |

<210> SEQ ID NO 36
<211> LENGTH: 987
<212> TYPE: DNA
<213> ORGANISM: Homo sapiens

<400> SEQUENCE: 36

| | |
|---|---|
| atgtgtcacc agcagttggt catctcttgg ttttccctgg tttttctggc atctcccctc | 60 |
| gtggccatat gggaactgaa gaaagatgtt tatgtcgtag aattggattg gtatccggat | 120 |
| gcccctggag aaatggtggt cctcacctgt gacacccctg aagaagatgg tatcacctgg | 180 |
| accttggacc agagcagtga ggtcttaggc tctggcaaaa ccctgaccat ccaagtcaaa | 240 |
| gagtttggag atgctggcca gtacacctgt cacaaaggag gcgaggttct aagccattcg | 300 |
| ctcctgctgc ttcacaaaaa ggaagatgga atttggtcca ctgatatttt aaaggaccag | 360 |
| aaagaaccca aaaataagac ctttctaaga tgcgaggcca agaattattc tggacgtttc | 420 |
| acctgctggt ggctgacgac aatcagtact gatttgacat tcagtgtcaa aagcagcaga | 480 |
| ggctcttctg acccccaagg ggtgacgtgc ggagctgcta cactctctgc agagagagtc | 540 |
| agagggaca acaaggagta tgagtactca gtggagtgcc aggaggacag tgcctgccca | 600 |
| gctgctgagg agagtctgcc cattgaggtc atggtggatg ccgttcacaa gctcaagtat | 660 |
| gaaaactaca ccagcagctt cttcatcagg gacatcatca acctgacccc acccaagaac | 720 |
| ttgcagctga gccattaaaa gaattctcgg caggtgagg tcagctggga gtaccctgac | 780 |
| acctggagta ctccacattc ctacttctcc ctgacattct gcgttcaggt ccagggcaag | 840 |
| agcaagagag aaaagaaaga tagagtcttc acggacaaga cctcagccac ggtcatctgc | 900 |
| cgcaaaaatg ccagcattag cgtgcgggcc caggaccgct actatagctc atcttggagc | 960 |
| gaatgggcat ctgtgccctg cagttag | 987 |

<210> SEQ ID NO 37
<211> LENGTH: 441
<212> TYPE: DNA
<213> ORGANISM: Homo sapiens

<400> SEQUENCE: 37

```
atgcatccgc tcctcaatcc tctcctgttg gcactgggcc tcatggcgct tttgttgacc      60
acggtcattg ctctcacttg ccttggcggc tttgcctccc caggccctgt gcctccctct     120
acagccctca gggagctcat tgaggagctg gtcaacatca cccagaacca gaaggctccg     180
ctctgcaatg gcagcatggt atggagcatc aacctgacag ctggcatgta ctgtgcagcc     240
ctggaatccc tgatcaacgt gtcaggctgc agtgccatcg agaagaccca gaggatgctg     300
agcggattct gcccgcacaa ggtctcagct gggcagtttt ccagcttgca tgtccgagac     360
accaaaatcg aggtggccca gtttgtaaag gacctgctct acatttaaa gaaactttt      420 cgcgagggac agttcaactg a                                              441
```

<210> SEQ ID NO 38
<211> LENGTH: 489
<212> TYPE: DNA
<213> ORGANISM: Homo sapiens

<400> SEQUENCE: 38

```
atgagaattt cgaaaccaca tttgagaagt atttccatcc agtgctactt gtgtttactt      60
ctaaacagtc attttctaac tgaagctggc attcatgtct tcattttggg ctgtttcagt     120
gcagggcttc ctaaaacaga agccaactgg gtgaatgtaa taagtgattt gaaaaaaatt     180
gaagatctta ttcaatctat gcatattgat gctactttat atacggaaag tgatgttcac     240
cccagttgca aagtaacagc aatgaagtgc tttctcttgg agttacaagt tatttcactt     300
gagtccggag atgcaagtat tcatgataca gtagaaaatc tgatcatcct agcaaacaac     360
agtttgtctt ctaatgggaa tgtaacagaa tctggatgca agaatgtga ggaactggag      420 gaaaaaaata ttaagaatt tttgcagagt tttgtacata ttgtccaaat gttcatcaac      480
acttcttga                                                            489
```

<210> SEQ ID NO 39
<211> LENGTH: 468
<212> TYPE: DNA
<213> ORGANISM: Homo sapiens

<400> SEQUENCE: 39

```
atgactcctg ggaagacctc attggtgtca ctgctactgc tgctgagcct ggaggccata      60
gtgaaggcag gaatcacaat cccacgaaat ccaggatgcc aaattctga ggacaagaac      120 ttcccccgga ctgtgatggt caacctgaac atccataacc ggaataccaa taccaatccc     180
aaaaggtcct cagattacta caaccgatcc acctcacctt ggaatctcca ccgcaatgag     240
gaccctgaga gatatccctc tgtgatctgg gaggcaaagt gccgccactt gggctgcatc     300
aacgctgatg gaacgtgga ctaccacatg aactctgtcc ccatccagca agagatcctg      360
gtcctgcgca gggagcctcc acactgcccc aactccttcc ggctggagaa gatactggtg     420
tccgtgggct gcacctgtgt caccccgatt gtccaccatg tggcctaa                  468
```

<210> SEQ ID NO 40
<211> LENGTH: 582
<212> TYPE: DNA

<213> ORGANISM: Homo sapiens

<400> SEQUENCE: 40

| | |
|---|---|
| atggctgctg aaccagtaga agacaattgc atcaactttg tggcaatgaa atttattgac | 60 |
| aatacgcttt actttatagc tgaagatgat gaaaacctgg aatcagatta ctttggcaag | 120 |
| cttgaatcta aattatcagt cataagaaat ttgaatgacc aagttctctt cattgaccaa | 180 |
| ggaaatcggc ctctatttga agatatgact gattctgact gtagagataa tgcaccccgg | 240 |
| accatattta ttataagtat gtataaagat agccagccta gaggtatggc tgtaactatc | 300 |
| tctgtgaagt gtgagaaaat ttcaactctc tcctgtgaga acaaaattat ttcctttaag | 360 |
| gaaatgaatc ctcctgataa catcaaggat acaaaaagtg acatcatatt ctttcagaga | 420 |
| agtgtcccag acatgataa taagatgcaa tttgaatctt catcatacga aggatacttt | 480 |
| ctagcttgtg aaaagagag agaccttttt aaactcattt tgaaaaaga ggatgaattg | 540 |
| ggggatagat ctataatgtt cactgttcaa acgaagact ag | 582 |

<210> SEQ ID NO 41
<211> LENGTH: 603
<212> TYPE: DNA
<213> ORGANISM: Homo sapiens

<400> SEQUENCE: 41

| | |
|---|---|
| atgaaactag acatgactgg ggactgcacg ccagtgctgg tgctgatggc cgcagtgctg | 60 |
| accgtgactg gagcagttcc tgtcgccagg ctccacgggg ctctcccgga tgcaaggggc | 120 |
| tgccacatag cccagttcaa gtccctgtct ccacaggagc tgcaggcctt taagagggcc | 180 |
| aaagatgcct tagaagagtc gcttctgctg aaggactgca ggtgccactc ccgcctcttc | 240 |
| cccaggacct gggacctgag gcagctgcag gtgagggagc gccccatggc tttggaggct | 300 |
| gagctggccc tgacgctgaa ggttctggag gccaccgctg acactgaccc agccctggtg | 360 |
| gacgtcttgg accagcccct tcacaccctg caccatatcc tctcccagtt ccgggcctgt | 420 |
| atccagcctc agcccacggc agggcccagg accggggcc gcctccacca ttggctgtac | 480 |
| cggctccagg aggccccaaa aaaggagtcc cctggctgcc tcgaggcctc tgtcaccttc | 540 |
| aacctcttcc gcctcctcac gcgagacctg aattgtgttg ccagtgggga cctgtgtgtc | 600 |
| tga | 603 |

<210> SEQ ID NO 42
<211> LENGTH: 603
<212> TYPE: DNA
<213> ORGANISM: Homo sapiens

<400> SEQUENCE: 42

| | |
|---|---|
| atgaaactag acatgaccgg ggactgcatg ccagtgctgg tgctgatggc cgcagtgctg | 60 |
| accgtgactg gagcagttcc tgtcgccagg ctccgcgggg ctctcccgga tgcaaggggc | 120 |
| tgccacatag cccagttcaa gtccctgtct ccacaggagc tgcaggcctt taagagggcc | 180 |
| aaagatgcct tagaagagtc gcttctgctg aaggactgca agtgccgctc ccgcctcttc | 240 |
| cccaggacct gggacctgag gcagctgcag gtgagggagc gccccgtggc tttggaggct | 300 |
| gagctggccc tgacgctgaa ggttctggag gccaccgctg acactgaccc agccctgggg | 360 |
| gatgtcttgg accagcccct tcacaccctg caccatatcc tctcccagct ccgggcctgt | 420 |
| atccagcctc agcccacggc agggcccagg accggggcc gcctccacca ttggctgcac | 480 |
| cggctccagg aggccccaaa aaaggagtcc cctggctgcc tcgaggcctc tgtcaccttc | 540 |

```
aacctcttcc gcctcctcac gcgagacctg aattgtgttg ccagcgggga cctgtgtgtc    600
tga                                                                  603

<210> SEQ ID NO 43
<211> LENGTH: 567
<212> TYPE: DNA
<213> ORGANISM: Homo sapiens

<400> SEQUENCE: 43
atgtgcttcc cgaaggtcct ctctgatgac atgaagaagc tgaaggcccg aatgcaccag     60
gccatagaaa gattttatga taaaatgcaa aatgcagaat caggacgtgg acaggtgatg    120
tcgagcctgg cagagctgga ggacgacttc aaagagggct acctggagac agtggcggct    180
tattatgagg agcagcaccc agagctcact cctctacttg aaaaagaaag agatggatta    240
cggtgccgag gcaacagatc ccctgtcccg gatgttgagg atcccgcaac cgaggagcct    300
ggggagagct tttgtgacaa ggtcatgaga tggttccagg ccatgctgca gcggctgcag    360
acctggtggc acggggttct ggcctgggtg aaggagaagg tggtggccct ggtccatgca    420
gtgcaggccc tctggaaaca gttccagagt ttctgctgct ctctgtcaga gctcttcatg    480
tcctctttcc agtcctacgg agcccacgg ggggacaagg aggagctgac accccagaag    540
tgctctgaac cccaatcctc aaaatga                                        567

<210> SEQ ID NO 44
<211> LENGTH: 813
<212> TYPE: DNA
<213> ORGANISM: Homo sapiens

<400> SEQUENCE: 44
atgaagccta aaatgaagta ttcaaccaac aaaatttcca cagcaaagtg gaagaacaca     60
gcaagcaaag ccttgtgttt caagctggga aatcccaac agaaggccaa agaagtttgc    120
cccatgtact ttatgaagct ccgctctggc cttatgataa aaaggaggc ctgttacttt    180 aggagagaaa ccaccaaaag gccttcactg aaaacaggta aaagcacaa aagacatctg    240 gtactcgctg cctgtcaaca gcagtctact gtggagtgct ttgcctttgg tatatcaggg    300
gtccagaaat atactagagc acttcatgat tcaagtatca caggaatttc acctattaca    360
gagtatcttg cttctctaag cacatacaat gatcaatcca ttactttgc tttggaggat    420 gaaagttatg agatatatgt tgaagacttg aaaaagatg aaaagaaaga taggtgtta    480 ctgagttact atgagtctca acacccctca atgaatcag gtgacggtgt tgatggtaag    540
atgttaatgg taaccctgag tcctacaaaa gacttctggt tgcatgccaa caacaaggaa    600
cactctgtgg agctccataa gtgtgaaaaa ccactgccag accaggcctt ctttgtcctt    660
cataatatgc actccaactg tgtttcattt gaatgcaaga ctgatcctgg agtgtttata    720
ggtgtaaagg ataatcatct tgctctgatt aaagtagact cttctgagaa tttgtgtact    780
gaaaatatct tgtttaagct ctctgaaact tag                                 813

<210> SEQ ID NO 45
<211> LENGTH: 729
<212> TYPE: DNA
<213> ORGANISM: Homo sapiens

<400> SEQUENCE: 45
atgccccggg gcttcacctg gctgcgctat cttgggatct tccttggcgt ggccttgggg     60
```

-continued

```
aatgagcctt tggagatgtg gcccttgacg cagaatgagg agtgcactgt cacgggtttt      120
ctgcgggaca agctgcagta caggagccga cttcagtaca tgaaacacta cttccccatc      180
aactacaaga tcagtgtgcc ttacgagggg gtgttcagaa tcgccaacgt caccaggctg      240
cagagggccc aggtgagcga gcgggagctg cggtatctgt gggtcttggt gagcctcagt      300
gccactgagt cggtgcagga cgtgctgctc gagggccacc catcctggaa gtacctgcag      360
gaggtggaga cgctgctgct gaatgtccag cagggcctca cggatgtgga ggtcagcccc      420
aaggtggaat ccgtgttgtc cctcttgaat gccccagggc aaaacctgaa gctggtgcgg      480
cccaaagccc tgctggacaa ctgcttccgg gtcatggagc tgctgtactg ctcctgctgt      540
aaacaaagct ccgtcctaaa ctggcaggac tgtgaggtgc caagtcctca gtcttgcagc      600
ccagagccct cattgcagta tgcggccacc cagctgtacc ctccgccccc gtggtccccc      660
agctccccgc ctcactccac gggctcggtg aggccggtca gggcacaggg cgagggcctc      720
ttgccctga                                                              729
```

<210> SEQ ID NO 46
<211> LENGTH: 702
<212> TYPE: DNA
<213> ORGANISM: Homo sapiens

<400> SEQUENCE: 46

```
atgagcactg aaagcatgat ccgggacgtg gagctggccg aggaggcgct ccccaagaag       60 acagggggc cccagggctc caggcggtgc ttgttcctca gcctcttctc cttcctgatc      120
gtggcaggcg ccaccacgct cttctgcctg ctgcactttg gagtgatcgg ccccagagg      180 gaagagttcc ccagggacct ctctctaatc agccctctgg cccaggcagt cagatcatct      240
tctcgaaccc cgagtgacaa gcctgtagcc catgttgtag caaaccctca agctgagggg      300
cagctccagt ggctgaaccg ccgggccaat gccctcctgg ccaatggcgt ggagctgaga      360
gataaccagc tggtggtgcc atcagagggc ctgtacctca tctactccca ggtcctcttc      420
aagggccaag gctgccccctc cacccatgtg ctcctcaccc acaccatcag ccgcatcgcc      480
gtctcctacc agaccaaggt caacctcctc tctgccatca gagccctg ccagagggag      540 acccagagg gggctgaggc caagccctgg tatgagccca tctatctggg aggggtcttc      600
cagctggaga agggtgaccg actcagcgct gagatcaatc ggcccgacta tctcgacttt      660
gccgagtctg ggcaggtcta ctttgggatc attgccctgt ga                        702
```

<210> SEQ ID NO 47
<211> LENGTH: 501
<212> TYPE: DNA
<213> ORGANISM: Homo sapiens

<400> SEQUENCE: 47

```
atgaaatata caagttatat cttggctttt cagctctgca tcgttttggg ttctcttggc       60
tgttactgcc aggacccata tgtaaaagaa gcagaaaacc ttaagaaata ttttaatgca      120
ggtcattcag atgtagcgga taatggaact cttttcttag gcattttgaa gaattggaaa      180
gaggagagtg acagaaaaat aatgcagagc caaattgtct cctttactt caaactttt       240 aaaaacttta agatgaccca gagcatccaa aagagtgtgg agaccatcaa ggaagacatg      300
aatgtcaagt ttttcaatag caacaaaaag aaacgagatg acttcgaaaa gctgactaat      360
tattcggtaa ctgacttgaa tgtccaacgc aaagcaatac atgaactcat ccaagtgatg      420
gctgaactgt cgccagcagc taaaacaggg aagcgaaaaa ggagtcagat gctgtttcga      480
```

```
ggtcgaagag catcccagta a                                           501
```

<210> SEQ ID NO 48
<211> LENGTH: 624
<212> TYPE: DNA
<213> ORGANISM: Homo sapiens

<400> SEQUENCE: 48

```
atggctggac ctgccaccca gagcccatg aagctgatgg ccctgcagct gctgctgtgg    60
cacagtgcac tctggacagt gcaggaagcc acccccctgg ccctgccag ctccctgccc   120 cagagcttcc tgctcaagtg cttagagcaa gtgaggaaga tccagggcga tggcgcagcg   180
ctccaggaga agctggtgag tgagtgtgcc acctacaagc tgtgccaccc cgaggagctg   240
gtgctgctcg acactctct gggcatcccc tgggctcccc tgagcagctg ccccagccag   300
gccctgcagc tggcaggctg cttgagccaa ctccatagcg gcctttttcct ctaccagggg   360 ctcctgcagg ccctggaagg gatctccccc gagttgggtc ccaccttgga cacactgcag   420
ctggacgtcg ccgactttgc caccaccatc tggcagcaga tggaagaact gggaatggcc   480
cctgccctgc agcccaccca gggtgccatg ccggccttcg cctctgcttt ccagcgccgg   540
gcaggagggg tcctggttgc ctcccatctg cagagcttcc tggaggtgtc gtaccgcgtt   600
ctacgccacc ttgcccagcc ctga                                           624
```

<210> SEQ ID NO 49
<211> LENGTH: 435
<212> TYPE: DNA
<213> ORGANISM: Homo sapiens

<400> SEQUENCE: 49

```
atgtggctgc agagcctgct gctcttgggc actgtggcct gcagcatctc tgcacccgcc    60
cgctcgccca gccccagcac gcagccctgg gagcatgtga atgccatcca ggaggcccgg   120
cgtctcctga acctgagtag agacactgct gctgagatga atgaaacagt agaagtcatc   180
tcagaaatgt ttgacctcca ggagccgacc tgcctacaga cccgcctgga gctgtacaag   240
cagggcctgc ggggcagcct caccaagctc aagggcccct tgaccatgat ggccagccac   300
tacaagcagc actgccctcc aaccccggaa acttcctgtg caacccagat tatcaccttt   360
gaaagtttca agagaaacct gaaggacttt ctgcttgtca tcccctttga ctgctgggag   420
ccagtccagg agtga                                                     435
```

<210> SEQ ID NO 50
<211> LENGTH: 324
<212> TYPE: DNA
<213> ORGANISM: Homo sapiens

<400> SEQUENCE: 50

```
atggcccgcg ctgctctctc cgccgccccc agcaatcccc ggctcctgcg agtggcactg    60
ctgctcctgc tcctggtagc cgctggccgg cgcgcagcag gagcgtccgt ggccactgaa   120
ctgcgctgcc agtgcttgca gaccctgcag ggaattcacc ccaagaacat ccaaagtgtg   180
aacgtgaagt cccccggacc ccactgcgcc caaaccgaag tcatagccac actcaagaat   240
gggcggaaag cttgcctcaa tcctgcatcc cccatagtta gaaaatcat cgaaaagatg   300 ctgaacagtg acaaatccaa ctga                                           324
```

<210> SEQ ID NO 51

```
<211> LENGTH: 324
<212> TYPE: DNA
<213> ORGANISM: Homo sapiens

<400> SEQUENCE: 51
atggcccgcg ccacgctctc cgccgccccc agcaatcccc ggctcctgcg ggtggcgctg      60
ctgctcctgc tcctggtggc cgccagccgg cgcgcagcag gagcgcccct ggccactgaa     120
ctgcgctgcc agtgcttgca gaccctgcag ggaattcacc tcaagaacat ccaaagtgtg     180
aaggtgaagt cccccggacc ccactgcgcc caaaccgaag tcatagccac actcaagaat     240
gggcagaaag cttgtctcaa ccccgcatcg cccatggtta agaaaatcat cgaaaagatg     300
ctgaaaaatg gcaaatccaa ctga                                            324

<210> SEQ ID NO 52
<211> LENGTH: 300
<212> TYPE: DNA
<213> ORGANISM: Homo sapiens

<400> SEQUENCE: 52
atgacttcca agctggccgt ggctctcttg gcagccttcc tgatttctgc agctctgtgt      60
gaaggtgcag ttttgccaag gagtgctaaa gaacttagat gtcagtgcat aaagacatac     120
tccaaacctt tccaccccaa atttatcaaa gaactgagag tgattgagag tggaccacac     180
tgcgccaaca cagaaattat tgtaaagctt tctgatggaa gagagctctg tctggacccc     240
aaggaaaact gggtgcagag ggttgtggag aagttttga agagggctga gaattcataa     300

<210> SEQ ID NO 53
<211> LENGTH: 378
<212> TYPE: DNA
<213> ORGANISM: Homo sapiens

<400> SEQUENCE: 53
atgaagaaaa gtggtgttct tttcctcttg ggcatcatct tgctggttct gattggagtg      60
caaggaaccc cagtagtgag aaagggtcgc tgttcctgca tcagcaccaa ccaagggact     120
atccacctac aatccttgaa agaccttaaa caatttgccc aagcccttc ctgcgagaaa     180 attgaaatca ttgctacact gaagaatgga gttcaaacat gtctaaaccc agattcagca     240
gatgtgaagg aactgattaa aaagtgggag aaacaggtca gccaaaagaa aaagcaaaag     300
aatgggaaaa acatcaaaaa aagaaagtt ctgaaagttc gaaaatctca acgttctcgt     360
caaaagaaga ctacataa                                                   378

<210> SEQ ID NO 54
<211> LENGTH: 285
<212> TYPE: DNA
<213> ORGANISM: Homo sapiens

<400> SEQUENCE: 54
atgagtgtga agggcatggc tatagccttg gctgtgatat tgtgtgctac agttgttcaa      60
ggcttcccca tgttcaaaag aggacgctgt ctttgcatag gccctggggt aaaagcagtg     120
aaagtggcag atattgagaa agcctccata atgtacccaa gtaacaactg tgacaaaata     180
gaagtgatta ttaccctgaa agaaaataaa ggacaacgat gcctaaatcc caaatcgaag     240 caagcaggc ttataatcaa aaaagttgaa agaaagaatt tttaa                      285

<210> SEQ ID NO 55
<211> LENGTH: 822
```

<212> TYPE: DNA
<213> ORGANISM: Homo sapiens

<400> SEQUENCE: 55

```
atgtctggga gtcagagcga ggtggctcca tccccgcaga gtccgcggag ccccgagatg      60
ggacgggact tgcggcccgg gtcccgcgtg ctcctgctcc tgcttctgct cctgctggtg     120
tacctgactc agccaggcaa tggcaacgag ggcagcgtca ctggaagttg ttattgtggt     180
aaaagaattt cttccgactc cccgccatcg gttcagttca tgaatcgtct ccggaaacac     240
ctgagagctt accatcggtg tctatactac acgaggttcc agctcctttc ctggagcgtg     300
tgtgggggca acaaggaccc atgggttcag gaattgatga gctgtcttga tctcaaagaa     360
tgtggacatg cttactcggg gattgtggcc caccagaagc atttacttcc taccagcccc     420
ccaatttctc aggcctcaga gggggcatct tcagatatcc acaccctgc  ccagatgctc     480
ctgtccacct tgcagtccac tcagcgcccc accctcccag taggatcact gtcctcggac     540
aaagagctca ctcgtcccaa tgaaaccacc attcacactg cgggccacag tctggcagct     600
gggcctgagg ctggggagaa ccagaagcag ccggaaaaaa atgctggtcc cacagccagg     660
acatcagcca cagtgccagt cctgtgcctc ctggccatca tcttcatcct caccgcagcc     720
ctttcctatg tgctgtgcaa gaggaggagg gggcagtcac cgcagtcctc tccagatctg     780
ccggttcatt atatacctgt ggcacctgac tctaataccg a                         822
```

<210> SEQ ID NO 56
<211> LENGTH: 300
<212> TYPE: DNA
<213> ORGANISM: Homo sapiens

<400> SEQUENCE: 56

```
atgaaagtct ctgccgccct tctgtgcctg ctgctcatag cagccacctt cattccccaa      60
gggctcgctc agccagatgc aatcaatgcc ccagtcacct gctgttataa cttcaccaat     120
aggaagatct cagtgcagag gctcgcgagc tatagaagaa tcaccagcag caagtgtccc     180
aaagaagctg tgatcttcaa gaccattgtg gccaaggaga tctgtgctga ccccaagcag     240
aagtgggttc aggattccat ggaccacctg gacaagcaaa cccaaactcc gaagacttga     300
```

<210> SEQ ID NO 57
<211> LENGTH: 279
<212> TYPE: DNA
<213> ORGANISM: Homo sapiens

<400> SEQUENCE: 57

```
atgcaggtct ccactgctgc ccttgctgtc ctcctctgca ccatggctct ctgcaaccag      60
ttctctgcat cacttgctgc tgacacgccg accgcctgct gcttcagcta cacctcccgg     120
cagattccac agaatttcat agctgactac tttgagacga gcagccagtg ctccaagccc     180
ggtgtcatct tcctaaccaa gcgaagccgg caggtctgtg ctgaccccag tgaggagtgg     240
gtccagaaat atgtcagcga cctggagctg agtgcctga                            279
```

<210> SEQ ID NO 58
<211> LENGTH: 279
<212> TYPE: DNA
<213> ORGANISM: Homo sapiens

<400> SEQUENCE: 58

```
atgaagctct gcgtgactgt cctgtctctc ctcatgctag tagctgcctt ctgctctcca    60
```

```
gcgctctcag caccaatggg ctcagaccct cccaccgcct gctgcttttc ttacaccgcg    120
aggaagcttc ctcgcaactt tgtggtagat tactatgaga ccagcagcct ctgctcccag    180
ccagctgtgg tattccaaac caaaagaagc aagcaagtct gtgctgatcc cagtgaatcc    240
tgggtccagg agtacgtgta tgacctggaa ctgaactga                          279
```

<210> SEQ ID NO 59
<211> LENGTH: 276
<212> TYPE: DNA
<213> ORGANISM: Homo sapiens

<400> SEQUENCE: 59

```
atgaaggtct ccgcggcagc cctcgctgtc atcctcattg ctactgccct ctgcgctcct     60
gcatctgcct ccccatattc ctcggacacc acaccctgct gctttgccta cattgcccgc    120
ccactgcccc gtgcccacat caaggagtat ttctacacca gtggcaagtg ctccaaccca    180
gcagtcgtct ttgtcacccg aaagaaccgc aagtgtgtg ccaacccaga gaagaaatgg     240
gttcgggagt acatcaactc tttggagatg agctag                             276
```

<210> SEQ ID NO 60
<211> LENGTH: 294
<212> TYPE: DNA
<213> ORGANISM: Homo sapiens

<400> SEQUENCE: 60

```
atgaaggtct ccgcagcact tctgtggctg ctgctcatag cagctgcctt cagcccccag     60
gggctcgctg ggccagcttc tgtcccaacc acctgctgct taacctggc caataggaag    120 ataccccttc agcgactaga gagctacagg agaatcacca gtggcaaatg tccccagaaa    180
gctgtgatct tcaagaccaa actggccaag gatatctgtg ccgaccccaa gaagaagtgg    240
gtgcaggatt ccatgaagta tctggaccaa aaatctccaa ctccaaagcc ataa          294
```

<210> SEQ ID NO 61
<211> LENGTH: 462
<212> TYPE: DNA
<213> ORGANISM: Artificial Sequence
<220> FEATURE:
<223> OTHER INFORMATION: Synthetic Construct

<400> SEQUENCE: 61

```
atgtaccgga tgcagctgct gagctgtatc gccctgtctc tggccctggt cacaaatagc     60 gccccctacca gcagcagcac caagaaaaca cagctgcaac tggaacacct cctgctggac    120
ctgcagatga tcctgaacgg catcaacaac tacaagaacc ccaagctgac ccggatgctg    180
accttcaagt tctacatgcc caagaaggcc accgagctga agcacctcca gtgcctggaa    240
gaggaactga agcccctgga agaagtgctg aatctggccc agagcaagaa cttccacctg    300
aggcctaggg acctgatcag caacatcaac gtgatcgtgc tggaactgaa aggcagcgag    360
acaaccttca tgtgcgagta cgccgacgag acagctacca tcgtggaatt tctgaaccgg    420
tggatcacct tctgccagag catcatcagc accctgacct ga                       462
```

<210> SEQ ID NO 62
<211> LENGTH: 762
<212> TYPE: DNA
<213> ORGANISM: Artificial Sequence
<220> FEATURE:
<223> OTHER INFORMATION: Synthetic Construct

<400> SEQUENCE: 62

```
atgtggcctc ctggatctgc ttctcagcct cctccatctc ctgccgctgc tacaggactt    60
catcctgccg caagacccgt gtctctgcag tgcagactga gcatgtgccc cgccagatct   120
ctgctgctgg tggctacact ggtgctgctg gatcatctga gcctggccag aaacctgcca   180
gtggccacgc ctgatcctgg catgtttcct tgtctgcacc acagccagaa cctgctgaga   240
gccgtgtcca acatgctgca gaaggccaga cagaccctcg agttctaccc ctgcaccagc   300
gaggaaatcg accacgagga catcaccaag gacaagacca gcaccgtgga agcctgcctg   360
cctctggaac tgaccaagaa cgagagctgc ctgaacagca gagagacaag cttcatcacc   420
aacggctctt gcctggcctc agaaagacc tccttcatga tggccctgtg cctgagcagc   480
atctacgagg acctgaagat gtaccaggtc gagttcaaga ccatgaacgc caagctgctg   540
atggacccca gcggcagat cttcctggac cagaatatgc tggccgtgat cgacgagctg   600
atgcaggccc tgaacttcaa cagcgagaca gtgccccaga gtccagcct ggaagaaccc   660 gacttctaca gaccaagat caagctgtgc atcctgctgc acgccttccg gatcagagcc   720
gtgaccatcg acagagtgat gagctacctg aacgcctcct ga                     762
```

<210> SEQ ID NO 63
<211> LENGTH: 987
<212> TYPE: DNA
<213> ORGANISM: Artificial Sequence
<220> FEATURE:
<223> OTHER INFORMATION: Synthetic Construct

<400> SEQUENCE: 63

```
atgtgtcacc agcagctggt catcagctgg ttcagcctgg tgttcctggc ctctcctctg    60
gtggccatct gggagctgaa gaaagacgtg tacgtggtgg aactggactg gtatcccgat   120
gctcctggcg agatggtggt gctgacctgc gataccctg aagaggacgg catcacctgg   180
acactggatc agtctagcga ggtgctcggc agcggcaaga ccctgaccat ccaagtgaaa   240
gagtttggcg acgccggcca gtacacctgt cacaaaggcg agaagtgct gagccacagc   300 ctgctgctgc tccacaagaa agaggatggc atttggagca ccgacatcct gaaggaccag   360
aaagagccca gaacaagac cttcctgaga tgcgaggcca agaactacag cggccggttc   420
acatgttggt ggctgaccac catcagcacc gacctgacct tcagcgtgaa gtccagcaga   480
ggcagcagtg atcctcaggg cgttacatgt ggcgccgcta cactgtctgc gaaagagtg   540 cgggcgaca caaagaata cgagtacagc gtggaatgcc agaggacag cgcctgtcca   600 gccgccgaag agtctctgcc tatcgaagtg atggtggacg ccgtgcacaa gctgaagtac   660
gagaactaca cctccagctt tttcatccgg gacatcatca gcccgatcc tccaaagaac   720 ctgcagctga gcctctgaa gaacagcaga caggtggaag tgtcctggga gtaccccgac   780
acctggtcta caccccacag ctacttcagc ctgaccttt gcgtgcaagt gcagggcaag   840
tccaagcgcg agaaaaagga ccgggtgttc accgacaaga ccagcgccac cgtgatctgc   900
agaaagaacg ccagcatcag cgtcagagcc caggaccggt actacagcag ctcttggagc   960
gaatgggcca gcgtgccatg tagctaa                                      987
```

<210> SEQ ID NO 64
<211> LENGTH: 75
<212> TYPE: DNA
<213> ORGANISM: Artificial Sequence
<220> FEATURE:
<223> OTHER INFORMATION: Synthetic Construct

```
<400> SEQUENCE: 64
agggccaaga ggggcagcgg cgagggcagg ggcagcctgc tgacctgcgg cgacgtggag    60 gagaacccccg gcccc                                                    75

<210> SEQ ID NO 65
<211> LENGTH: 66
<212> TYPE: DNA
<213> ORGANISM: Artificial Sequence
<220> FEATURE:
<223> OTHER INFORMATION: Synthetic Construct

<400> SEQUENCE: 65
ggaagcggag ctactaactt cagcctgctg aagcaggctg agacgtgga ggagaaccct    60 ggacct                                                               66

<210> SEQ ID NO 66
<211> LENGTH: 69
<212> TYPE: DNA
<213> ORGANISM: Artificial Sequence
<220> FEATURE:
<223> OTHER INFORMATION: Synthetic Construct

<400> SEQUENCE: 66
ggaagcggac agtgtactaa ttatgctctc ttgaaattgg ctggagatgt tgagagcaac    60
cctggacct                                                            69

<210> SEQ ID NO 67
<211> LENGTH: 75
<212> TYPE: DNA
<213> ORGANISM: Artificial Sequence
<220> FEATURE:
<223> OTHER INFORMATION: Synthetic Construct

<400> SEQUENCE: 67
ggaagcggag tgaaacagac tttgaatttt gaccttctca gttggcggg agacgtggag     60 tccaaccctg gacct                                                     75

<210> SEQ ID NO 68
<211> LENGTH: 25
<212> TYPE: PRT
<213> ORGANISM: Artificial Sequence
<220> FEATURE:
<223> OTHER INFORMATION: Synthetic Construct

<400> SEQUENCE: 68

Arg Ala Lys Arg Gly Ser Gly Glu Gly Arg Gly Ser Leu Leu Thr Cys
1               5                   10                  15

Gly Asp Val Glu Glu Asn Pro Gly Pro
            20                  25

<210> SEQ ID NO 69
<211> LENGTH: 22
<212> TYPE: PRT
<213> ORGANISM: Artificial Sequence
<220> FEATURE:
<223> OTHER INFORMATION: Synthetic Construct

<400> SEQUENCE: 69

Gly Ser Gly Ala Thr Asn Phe Ser Leu Leu Lys Gln Ala Gly Asp Val
1               5                   10                  15

Glu Glu Asn Pro Gly Pro
            20
```

<210> SEQ ID NO 70
<211> LENGTH: 23
<212> TYPE: PRT
<213> ORGANISM: Artificial Sequence
<220> FEATURE:
<223> OTHER INFORMATION: Synthetic Construct

<400> SEQUENCE: 70

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 71
<211> LENGTH: 25
<212> TYPE: PRT
<213> ORGANISM: Artificial Sequence
<220> FEATURE:
<223> OTHER INFORMATION: Synthetic Construct

<400> SEQUENCE: 71

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 72
<211> LENGTH: 15
<212> TYPE: PRT
<213> ORGANISM: Artificial Sequence
<220> FEATURE:
<223> OTHER INFORMATION: Synthetic Construct

<400> SEQUENCE: 72

Gly Gly Gly Gly Ser Gly Gly Gly Ser Gly Gly Gly Gly Ser
1               5                   10                  15

<210> SEQ ID NO 73
<211> LENGTH: 18
<212> TYPE: PRT
<213> ORGANISM: Artificial Sequence
<220> FEATURE:
<223> OTHER INFORMATION: Synthetic Construct

<400> SEQUENCE: 73

Gly Gly Ser Ser Arg Ser Ser Ser Gly Gly Gly Ser Gly Gly
1               5                   10                  15

Gly Gly

<210> SEQ ID NO 74
<211> LENGTH: 20
<212> TYPE: PRT
<213> ORGANISM: Artificial Sequence
<220> FEATURE:
<223> OTHER INFORMATION: Synthetic Construct

<400> SEQUENCE: 74

Gly Gly Gly Gly Ser Gly Gly Gly Gly Ser Gly Gly Gly Gly Ser Gly
1               5                   10                  15

Gly Gly Gly Ser
            20

<210> SEQ ID NO 75

```
<211> LENGTH: 15
<212> TYPE: PRT
<213> ORGANISM: Artificial Sequence
<220> FEATURE:
<223> OTHER INFORMATION: Synthetic Construct

<400> SEQUENCE: 75

Cys Gly Gly Gly Ser Gly Gly Gly Ser Gly Gly Gly Gly Gly Ser
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Synthetic Construct

<400> SEQUENCE: 76

Ser His Gly Gly His Gly Gly Gly Ser Gly Gly Gly Gly Gly Ser
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Synthetic Construct

<400> SEQUENCE: 77

Met Gly Gly Met Ser Gly Gly Gly Ser Gly Gly Gly Gly Gly Ser
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Synthetic Construct

<400> SEQUENCE: 78

Tyr Gly Gly Tyr Ser Gly Gly Gly Gly Ser Gly Gly Gly Gly Ser
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Synthetic Construct

<400> SEQUENCE: 79

Trp Gly Gly Tyr Ser Gly Gly Gly Gly Ser Gly Gly Gly Gly Ser
1               5                   10                  15

<210> SEQ ID NO 80
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 80

Ser Val Ser Val Gly Met Lys Pro Ser Pro Arg Pro
1               5                   10

<210> SEQ ID NO 81
<211> LENGTH: 12
```

```
<212> TYPE: PRT
<213> ORGANISM: Artificial Sequence
<220> FEATURE:
<223> OTHER INFORMATION: Synthetic Sequence

<400> SEQUENCE: 81

Val Ile Ser Asn His Ala Gly Ser Ser Arg Arg Leu
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Synthetic Construct

<400> SEQUENCE: 82

Pro Trp Ile Pro Thr Pro Arg Pro Thr Phe Thr Gly
1               5                   10

<210> SEQ ID NO 83
<211> LENGTH: 11
<212> TYPE: PRT
<213> ORGANISM: Artificial Sequence
<220> FEATURE:
<223> OTHER INFORMATION: Synthetic Construct

<400> SEQUENCE: 83

Arg Gly Arg Gly Arg Gly Arg Gly Arg Gly Arg
1               5                   10

<210> SEQ ID NO 84
<211> LENGTH: 1638
<212> TYPE: DNA
<213> ORGANISM: Artificial Sequence
<220> FEATURE:
<223> OTHER INFORMATION: Synthetic Construct

<400> SEQUENCE: 84
atgtgtcacc agcagctggt catcagctgg ttcagcctgg tgttcctggc ctctcctctg     60
gtggccatct gggagctgaa gaaagacgtg tacgtggtgg aactggactg gtatcccgat    120
gctcctggcg agatggtggt gctgacctgc gataccctg aagaggacgg catcacctgg     180
acactggatc agtctagcga ggtgctcggc agcggcaaga ccctgaccat ccaagtgaaa    240
gagtttggcg acgccggcca gtacacctgt cacaaaggcg agaagtgct gagccacagc     300 ctgctgctgc tccacaagaa agaggatggc atttggagca ccgacatcct gaaggaccag    360
aaagagccca gaacaagac cttcctgaga tgcgaggcca gaactacag cggccggttc      420 acatgttggt ggctgaccac catcagcacc gacctgacct tcagcgtgaa gtccagcaga    480
ggcagcagtg atcctcaggg cgttacatgt ggcgccgcta cactgtctgc cgaaagagtg    540
cggggcgaca caaagaata cgagtacagc gtggaatgcc aagaggacag cgcctgtcca    600
gccgccgaag agtctctgcc tatcgaagtg atggtggacg ccgtgcacaa gctgaagtac    660
gagaactaca cctccagctt tttcatccgg gacatcatca gcccgatcc tccaaagaac    720 ctgcagctga gcctctgaa gaacagcaga caggtggaag tgtcctggga gtaccccgac    780
acctggtcta caccccacag ctacttcagc ctgacctttt gcgtgcaagt cagggcaag     840 tccaagcgcg agaaaaagga ccgggtgttc accgacaaga ccagcgccac cgtgatctgc    900
agaaagaacg ccagcatcag cgtcagagcc caggaccggt actacagcag ctcttggagc    960
gaatgggcca gcgtgccatg ttctggtggc ggaggatctg gcggaggtgg aagcggcgga   1020
```

```
ggcggcagcg gaggtggtgg atctagaaat ctgccagtgg ccacgcctga tcctggcatg    1080
tttccttgtc tgcaccacag ccagaacctg ctgagagccg tgtccaacat gctgcagaag    1140
gccagacaga ccctcgagtt ctaccccctgc accagcgagg aaatcgacca cgaggacatc    1200
accaaggata agaccagcac cgtggaagcc tgcctgcctc tggaactgac caagaacgag    1260
agctgcctga cagccggga accagcttc atcaccaacg ctcttgcct ggccagcaga    1320 aagacctcct tcatgatggc cctgtgcctg agcagcatct acgaggacct gaagatgtac    1380
caggtcgagt tcaagaccat gaacgccaag ctgctgatgg accccaagcg cagatcttc    1440 ctggaccaga atatgctggc cgtgatcgac gagctgatgc aggccctgaa cttcaacagc    1500
gagacagtgc cccagaagtc tagcctggaa gaacccgact tctacaagac caagatcaag    1560
ctgtgcatcc tgctgcacgc cttccggatc agagccgtga ccatcgacag agtgatgagc    1620
tacctgaacg cctcctga                                                  1638
```

<210> SEQ ID NO 85
<211> LENGTH: 545
<212> TYPE: PRT
<213> ORGANISM: Artificial Sequence
<220> FEATURE:
<223> OTHER INFORMATION: Synthetic Construct

<400> SEQUENCE: 85

```
Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
```

-continued

```
                245                 250                 255
Glu Tyr Pro Asp Thr Trp Ser Thr Pro His Ser Tyr Phe Ser Leu Thr
            260                 265                 270
Phe Cys Val Gln Val Gln Gly Lys Ser Lys Arg Glu Lys Lys Asp Arg
        275                 280                 285
Val Phe Thr Asp Lys Thr Ser Ala Thr Val Ile Cys Arg Lys Asn Ala
    290                 295                 300
Ser Ile Ser Val Arg Ala Gln Asp Arg Tyr Tyr Ser Ser Ser Trp Ser
305                 310                 315                 320
Glu Trp Ala Ser Val Pro Cys Ser Gly Gly Gly Ser Gly Gly Gly
                325                 330                 335
Gly Ser Gly Gly Gly Ser Gly Gly Gly Ser Arg Asn Leu Pro
                340                 345                 350
Val Ala Thr Pro Asp Pro Gly Met Phe Pro Cys Leu His His Ser Gln
            355                 360                 365
Asn Leu Leu Arg Ala Val Ser Asn Met Leu Gln Lys Ala Arg Gln Thr
            370                 375                 380
Leu Glu Phe Tyr Pro Cys Thr Ser Glu Glu Ile Asp His Glu Asp Ile
385                 390                 395                 400
Thr Lys Asp Lys Thr Ser Thr Val Glu Ala Cys Leu Pro Leu Glu Leu
                405                 410                 415
Thr Lys Asn Glu Ser Cys Leu Asn Ser Arg Glu Thr Ser Phe Ile Thr
            420                 425                 430
Asn Gly Ser Cys Leu Ala Ser Arg Lys Thr Ser Phe Met Met Ala Leu
            435                 440                 445
Cys Leu Ser Ser Ile Tyr Glu Asp Leu Lys Met Tyr Gln Val Glu Phe
    450                 455                 460
Lys Thr Met Asn Ala Lys Leu Leu Met Asp Pro Lys Arg Gln Ile Phe
465                 470                 475                 480
Leu Asp Gln Asn Met Leu Ala Val Ile Asp Glu Leu Met Gln Ala Leu
            485                 490                 495
Asn Phe Asn Ser Glu Thr Val Pro Gln Lys Ser Ser Leu Glu Glu Pro
            500                 505                 510
Asp Phe Tyr Lys Thr Lys Ile Lys Leu Cys Ile Leu Leu His Ala Phe
        515                 520                 525
Arg Ile Arg Ala Val Thr Ile Asp Arg Val Met Ser Tyr Leu Asn Ala
    530                 535                 540
Ser
545
```

US 11,779,660 B2

VIRAL VECTORS FOR CANCER THERAPY

CROSS REFERENCE TO RELATED APPLICATIONS

This application claims the priority benefit of U.S. Provisional Application Ser. No. 63/170,103, filed Apr. 2, 2021, which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CFR) of the Sequence Listing (file name 761342001500.txt, date recorded: Apr. 1, 2022, size: 86,233 bytes).

FIELD OF THE INVENTION

The present disclosure relates, in part, to recombinant nucleic acids comprising one or more polynucleotides encoding an immunomodulatory polypeptide, viruses comprising the same, pharmaceutical compositions and formulations thereof, and methods of their use (e.g., for treating cancer, such as lung cancer).

BACKGROUND

Cancer is among the leading causes of death worldwide. Despite significant advances in clinical care and treatment methods, more effective cancer treatment options are still needed to prolong survival and decrease cancer death rates.

All references cited herein, including patent applications, patent publications, non-patent literature, and NCBI/UniProtKB/Swiss-Prot Accession numbers are herein incorporated by reference in their entirety, as if each individual reference were specifically and individually indicated to be incorporated by reference.

BRIEF SUMMARY

In order to meet these and other needs, provided herein are recombinant nucleic acids (e.g., recombinant herpes virus genomes) encoding one or more polypeptides (e.g., one or more immunomodulatory polypeptides such as cytokines and chemokines) for use in viruses (e.g., herpes viruses), pharmaceutical compositions and formulations, medicaments, and/or methods useful for treating cancer in a subject in need thereof.

Accordingly, certain aspects of the present disclosure relate to a recombinant herpes virus genome comprising one or more polynucleotides encoding an immunomodulatory polypeptide. In some embodiments, the recombinant herpes virus genome comprises two or more polynucleotides encoding an immunomodulatory polypeptide. In some embodiments, the recombinant herpes virus genome is replication competent. In some embodiments, the recombinant herpes virus genome is replication defective. In some embodiments that may be combined with any of the preceding embodiments, the recombinant herpes virus genome comprises the one or more polynucleotides encoding the immunomodulatory polypeptide within one or more viral gene loci. In some embodiments that may be combined with any of the preceding embodiments, the recombinant herpes virus genome is selected from a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, an Epstein-Barr virus genome, a recombinant Kaposi's sarcoma-associated herpesvirus genome, and any combinations or derivatives thereof.

In some embodiments that may be combined with any of the preceding embodiments, the recombinant herpes virus genome is a recombinant herpes simplex virus genome. In some embodiments, the recombinant herpes simplex virus genome is a recombinant type 1 herpes simplex virus (HSV-1) genome, a recombinant type 2 herpes simplex virus (HSV-2) genome, or any combinations or derivatives thereof. In some embodiments, the recombinant herpes simplex virus genome is a recombinant HSV-1 genome.

In some embodiments that may be combined with any of the preceding embodiments, the recombinant herpes simplex virus genome has been engineered to reduce or eliminate expression of one or more herpes simplex virus genes (e.g., one or more toxic herpes simplex virus genes). In some embodiments that may be combined with any of the preceding embodiments, the recombinant herpes simplex virus genome comprises an inactivating mutation. In some embodiments, the inactivating mutation is in a herpes simplex virus gene. In some embodiments, the inactivating mutation is a deletion of the coding sequence of the herpes simplex virus gene. In some embodiments, the herpes simplex virus gene is selected from Infected Cell Protein (ICP) 0 (one or both copies), ICP4 (one or both copies), ICP22, ICP27, ICP47, thymidine kinase (tk), Long Unique Region (UL) 41, and UL55. In some embodiments that may be combined with any of the preceding embodiments, the recombinant herpes simplex virus genome comprises an inactivating mutation in one or both copies of the ICP4 gene. In some embodiments that may be combined with any of the preceding embodiments, the recombinant herpes simplex virus genome comprises an inactivating mutation in the ICP22 gene. In some embodiments that may be combined with any of the preceding embodiments, the recombinant herpes simplex virus genome comprises an inactivating mutation in the UL41 gene. In some embodiments that may be combined with any of the preceding embodiments, the recombinant herpes simplex virus genome comprises an inactivating mutation in one or both copies of the ICP0 gene. In some embodiments that may be combined with any of the preceding embodiments, the recombinant herpes simplex virus genome comprises an inactivating mutation in the ICP27 gene. In some embodiments that may be combined with any of the preceding embodiments, the recombinant herpes simplex virus genome comprises an inactivating mutation in the UL55 gene. In some embodiments that may be combined with any of the preceding embodiments, the recombinant herpes simplex virus genome does not comprise an inactivating mutation in the ICP47 gene. In some embodiments, the recombinant herpes simplex virus genome does not comprise an inactivating mutation in one or both copies of the ICP34.5 gene. In some embodiments that may be combined with any of the preceding embodiments, the recombinant herpes simplex virus genome does not comprise an inactivating mutation in the UL36 gene.

In some embodiments that may be combined with any of the preceding embodiments, the recombinant herpes simplex virus genome comprises the one or more polynucleotides encoding the immunomodulatory polypeptide within one or more viral gene loci. In some embodiments that may be combined with any of the preceding embodiments, the recombinant herpes simplex virus genome comprises the one or more polynucleotides encoding the immunomodulatory polypeptide within one or both of the ICP4 viral gene loci. In some embodiments that may be combined with any of the preceding embodiments, the recombinant herpes simplex virus genome comprises the one or more polynucleotides encoding the immunomodulatory polypeptide within the ICP22 viral gene locus. In some embodiments that may be combined with any of the preceding embodiments, the recombinant herpes simplex virus genome comprises the one or more polynucleotides encoding the immunomodulatory polypeptide within the UL41 viral gene locus. In some embodiments that may be combined with any of the preceding embodiments, the recombinant herpes simplex virus genome comprises the one or more polynucleotides encoding the immunomodulatory polypeptide within one or both of the ICP0 viral gene loci. In some embodiments that may be combined with any of the preceding embodiments, the recombinant herpes simplex virus genome comprises the one or more polynucleotides encoding the immunomodulatory polypeptide within the ICP27 viral gene locus. In some embodiments that may be combined with any of the preceding embodiments, the recombinant herpes simplex virus genome comprises the one or more polynucleotides encoding the immunomodulatory polypeptide within the UL55 viral gene locus.

In some embodiments that may be combined with any of the preceding embodiments, the immunomodulatory polypeptide is a human immunomodulatory polypeptide. In some embodiments that may be combined with any of the preceding embodiments, the immunomodulatory polypeptide is a secreted immunomodulatory polypeptide. In some embodiments that may be combined with any of the preceding embodiments, the immunomodulatory polypeptide is a cytokine or chemokine. In some embodiments that may be combined with any of the preceding embodiments, the cytokine is a pro-inflammatory cytokine. In some embodiments that may be combined with any of the preceding embodiments, the cytokine is selected from Interleukin-1 (IL-1), Interleukin-2 (IL-2), Interleukin-7 (IL-7), Interleukin-12 (IL-12), Interleukin-13 (IL-13), Interleukin-15 (IL-15), Interleukin-17 (IL-17), Interleukin-18 (IL-18), Interleukin-28 (IL-28), Interleukin-32 (IL-32), Interleukin-33 (IL-33), Interleukin-34 (IL-34), Tumor Necrosis Factor alpha (TNFα), Interferon gamma (IFNγ), Granulocyte Colony-Stimulating Factor (G-CSF), and Granulocyte-Macrophage Colony-Stimulating Factor (GM-CSF). In some embodiments that may be combined with any of the preceding embodiments, the cytokine is IL-2. In some embodiments that may be combined with any of the preceding embodiments, the cytokine is IL-12. In some embodiments that may be combined with any of the preceding embodiments, the cytokine is not GM-CSF. In some embodiments that may be combined with any of the preceding embodiments, the chemokine is a pro-inflammatory chemokine. In some embodiments that may be combined with any of the preceding embodiments, the chemokine is selected from Chemokine (C—X—C motif) Ligand 1 (CXCL1), Chemokine (C—X—C motif) Ligand 2 (CSCL2), Chemokine (C—X—C motif) Ligand 8 (CXCL8), Chemokine (C—X—C motif) Ligand 9 (CXCL9), Chemokine (C—X—C motif) Ligand 11 (CXCL11), Chemokine (C—X—C motif) Ligand 16 (CXCL16), C—C Motif Chemokine Ligand 2 (CCL2), C—C Motif Chemokine Ligand 3 (CCL3), C—C Motif Chemokine Ligand 4 (CCL4), C—C Motif Chemokine Ligand 5 (CCL5), and C—C Motif Chemokine Ligand 11 (CCL11). In some embodiments that may be combined with any of the preceding embodiments, the immunomodulatory polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 1-30. In some embodiments, the immunomodulatory polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 1-19. In some embodiments, the immunomodulatory polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 20-30. In some embodiments, the immunomodulatory polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 3. In some embodiments, the immunomodulatory polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 5-6.

In some embodiments that may be combined with any of the preceding embodiments, the recombinant herpes virus genome has reduced cytotoxicity when introduced into a target cell as compared to a corresponding wild-type herpes virus genome. In some embodiments, the target cell is a human cell. In some embodiments, the target cell is a cell of the respiratory tract. In some embodiments, the target cell is an airway epithelial cell.

Other aspects of the present disclosure relate to a herpes virus comprising any of the recombinant herpes virus genomes described herein. In some embodiments, the herpes virus is replication competent. In some embodiments, the herpes virus is replication defective. In some embodiments that may be combined with any of the preceding embodiments, the herpes virus is not oncolytic. In some embodiments that may be combined with any of the preceding embodiments, the herpes virus is a pseudotyped virus. In some embodiments that may be combined with any of the preceding embodiments, the herpes virus is not a pseudotyped virus. In some embodiments that may be combined with any of the preceding embodiments, the herpes virus is not a pseudotyped oncolytic virus. In some embodiments that may be combined with any of the preceding embodiments, the herpes virus has reduced cytotoxicity as compared to a corresponding wild-type herpes virus. In some embodiments that may be combined with any of the preceding embodiments, the herpes virus is selected from a herpes simplex virus, a varicella zoster virus, a human cytomegalovirus, a herpesvirus 6A, a herpesvirus 6B, a herpesvirus 7, an Epstein-Barr virus, a Kaposi's sarcoma-associated herpesvirus, and any combinations or derivatives thereof. In some embodiments that may be combined with any of the preceding embodiments, the herpes virus is a herpes simplex virus. In some embodiments, the herpes simplex virus is not oncolytic. In some embodiments, the herpes simplex virus is an HSV-1, an HSV-2, or any combinations or derivatives thereof. In some embodiments, the herpes simplex virus is an HSV-1. In some embodiments, the HSV-1 is not oncolytic.

Other aspects of the present disclosure relate to a pharmaceutical composition comprising any of the recombinant herpes virus genomes and/or any of the recombinant herpes viruses described herein and a pharmaceutically acceptable carrier or excipient. In some embodiments that may be combined with any of the preceding embodiments, the pharmaceutical composition is suitable for topical, transdermal, subcutaneous, intradermal, oral, intranasal, intratracheal, sublingual, buccal, rectal, vaginal, inhaled, intravenous, intraarterial, intramuscular, intracardiac, intraosseous, intraperitoneal, transmucosal, intravitreal, subretinal, intraarticular, peri-articular, local, or epicutaneous administration. In some embodiments that may be combined with any of the preceding embodiments, the pharmaceutical composition is suitable for oral, intranasal, intratracheal, or inhaled administration. In some embodiments, the pharmaceutical composition is suitable for intranasal or inhaled administration. In some embodiments, the pharmaceutical composition is suitable for inhaled administration. In some embodiments that may be combined with any of the preceding embodiments, the pharmaceutical composition is suitable for use in a dry powder inhaler, a pressurized metered dose inhaler, a soft mist inhaler, a nebulizer, an electrohydrodynamic aerosol device, or any combinations thereof. In some embodiments that may be combined with any of the preceding embodiments, the pharmaceutical composition is suitable for use in a nebulizer. In some embodiments, the nebulizer is a vibrating mesh nebulizer. In some embodiments that may be combined with any of the preceding embodiments, the pharmaceutical composition comprises a phosphate buffer. In some embodiments that may be combined with any of the preceding embodiments, the pharmaceutical composition comprises glycerol. In some embodiments that may be combined with any of the preceding embodiments, the pharmaceutical composition comprises a lipid carrier. In some embodiments that may be combined with any of the preceding embodiments, the pharmaceutical composition comprises a nanoparticle carrier.

Other aspects of the present disclosure relate to the use of any of the recombinant nucleic acids (e.g., recombinant herpes virus genomes), recombinant viruses (e.g., recombinant herpes viruses), and/or pharmaceutical compositions described herein as a medicament.

Other aspects of the present disclosure relate to the use of any of the recombinant nucleic acids (e.g., recombinant herpes virus genomes), recombinant viruses (e.g., recombinant herpes viruses), and/or pharmaceutical compositions described herein in a therapy.

Other aspects of the present disclosure relate to the use of any of the recombinant nucleic acids (e.g., recombinant herpes virus genomes), recombinant viruses (e.g., recombinant herpes viruses), and/or pharmaceutical compositions described herein in the preparation of a medicament for treating cancer (e.g., lung cancer).

Other aspects of the present disclosure relate to a method of expressing, enhancing, increasing, augmenting, and/or supplementing the levels of an immunomodulatory polypeptide in one or more cells of a subject comprising administering to the subject an effective amount of any of the recombinant herpes viruses and/or pharmaceutical compositions described herein. In some embodiments, the one or more cells are one or more cells of the respiratory tract, airway epithelial, and/or lung. In some embodiments that may be combined with any of the preceding embodiments, the subject is a human. In some embodiments that may be combined with any of the preceding embodiments, the herpes virus or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, peri-articularly, intratumorally, locally, or via inhalation to the subject. In some embodiments that may be combined with any of the preceding embodiments, the herpes virus or pharmaceutical composition is administered orally, intranasally, intratracheally, or via inhalation to the subject. In some embodiments, the herpes virus or pharmaceutical composition is administered intranasally or via inhalation to the subject. In some embodiments, the herpes virus or pharmaceutical composition is administered via inhalation to the subject. In some embodiments, the herpes virus or pharmaceutical composition is administered using a dry powder inhaler, a pressurized metered dose inhaler, a soft mist inhaler, a nebulizer, or an electrohydrodynamic aerosol device. In some embodiments, the herpes virus or pharmaceutical composition is administered using a nebulizer. In some embodiments, the nebulizer is a vibrating mesh nebulizer.

Other aspects of the present disclosure relate to a method of providing prophylactic, palliative, or therapeutic relief of one or more signs or symptoms of cancer in a subject in need thereof comprising administering to the subject an effective amount of any of the recombinant herpes viruses and/or pharmaceutical compositions described herein. In some embodiments, the cancer is selected from a solid tumor, a hematologic cancer, bladder cancer, brain cancer, breast cancer, colon cancer, gastric cancer, glioma, head cancer, leukemia, liver cancer, lung cancer, lymphoma, myeloma, neck cancer, ovarian cancer, melanoma, pancreatic cancer, renal cancer, salivary cancer, skin cancer, stomach cancer, thymic epithelial cancer, and thyroid cancer. In some embodiments, the cancer is small-cell lung cancer, non-small cell lung cancer, adenocarcinoma of the lung, or squamous carcinoma of the lung. In some embodiments, the cancer is non-small cell lung cancer. In some embodiments, the cancer is osteosarcoma. In some embodiments that may be combined with any of the preceding embodiments, the subject is a human. In some embodiments that may be combined with any of the preceding embodiments, the herpes virus or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, peri-articularly, intratumorally, locally, or via inhalation to the subject. In some embodiments that may be combined with any of the preceding embodiments, the herpes virus or pharmaceutical composition is administered orally, intranasally, intratracheally, or via inhalation to the subject. In some embodiments that may be combined with any of the preceding embodiments, the herpes virus or pharmaceutical composition is administered orally, intranasally, intratracheally, or via inhalation to the subject. In some embodiments, the herpes virus or pharmaceutical composition is administered intranasally or via inhalation to the subject. In some embodiments, the herpes virus or pharmaceutical composition is administered via inhalation to the subject. In some embodiments, the herpes virus or pharmaceutical composition is administered using a dry powder inhaler, a pressurized metered dose inhaler, a soft mist inhaler, a nebulizer, or an electrohydrodynamic aerosol device. In some embodiments, the herpes virus or pharmaceutical composition is administered using a nebulizer. In some embodiments, the nebulizer is a vibrating mesh nebulizer.

Other aspects of the present disclosure relate to a method of treating cancer in a subject in need thereof comprising administering to the subject an effective amount of any of the recombinant herpes viruses and/or pharmaceutical compositions described herein. In some embodiments, the cancer is selected from carcinoma, lymphoma, blastoma, sarcoma, a neuroendocrine tumor, mesothelioma, schwannoma, meningioma, adenocarcinoma, melanoma, leukemia, and lymphoid malignancy. In some embodiments, the cancer is selected from a solid tumor, a hematologic cancer, bladder cancer, brain cancer, breast cancer, colon cancer, gastric cancer, glioma, head cancer, leukemia, liver cancer, lung cancer, lymphoma, myeloma, neck cancer, ovarian cancer, melanoma, pancreatic cancer, renal cancer, salivary cancer, skin cancer, stomach cancer, thymic epithelial cancer, and thyroid cancer. In some embodiments, the cancer is small-cell lung cancer, non-small cell lung cancer, adenocarcinoma of the lung, or squamous carcinoma of the lung. In some embodiments, the cancer is non-small cell lung cancer. In some embodiments, the cancer is osteosarcoma. In some embodiments that may be combined with any of the preceding embodiments, the subject is a human. In some embodiments that may be combined with any of the preceding embodiments, the herpes virus or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, peri-articularly, intratumorally, locally, or via inhalation to the subject. In some embodiments that may be combined with any of the preceding embodiments, the herpes virus or pharmaceutical composition is administered orally, intranasally, intratracheally, or via inhalation to the subject. In some embodiments, the herpes virus or pharmaceutical composition is administered intranasally or via inhalation to the subject. In some embodiments, the herpes virus or pharmaceutical composition is administered via inhalation to the subject. In some embodiments, the herpes virus or pharmaceutical composition is administered using a dry powder inhaler, a pressurized metered dose inhaler, a soft mist inhaler, a nebulizer, or an electrohydrodynamic aerosol device. In some embodiments, the herpes virus or pharmaceutical composition is administered using a nebulizer. In some embodiments, the nebulizer is a vibrating mesh nebulizer.

Other aspects of the present disclosure relate to a method of delivering a polypeptide (e.g., an immune modulator polypeptide) to one or more cells of the respiratory tract of a subject comprising administering to the subject a pharmaceutical composition comprising (a) a herpes virus comprising a recombinant herpes virus genome, wherein the recombinant herpes virus genome comprises one or more polynucleotides encoding the polypeptide, and (b) a pharmaceutically acceptable carrier. In some embodiments, the subject suffers from a disease or condition affecting one or more cells of the respiratory tract, such as a cancer or neoplasm affecting the airways and/or lungs which has either originated from the respiratory tract or metastasized from other tissues or organs. In some embodiments, the subject does not suffer from a genetic pulmonary disease. In some embodiments, the subject does not suffer from a disease selected from alpha-1-antitrypsin deficiency, pulmonary alveolar microlithiasis, primary ciliary dyskinesia, congenital pulmonary alveolar proteinosis, pulmonary arterial hypertension, and pulmonary fibrosis. In some embodiments, the lack or a reduced level of expression and/or activity of the polypeptide in the subject is not associated with a genetic pulmonary disease. In some embodiments, the lack or a reduced level of expression and/or activity of the polypeptide in the subject is not associated with a disease selected from alpha-1-antitrypsin deficiency, pulmonary alveolar microlithiasis, primary ciliary dyskinesia, congenital pulmonary alveolar proteinosis, pulmonary arterial hypertension, and pulmonary fibrosis.

In some embodiments that may be combined with any of the preceding embodiments, the herpes virus is a pseudotyped virus. In some embodiments that may be combined with any of the preceding embodiments, the herpes virus is not a pseudotyped virus. In some embodiments that may be combined with any of the preceding embodiments, the herpes virus is not a pseudotyped oncolytic virus.

Other aspects of the present disclosure relate to an article of manufacture or kit comprising any of the recombinant nucleic acids, viruses, medicaments, and/or pharmaceutical compositions or formulations described herein and instructions for administration thereof.

BRIEF DESCRIPTION OF THE DRAWINGS

FIGS. 1A-1I show schematics of wild-type and modified herpes simplex virus genomes. FIG. 1A shows a wild-type herpes simplex virus genome. FIG. 1B shows a modified herpes simplex virus genome comprising deletions of the coding sequence of ICP4 (both copies), with an expression cassette containing a nucleic acid encoding an immunomodulatory polypeptide integrated at each of the ICP4 loci. FIG. 1C shows a modified herpes simplex virus genome comprising deletions of the coding sequences of ICP4 (both copies) and UL41, with an expression cassette containing a nucleic acid encoding an immunomodulatory polypeptide integrated at each of the ICP4 loci. FIG. 1D shows a modified herpes simplex virus genome comprising deletions of the coding sequences of ICP4 (both copies) and UL41, with an expression cassette containing a nucleic acid encoding an immunomodulatory polypeptide integrated at the UL41 locus. FIG. 1E shows a modified herpes simplex virus genome comprising deletions of the coding sequences of ICP4 (both copies) and ICP22, with an expression cassette containing a nucleic acid encoding an immunomodulatory polypeptide integrated at each of the ICP4 loci. FIG. 1F shows a modified herpes simplex virus genome comprising deletions of the coding sequences of ICP4 (both copies) and ICP22, with an expression cassette containing a nucleic acid encoding an immunomodulatory polypeptide integrated at the ICP22 locus. FIG. 1G shows a modified herpes simplex virus genome comprising deletions of the coding sequences of ICP4 (both copies), UL41, and ICP22, with an expression cassette containing a nucleic acid encoding an immunomodulatory polypeptide integrated at each of the ICP4 loci. FIG. 1H shows a modified herpes simplex virus genome comprising deletions of the coding sequences of ICP4 (both copies), UL41, and ICP22, with an expression cassette containing a nucleic acid encoding an immunomodulatory polypeptide integrated at the UL41 locus. FIG. 1I shows a modified herpes simplex virus genome comprising deletions of the coding sequences of ICP4 (both copies), UL41, and ICP22, with an expression cassette containing a nucleic acid encoding an immunomodulatory polypeptide integrated at the ICP22 locus.

FIG. 2A: lane 1 ladder; lane 2 recombinant IL-12; lanes 3-6 HSV-IL12; lane 7 mock. FIG. 2B: lane 1 ladder; lane 2 recombinant IL-2; lanes 3-5 HSV-IL2; lane 6 mock.

FIGS. 4A-4M show the in vivo evaluation of HSV-IL12 in healthy mice. FIG. 4A depicts animal weights following HSV-IL12 intratracheal administration. Data are presented as mean±standard error of the mean (SEM); n=2-3 animals per group per time point. FIGS. 4B-4C show genome (FIG. 4B) and transcript (FIG. 4C) levels in lungs of BALB/c animals post-intratracheal administration of HSV-IL12. qPCR (FIG. 4B) and qRT-PCR (FIG. 4C) were performed to measure il12 genomes and transcripts; respectively. Data are indicative of samples run in duplicate, and displayed as mean±SEM of n=2-3 animals per group. FIGS. 4D-4E show IL-12 protein concentrations in serum (FIG. 4D) and bronchoalveolar lavage fluid (BALF; FIG. 4E) analyzed by ELISA. Serum samples are shown as mean±SD of one animal sample assayed in duplicate. BALF data are shown as mean±SEM of n=2-3 animals per group. FIG. 4F depicts IL-12 concentration in lung homogenates following HSV-IL12 intratracheal administration. Biopsies were cut from frozen lung tissue, homogenized, and assayed by ELISA in duplicate. Protein concentrations of homogenates were determined by BCA assay, and IL-12 concentrations were normalized to total protein. Data are displayed as mean±SEM of n=2-3 animals per group. FIG. 4G depicts animal weights following once weekly HSV-IL12 intratracheal administration. Animals were weighed prior to HSV-IL12 administration at the indicated time points. Data are presented as mean±SEM; n=4-6 animals per group. FIGS. 4H-4I depict il12 genome (FIG. 4H) and transcript (FIG. 4I) levels in lungs of BALB/c animals following once weekly treatment for three consecutive weeks. Data are indicative of samples run in duplicate. Values from individual animals are displayed in conjunction with the mean±SEM of n=2-3 animals per group. FIGS. 4J-4K depict IL-12 protein concentrations in BALF and lung homogenates. BALF (FIG. 4J) and lung homogenates (FIG. 4K) were analyzed by ELISA for mIL-12 protein concentration. All samples were assayed in duplicate. Values from individual animals are shown in conjunction with the mean±SEM of n=2-3 animals per group. FIGS. 4L-4M depict analysis of BALF cells as a measure of inflammation. Biopsies were cut from frozen lung tissue, homogenized, and assayed by ELISA in duplicate. Data are displayed as mean SEM of n=2-3 animals per group.

FIGS. 5A-5I show the in vivo evaluation of HSV-IL2 in healthy mice. FIG. 5A depicts animal weights following HSV-IL2 intratracheal administration. Data are presented as mean±SEM; n=2-3 animals per group per time point. FIGS. 5B-5C show il2 genome (FIG. 5B) and transcript (FIG. 5C) levels in lungs of BALB/c animals post-intratracheal administration of HSV-IL2. Data are indicative of samples run in duplicate and displayed as mean±SEM of n=2-3 animals per group. FIGS. 5D-5E show IL-2 protein concentrations in serum (FIG. 5D) and bronchoalveolar lavage fluid (BALF; FIG. 5E) analyzed by ELISA. Serum samples are shown as mean±SEM of 2-3 animals per group with samples assayed in duplicate. BALF data are shown as mean±SEM of n=2-3 animals per group. FIG. 5F depicts IL-2 concentration in lung homogenates following HSV-IL2 intratracheal administration. Biopsies were cut from frozen lung tissue, homogenized, and assayed by ELISA in duplicate. Protein concentrations of homogenates were determined by BCA assay, and IL-2 concentrations were normalized to total protein. Data are displayed as mean±SEM of n=2-3 animals per group. FIGS. 5G-5I depict IL-2 pharmacokinetics in serum (FIG. 5G), bronchoalveolar lavage fluid (BALF; FIG. 5H), and lysate (FIG. 5I). Data are displayed as mean±SEM of n=2-3 animals per group.

FIG. 6A depicts animal weights following HSV-GMCSF intratracheal administration. Data are presented as mean±SEM; n=2-3 animals per group per time point. FIG. 6E) analyzed by ELISA. Serum and BALF data are shown as mean±SEM of n=2-3 animals per group. FIGS. 6M-6N depict analysis of BALF cells as a measure of inflammation. Cells isolated from BALF were enumerated using a hemocytometer, and viability was determined based on Trypan blue exclusion. Data are displayed as mean±SEM of n=2-3 animals per group.

FIG. 7A shows body weights in control (vehicle) versus K7M2 (murine tumor cell line) infused mice. Data are presented as mean±SEM; n=2-5 animals per group per time point. FIGS. 7B-7C depict lung weights in control vs. tumor cell line-exposed mice at three weeks (FIG. 7B) or six weeks (FIG. 7C) post-inoculation of the K7M2 cells. Values from individual animals are shown in conjunction with the mean±SEM of n=2-5 animals per group. FIGS. 7D-7F depict hematoxylin and eosin (H&E) histological staining of lung sections 6-weeks post inoculation of the K7M2 cells. Magnification is 2.5× (FIG. 7D), 20× (FIG. 7E), 10× (FIG. 7F), and 20× (FIG. 7G).

FIG. 8A shows body weights in control versus HSV-IL12 dosed mice. Data are presented as mean±SEM; n=5 animals per group per time point. FIG. 8B depicts lung weights in control versus HSV-IL12 dosed mice. Values from individual animals are shown in conjunction with the mean±SEM; n=3-5 animals per group.

FIG. 9A depicts animal weights following once weekly HSV-IL12/GMCSF combinatorial intratracheal administration. Animals were weighed prior to HSV-IL12/GMCSF administration on days 0 and 7 and at sacrifice on day 8. Data are presented as mean±SEM; n=3-4 animals per group. FIGS. 9B-9E depict IL-12 and GMCSF protein concentrations in BALF and lung homogenates. BALF (FIGS. 9B-9C) and lung homogenates (FIGS. 9D-9E) were analyzed by ELISA for mIL-12 and mGM-CSF protein concentration. All samples were assayed in duplicate. Values from individual animals are shown in conjunction with the mean±SEM of n=3-4 animals per group. FIG. 9F depicts analysis of BALF cells as a measure of inflammation. Cells isolated from BALF were enumerated using a hemocytometer, and viability was determined based on Trypan blue exclusion. Data are displayed as mean±SEM of n=3-4 animals per group.

FIG. 10A shows body weight in control versus HSV-IL12 alone, HSV-GMCSF alone, and combinatorial HSV-IL12 and HSV-GMCSF dosed mice. Data are presented as mean±SEM; n=2-5 animals per group per time point. FIG. 10B depicts survival curves in control versus HSV-IL12 alone, HSV-GMCSF alone, and combinatorial HSV-IL12 and HSV-GMCSF dosed mice. Data are presented as mean±SEM; n=5 animals per group.

DETAILED DESCRIPTION

Figure 1A:
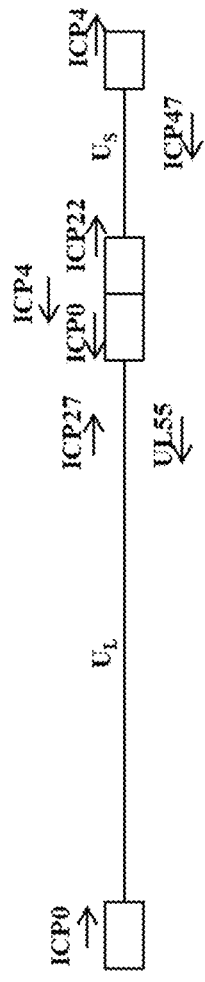
Figure 1B:
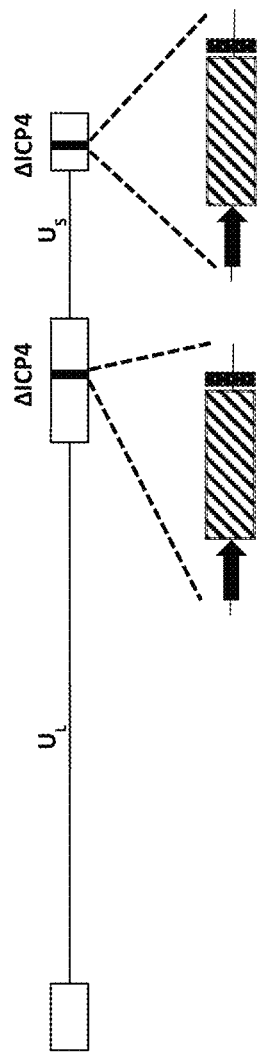
Figure 1C:
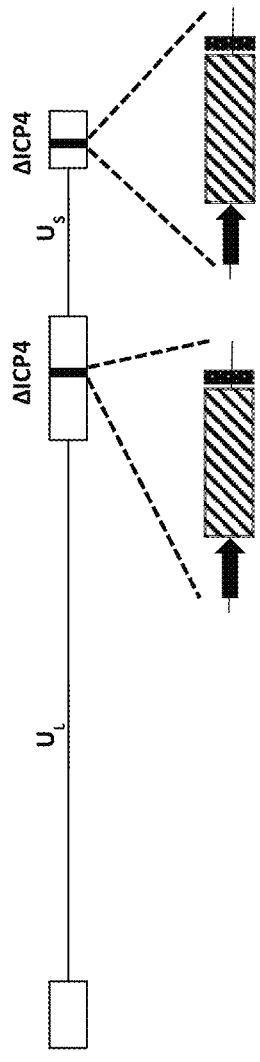
Figure 1D:
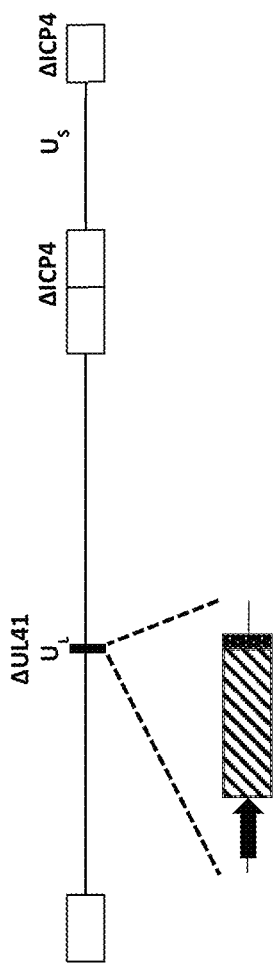
Figure 1E:
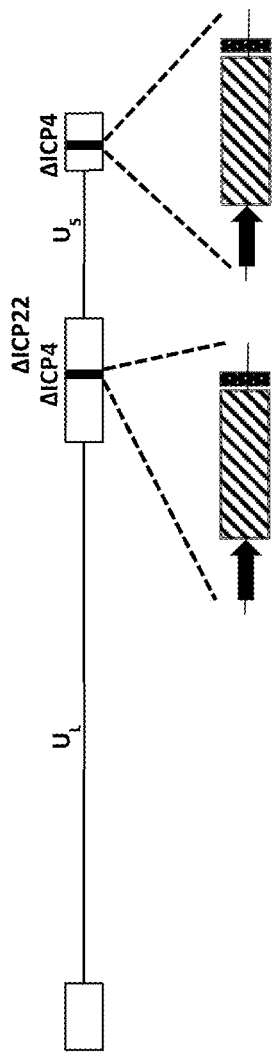
Figure 1F:
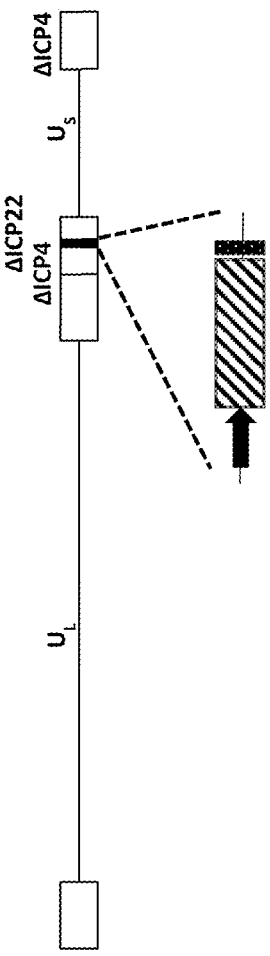
Figure 1I:
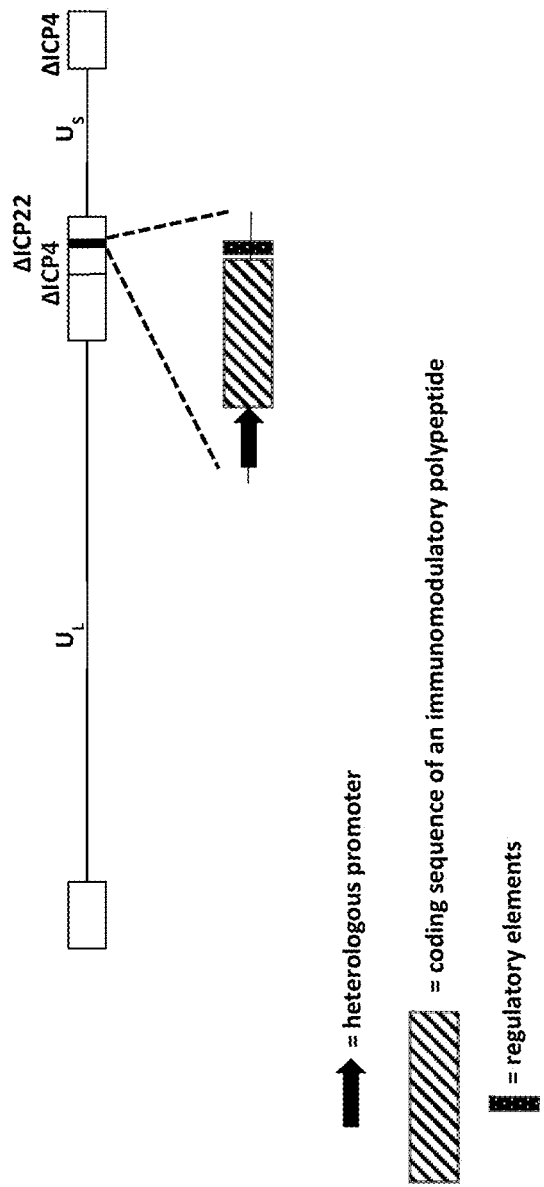

The following description sets forth exemplary methods, parameters, and the like. It should be recognized, however, that such a description is not intended as a limitation on the scope of the present disclosure but is instead provided as a description of exemplary embodiments.

I. General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Gene Transfer Vectors for Mammalian Cells* (J. M. Miller and M. P. Calos, eds., 1987); *PCR: The Polymerase Chain Reaction*, (Mullis et al., eds., 1994); *Short Protocols in Molecular Biology* (Wiley and Sons, 1999).

II. Definitions

Before describing the present disclosure in detail, it is to be understood that the present disclosure is not limited to particular compositions or biological systems, which can, of course, vary. It is also to be understood that the terminology used herein is for the purpose of describing particular embodiments only and is not intended to be limiting.

As used herein, the singular forms "a", "an" and "the" include plural referents unless the content clearly dictates otherwise. Thus, for example, reference to "a molecule" optionally includes a combination of two or more such molecules, and the like.

As used herein, the term "and/or" may include any and all combinations of one or more of the associated listed items. For example, the term "a and/or b" may refer to "a alone", "b alone", "a or b", or "a and b"; the term "a, b, and/or c" may refer to "a alone", "b alone", "c alone", "a or b", "a or c", "b or c", "a, b, or c", "a and b", "a and c", "b and c", or "a, b, and c"; etc.

As used herein, the term "about" refers to the usual error range for the respective value readily known to the skilled person in this technical field. Reference to "about" a value or parameter herein includes (and describes) embodiments that are directed to that value or parameter per se.

It is understood that aspects and embodiments of the present disclosure include "comprising", "consisting", and "consisting essentially of" aspects and embodiments.

As used herein, the terms "polynucleotide", "nucleic acid sequence", "nucleic acid", and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog, and inter-nucleotide modifications.

As used herein, a nucleic acid is "operatively linked" or "operably linked" when it is placed into a functional relationship with another nucleic acid sequence. For example, a promoter or enhancer is operably linked to a coding sequence if it affects the transcription of the sequence, or a ribosome binding site is operably linked to a coding sequence if it is positioned so as to facilitate translation. Generally, "operatively linked" or "operably linked" means that the DNA or RNA sequences being linked are contiguous.

As used herein, the term "vector" refers to discrete elements that are used to introduce heterologous nucleic acids into cells for either expression or replication thereof. An expression vector includes vectors capable of expressing nucleic acids that are operatively linked with regulatory sequences, such as promoter regions, that are capable of effecting expression of such nucleic acids. Thus, an expression vector may refer to a DNA or RNA construct, such as a plasmid, a phage, recombinant virus, or other vector that, upon introduction into an appropriate host cell, results in expression of the nucleic acids. Appropriate expression vectors are well known to those of skill in the art and include those that are replicable in eukaryotic cells and those that remain episomal or those which integrate into the host cell genome.

As used herein, an "open reading frame" or "ORF" refers to a continuous stretch of nucleic acids, either DNA or RNA, that encode a protein or polypeptide. Typically, the nucleic acids comprise a translation start signal or initiation codon, such as ATG or AUG, and a termination codon.

As used herein, an "untranslated region" or "UTR" refers to untranslated nucleic acids at the 5' and/or 3' ends of an open reading frame. The inclusion of one or more UTRs in a polynucleotide may affect post-transcriptional regulation, mRNA stability, and/or translation of the polynucleotide.

As used herein, the term "transgene" refers to a polynucleotide that is capable of being transcribed into RNA and translated and/or expressed under appropriate conditions after being introduced into a cell. In some aspects, it confers a desired property to a cell into which it was introduced, or otherwise leads to a desired therapeutic or diagnostic outcome.

As used herein, the terms "polypeptide," "protein," and "peptide" are used interchangeably and may refer to a polymer of two or more amino acids.

As used herein, a "subject", "host", or an "individual" refers to any animal classified as a mammal, including humans, domestic and farm animals, and zoo, sports, or pet animals, such as dogs, horses, cats, cows, as well as animals used in research, such as mice, rats, hamsters, rabbits, and non-human primates, etc. In some embodiments, the mammal is human.

As used herein, the terms "pharmaceutical formulation" or "pharmaceutical composition" refer to a preparation which is in such a form as to permit the biological activity of the active ingredient(s) to be effective, and which contains no additional components which are unacceptably toxic to a subject to which the composition or formulation would be administered. "Pharmaceutically acceptable" excipients (e.g., vehicles, additives) are those which can reasonably be administered to a subject mammal to provide an effective dose of the active ingredient(s) employed.

As used herein, an "effective amount" is at least the minimum amount required to affect a measurable improvement or prevention of one or more symptoms of a particular disorder. An "effective amount" may vary according to factors such as the disease state, age, sex, and weight of the patient. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications used to treat symptoms of the disease, delaying the progression of the disease, and/or prolonging survival. An effective amount can be administered in one or more administrations. For purposes of the present disclosure, an effective amount of a recombinant nucleic acid, virus, and/or pharmaceutical composition is an amount sufficient to accomplish prophylactic or therapeutic treatment either directly or indirectly. As is understood in the clinical context, an effective amount of a recombinant nucleic acid, virus, and/or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "treatment" refers to clinical intervention designed to alter the natural course of the individual or cell being treated during the course of clinical pathology. Desirable effects of treatment include decreasing the rate of disease/disorder/defect progression, ameliorating, or palliating the disease/disorder/defect state, and remission or improved prognosis.

As used herein, the term "delaying progression of" a disease/disorder/defect refers to deferring, hindering, slowing, retarding, stabilizing, and/or postponing development of the disease/disorder/defect. This delay can be of varying lengths or time, depending on the history of the disease/disorder/defect and/or the individual being treated. As is evident to one of ordinary skill in the art, a sufficient or significant delay can, in effect, encompass prevention, in that the individual does not develop the disease.

Throughout the present disclosure, various aspects are presented in a range format. It should be understood that the description in range format is merely for convenience and brevity and should not be construed as an inflexible limitation on the scope of the present disclosure. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the present disclosure. The upper and lower limits of these smaller ranges may independently be comprised in the smaller ranges, and are also encompassed within the present disclosure, subject to any specifically excluded limit in the stated range. Where the stated range comprises one or both of the limits, ranges excluding either or both of those comprised limits are also comprised in the present disclosure. This applies regardless of the breadth of the range.

III. Recombinant Nucleic Acids

Certain aspects of the present disclosure relate to recombinant nucleic acids (e.g., isolated recombinant nucleic acids) comprising one or more (e.g., one or more, two or more, three or more, four or more, five or more, ten or more, etc.) polynucleotides encoding an immunomodulatory polypeptide. In some embodiments, the recombinant nucleic acid comprises one polynucleotide encoding an immunomodulatory polypeptide. In some embodiments, the recombinant nucleic acid comprises two polynucleotides encoding an immunomodulatory polypeptide. In some embodiments, the recombinant nucleic acid comprises three or more polynucleotides encoding an immunomodulatory polypeptide. In some embodiments, the recombinant nucleic acid comprises one or more polynucleotides encoding two or more immunomodulatory polypeptides. In some embodiments, the recombinant nucleic acid comprises two or more polynucleotides encoding two or more immunomodulatory polypeptides. In some embodiments, the two or more immunomodulatory polypeptides are identical. In some embodiments, the two or more immunomodulatory polypeptides are different.

In some embodiments, the present disclosure relates to recombinant nucleic acids comprising a polynucleotide encoding a chimeric polypeptide comprising: a first immunomodulatory polypeptide, a linker polypeptide, and a second immunomodulatory polypeptide. In some embodiments, the first and second immunomodulatory polypeptides are the same. In some embodiments, the first and second immunomodulatory polypeptides are different. In some embodiments, the linker polypeptide is a cleavable linker polypeptide. In some embodiments, the linker polypeptide is a non-cleavable linker polypeptide.

In some embodiments, the recombinant nucleic acid is a vector. In some embodiments, the recombinant nucleic acid is a viral vector. In some embodiments, the recombinant nucleic acid is a herpes viral vector. In some embodiments, the recombinant nucleic acid is a herpes simplex virus amplicon. In some embodiments, the recombinant nucleic acid is a recombinant herpes virus genome. In some embodiments, the recombinant herpes virus genome is a recombinant herpes simplex virus genome. In some embodiments, the recombinant herpes simplex virus genome is a recombinant herpes simplex virus type 1 (HSV-1) genome.

Polynucleotides Encoding Immunomodulatory Polypeptides

In some embodiments, the present disclosure relates to recombinant nucleic acids comprising one or more polynucleotides encoding one or more immunomodulatory polypeptides (e.g., one or more human immunomodulatory polypeptides). Any suitable immunomodulatory polypeptide described herein or known in the art may be encoded by a polynucleotide of the present disclosure, including, for example, human cytokines and chemokines, such as human pro-inflammatory cytokines and chemokines.

In some embodiments, a polynucleotide of the present disclosure comprises the wild-type coding sequence of any immunomodulatory gene described herein or known in the art (including any isoform thereof). In some embodiments, a polynucleotide of the present disclosure comprises a codon-optimized variant of the wild-type coding sequence of any immunomodulatory gene described herein or known in the art. In some embodiments, use of a codon-optimized variant of the coding sequence of a gene increases stability and/or yield of heterologous expression (RNA and/or protein) of the encoded polypeptide in a target cell, as compared to the stability and/or yield of heterologous expression of a corresponding, non-codon-optimized, wild-type sequence. Any suitable method known in the art for performing codon optimization of a sequence for expression in one or more target cells (e.g., one or more human cells) may be used, including, for example, by the methods described by Fath et al. (PLoS One. 2011 Mar. 3; 6(3): e17596).

In some embodiments, the present disclosure relates to a recombinant nucleic acid comprising one or more polynucleotides comprising the coding sequence of a human cytokine. Any suitable human cytokine gene (including any isoform thereof) known in the art may be encoded by a polynucleotide of the present disclosure, including, for example, an IL1A gene (see e.g., NCBI Gene ID: 3552; SEQ ID NO: 31), an IL1B gene (see e.g., NCBI Gene ID: 3553; SEQ ID NO: 32), an 112 gene (see e.g., NCBI Gene ID: 3558; SEQ ID NO: 33), an IL3 gene (see e.g., NCBI Gene ID: 3562), an IL4 gene (see e.g., NCBI Gene ID: 3565), an IL5 gene (see e.g., NCBI Gene ID: 3567), an IL6 gene (see e.g., NCBI Gene ID: 3569), an IL7 gene (see e.g., NCBI Gene ID: 3574; SEQ ID NO: 34), an IL9 gene (see e.g., NCBI Gene ID: 3578), and IL10 gene (see e.g., NCBI Gene ID: 3586), an IL11 gene (see e.g., NCBI Gene ID: 3589), an IL12A gene (see e.g., NCBI Gene ID: 3592; SEQ ID NO: 35), an IL12B gene (see e.g., NCBI Gene ID: 3593; SEQ ID NO: 36), an IL13 gene (see e.g., NCBI Gene ID: 3596; SEQ ID NO: 317), an IL15 gene (see e.g., NCBI Gene ID: 3600; SEQ ID NO: 38), an IL17A gene (see e.g., NCBI Gene ID: 3605; SEQ ID NO: 39), an IL17B gene (see e.g., NCBI Gene ID: 27190), an IL17C gene (see e.g., NCBI Gene ID: 27189), an IL17D gene (see e.g., NCBI Gene ID: 53342), an IL25 gene (see e.g., NCBI Gene ID: 64806), an IL17F gene (see e.g., NCBI Gene ID: 112744), an IL18 gene (see e.g., NCBI Gene ID: 3606; SEQ ID NO: 40), an IFNL2 gene (see e.g., NCBI Gene ID: 282616; SEQ ID NO: 41), an IFNL3 gene (see e.g., NCBI Gene ID: 282617; SEQ ID NO: 42), an IFNL1 gene (see e.g., NCBI Gene ID: 282618), an IL32 gene (see e.g., NCBI Gene ID: 9235; SEQ ID NO: 43), an IL33 gene (see e.g., NCBI Gene ID: 90865; SEQ ID NO: 44), an IL34 gene (see e.g., NCBI Gene ID: 146433; SEQ ID NO: 45), an IL36A gene (see e.g., NCBI Gene ID: 27179), an IL36B gene (see e.g., NCBI Gene ID: 27177), an IL36G gene (see e.g., NCBI Gene ID: 56300), an IFNA1 gene (see e.g., NCBI Gene ID: 3439), an IFNA13 gene (see e.g., NCBI Gene ID: 3447), an IFNA2 gene (see e.g., NCBI Gene ID: 3440), an IFNA4 gene (see e.g., NCBI Gene ID: 3441), an IFNA5 gene (see e.g., NCBI Gene ID: 3442), an IFNA6 gene (see e.g., NCBI Gene ID: 3443), an IFNA7 gene (see e.g., NCBI Gene ID: 3444), an IFNA8 gene (see e.g., NCBI Gene ID: 3445), an IFNA10 gene (see e.g., NCBI Gene ID: 3446), an IFNA14 gene (see e.g., NCBI Gene ID: 3448), IFNA16 gene (see e.g., NCBI Gene ID: 3449), IFNA17 gene (see e.g., NCBI Gene ID: 3451), an IFNA21 gene (see e.g., NCBI Gene ID: 3452), an IFNB1 gene (see e.g., NCBI Gene ID: 3456), an IFNB3 gene (see e.g., NCBI Gene ID: 618946), an IFNG gene (see e.g., NCBI Gene ID: 3458; SEQ ID NO: 46), a TNF gene (see e.g., NCBI Gene ID: 7124; SEQ ID NO: 47), aLTA gene (see e.g., NCBI Gene ID: 4'49), a CSF3 gene (see e.g., NCBI Gene ID: 1440; SEQ ID NO: 48), a CSF2 gene (see e.g., NCBI Gene ID: 1437; SEQ ID NO: 49), a CSF1 gene (see e.g., NCBI Gene ID: 1435), etc. In some embodiments, a polynucleotide of the present disclosure does not comprise a sequence encoding an IL4 gene. In some embodiments, a polynucleotide of the present disclosure does not comprise a sequence encoding an IL10 gene. In some embodiments, a polynucleotide of the present disclosure does not comprise a sequence encoding an GM-CSF gene. In some embodiments, a polynucleotide of the present disclosure does not comprise a sequence encoding an IL4, IL10, and/or GM-CSF gene. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the human cytokine genes (and/or coding sequences thereof) described herein or known in the art. In some embodiments, the cytokine is a pro-inflammatory cytokine. In some embodiments, the cytokine is selected from human IL-1, IL-2, IL-7, IL-12, IL-13, IL-15, IL-17, IL-18, IL-28 (e.g., IL-28a and/or IL-28O), IL-32, IL-33, IL-34, TNFα, IFNγ, G-CSF, and/or GM-CSF.

In some embodiments, a polynucleotide of the present disclosure encodes an IL-1α polypeptide. In some embodiments, the IL-1α polypeptide is a human IL-1α polypeptide (see e.g., UniProt accession number: P01583). In some embodiments, the polynucleotide comprises the coding sequence of a wild-type IL1A gene (see e.g., NCBI Gene ID: 3552, SEQ ID NO: 31), or a codon-optimized variant thereof. In some embodiments, a polynucleotide encoding an IL-1α polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 1. In some embodiments, a polynucleotide encoding an IL-1α polypeptide is a polynucleotide that encodes a polypeptide comprising the amino acid sequence of SEQ ID NO: 1.

In some embodiments, a polynucleotide encoding an IL-1α polypeptide is a polynucleotide that encodes an N-terminal truncation, a C-terminal truncation, or a fragment of the amino acid sequence of SEQ ID NO: 1. N-terminal truncations, C-terminal truncations, or fragments may comprise at least 10, at least 12, at least 14, at least 16, at least 18, at least 20, at least 30, at least 40, at least 50, at least 75, at least 100, at least 200, but fewer than 271, consecutive amino acids of SEQ ID NO: 1.

In some embodiments, a polynucleotide of the present disclosure encodes an IL-1β polypeptide. In some embodiments, the IL-1β polypeptide is a human IL-1β polypeptide (see e.g., UniProt accession number: P01584). In some embodiments, the polynucleotide comprises the coding sequence of a wild-type IL1B gene (see e.g., NCBI Gene ID: 3553, SEQ ID NO: 32), or a codon-optimized variant thereof. In some embodiments, a polynucleotide encoding an IL-1 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 2. In some embodiments, a polynucleotide encoding an IL-1β polypeptide is a polynucleotide that encodes a polypeptide comprising the amino acid sequence of SEQ ID NO: 2.

In some embodiments, a polynucleotide encoding an IL-1β polypeptide is a polynucleotide that encodes an N-terminal truncation, a C-terminal truncation, or a fragment of the amino acid sequence of SEQ ID NO: 2. N-terminal truncations, C-terminal truncations, or fragments may comprise at least 10, at least 12, at least 14, at least 16, at least 18, at least 20, at least 30, at least 40, at least 50, at least 75, at least 100, at least 200, but fewer than 269, consecutive amino acids of SEQ ID NO: 2.

In some embodiments, a polynucleotide of the present disclosure encodes an IL-2 polypeptide. In some embodiments, the IL-2 polypeptide is a human IL-2 polypeptide (see e.g., UniProt accession number: P60568). In some embodiments, the polynucleotide comprises the coding sequence of a wild-type IL2 gene (see e.g., NCBI Gene ID: 3558, SEQ ID NO: 33), or a codon-optimized variant thereof (see e.g., SEQ ID NO: 61). In some embodiments, a polynucleotide encoding an IL-2 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 3. In some embodiments, a polynucleotide encoding an IL-2 polypeptide is a polynucleotide that encodes a polypeptide comprising the amino acid sequence of SEQ ID NO: 3.

In some embodiments, a polynucleotide encoding an IL-2 polypeptide is a polynucleotide that encodes an N-terminal truncation, a C-terminal truncation, or a fragment of the amino acid sequence of SEQ ID NO: 3. N-terminal truncations, C-terminal truncations, or fragments may comprise at least 10, at least 12, at least 14, at least 16, at least 18, at least 20, at least 30, at least 40, at least 50, at least 75, at least 100, but fewer than 153, consecutive amino acids of SEQ ID NO: 3.

In some embodiments, a polynucleotide of the present disclosure encodes an IL-7 polypeptide. In some embodiments, the IL-7 polypeptide is a human IL-7 polypeptide (see e.g., UniProt accession number: P13232). In some embodiments, the polynucleotide comprises the coding sequence of a wild-type IL7 gene (see e.g., NCBI Gene ID: 3574, SEQ ID NO: 34), or a codon-optimized variant thereof. In some embodiments, a polynucleotide encoding an IL-7 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 4. In some embodiments, a polynucleotide encoding an IL-7 polypeptide is a polynucleotide that encodes a polypeptide comprising the amino acid sequence of SEQ ID NO: 4.

In some embodiments, a polynucleotide encoding an IL-7 polypeptide is a polynucleotide that encodes an N-terminal truncation, a C-terminal truncation, or a fragment of the amino acid sequence of SEQ ID NO: 4. N-terminal truncations, C-terminal truncations, or fragments may comprise at least 10, at least 12, at least 14, at least 16, at least 18, at least 20, at least 30, at least 40, at least 50, at least 75, at least 100, but fewer than 177, consecutive amino acids of SEQ ID NO: 4.

In some embodiments, a polynucleotide of the present disclosure encodes an IL-12 subunit α polypeptide. In some embodiments, the IL-12 subunit α polypeptide is a human IL-12 subunit α polypeptide (see e.g., UniProt accession number: P29459). In some embodiments, the polynucleotide comprises the coding sequence of a wild-type IL12A gene (see e.g., NCBI Gene ID: 3592, SEQ ID NO: 35), or a codon-optimized variant thereof (see e.g., SEQ ID NO: 62). In some embodiments, a polynucleotide encoding an IL-12 subunit α polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 5. In some embodiments, a polynucleotide encoding an IL-12 subunit α polypeptide is a polynucleotide that encodes a polypeptide comprising the amino acid sequence of SEQ ID NO: 5.

In some embodiments, a polynucleotide encoding an IL-12 subunit α polypeptide is a polynucleotide that encodes an N-terminal truncation, a C-terminal truncation, or a fragment of the amino acid sequence of SEQ ID NO: 5. N-terminal truncations, C-terminal truncations, or fragments may comprise at least 10, at least 12, at least 14, at least 16, at least 18, at least 20, at least 30, at least 40, at least 50, at least 75, at least 100, at least 200, but fewer than 219, consecutive amino acids of SEQ ID NO: 5.

In some embodiments, a polynucleotide of the present disclosure encodes an IL-12 subunit β polypeptide. In some embodiments, the IL-12 subunit R polypeptide is a human IL-12 subunit polypeptide (see e.g., UniProt accession number: P29460). In some embodiments, the polynucleotide comprises the coding sequence of a wild-type IL12B gene (see e.g., NCBI Gene ID: 3593, SEQ ID NO: 36), or a codon-optimized variant thereof (see e.g., SEQ ID NO: 63). In some embodiments, a polynucleotide encoding an IL-12 subunit R polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 6. In some embodiments, a polynucleotide encoding an IL-12 subunit R polypeptide is a polynucleotide that encodes a polypeptide comprising the amino acid sequence of SEQ ID NO: 6.

In some embodiments, a polynucleotide encoding an IL-12 subunit R polypeptide is a polynucleotide that encodes an N-terminal truncation, a C-terminal truncation, or a fragment of the amino acid sequence of SEQ ID NO: 6. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, but fewer than 328, consecutive amino acids of SEQ ID NO: 6.

In some embodiments, a polynucleotide of the present disclosure encodes an IL-13 polypeptide. In some embodiments, the IL-13 polypeptide is a human IL-13 polypeptide (see e.g., UniProt accession number: P35225). In some embodiments, the polynucleotide comprises the coding sequence of a wild-type IL13 gene (see e.g., NCBI Gene ID: 3596, SEQ ID NO: 37), or a codon-optimized variant thereof. In some embodiments, a polynucleotide encoding an IL-13 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 7. In some embodiments, a polynucleotide encoding an IL-13 polypeptide is a polynucleotide that encodes a polypeptide comprising the amino acid sequence of SEQ ID NO: 7.

In some embodiments, a polynucleotide encoding an IL-13 polypeptide is a polynucleotide that encodes an N-terminal truncation, a C-terminal truncation, or a fragment of the amino acid sequence of SEQ ID NO: 7. N-terminal truncations, C-terminal truncations, or fragments may comprise at least 10, at least 12, at least 14, at least 16, at least 18, at least 20, at least 30, at least 40, at least 50, at least 75, at least 100, but fewer than 146, consecutive amino acids of SEQ ID NO: 7.

In some embodiments, a polynucleotide of the present disclosure encodes an IL-15 polypeptide. In some embodiments, the IL-15 polypeptide is a human IL-15 polypeptide (see e.g., UniProt accession number: P40933). In some embodiments, the polynucleotide comprises the coding sequence of a wild-type IL15 gene (see e.g., NCBI Gene ID: 3600, SEQ ID NO: 38), or a codon-optimized variant thereof. In some embodiments, a polynucleotide encoding an IL-15 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 8. In some embodiments, a polynucleotide encoding an IL-15 polypeptide is a polynucleotide that encodes a polypeptide comprising the amino acid sequence of SEQ ID NO: 8.

In some embodiments, a polynucleotide encoding an IL-15 polypeptide is a polynucleotide that encodes an N-terminal truncation, a C-terminal truncation, or a fragment of the amino acid sequence of SEQ ID NO: 8. N-terminal truncations, C-terminal truncations, or fragments may comprise at least 10, at least 12, at least 14, at least 16, at least 18, at least 20, at least 30, at least 40, at least 50, at least 75, at least 100, but fewer than 162, consecutive amino acids of SEQ ID NO: 8.

In some embodiments, a polynucleotide of the present disclosure encodes an IL-17A polypeptide. In some embodiments, the IL-17A polypeptide is a human IL-17A polypeptide (see e.g., UniProt accession number: Q16552). In some embodiments, the polynucleotide comprises the coding sequence of a wild-type IL17A gene (see e.g., NCBI Gene ID: 3605, SEQ ID NO: 39), or a codon-optimized variant thereof. In some embodiments, a polynucleotide encoding an IL-17A polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 9. In some embodiments, a polynucleotide encoding an IL-17A polypeptide is a polynucleotide that encodes a polypeptide comprising the amino acid sequence of SEQ ID NO: 9.

In some embodiments, a polynucleotide encoding an IL-17A polypeptide is a polynucleotide that encodes an N-terminal truncation, a C-terminal truncation, or a fragment of the amino acid sequence of SEQ ID NO: 9. N-terminal truncations, C-terminal truncations, or fragments may comprise at least 10, at least 12, at least 14, at least 16, at least 18, at least 20, at least 30, at least 40, at least 50, at least 75, at least 100, but fewer than 155, consecutive amino acids of SEQ ID NO: 9.

In some embodiments, a polynucleotide of the present disclosure encodes an IL-18 polypeptide. In some embodiments, the IL-18 polypeptide is a human IL-18 polypeptide (see e.g., UniProt accession number: Q14116). In some embodiments, the polynucleotide comprises the coding sequence of a wild-type IL18 gene (see e.g., NCBI Gene ID: 3606, SEQ ID NO: 40), or a codon-optimized variant thereof. In some embodiments, a polynucleotide encoding an IL-18 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 10. In some embodiments, a polynucleotide encoding an IL-18 polypeptide is a polynucleotide that encodes a polypeptide comprising the amino acid sequence of SEQ ID NO: 10.

In some embodiments, a polynucleotide encoding an IL-18 polypeptide is a polynucleotide that encodes an N-terminal truncation, a C-terminal truncation, or a fragment of the amino acid sequence of SEQ ID NO: 10. N-terminal truncations, C-terminal truncations, or fragments may comprise at least 10, at least 12, at least 14, at least 16, at least 18, at least 20, at least 30, at least 40, at least 50, at least 75, at least 100, at least 150, but fewer than 193, consecutive amino acids of SEQ ID NO: 10.

In some embodiments, a polynucleotide of the present disclosure encodes an IL-28A polypeptide. In some embodiments, the IL-28A polypeptide is a human IL-28A polypeptide (see e.g., UniProt accession number: Q8IZJ0). In some embodiments, the polynucleotide comprises the coding sequence of a wild-type IFNL2 gene (see e.g., NCBI Gene ID: 282616, SEQ ID NO: 41), or a codon-optimized variant thereof. In some embodiments, a polynucleotide encoding an IL-28A polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 11. In some embodiments, a polynucleotide encoding an IL-28A polypeptide is a polynucleotide that encodes a polypeptide comprising the amino acid sequence of SEQ ID NO: 11.

In some embodiments, a polynucleotide encoding an IL-28A polypeptide is a polynucleotide that encodes an N-terminal truncation, a C-terminal truncation, or a fragment of the amino acid sequence of SEQ ID NO: 11. N-terminal truncations, C-terminal truncations, or fragments may comprise at least 10, at least 12, at least 14, at least 16, at least 18, at least 20, at least 30, at least 40, at least 50, at least 75, at least 100, at least 150, but fewer than 200, consecutive amino acids of SEQ ID NO: 11.

In some embodiments, a polynucleotide of the present disclosure encodes an IL-28B polypeptide. In some embodiments, the IL-28B polypeptide is a human IL-28B polypeptide (see e.g., UniProt accession number: Q8IZI9). In some embodiments, the polynucleotide comprises the coding sequence of a wild-type IFNL3 gene (see e.g., NCBI Gene ID: 282617, SEQ ID NO: 42), or a codon-optimized variant thereof. In some embodiments, a polynucleotide encoding an IL-28B polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 12. In some embodiments, a polynucleotide encoding an IL-28B polypeptide is a polynucleotide that encodes a polypeptide comprising the amino acid sequence of SEQ ID NO: 12.

In some embodiments, a polynucleotide encoding an IL-28B polypeptide is a polynucleotide that encodes an N-terminal truncation, a C-terminal truncation, or a fragment of the amino acid sequence of SEQ ID NO: 12. N-terminal truncations, C-terminal truncations, or fragments may comprise at least 10, at least 12, at least 14, at least 16, at least 18, at least 20, at least 30, at least 40, at least 50, at least 75, at least 100, but fewer than 196, consecutive amino acids of SEQ ID NO: 12.

In some embodiments, a polynucleotide of the present disclosure encodes an IL-32 polypeptide. In some embodiments, the IL-32 polypeptide is a human IL-32 polypeptide (see e.g., UniProt accession number: P24001). In some embodiments, the polynucleotide comprises the coding sequence of a wild-type IL32 gene (see e.g., NCBI Gene ID: 9235, SEQ ID NO: 43), or a codon-optimized variant thereof. In some embodiments, a polynucleotide encoding an IL-32 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 13. In some embodiments, a polynucleotide encoding an IL-32 polypeptide is a polynucleotide that encodes a polypeptide comprising the amino acid sequence of SEQ ID NO: 13.

In some embodiments, a polynucleotide encoding an IL-32 polypeptide is a polynucleotide that encodes an N-terminal truncation, a C-terminal truncation, or a fragment of the amino acid sequence of SEQ ID NO: 13. N-terminal truncations, C-terminal truncations, or fragments may comprise at least 10, at least 12, at least 14, at least 16, at least 18, at least 20, at least 30, at least 40, at least 50, at least 75, at least 100, at least 200, but fewer than 234, consecutive amino acids of SEQ ID NO: 13.

In some embodiments, a polynucleotide of the present disclosure encodes an IL-33 polypeptide. In some embodiments, the IL-33 polypeptide is a human IL-33 polypeptide (see e.g., UniProt accession number: O95760). In some embodiments, the polynucleotide comprises the coding sequence of a wild-type IL33 gene (see e.g., NCBI Gene ID: 90865, SEQ ID NO: 44), or a codon-optimized variant thereof. In some embodiments, a polynucleotide encoding an IL-33 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 14. In some embodiments, a polynucleotide encoding an IL-33 polypeptide is a polynucleotide that encodes a polypeptide comprising the amino acid sequence of SEQ ID NO: 14.

In some embodiments, a polynucleotide encoding an IL-33 polypeptide is a polynucleotide that encodes an N-terminal truncation, a C-terminal truncation, or a fragment of the amino acid sequence of SEQ ID NO: 14. N-terminal truncations, C-terminal truncations, or fragments may comprise at least 10, at least 12, at least 14, at least 16, at least 18, at least 20, at least 30, at least 40, at least 50, at least 75, at least 100, at least 200, but fewer than 270, consecutive amino acids of SEQ ID NO: 14.

In some embodiments, a polynucleotide of the present disclosure encodes an IL-34 polypeptide. In some embodiments, the IL-34 polypeptide is a human IL-34 polypeptide (see e.g., UniProt accession number: Q6ZMJ4). In some embodiments, the polynucleotide comprises the coding sequence of a wild-type IL34 gene (see e.g., NCBI Gene ID: 146433, SEQ ID NO: 45), or a codon-optimized variant thereof. In some embodiments, a polynucleotide encoding an IL-34 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 15. In some embodiments, a polynucleotide encoding an IL-34 polypeptide is a polynucleotide that encodes a polypeptide comprising the amino acid sequence of SEQ ID NO: 15.

In some embodiments, a polynucleotide encoding an IL-34 polypeptide is a polynucleotide that encodes an N-terminal truncation, a C-terminal truncation, or a fragment of the amino acid sequence of SEQ ID NO: 15. N-terminal truncations, C-terminal truncations, or fragments may comprise at least 10, at least 12, at least 14, at least 16, at least 18, at least 20, at least 30, at least 40, at least 50, at least 75, at least 100, at least 200, but fewer than 242, consecutive amino acids of SEQ ID NO: 15.

In some embodiments, a polynucleotide of the present disclosure encodes a TNFα polypeptide. In some embodiments, the TNFα polypeptide is a human TNFα polypeptide (see e.g., UniProt accession number: P01375). In some embodiments, the polynucleotide comprises the coding sequence of a wild-type TNF gene (see e.g., NCBI Gene ID: 7124, SEQ ID NO: 46), or a codon-optimized variant thereof. In some embodiments, a polynucleotide encoding a TNFα polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 16. In some embodiments, a polynucleotide encoding a TNFα polypeptide is a polynucleotide that encodes a polypeptide comprising the amino acid sequence of SEQ ID NO: 16.

In some embodiments, a polynucleotide encoding a TNFα polypeptide is a polynucleotide that encodes an N-terminal truncation, a C-terminal truncation, or a fragment of the amino acid sequence of SEQ ID NO: 16. N-terminal truncations, C-terminal truncations, or fragments may comprise at least 10, at least 12, at least 14, at least 16, at least 18, at least 20, at least 30, at least 40, at least 50, at least 75, at least 100, at least 200, but fewer than 233, consecutive amino acids of SEQ ID NO: 16.

In some embodiments, a polynucleotide of the present disclosure encodes an IFNγ polypeptide. In some embodiments, the IFNγ polypeptide is a human IFNγ polypeptide (see e.g., UniProt accession number: P01579). In some embodiments, the polynucleotide comprises the coding sequence of a wild-type IFNG gene (see e.g., NCBI Gene ID: 3458, SEQ ID NO: 47), or a codon-optimized variant thereof. In some embodiments, a polynucleotide encoding a IFNγ polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 17. In some embodiments, a polynucleotide encoding a IFNγ polypeptide is a polynucleotide that encodes a polypeptide comprising the amino acid sequence of SEQ ID NO: 17.

In some embodiments, a polynucleotide encoding an IFNγ polypeptide is a polynucleotide that encodes an N-terminal truncation, a C-terminal truncation, or a fragment of the amino acid sequence of SEQ ID NO: 17. N-terminal truncations, C-terminal truncations, or fragments may comprise at least 10, at least 12, at least 14, at least 16, at least 18, at least 20, at least 30, at least 40, at least 50, at least 75, at least 100, but fewer than 166, consecutive amino acids of SEQ ID NO: 17.

In some embodiments, a polynucleotide of the present disclosure encodes a G-CSF polypeptide. In some embodiments, the G-CSF polypeptide is a human G-CSF polypeptide (see e.g., UniProt accession number: P09919). In some embodiments, the polynucleotide comprises the coding sequence of a wild-type CSF3 gene (see e.g., NCBI Gene ID: 1440, SEQ ID NO: 48), or a codon-optimized variant thereof. In some embodiments, a polynucleotide encoding a G-CSF polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 18. In some embodiments, a polynucleotide encoding a G-CSF polypeptide is a polynucleotide that encodes a polypeptide comprising the amino acid sequence of SEQ ID NO: 18.

In some embodiments, a polynucleotide encoding a G-CSF polypeptide is a polynucleotide that encodes an N-terminal truncation, a C-terminal truncation, or a fragment of the amino acid sequence of SEQ ID NO: 18. N-terminal truncations, C-terminal truncations, or fragments may comprise at least 10, at least 12, at least 14, at least 16, at least 18, at least 20, at least 30, at least 40, at least 50, at least 75, at least 100, at least 200, but fewer than 207, consecutive amino acids of SEQ ID NO: 18.

In some embodiments, a polynucleotide of the present disclosure encodes a GM-CSF polypeptide. In some embodiments, the GM-CSF polypeptide is a human GM-CSF polypeptide (see e.g., UniProt accession number: P04141). In some embodiments, the polynucleotide comprises the coding sequence of a wild-type CSF2 gene (see e.g., NCBI Gene ID: 1437, SEQ ID NO: 49), or a codon-optimized variant thereof. In some embodiments, a polynucleotide encoding a GM-CSF polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 19. In some embodiments, a polynucleotide encoding a GM-CSF polypeptide is a polynucleotide that encodes a polypeptide comprising the amino acid sequence of SEQ ID NO: 19.

In some embodiments, a polynucleotide encoding a GM-CSF polypeptide is a polynucleotide that encodes an N-terminal truncation, a C-terminal truncation, or a fragment of the amino acid sequence of SEQ ID NO: 19. N-terminal truncations, C-terminal truncations, or fragments may comprise at least 10, at least 12, at least 14, at least 16, at least 18, at least 20, at least 30, at least 40, at least 50, at least 75, at least 100, but fewer than 144, consecutive amino acids of SEQ ID NO: 19.

In some embodiments, the present disclosure relates to a recombinant nucleic acid comprising one or more polynucleotides comprising the coding sequence of a human chemokine. Any suitable human chemokine gene (including any isoform thereof) known in the art may be encoded by a polynucleotide of the present disclosure, including, for example, a CCL1 gene (see e.g., NCBI Gene ID: 6346), a CCL2 gene (see e.g., NCBI Gene ID: 6347; SEQ ID NO: 56), a CCL3 gene (see e.g., NCBI Gene ID: 6348; SEQ ID NO: 57), a CCL4 gene (see e.g., NCBI Gene ID: 6351; SEQ ID NO: 58), a CCL5 gene (see e.g., NCBI Gene ID: 6352; SEQ ID NO: 59, a CCL7 gene (see e.g., NCBI Gene ID: 6354), a CCL8 gene (see e.g., NCBI Gene ID: 6355), a CCL11 gene (see e.g., NCBI Gene ID: 6356; SEQ ID NO: 60), a CCL13 gene (see e.g., NCBI Gene ID: 6357), a CCL14 gene (see e.g., NCBI Gene ID: 6358), a CCL15 gene (see e.g., NCBI Gene ID: 6359), a CCL16 gene (see e.g., NCBI Gene ID: 6360), a CCL17 gene (see e.g., NCBI Gene ID: 6361), a CCL18 gene (see e.g., NCBI Gene ID: 6362), a CCL19 gene (see e.g., NCBI Gene ID: 6363), a CCL20 gene (see e.g., NCBI Gene ID: 6364), a CCL21 gene (see e.g., NCBI Gene ID: 6366), a CCL22 gene (see e.g., NCBI Gene ID: 6367), a CCL23 gene (see e.g., NCBI Gene ID:

6368), a CCL24 gene (see e.g., NCBI Gene ID: 6369), a CCL25 gene (see e.g., NCBI Gene ID: 6370), a CCL26 gene (see e.g., NCBI Gene ID: 10344), a CCL27 gene (see e.g., NCBI Gene ID: 10850), a CCL28 gene (see e.g., NCBI Gene ID: 56477), a CXCL1 gene (see e.g., NCBI Gene ID: 2919; SEQ ID NO: 50), a CXCL2 gene (see e.g., NCBI Gene ID: 2920; SEQ ID NO: 51), a CXCL3 gene (see e.g., NCBI Gene ID: 2921), a CXCL4 gene (see e.g., NCBI Gene ID: 5196), a CXCL5 gene (see e.g., NCBI Gene ID: 6374), a CXCL6 gene (see e.g., NCBI Gene ID: 6372), a PPBP gene (also known as CXCL7 gene, see e.g., NCBI Gene ID: 5473), a CXCL8 gene (see e.g., NCBI Gene ID: 3576; SEQ ID NO: 52), a CXCL9 gene (see e.g., NCBI Gene ID: 4283; SEQ ID NO: 53), a CXCL10 gene (see e.g., NCBI Gene ID: 3627), a CXCL11 gene (see e.g., NCBI Gene ID: 6373; SEQ ID NO: 54), a CXCL12 gene (see e.g., NCBI Gene ID: 6387), a CXCL13 gene (see e.g., NCBI Gene ID: 10563), a CXCL14 gene (see e.g., NCBI Gene ID: 9547), a CXCL16 gene (see e.g., NCBI Gene ID: 58191; SEQ ID NO: 55), a CXCL17 gene (see e.g., NCBI Gene ID: 284340), a XCL1 gene (see e.g., NCBI Gene ID: 6375), a XCL2 gene (see e.g., NCBI Gene ID: 6846), a CX3CL1 gene (see e.g., NCBI Gene ID: 6376), etc. In some embodiments, a polynucleotide (e.g., one or more first polynucleotides and/or one or more second polynucleotides) of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the human chemokine genes (and/or coding sequences thereof) described herein or known in the art. In some embodiments, the chemokine is a pro-inflammatory chemokine. In some embodiments, the chemokine is selected from human CXCL1, CXCL2, CXCL8, CXCL9, CXCL11, CXCL16, CCL2, CCL3, CCL4, CCL5, and/or CCL11.

In some embodiments, a polynucleotide of the present disclosure encodes a CXCL1 polypeptide. In some embodiments, the CXCL1 polypeptide is a human CXCL1 polypeptide (see e.g., UniProt accession number: P09341). In some embodiments, the polynucleotide comprises the coding sequence of a wild-type CXCL1 gene (see e.g., NCBI Gene ID: 2919, SEQ ID NO: 50), or a codon-optimized variant thereof. In some embodiments, a polynucleotide encoding a CXCL1 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 20. In some embodiments, a polynucleotide encoding a CXCL1 polypeptide is a polynucleotide that encodes a polypeptide comprising the amino acid sequence of SEQ ID NO: 20.

In some embodiments, a polynucleotide encoding a CXCL1 polypeptide is a polynucleotide that encodes an N-terminal truncation, a C-terminal truncation, or a fragment of the amino acid sequence of SEQ ID NO: 20. N-terminal truncations, C-terminal truncations, or fragments may comprise at least 10, at least 12, at least 14, at least 16, at least 18, at least 20, at least 30, at least 40, at least 50, at least 75, at least 100, but fewer than 107, consecutive amino acids of SEQ ID NO: 20.

In some embodiments, a polynucleotide of the present disclosure encodes a CXCL2 polypeptide. In some embodiments, the CXCL2 polypeptide is a human CXCL2 polypeptide (see e.g., UniProt accession number: P19875). In some embodiments, the polynucleotide comprises the coding sequence of a wild-type CXCL2 gene (see e.g., NCBI Gene ID: 2920, SEQ ID NO: 51), or a codon-optimized variant thereof. In some embodiments, a polynucleotide encoding a CXCL2 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 21. In some embodiments, a polynucleotide encoding a CXCL2 polypeptide is a polynucleotide that encodes a polypeptide comprising the amino acid sequence of SEQ ID NO: 21.

In some embodiments, a polynucleotide encoding a CXCL2 polypeptide is a polynucleotide that encodes an N-terminal truncation, a C-terminal truncation, or a fragment of the amino acid sequence of SEQ ID NO: 21. N-terminal truncations, C-terminal truncations, or fragments may comprise at least 10, at least 12, at least 14, at least 16, at least 18, at least 20, at least 30, at least 40, at least 50, at least 75, at least 100, but fewer than 107, consecutive amino acids of SEQ ID NO: 21.

In some embodiments, a polynucleotide of the present disclosure encodes a CXCL8 polypeptide. In some embodiments, the CXCL8 polypeptide is a human CXCL8 polypeptide (see e.g., UniProt accession number: P10145). In some embodiments, the polynucleotide comprises the coding sequence of a wild-type CXCL8 gene (see e.g., NCBI Gene ID: 3576, SEQ ID NO: 52), or a codon-optimized variant thereof. In some embodiments, a polynucleotide encoding a CXCL8 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 22. In some embodiments, a polynucleotide encoding a CXCL8 polypeptide is a polynucleotide that encodes a polypeptide comprising the amino acid sequence of SEQ ID NO: 22.

In some embodiments, a polynucleotide encoding a CXCL8 polypeptide is a polynucleotide that encodes an N-terminal truncation, a C-terminal truncation, or a fragment of the amino acid sequence of SEQ ID NO: 22. N-terminal truncations, C-terminal truncations, or fragments may comprise at least 10, at least 12, at least 14, at least 16, at least 18, at least 20, at least 30, at least 40, at least 50, at least 75, but fewer than 99, consecutive amino acids of SEQ ID NO: 22.

In some embodiments, a polynucleotide of the present disclosure encodes a CXCL9 polypeptide. In some embodiments, the CXCL9 polypeptide is a human CXCL9 polypeptide (see e.g., UniProt accession number: Q07325). In some embodiments, the polynucleotide comprises the coding sequence of a wild-type CXCL9 gene (see e.g., NCBI Gene ID: 4283, SEQ ID NO: 53), or a codon-optimized variant thereof. In some embodiments, a polynucleotide encoding a CXCL9 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 23. In some embodiments, a polynucleotide encoding a CXCL9 polypeptide is a polynucleotide that encodes a polypeptide comprising the amino acid sequence of SEQ ID NO: 23.

In some embodiments, a polynucleotide encoding a CXCL9 polypeptide is a polynucleotide that encodes an N-terminal truncation, a C-terminal truncation, or a fragment of the amino acid sequence of SEQ ID NO: 23. N-terminal truncations, C-terminal truncations, or fragments may comprise at least 10, at least 12, at least 14, at least 16, at least 18, at least 20, at least 30, at least 40, at least 50, at least 75, at least 100, but fewer than 125, consecutive amino acids of SEQ ID NO: 23.

In some embodiments, a polynucleotide of the present disclosure encodes a CXCL11 polypeptide. In some embodiments, the CXCL11 polypeptide is a human CXCL11 polypeptide (see e.g., UniProt accession number: O14625). In some embodiments, the polynucleotide comprises the coding sequence of a wild-type CXCL11 gene (see e.g., NCBI Gene ID: 6373, SEQ ID NO: 54), or a codon-optimized variant thereof. In some embodiments, a polynucleotide encoding a CXCL11 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 24. In some embodiments, a polynucleotide encoding a CXCL11 polypeptide is a polynucleotide that encodes a polypeptide comprising the amino acid sequence of SEQ ID NO: 24.

In some embodiments, a polynucleotide encoding a CXCL11 polypeptide is a polynucleotide that encodes an N-terminal truncation, a C-terminal truncation, or a fragment of the amino acid sequence of SEQ ID NO: 24. N-terminal truncations, C-terminal truncations, or fragments may comprise at least 10, at least 12, at least 14, at least 16, at least 18, at least 20, at least 30, at least 40, at least 50, at least 75, but fewer than 94, consecutive amino acids of SEQ ID NO: 24.

In some embodiments, a polynucleotide of the present disclosure encodes a CXCL16 polypeptide. In some embodiments, the CXCL16 polypeptide is a human CXCL16 polypeptide (see e.g., UniProt accession number: Q9H2A7). In some embodiments, the polynucleotide comprises the coding sequence of a wild-type CXCL16 gene (see e.g., NCBI Gene ID: 58191, SEQ ID NO: 55), or a codon-optimized variant thereof. In some embodiments, a polynucleotide encoding a CXCL16 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 25. In some embodiments, a polynucleotide encoding a CXCL16 polypeptide is a polynucleotide that encodes a polypeptide comprising the amino acid sequence of SEQ ID NO: 25.

In some embodiments, a polynucleotide encoding a CXCL16 polypeptide is a polynucleotide that encodes an N-terminal truncation, a C-terminal truncation, or a fragment of the amino acid sequence of SEQ ID NO: 25. N-terminal truncations, C-terminal truncations, or fragments may comprise at least 10, at least 12, at least 14, at least 16, at least 18, at least 20, at least 30, at least 40, at least 50, at least 75, at least 100, at least 200, but fewer than 254, consecutive amino acids of SEQ ID NO: 25.

In some embodiments, a polynucleotide of the present disclosure encodes a CCL2 polypeptide. In some embodiments, the CCL2 polypeptide is a human CCL2 polypeptide (see e.g., UniProt accession number: P13500). In some embodiments, the polynucleotide comprises the coding sequence of a wild-type CCL2 gene (see e.g., NCBI Gene ID: 6347, SEQ ID NO: 56), or a codon-optimized variant thereof. In some embodiments, a polynucleotide encoding a CCL2 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 26. In some embodiments, a polynucleotide encoding a CCL2 polypeptide is a polynucleotide that encodes a polypeptide comprising the amino acid sequence of SEQ ID NO: 26.

In some embodiments, a polynucleotide encoding a CCL2 polypeptide is a polynucleotide that encodes an N-terminal truncation, a C-terminal truncation, or a fragment of the amino acid sequence of SEQ ID NO: 26. N-terminal truncations, C-terminal truncations, or fragments may comprise at least 10, at least 12, at least 14, at least 16, at least 18, at least 20, at least 30, at least 40, at least 50, at least 75, but fewer than 99, consecutive amino acids of SEQ ID NO: 26.

In some embodiments, a polynucleotide of the present disclosure encodes a CCL3 polypeptide. In some embodiments, the CCL3 polypeptide is a human CCL3 polypeptide (see e.g., UniProt accession number: P10147). In some embodiments, the polynucleotide comprises the coding sequence of a wild-type CCL3 gene (see e.g., NCBI Gene ID: 6348, SEQ ID NO: 57), or a codon-optimized variant thereof. In some embodiments, a polynucleotide encoding a CCL3 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 27. In some embodiments, a polynucleotide encoding a CCL3 polypeptide is a polynucleotide that encodes a polypeptide comprising the amino acid sequence of SEQ ID NO: 27.

In some embodiments, a polynucleotide encoding a CCL3 polypeptide is a polynucleotide that encodes an N-terminal truncation, a C-terminal truncation, or a fragment of the amino acid sequence of SEQ ID NO: 27. N-terminal truncations, C-terminal truncations, or fragments may comprise at least 10, at least 12, at least 14, at least 16, at least 18, at least 20, at least 30, at least 40, at least 50, at least 75, but fewer than 92, consecutive amino acids of SEQ ID NO: 27.

In some embodiments, a polynucleotide of the present disclosure encodes a CCL4 polypeptide. In some embodiments, the CCL4 polypeptide is a human CCL4 polypeptide (see e.g., UniProt accession number: P13236). In some embodiments, the polynucleotide comprises the coding sequence of a wild-type CCL4 gene (see e.g., NCBI Gene ID: 6351, SEQ ID NO: 58), or a codon-optimized variant thereof. In some embodiments, a polynucleotide encoding a CCL4 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 28. In some embodiments, a polynucleotide encoding a CCL4 polypeptide is a polynucleotide that encodes a polypeptide comprising the amino acid sequence of SEQ ID NO: 28.

In some embodiments, a polynucleotide encoding a CCL4 polypeptide is a polynucleotide that encodes an N-terminal truncation, a C-terminal truncation, or a fragment of the amino acid sequence of SEQ ID NO: 28. N-terminal truncations, C-terminal truncations, or fragments may comprise at least 10, at least 12, at least 14, at least 16, at least 18, at least 20, at least 30, at least 40, at least 50, at least 75, but fewer than 92, consecutive amino acids of SEQ ID NO: 28.

In some embodiments, a polynucleotide of the present disclosure encodes a CCL5 polypeptide. In some embodiments, the CCL5 polypeptide is a human CCL5 polypeptide (see e.g., UniProt accession number: P13501). In some embodiments, the polynucleotide comprises the coding sequence of a wild-type CCL5 gene (see e.g., NCBI Gene ID: 6352, SEQ ID NO: 59), or a codon-optimized variant thereof. In some embodiments, a polynucleotide encoding a CCL5 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 29. In some embodiments, a polynucleotide encoding a CCL5 polypeptide is a polynucleotide that encodes a polypeptide comprising the amino acid sequence of SEQ ID NO: 29.

In some embodiments, a polynucleotide encoding a CCL5 polypeptide is a polynucleotide that encodes an N-terminal truncation, a C-terminal truncation, or a fragment of the amino acid sequence of SEQ ID NO: 29. N-terminal truncations, C-terminal truncations, or fragments may comprise at least 10, at least 12, at least 14, at least 16, at least 18, at least 20, at least 30, at least 40, at least 50, at least 75, but fewer than 91, consecutive amino acids of SEQ ID NO: 29.

In some embodiments, a polynucleotide of the present disclosure encodes a CCL11 polypeptide. In some embodiments, the CCL11 polypeptide is a human CCL11 polypeptide (see e.g., UniProt accession number: P51671). In some embodiments, the polynucleotide comprises the coding sequence of a wild-type CCL11 gene (see e.g., NCBI Gene ID: 6356, SEQ ID NO: 60), or a codon-optimized variant thereof. In some embodiments, a polynucleotide encoding a CCL11 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 30. In some embodiments, a polynucleotide encoding a CCL11 polypeptide is a polynucleotide that encodes a polypeptide comprising the amino acid sequence of SEQ ID NO: 30.

In some embodiments, a polynucleotide encoding a CCL11 polypeptide is a polynucleotide that encodes an N-terminal truncation, a C-terminal truncation, or a fragment of the amino acid sequence of SEQ ID NO: 30. N-terminal truncations, C-terminal truncations, or fragments may comprise at least 10, at least 12, at least 14, at least 16, at least 18, at least 20, at least 30, at least 40, at least 50, at least 75, but fewer than 97, consecutive amino acids of SEQ ID NO: 30.

In some embodiments, a polynucleotide of the present disclosure encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an amino acid sequence selected from SEQ ID NOS: 1-30. In some embodiments, a polynucleotide of the present disclosure encodes a polypeptide comprising an amino acid sequence selected from SEQ ID NOS: 1-30.

In some embodiments, a polynucleotide of the present disclosure encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an amino acid sequence selected from SEQ ID NOS: 1-19. In some embodiments, a polynucleotide of the present disclosure encodes a polypeptide comprising an amino acid sequence selected from SEQ ID NOS: 1-19.

In some embodiments, a polynucleotide of the present disclosure encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an amino acid sequence selected from SEQ ID NOS: 20-30. In some embodiments, a polynucleotide of the present disclosure encodes a polypeptide comprising an amino acid sequence selected from SEQ ID NOS: 20-30.

In some embodiments, a polynucleotide of the present disclosure encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an amino acid sequence selected from SEQ ID NOS: 3, 5 and 6. In some embodiments, a polynucleotide of the present disclosure encodes a polypeptide comprising an amino acid sequence selected from SEQ ID NOS: 3, 5 and 6.

In some embodiments, a polynucleotide of the present disclosure encodes any one or more of an Interleukin-1 alpha (IL-1α) peptide, an Interleukin-1 beta (IL-1β) peptide, an Interleukin-2 (IL-2) peptide, an Interleukin-3 (IL-3) peptide, an Interleukin-4 (IL-4) peptide, an Interleukin-5 (IL-5) peptide, an Interleukin-6 (IL-6) peptide, an Interleukin-7 (IL-7) peptide, an Interleukin-8 (IL-8) peptide, an Interleukin-9 (IL-9) peptide, an Interleukin-10 (IL-10) peptide, an Interleukin-11(IL-11) peptide, an Interleukin-12 subunit alpha (IL-12α) peptide, an Interleukin-12 subunit beta (IL-12β) peptide, an Interleukin-13 (IL-13) peptide, an Interleukin-15 (IL-15) peptide, an Interleukin-17 (IL-17) peptide, an Interleukin-17B (IL-17B) peptide, an Interleukin-17C (IL-17C) peptide, an Interleukin-17D (IL-17D) peptide, an Interleukin-25 (IL-25) peptide, an Interleukin-17F (IL-17F) peptide, an Interleukin-18 (IL-18) peptide, an Interleukin-28A (IL-28A) peptide, an Interleukin-28B (IL-28B) peptide, an Interleukin-29 (IL-29) peptide, an Interleukin-32 (IL-32) peptide, an Interleukin-33 (IL-33) peptide, an Interleukin-34 (IL-34) peptide, an Interleukin-36 alpha (IL-36α) peptide, an Interleukin-36 (IL-36β) beta peptide, an Interleukin-36 gamma (IL-36γ) peptide, an Interferon alpha-1 (IFNα-1) peptide, an Interferon alpha-2 (IFNα-2) peptide, an Interferon alpha-4 (IFNα-4) peptide, an Interferon alpha-5 (IFNα-5) peptide, an Interferon alpha-6 (IFNα-6) peptide, an Interferon alpha-7 (IFNα-7) peptide, an Interferon alpha-8 (IFNα-8) peptide, an Interferon alpha-10 (IFNα-10) peptide, an Interferon alpha-14 (IFNα-14) peptide, an Interferon alpha-16 (IFNα-16) peptide, an Interferon alpha-17 (IFNα-17) peptide, an Interferon alpha-21 (IFNα-21) peptide, an Interferon beta-1 (IFNβ-1) peptide, an Interferon beta-3 (IFNβ-3) peptide, an Interferon gamma (IFNγ) peptide, a Tumor Necrosis Factor alpha (TNFα) peptide, a Tumor Necrosis Factor beta (TNFβ) peptide, a Granulocyte Colony-Stimulating Factor (G-CSF) peptide, a Granulocyte-Macrophage Colony-Stimulating Factor (GM-CSF) peptide, a Macrophage Colony-Stimulating Factor (M-CSF) peptide, a C—C Motif Chemokine 1 (CCL1) peptide, a C—C Motif Chemokine 2 (CCL2) peptide, a C—C Motif Chemokine 3 (CCL3)peptide, a C—C Motif Chemokine 4 (CCL4) peptide, a C—C Motif Chemokine 5 (CCL5) peptide, a C—C Motif Chemokine 7 (CCL7)peptide, a C—C Motif Chemokine 8 (CCL8) peptide, a C—C Motif Chemokine 11 (CCL11) peptide, a C—C Motif Chemokine 13 (CCL13) peptide, a C—C Motif Chemokine 14 (CCL14) peptide, a C—C Motif Chemokine 15 (CCL15) peptide, a C—C Motif Chemokine 16 (CCL16) peptide, a C—C Motif Chemokine 17 (CCL17) peptide, a C—C Motif Chemokine 18 (CCL18) peptide, a C—C Motif Chemokine 19 (CCL19) peptide, a C—C Motif Chemokine 20 (CCL20) peptide, a C—C Motif Chemokine 21 (CCL21) peptide, a C—C Motif Chemokine 22 (CCL22) peptide, a C—C Motif Chemokine 23 (CCL23) peptide, a C—C Motif Chemokine 24 (CCL24) peptide, a C—C Motif Chemokine 25 (CCL25) peptide, a C—C Motif Chemokine 26 (CCL26) peptide, a C—C Motif Chemokine 27 (CCL27) peptide, a C—C Motif Chemokine 28 (CCL28) peptide, a C—X—C Motif Chemokine 1 (CXCL1) peptide, a C—X—C Motif Chemokine 2 (CXCL2) peptide, a C—X—C Motif Chemokine 3 (CXCL3) peptide, a C—X—C Motif Chemokine 4 (CXCL4) peptide, a C—X—C Motif Chemokine 5 (CXCL5) peptide, a C—X—C Motif Chemokine 6 (CXCL6) peptide, a C—X—C Motif Chemokine 7 (CXCL7) peptide, a C—X—C Motif Chemokine 9 (CXCL9) peptide, a C—X—C Motif Chemokine 10 (CXCL10) peptide, a C—X—C Motif Chemokine 11 (CXCL11) peptide, a C—X—C Motif Chemokine 12 (CXCL12) peptide, a C—X—C Motif Chemokine 13 (CXCL13) peptide, a C—X—C Motif Chemokine 14 (CXCL14) peptide, a C—X—C Motif Chemokine 16 (CXCL16) peptide, a C—X—C Motif Chemokine 17 (CXCL17) peptide, a C Motif Chemokine 1 (XCL1) peptide, a C Motif Chemokine 2 (XCL2) peptide, a C—X3-C Motif Chemokine 1 (CX3CL1) peptide, and/or any chimeric polypeptides thereof, in any suitable combination. In some embodiments, a polynucleotide of the present disclosure does not encode an Interleukin-4 (IL-4) peptide. In some embodiments, a polynucleotide of the present disclosure does not encode an Interleukin-10 (IL-10) peptide. In some embodiments, a polynucleotide of the present disclosure does not encode a Granulocyte-Macrophage Colony-Stimulating Factor (GM-CSF) peptide. In some embodiments, a polynucleotide of the present disclosure does not encode an Interleukin-4 (IL-4) peptide, an Interleukin-10 (IL-10) peptide, and/or a Granulocyte-Macrophage Colony-Stimulating Factor (GM-CSF) peptide.

A polynucleotide of the present disclosure encoding a polypeptide (e.g., an immunomodulatory polypeptide) may further encode additional coding and non-coding sequences. Examples of additional coding and non-coding sequences may include, but are not limited to, sequences encoding additional polypeptide tags (e.g., encoded in-frame with the polypeptide in order to produce a fusion protein), introns (e.g., native, modified, or heterologous introns), 5' and/or 3' UTRs (e.g., native, modified, or heterologous 5' and/or 3' UTRs), and the like. Examples of suitable polypeptide tags may include, but are not limited, to any combination of purification tags, such as his-tags, flag-tags, maltose binding protein and glutathione-S-transferase tags, detection tags, such as tags that may be detected photometrically (e.g., green fluorescent protein, red fluorescent protein, etc.) and tags that have a detectable enzymatic activity (e.g., alkaline phosphatase, etc.), tags containing secretory sequences, signal sequences, leader sequences, and/or stabilizing sequences, protease cleavage sites (e.g., furin cleavage sites, TEV cleavage sites, Thrombin cleavage sites, etc.), and the like. In some embodiments, the 5' and/or 3'UTRs increase the stability, localization, and/or translational efficiency of the polynucleotides. In some embodiments, the 5' and/or 3'UTRs improve the level and/or duration of protein expression. In some embodiments, the 5' and/or 3'UTRs include elements (e.g., one or more miRNA binding sites, etc.) that may block or reduce off-target expression (e.g., inhibiting expression in specific cell types (e.g., neuronal cells), at specific times in the cell cycle, at specific developmental stages, etc.). In some embodiments, the 5' and/or 3'UTRs include elements (e.g., one or more miRNA binding sites, etc.) that may enhance expression of the encoded polypeptide in specific cell types.

In some embodiments, a polynucleotide of the present disclosure encoding a polypeptide (e.g., an immunomodulatory polypeptide) is operably linked to one or more (e.g., one or more, two or more, three or more, four or more, five or more, ten or more, etc.) regulatory sequences. The term "regulatory sequence" may include enhancers, insulators, promoters, and other expression control elements (e.g., polyadenylation signals). Any suitable enhancer(s) known in the art may be used, including, for example, enhancer sequences from mammalian genes (such as globin, elastase, albumin, α-fetoprotein, insulin and the like), enhancer sequences from a eukaryotic cell virus (such as SV40 enhancer on the late side of the replication origin (bp 100-270), the cytomegalovirus early promoter enhancer, the polyoma enhancer on the late side of the replication origin, adenovirus enhancers, and the like), and any combinations thereof. Any suitable insulator(s) known in the art may be used, including, for example, HSV chromatin boundary (CTRL/CTCF-binding/insulator) elements CTRL1 and/or CTRL2, chicken hypersensitive site 4 insulator (cHS4), human HNRPA2B1-CBX3 ubiquitous chromatin opening element (UCOE), the scaffold/matrix attachment region (S/MAR) from the human interferon beta gene (IFNB1), and any combinations thereof. Any suitable promoter (e.g., suitable for transcription in mammalian host cells) known in the art may be used, including, for example, promoters obtained from the genomes of viruses (such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), and the like), promoters from heterologous mammalian genes (such as the actin promoter (e.g., the β-actin promoter), a ubiquitin promoter (e.g., a ubiquitin C (UbC) promoter), a phosphoglycerate kinase (PGK) promoter, an immunoglobulin promoter, from heat-shock promoters, and the like), promoters from homologous mammalian genes, synthetic promoters (such as the CAG promoter), and any combinations thereof, provided such promoters are compatible with the host cells. Regulatory sequences may include those which direct constitutive expression of a nucleic acid, as well as tissue-specific regulatory and/or inducible or repressible sequences.

In some embodiments, a polynucleotide of the present disclosure is operably linked to one or more heterologous promoters. In some embodiments, the one or more heterologous promoters are one or more of constitutive promoters, tissue-specific promoters, temporal promoters, spatial promoters, inducible promoters, and repressible promoters. In some embodiments, the one or more heterologous promoters are one or more of the human cytomegalovirus (HCMV) immediate early promoter, the human elongation factor-1 (EF1) promoter, the human β-actin promoter, the human UbC promoter, the human PGK promoter, the synthetic CAGG promoter, and any combinations thereof. In some embodiments, a polynucleotide of the present disclosure encoding a polypeptide (e.g., an immunomodulatory polypeptide) is operably linked to an HCMV promoter.

In some embodiments, a polynucleotide of the present disclosure encoding a polypeptide (e.g., an immunomodulatory polypeptide, such as IL-2 and/or IL-12) expresses the polypeptide when the polynucleotide is delivered into one or more target cells of a subject (e.g., one or more cells of the respiratory tract, airway, lungs, etc. of the subject). In some embodiments, expression of the polypeptide (e.g., an immunomodulatory polypeptide, such as IL-2 and/or IL-12) enhances, increases, augments, and/or supplements the levels, function, and/or activity of the polypeptide in one or more target cells of a subject (e.g., as compared to prior to expression of the polypeptide, as compared to levels of the endogenous polypeptide expressed in the cell, etc.). In some embodiments, expression of the polypeptide (e.g., an immunomodulatory polypeptide, such as IL-2 and/or IL-12) provides prophylactic, palliative, or therapeutic relief of one or more signs or symptoms of cancer (e.g., solid tumor, hematologic cancer, bladder cancer, brain cancer, breast cancer, colon cancer, gastric cancer, glioma, head cancer, leukemia, liver cancer, lung cancer, lymphoma, myeloma, neck cancer, ovarian cancer, melanoma, pancreatic cancer, renal cancer, salivary cancer, skin cancer, stomach cancer, thymic epithelial cancer, thyroid cancer, etc.) in a subject (e.g., as compared to prior to expression of the polypeptide).

Chimeric Polypeptides

In some embodiments, a polynucleotide of the present disclosure encodes a chimeric polypeptide comprising a first immunomodulatory polypeptide and a second immunomodulatory polypeptide. In some embodiments, the first and second immunomodulatory polypeptides are the same. In some embodiments, the first and second immunomodulatory polypeptides are different. In some embodiments, the chimeric polypeptide further comprises a linker polypeptide linking the first and second immunomodulatory polypeptides. In some embodiments, the chimeric polypeptide comprises, from N-terminus to C-terminus, the first immunomodulatory polypeptide—the linker polypeptide—the second immunomodulatory polypeptide. The first and/or second immunomodulatory polypeptides may be any of the immunomodulatory polypeptides described herein or known in the art.

In some embodiments, the linker polypeptide is a cleavable linker polypeptide. Any cleavable linker polypeptide known in the art may be used in the chimeric polypeptides of the present disclosure, including, for example, a T2A linker, a P2A linker, a E2A linker, and F2A linker, etc. In some embodiments, the linker polypeptide is a T2A linker polypeptide. An exemplary nucleic acid sequence encoding a T2A linker polypeptide is provided as SEQ ID NO: 64. An exemplary amino acid sequence of a T2A linker polypeptide is provided as SEQ ID NO: 68. In some embodiments, the linker polypeptide is a P2A linker polypeptide. An exemplary nucleic acid sequence encoding a P2A linker polypeptide is provided as SEQ ID NO: 65. An exemplary amino acid sequence of a P2A linker polypeptide is provided as SEQ ID NO: 69. In some embodiments, the linker polypeptide is an E2A linker polypeptide. An exemplary nucleic acid sequence encoding an E2A linker polypeptide is provided as SEQ ID NO: 66. An exemplary amino acid sequence of an E2A linker polypeptide is provided as SEQ ID NO: 70. In some embodiments, the linker polypeptide is an F2A linker polypeptide. An exemplary nucleic acid sequence encoding an F2A linker polypeptide is provided as SEQ ID NO: 67. An exemplary amino acid sequence of an F2A linker polypeptide is provided as SEQ ID NO: 71. In some embodiments, the linker polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 68-71. In some embodiments, the linker polypeptide comprises a sequence selected from SEQ ID NOS: 68-71.

In some embodiments, the linker polypeptide is a non-cleavable linker polypeptide. Any non-cleavable linker polypeptide known in the art may be used in the chimeric polypeptides of the present disclosure, including, for example, a GGGGSGGGGSGGGGS (SEQ ID NO: 72) linker, a GGSSRSSSSGGGGSGGGG (SEQ ID NO: 73) linker, a GGGGSGGGGSGGGGSGGGGS (SEQ ID NO: 74) linker, a CGGGSGGGGSGGGGS (SEQ ID NO: 75) linker, a SHGGHGGGGSGGGGS (SEQ ID NO: 76) linker, a MGGMSGGGGSGGGGS (SEQ ID NO: 77) linker, a YGGYSGGGGSGGGGS (SEQ ID NO: 78) linker, a WGGYSGGGGSGGGGS (SEQ ID NO: 79) linker, a SVSVGMKPSPRP (SEQ ID NO: 80) linker, a VISNHA-GSSRRL (SEQ ID NO: 81) linker, a PWIPTPRPTFTG (SEQ ID NO: 82) linker, a RGRGRGRGRGR (SEQ ID NO: 83) linker, etc. In some embodiments, the linker polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 72-83. In some embodiments, the linker polypeptide comprises a sequence selected from SEQ ID NOS: 72-83.

An exemplary nucleic acid sequence encoding a chimeric polypeptide comprising a first human immunomodulatory polypeptide, a linker polypeptide, and a second human immunomodulatory polypeptide is provided as SEQ ID NO: 84. An exemplary amino acid sequence of a chimeric polypeptide comprising a first human immunomodulatory polypeptide, a linker polypeptide, and a second human immunomodulatory polypeptide is provided as SEQ ID NO: 85. In some embodiments, a polynucleotide of the present disclosure encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 85. In some embodiments, a polynucleotide of the present disclosure encodes a polypeptide comprising the amino acid sequence of SEQ ID NO: 85.

In some embodiments, a polynucleotide of the present disclosure does not comprise the coding sequence of (e.g., a transgene encoding) a Collagen alpha-1 (VII) chain polypeptide (COL7). In some embodiments, a polynucleotide of the present disclosure does not comprise the coding sequence of (e.g., a transgene encoding) a Lysyl hydroxylase 3 polypeptide (LH3). In some embodiments, a polynucleotide of the present disclosure does not comprise the coding sequence of (e.g., a transgene encoding) a Keratin type I cytoskeletal 17 polypeptide (KRT17). In some embodiments, a polynucleotide of the present disclosure does not comprise the coding sequence of (e.g., a transgene encoding) a transglutaminase (TGM) polypeptide (e.g., a human transglutaminase polypeptide such as a human TGM1 polypeptide and/or a human TGM5 polypeptide). In some embodiments, a polynucleotide of the present disclosure does not comprise the coding sequence of (e.g., a transgene encoding) a cosmetic protein (e.g., collagen proteins, fibronectins, elastins, lumicans, vitronectins/vitronectin receptors, laminins, neuromodulators, fibrillins, additional dermal extracellular matrix proteins, etc.). In some embodiments, a polynucleotide of the present disclosure does not comprise the coding sequence of (e.g., a transgene encoding) an antibody (e.g., a full-length antibody, an antibody fragment, etc.). In some embodiments, a polynucleotide of the present disclosure does not comprise the coding sequence of (e.g., a transgene encoding) a Serine Protease Inhibitor Kazal-type (SPINK) polypeptide (e.g., a human SPINK polypeptide, such as a SPINK5 polypeptide). In some embodiments, a polynucleotide of the present disclosure does not comprise the coding sequence of (e.g., a transgene encoding) a filaggrin or filaggrin 2 polypeptide (e.g., a human filaggrin or filaggrin 2 polypeptide). In some embodiments, a polynucleotide of the present disclosure does not comprise the coding sequence of (e.g., a transgene encoding) a Cystic Fibrosis Transmembrane Conductance Regulator (CFTR) polypeptide (e.g., a human CFTR polypeptide). In some embodiments, a polynucleotide of the present disclosure does not comprise the coding sequence of (e.g., a transgene encoding) an ichthyosis-associated polypeptide (e.g., an ATP-binding cassette sub-family A member 12 polypeptide, a 1-acylglycerol-3-phosphate O-acyltransferase ABHD5 polypeptide, an Aldehyde dehydrogenase family 3 member A2 polypeptide, an Arachidonate 12-lipoxygenase 12R-type polypeptide, a Hydroperoxide isomerase ALOXE3 polypeptide, an AP-1 complex subunit sigma-1A polypeptide, an Arylsulfatase E polypeptide, a Caspase-14 polypeptide, a Comeodesmosin polypeptide, a Ceramide synthase 3 polypeptide, a Carbohydrate sulfotransferase 8 polypeptide, a Claudin-1 polypeptide, a Cystatin-A polypeptide, a Cytochrome P450 4F22 polypeptide, a 3-beta-hydroxysteroid-Delta(8), Delta(7)-isomerase polypeptide, an Elongation of very long chain fatty acids protein 4 polypeptide, a Filaggrin polypeptide, a Filaggrin 2 polypeptide, a Gap junction beta-2 polypeptide, a Gap junction beta-3 polypeptide, a Gap junction beta-4 polypeptide, a Gap junction beta-6 polypeptide, a 3-ketodihydrosphingosine reductase polypeptide, a Keratin, type II cytoskeletal 1 polypeptide, a Keratin, type II cytoskeletal 2 epidermal polypeptide, a Keratin, type I cytoskeletal 9 polypeptide, a Keratin, type I cytoskeletal 10 polypeptide, a Lipase member N polypeptide, a Loricrin polypeptide, a Membrane-bound transcription factor site-2 protease polypeptide, a Magnesium transporter NIPA4 polypeptide, a Sterol-4-alpha-carboxylate 3-dehydrogenase, decarboxylating polypeptide, a Peroxisomal targeting signal 2 receptor polypeptide, a D-3-phosphoglycerate dehydrogenase polypeptide, a Phytanoyl-CoA dioxygenase, peroxisomal polypeptide, Patatin-like phospholipase domain-containing protein 1 polypeptide, a Proteasome maturation protein polypeptide, a Phosphoserine aminotransferase polypeptide, a Short-chain dehydrogenase/reductase family 9C member 7 polypeptide, a Serpin B8 polypeptide, a Long-chain fatty acid transport protein 4 polypeptide, a Synaptosomal-associated protein 29 polypeptide, a Suppressor of tumorigenicity 14 protein polypeptide, a Steryl-sulfatase polypeptide, a Vacuolar protein sorting-associated protein 33B polypeptide, and a CAAX prenyl protease 1 homolog polypeptide). In some embodiments, a polynucleotide of the present disclosure does not comprise the coding sequence of (e.g., a transgene encoding) a Collagen alpha-1 (VII) chain polypeptide, a Lysyl hydroxylase 3 polypeptide, a Keratin type I cytoskeletal 17 polypeptide, and/or any chimeric polypeptides thereof. In some embodiments, a polynucleotide of the present disclosure does not comprise the coding sequence of (e.g., a transgene encoding) a Collagen alpha-1 (VII) chain polypeptide, a Lysyl hydroxylase 3 polypeptide, a Keratin type I cytoskeletal 17 polypeptide, a transglutaminase (TGM) polypeptide, a filaggrin polypeptide, a cosmetic protein, an antibody, a SPINK polypeptide, a CFTR polypeptide, an ichthyosis-associated polypeptide, an Alpha-1-antitrypsin polypeptide, a Sodium-dependent phosphate transport protein 2B polypeptide, a Dynein heavy chain 5 axonemal polypeptide, a Dynein heavy chain 11 axonemal polypeptide, a Coiled-coil domain-containing protein 39 polypeptide, a Dynein intermediate chain 1 axonemal polypeptide, a Coiled-coil domain-containing protein 40 polypeptide, a Coiled-coil domain containing protein 103 polypeptide, a Sperm-associated antigen 1 polypeptide, a Zinc finger MYND domain-containing protein 10 polypeptide, an Armadillo repeat containing protein 4 polypeptide, a Coiled-coil domain-containing protein 151 polypeptide, a Dynein intermediate chain 2 axonemal polypeptide, a Radial spoke head 1 homolog polypeptide, a Coiled-coil domain-containing protein 114 polypeptide, a Radial spoke head protein 4 homolog A polypeptide, a Dynein assembly factor 1 axonemal polypeptide, a Dynein assembly factor 2 axonemal polypeptide, a Leucine-rich repeat-containing protein 6 polypeptide, a Pulmonary surfactant-associated protein B polypeptide, a Pulmonary surfactant-associated protein C polypeptide, a Homeobox protein Nkx-2.1 polypeptide, an ATP-binding cassette sub-family A member 3 polypeptide, a Cytokine receptor common subunit beta polypeptide, a Granulocyte-macrophage colony-stimulating factor receptor subunit alpha polypeptide, a Bone morphogenetic protein receptor type-2 polypeptide, a Sarcoplasmic/endoplasmic reticulum calcium ATPase 2 polypeptide, a serine/threonine-protein kinase receptor R3 polypeptide, an Endoglin polypeptide, a Mothers against decapentaplegic homolog 9 polypeptide, a Caveolin-1 polypeptide, a Potassium channel subfamily K member 3 polypeptide, an eIF-2-alpha kinase GCN2 polypeptide, a Pulmonary surfactant-associated protein A2 polypeptide, a Telomerase reverse transcriptase polypeptide, a Dyskerin polypeptide, a Regulator of telomere elongation helicase 1 polypeptide, a Poly(A)-specific ribonuclease PARN polypeptide, a TERF1-interacting nuclear factor 2 polypeptide, an H/ACA ribonucleoprotein complex non-core subunit NAF1 polypeptide, a Mucin-5B polypeptide, a Desmoplakin polypeptide, a CST complex subunit STN1 polypeptide, a Dipeptidyl peptidase 9 polypeptide, and/or any chimeric polypeptides thereof.

Recombinant Nucleic Acids

In some embodiments, the present disclosure relates to recombinant nucleic acids comprising any one or more of the polynucleotides described herein. In some embodiments, the recombinant nucleic acid is a vector (e.g., an expression vector, a display vector, etc.). In some embodiments, the vector is a DNA vector or an RNA vector. Generally, vectors suitable to maintain, propagate, and/or express polynucleotides to produce one or more polypeptides in a subject may be used. Examples of suitable vectors may include, for example, plasmids, cosmids, episomes, transposons, and viral vectors (e.g., adenoviral vectors, adeno-associated viral vectors, vaccinia viral vectors, Sindbis-viral vectors, measles vectors, herpes viral vectors, lentiviral vectors, retroviral vectors, etc.). In some embodiments, the vector is a herpes viral vector. In some embodiments, the vector is capable of autonomous replication in a host cell. In some embodiments, the vector is incapable of autonomous replication in a host cell. In some embodiments, the vector can integrate into a host DNA. In some embodiments, the vector cannot integrate into a host DNA (e.g., is episomal). Methods of making vectors containing one or more polynucleotides of interest are well known to one of ordinary skill in the art, including, for example, by chemical synthesis or by artificial manipulation of isolated segments of nucleic acids (e.g., by genetic engineering techniques).

In some embodiments, a recombinant nucleic acid of the present disclosure is a herpes simplex virus (HSV) amplicon. Herpes virus amplicons, including the structural features and methods of making the same, are generally known to one of ordinary skill in the art (see e.g., de Silva S. and Bowers W. "Herpes Virus Amplicon Vectors". *Viruses* 2009, 1, 594-629). In some embodiments, the herpes simplex virus amplicon is an HSV-1 amplicon. In some embodiments, the herpes simplex virus amplicon is an HSV-1 hybrid amplicon. Examples of HSV-1 hybrid amplicons may include, but are not limited to, HSV/AAV hybrid amplicons, HSV/EBV hybrid amplicons, HSV/EBV/RV hybrid amplicons, and/or HSV/Sleeping Beauty hybrid amplicons. In some embodiments, the amplicon is an HSV/AAV hybrid amplicon. In some embodiments, the amplicon is an HSV/Sleeping Beauty hybrid amplicon.

In some embodiments, a recombinant nucleic acid of the present disclosure is a recombinant herpes virus genome. The recombinant herpes virus genome may be a recombinant genome from any member of the Herpesviridae family of DNA viruses known in the art, including, for example, a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Epstein-Barr virus genome, a recombinant Kaposi's sarcoma-associated herpesvirus genome, and any combinations or derivatives thereof. In some embodiments, the recombinant herpes virus genome comprises one or more (e.g., one or more, two or more, three or more, four or more, five or more, six or more, seven or more, eight or more, nine or more, ten or more, etc.) inactivating mutations. As used herein, an "inactivating mutation" may refer to any mutation that results in a gene or regulon product (RNA or protein) having reduced, undetectable, or eliminated quantity and/or function (e.g., as compared to a corresponding sequence lacking the inactivating mutation). Examples of inactivating mutations may include, but are not limited to, deletions, insertions, point mutations, and rearrangements in transcriptional control sequences (promoters, enhancers, insulators, etc.) and/or coding sequences of a given gene or regulon. Any suitable method of measuring the quantity of a gene or regulon product known in the art may be used, including, for example, qPCR, Northern blots, RNAseq, western blots, ELISAs, etc. In some embodiments, the one or more inactivating mutations are in one or more (e.g., one or more, two or more, three or more, four or more, five or more, six or more, seven or more, eight or more, nine or more, ten or more, etc.) herpes virus genes. In some embodiments, the recombinant herpes virus genome is attenuated (e.g., as compared to a corresponding, wild-type herpes virus genome). In some embodiments, the recombinant herpes virus genome is replication competent. In some embodiments, the recombinant herpes virus genome is replication defective. In some embodiments, the recombinant herpes virus genome is not oncolytic.

In some embodiments, the recombinant nucleic acid is a recombinant herpes simplex virus (HSV) genome. In some embodiments, the recombinant herpes simplex virus genome comprises one or more (e.g., one or more, two or more, three or more, four or more, five or more, six or more, seven or more, eight or more, nine or more, ten or more, etc.) inactivating mutations. In some embodiments, the one or more inactivating mutations are in one or more (e.g., one or more, two or more, three or more, four or more, five or more, six or more, seven or more, eight or more, nine or more, ten or more, etc.) herpes simplex virus genes. In some embodiments, the recombinant herpes simplex virus genome is attenuated (e.g., as compared to a corresponding, wild-type herpes simplex virus genome). In some embodiments, the recombinant herpes simplex virus genome is replication competent. In some embodiments, the recombinant herpes simplex virus genome is replication defective. In some embodiments, the recombinant herpes simplex virus genome is not oncolytic.

In some embodiments, the recombinant herpes virus genome is a recombinant herpes simplex virus type 1 (HSV-1) genome, a recombinant herpes simplex virus type 2 (HSV-2) genome, or any derivatives thereof. In some embodiments, the recombinant herpes simplex virus genome is a recombinant HSV-1 genome. In some embodiments, the recombinant HSV-1 genome may be from any HSV-1 strain known in the art, including, for example, strains 17, Ty25, R62, S25, Ku86, S23, R11, Ty148, Ku47, H166$_{syn}$, 1319-2005, F-13, M-12, 90237, F-17, KOS, 3083-2008, F12g, L2, CD38, H193, M-15, India 2011, 0116209, F-11I, 66-207, 2762, 369-2007, 3355, MacIntyre, McKrae, 7862, 7-hse, HF10, 1394, 2005, 270-2007, OD4, SC16, M-19, 4J1037, 5J1060, J1060, KOS79, 132-1988, 160-1982, H166, 2158-2007, RE, 78326, F18g, F11, 172-2010, H129, F, E4, CJ994, F14g, E03, E22, E10, E06, E11, E25, E23, E35, E15, E07, E12, E14, E08, E19, E13, ATCC 2011, etc. (see e.g., Bowen et al. J Virol. 2019 Apr. 3; 93(8)). In some embodiments, the recombinant HSV-1 genome is from the KOS strain. In some embodiments, the recombinant HSV-1 genome is not from the McKrae strain. In some embodiments, the recombinant HSV-1 genome is attenuated (e.g., as compared to a corresponding, wild-type HSV-1 genome). In some embodiments, the recombinant HSV-1 genome is replication competent. In some embodiments, the recombinant HSV-1 genome is replication defective. In some embodiments, the recombinant HSV-1 genome is not oncolytic.

In some embodiments, the recombinant herpes simplex virus genome comprises an inactivating mutation in at least one, at least two, at least three, at least four, at least five, at least six, at least seven, or all eight of the Infected Cell Protein (or Infected Cell Polypeptide) (ICP) 0, ICP4, ICP22, ICP27, ICP47, thymidine kinase (tk), Long Unique Region (UL) 41 and/or UL55 herpes simplex virus genes. In some embodiments, the recombinant herpes simplex virus genome does not comprise an inactivating mutation in the ICP34.5 (one or both copies) and/or ICP47 herpes simplex virus genes (e.g., to avoid production of an immune-stimulating virus). In some embodiments, the recombinant herpes simplex virus genome does not comprise an inactivating mutation in the ICP34.5 (one or both copies) herpes simplex virus gene. In some embodiments, the recombinant herpes simplex virus genome does not comprise an inactivating mutation in the ICP47 herpes simplex virus gene. In some embodiments, the recombinant herpes simplex virus genome does not comprise an inactivating mutation in the ICP34.5 (one or both copies) and ICP47 herpes simplex virus genes. In some embodiments, the recombinant herpes simplex virus genome is not oncolytic. In some embodiments, the recombinant herpes simplex virus genome is not conditionally replication competent. In some embodiments, the recombinant herpes simplex virus genome is not conditionally replication competent in a cancerous cell.

In some embodiments, the recombinant herpes simplex virus genome comprises an inactivating mutation in the ICP0 gene (one or both copies). In some embodiments, the recombinant herpes simplex virus genome comprises an inactivating mutation in the ICP0 gene (one or both copies), and further comprises an inactivating mutation in the ICP4 (one or both copies), ICP22, ICP27, ICP47, UL41, and/or UL55 genes. In some embodiments, the recombinant herpes simplex virus genome comprises an inactivating mutation in the ICP0 gene (one or both copies), and an inactivating mutation in the ICP4 gene (one or both copies). In some embodiments, the recombinant herpes simplex virus genome comprises an inactivating mutation in the ICP0 gene (one or both copies), and an inactivating mutation in the ICP22 gene. In some embodiments, the recombinant herpes simplex virus genome comprises an inactivating mutation in the ICP0 gene (one or both copies), and an inactivating mutation in the UL41 gene. In some embodiments, the recombinant herpes simplex virus genome comprises an inactivating mutation in the ICP0 gene (one or both copies), an inactivating mutation in the ICP4 gene (one or both copies), and an inactivating mutation in the ICP22 gene. In some embodiments, the recombinant herpes simplex virus genome comprises an inactivating mutation in the ICP0 gene (one or both copies), an inactivating mutation in the ICP4 gene (one or both copies), and an inactivating mutation in the UL41 gene. In some embodiments, the recombinant herpes simplex virus genome comprises an inactivating mutation in the ICP0 gene (one or both copies), an inactivating mutation in the ICP22 gene, and an inactivating mutation in the UL41 gene. In some embodiments, the recombinant herpes simplex virus genome comprises an inactivating mutation in the ICP0 gene (one or both copies), an inactivating mutation in the ICP4 gene (one or both copies), an inactivating mutation in the ICP22 gene, and an inactivating mutation in the UL41 gene. In some embodiments, the inactivating mutation is a deletion of the coding sequence of the ICP0 (one or both copies), ICP4 (one or both copies), ICP22, and/or UL41 genes. In some embodiments, the recombinant herpes simplex virus genome further comprises an inactivating mutation in the ICP27, ICP47, and/or UL55 genes.

In some embodiments, the recombinant herpes simplex virus genome comprises an inactivating mutation in the ICP4 gene (one or both copies). In some embodiments, the recombinant herpes simplex virus genome comprises an inactivating mutation in the ICP4 gene (one or both copies), and further comprises an inactivating mutation in the ICP0 (one or both copies), ICP22, ICP27, ICP47, UL41, and/or UL55 genes. In some embodiments, the recombinant herpes simplex virus genome comprises an inactivating mutation in the ICP4 gene (one or both copies), and an inactivating mutation in the ICP22 gene. In some embodiments, the recombinant herpes simplex virus genome comprises an inactivating mutation in the ICP4 gene (one or both copies), and an inactivating mutation in the UL41 gene. In some embodiments, the recombinant herpes simplex virus genome comprises an inactivating mutation in the ICP4 gene (one or both copies), an inactivating mutation in the ICP22 gene, and an inactivating mutation in the UL41 gene. In some embodiments, the inactivating mutation is a deletion of the coding sequence of the ICP4 (one or both copies), ICP22, and/or UL41 genes. In some embodiments, the recombinant herpes simplex virus genome further comprises an inactivating mutation in the ICP0 (one or both copies), ICP27, ICP47, and/or UL55 genes.

In some embodiments, the recombinant herpes simplex virus genome comprises an inactivating mutation in the ICP22 gene. In some embodiments, the recombinant herpes simplex virus genome comprises an inactivating mutation in the ICP22 gene, and further comprises an inactivating mutation in the ICP0 (one or both copies), ICP4 (one or both copies), ICP27, ICP47, UL41, and/or UL55 genes. In some embodiments, the recombinant herpes simplex virus genome comprises an inactivating mutation in the ICP22 gene, and an inactivating mutation UL41 gene. In some embodiments, the inactivating mutation is a deletion of the coding sequence of the ICP22 and/or UL41 genes. In some embodiments, the recombinant herpes simplex virus genome further comprises an inactivating mutation in the ICP0 (one or both copies), ICP4 (one or both copies), ICP27, ICP47, and/or UL55 genes.

In some embodiments, the recombinant herpes simplex virus genome comprises an inactivating mutation in the ICP27 gene. In some embodiments, the recombinant herpes simplex virus genome comprises an inactivating mutation in the ICP27 gene, and further comprises an inactivating mutation in the ICP0 (one or both copies), ICP4 (one or both copies), ICP22, ICP47, UL41, and/or UL55 genes. In some embodiments, the inactivating mutation is a deletion of the coding sequence of the ICP27 gene.

In some embodiments, the recombinant herpes simplex virus genome comprises an inactivating mutation in the ICP47 gene. In some embodiments, the recombinant herpes simplex virus genome comprises an inactivating mutation in the ICP47 gene, and further comprises an inactivating mutation in the ICP0 (one or both copies), ICP4 (one or both copies), ICP22, ICP27, UL41, and/or UL55 genes. In some embodiments, the inactivating mutation is a deletion of the coding sequence of the ICP47 gene.

In some embodiments, the recombinant herpes simplex virus genome comprises an inactivating mutation in the UL41 gene. In some embodiments, the recombinant herpes simplex virus genome comprises an inactivating mutation in the UL41 gene, and further comprises an inactivating mutation in the ICP0 (one or both copies), ICP4 (one or both copies), ICP22, ICP27, ICP47, and/or UL55 genes. In some embodiments, the inactivating mutation is a deletion of the coding sequence of the UL41 gene.

In some embodiments, the recombinant herpes simplex virus genome comprises an inactivating mutation in the UL55 gene. In some embodiments, the recombinant herpes simplex virus genome comprises an inactivating mutation in the UL55 gene, and further comprises an inactivating mutation in the ICP0 (one or both copies), ICP4 (one or both copies), ICP22, ICP27, ICP47, and/or UL41 genes. In some embodiments, the inactivating mutation is a deletion of the coding sequence of the UL55 gene.

In some embodiments, the recombinant herpes simplex virus genome comprises an inactivating mutation in (e.g., a deletion of) the internal repeat (Joint) region comprising the internal repeat long ($IR_L$) and internal repeat short (IRs)

regions. In some embodiments, inactivation (e.g., deletion) of the Joint region eliminates one copy each of the ICP4 and ICP0 genes. In some embodiments, inactivation (e.g., deletion) of the Joint region further inactivates (e.g., deletes) the promoter for the ICP22 and ICP47 genes. If desired, expression of one or both of these genes can be restored by insertion of an immediate early promoter into the recombinant herpes simplex virus genome (see e.g., Hill et al. (1995). Nature 375(6530): 411-415; Goldsmith et al. (1998). J Exp Med 187(3): 341-348). Without wishing to be bound by theory, it is believed that inactivating (e.g., deleting) the Joint region may contribute to the stability of the recombinant herpes simplex virus genome and/or allow for the recombinant herpes simplex virus genome to accommodate more and/or larger transgenes.

In some embodiments, the recombinant herpes simplex virus genome comprises an inactivating mutation in the ICP4 (one or both copies), ICP22, and ICP27 genes. In some embodiments, the recombinant herpes simplex virus genome comprises an inactivating mutation in the ICP4 (one or both copies), ICP27, and UL55 genes. In some embodiments, the recombinant herpes simplex virus genome comprises an inactivating mutation in the ICP4 (one or both copies), ICP22, ICP27, ICP47, and UL55 genes. In some embodiments, the inactivating mutation in the ICP4 (one or both copies), ICP27, and/or UL55 genes is a deletion of the coding sequence of the ICP4 (one or both copies), ICP27, and/or UL55 genes. In some embodiments, the inactivating mutation in the ICP22 and ICP47 genes is a deletion in the promoter region of the ICP22 and ICP47 genes (e.g., the ICP22 and ICP47 coding sequences are intact but are not transcriptionally active). In some embodiments, the recombinant herpes simplex virus genome comprises a deletion in the coding sequence of the ICP4 (one or both copies), ICP27, and UL55 genes, and a deletion in the promoter region of the ICP22 and ICP47 genes. In some embodiments, the recombinant herpes simplex virus genome further comprises an inactivating mutation in the ICP0 (one or both copies) and/or UL41 genes.

In some embodiments, the recombinant herpes simplex virus genome comprises an inactivating mutation in the ICP0 (one or both copies) gene. In some embodiments, the recombinant herpes simplex virus genome comprises an inactivating mutation in the ICP0 (one or both copies) and ICP4 (one or both copies) genes. In some embodiments, the recombinant herpes simplex virus genome comprises an inactivating mutation in the ICP0 (one or both copies), ICP4 (one or both copies), and ICP22 genes. In some embodiments, the recombinant herpes simplex virus genome comprises an inactivating mutation in the ICP0 (one or both copies), ICP4 (one or both copies), ICP22, and ICP27 genes. In some embodiments, the recombinant herpes simplex virus genome comprises an inactivating mutation in the ICP0 (one or both copies), ICP4 (one or both copies), ICP22, ICP27 and UL55 genes. In some embodiments, the inactivating mutation in the ICP0 (one or both copies), ICP4 (one or both copies), ICP22, ICP27 and/or UL55 genes comprises a deletion of the coding sequence of the ICP0 (one or both copies), ICP4 (one or both copies), ICP22, ICP27 and/or UL55 genes. In some embodiments, the recombinant herpes simplex virus genome further comprises an inactivating mutation in the ICP47 and/or the UL41 genes.

In some embodiments, a recombinant herpes simplex virus genome comprises one or more polynucleotides of the present disclosure within one, two, three, four, five, six, seven or more viral gene loci. Examples of suitable viral loci may include, without limitation, the ICP0 (one or both copies), ICP4 (one or both copies), ICP22, ICP27, ICP47, tk, UL41 and UL55 herpes simplex viral gene loci. In some embodiments, a recombinant herpes simplex virus genome comprises one or more polynucleotides of the present disclosure within one or both of the viral ICP4 gene loci (e.g., a recombinant virus comprising a polynucleotide encoding a polypeptide (such as an immunomodulatory polypeptide) in one or both of the ICP4 loci). In some embodiments, a recombinant herpes simplex virus genome comprises one or more polynucleotides of the present disclosure within the viral ICP22 gene locus (e.g., a recombinant virus comprising a polynucleotide encoding a polypeptide (such as an immunomodulatory polypeptide) in the ICP22 locus). In some embodiments, a recombinant herpes simplex virus genome comprises one or more polynucleotides of the present disclosure within the viral UL41 gene locus (e.g., a recombinant virus comprising a polynucleotide encoding a polypeptide (such as an immunomodulatory polypeptide) in the UL41 locus). In some embodiments, a recombinant herpes simplex virus genome comprises one or more polynucleotides of the present disclosure within the viral ICP27 gene locus (e.g., a recombinant virus comprising a polynucleotide encoding a polypeptide (such as an immunomodulatory polypeptide) in the ICP27 locus). In some embodiments, a recombinant herpes simplex virus genome comprises one or more polynucleotides of the present disclosure within the viral ICP47 gene locus (e.g., a recombinant virus comprising a polynucleotide encoding a polypeptide (such as an immunomodulatory polypeptide) in the ICP47 locus). In some embodiments, a recombinant herpes simplex virus genome comprises one or more polynucleotides of the present disclosure within the viral UL55 gene locus (e.g., a recombinant virus comprising a polynucleotide encoding a polypeptide (such as an immunomodulatory polypeptide) in the UL55 locus). In some embodiments, a recombinant herpes simplex virus genome comprises one or more polynucleotides of the present disclosure within the viral tk gene locus (e.g., a recombinant virus comprising a polynucleotide encoding a polypeptide (such as an immunomodulatory polypeptide) in the tk locus).

In some embodiments, a recombinant herpes simplex virus genome comprises one or more polynucleotides of the present disclosure within one or both of the viral ICP4 gene loci, and one or more polynucleotides of the present disclosure within the viral ICP22 gene locus (e.g., a recombinant virus comprising a polynucleotide encoding an immunomodulatory polypeptide (such as a human IL-12 polypeptide) in one or both of the ICP4 loci, and a polynucleotide encoding an immunomodulatory polypeptide (such as a human GM-CSF polypeptide) in the ICP22 locus). In some embodiments, a recombinant herpes simplex virus genome comprises one or more polynucleotides of the present disclosure within one or both of the viral ICP4 gene loci, and one or more polynucleotides of the present disclosure within the viral UL41 gene locus (e.g., a recombinant virus comprising a polynucleotide encoding an immunomodulatory polypeptide (such as a human IL-12 polypeptide) in one or both of the ICP4 loci, and a polynucleotide encoding an immunomodulatory polypeptide (such as a human GM-CSF polypeptide) in the UL41 locus). In some embodiments, a recombinant herpes simplex virus genome comprises one or more polynucleotides of the present disclosure within the viral ICP22 gene locus, and one or more polynucleotides of the present disclosure within the viral UL41 gene locus (e.g., a recombinant virus comprising a polynucleotide encoding an immunomodulatory polypeptide (such as a human IL-12 polypeptide) in the ICP22 locus, and a polynucleotide encoding an immunomodulatory polypeptide (such as a human GM-CSF polypeptide) in the UL41 locus). In some embodiments, a recombinant herpes simplex virus genome comprises one or more polynucleotides of the present disclosure within one or both of the viral ICP4 gene loci, one or more polynucleotides of the present disclosure within the viral ICP22 gene locus, and one or more polynucleotides of the present disclosure within the viral UL41 gene locus (e.g., a recombinant virus comprising a polynucleotide encoding an immunomodulatory polypeptide (such as a human IL-12 polypeptide) in one or both of the ICP4 loci, a polynucleotide encoding an immunomodulatory polypeptide (such as a human GM-CSF polypeptide) in the ICP22 locus, and a polynucleotide encoding an immunomodulatory polypeptide (such as a human IL-2 polypeptide) in the UL41 locus). In some embodiments, a recombinant herpes simplex virus genome comprises one or more polynucleotides of the present disclosure within one or both of the viral ICP4 gene loci, one or more polynucleotides of the present disclosure within the viral ICP22 gene locus, one or more polynucleotides of the present disclosure within the viral UL41 gene locus, one or more polynucleotides of the present disclosure within the viral ICP27 gene locus, one or more polynucleotides of the present disclosure within the viral ICP47 gene locus, one or more polynucleotides of the present disclosure within the viral tk gene locus, and/or one or more polynucleotides of the present disclosure within the viral UL55 gene locus.

In some embodiments, the recombinant herpes virus genome (e.g., a recombinant herpes simplex virus genome) has been engineered to decrease or eliminate expression of one or more herpes virus genes (e.g., one or more toxic herpes virus genes), such as one or both copies of the HSV ICP0 gene, one or both copies of the HSV ICP4 gene, the HSV ICP22 gene, the HSV UL41 gene, the HSV ICP27 gene, the HSV ICP47 gene, the HSV tk gene, the HSV UL55 gene, etc. In some embodiments, the recombinant herpes virus genome (e.g., a recombinant herpes simplex virus genome) has been engineered to reduce cytotoxicity of the recombinant genome (e.g., when introduced into a target cell), as compared to a corresponding wild-type herpes virus genome (e.g., a wild-type herpes simplex virus genome). In some embodiments, the target cell is a human cell (primary cells or a cell line derived therefrom). In some embodiments, the target cell is a cell of the respiratory tract (primary cells or a cell line derived therefrom). In some embodiments, the target cell is an airway epithelial cell (primary cells or a cell line derived therefrom). In some embodiments, the target cell is a cell of the lung (primary cells or a cell line derived therefrom). In some embodiments, cytotoxicity (e.g., in a target cell) of the recombinant genome (e.g., a recombinant herpes simplex virus genome) is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% as compared to a corresponding wild-type herpes virus genome (e.g., measuring the relative cytotoxicity of a recombinant ΔICP4 (one or both copies) herpes simplex virus genome vs. a wild-type herpes simplex virus genome in a target cell; measuring the relative cytotoxicity of a recombinant ΔICP4 (one or both copies)/ΔICP22 herpes simplex virus genome vs. a wild-type herpes simplex virus genome in a target cell, etc.). In some embodiments, cytotoxicity (e.g., in a target cell) of the recombinant herpes genome (e.g., a recombinant herpes simplex virus genome) is reduced by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, at least about 1000-fold, or more as compared to a corresponding wild-type herpes virus genome (e.g., measuring the relative cytotoxicity of a recombinant ΔICP4 (one or both copies) herpes simplex virus genome vs. a wild-type herpes simplex virus genome in a target cell; measuring the relative cytotoxicity of a recombinant ΔICP4 (one or both copies)/ΔICP22 herpes simplex virus genome vs. a wild-type herpes simplex virus genome in a target cell, etc.). Methods of measuring cytotoxicity are known to one of ordinary skill in the art, including, for example, through the use of vital dyes (formazan dyes), protease biomarkers, an MTT assay (or an assay using related tetrazolium salts such as XTT, MTS, water-soluble tetrazolium salts, etc.), measuring ATP content, etc.

In some embodiments, the recombinant genome (e.g., a recombinant herpes simplex virus genome) has been engineered to reduce its impact on target cell proliferation after exposure of a target cell to the recombinant genome, as compared to a corresponding wild-type genome (e.g., a wild-type herpes simplex virus genome). In some embodiments, the target cell is a human cell (primary cells or a cell line derived therefrom). In some embodiments, the target cell is a cell of the respiratory tract (primary cells or a cell line derived therefrom). In some embodiments, the target cell is an airway epithelial cell (primary cells or a cell line derived therefrom). In some embodiments, the target cell is a cell of the lung (primary cells or a cell line derived therefrom). In some embodiments, target cell proliferation after exposure to the recombinant genome is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% faster as compared to target cell proliferation after exposure to a corresponding wild-type genome (e.g., measuring the relative cellular proliferation after exposure to a recombinant ΔICP4 (one or both copies) herpes simplex virus genome vs. cellular proliferation after exposure to a wild-type herpes simplex virus genome in target cells; measuring the relative cellular proliferation after exposure to a recombinant ΔICP4 (one or both copies)/ΔICP22 herpes simplex virus genome vs. cellular proliferation after exposure to a wild-type herpes simplex virus genome in target cells, etc.). In some embodiments, target cell proliferation after exposure to the recombinant genome is at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, or at least about 1000-fold faster as compared to target cell proliferation after exposure to a corresponding wild-type genome (e.g., measuring the relative cellular proliferation after exposure to a recombinant ΔICP4 (one or both copies) herpes simplex virus genome vs. cellular proliferation after exposure to a wild-type herpes simplex virus genome in target cells; measuring the relative cellular proliferation after exposure to a recombinant ΔICP4 (one or both copies)/ΔICP22 herpes simplex virus genome vs. cellular proliferation after exposure to a wild-type herpes simplex virus genome in target cells, etc.). Methods of measuring cellular proliferation are known to one of ordinary skill in the art, including, e.g., through the use of a Ki67 cell proliferation assay, a BrdU cell proliferation assay, etc.

A vector (e.g., herpes viral vector) may include one or more polynucleotides of the present disclosure in a form suitable for expression of the polynucleotide in a host cell. Vectors may include one or more regulatory sequences operatively linked to the polynucleotide to be expressed (e.g., as described above).

In some embodiments, the present disclosure relates to one or more heterologous polynucleotides (e.g., a bacterial artificial chromosome (BAC)) comprising any of the recombinant nucleic acids described herein.

In some embodiments, a recombinant nucleic acid (e.g., a recombinant herpes simplex virus genome) of the present disclosure comprises one or more of the polynucleotides described herein inserted in any orientation in the recombinant nucleic acid. If the recombinant nucleic acid comprises two or more polynucleotides described herein (e.g., two or more, three or more, etc.), the polynucleotides may be inserted in the same orientation or opposite orientations to one another. Without wishing to be bound be theory, incorporating two polynucleotides (e.g., two transgenes) into a recombinant nucleic acid (e.g., a vector) in an antisense orientation may help to avoid read-through and ensure proper expression of each polynucleotide.

In some embodiments, a recombinant nucleic of the present disclosure does not comprise a polynucleotide encoding a Collagen alpha-1 (VII) chain polypeptide (COL7). In some embodiments, a recombinant nucleic of the present disclosure does not comprise a polynucleotide encoding a Lysyl hydroxylase 3 polypeptide (LH3). In some embodiments, a recombinant nucleic of the present disclosure does not comprise a polynucleotide encoding a Keratin type I cytoskeletal 17 polypeptide (KRT17). In some embodiments, a recombinant nucleic of the present disclosure does not comprise a polynucleotide encoding a transglutaminase (TGM) polypeptide (e.g., a human transglutaminase polypeptide such as a human TGM1 polypeptide and/or a human TGM5 polypeptide). In some embodiments, a recombinant nucleic of the present disclosure does not comprise a polynucleotide encoding a cosmetic protein (e.g., collagen proteins, fibronectins, elastins, lumicans, vitronectins/vitronectin receptors, laminins, neuromodulators, fibrillins, additional dermal extracellular matrix proteins, etc.). In some embodiments, a recombinant nucleic of the present disclosure does not comprise a polynucleotide encoding an antibody (e.g., a full-length antibody, an antibody fragment, etc.). In some embodiments, a recombinant nucleic of the present disclosure does not comprise a polynucleotide encoding a Serine Protease Inhibitor Kazal-type (SPINK) polypeptide (e.g., a human SPINK polypeptide, such as a SPINK5 polypeptide). In some embodiments, a recombinant nucleic of the present disclosure does not comprise a polynucleotide encoding a filaggrin or filaggrin 2 polypeptide (e.g., a human filaggrin or filaggrin 2 polypeptide). In some embodiments, a recombinant nucleic of the present disclosure does not comprise a polynucleotide encoding a Cystic Fibrosis Transmembrane Conductance Regulator (CFTR) polypeptide (e.g., a human CFTR polypeptide). In some embodiments, a recombinant nucleic of the present disclosure does not comprise a polynucleotide encoding an ichthyosis-associated polypeptide (e.g., an ATP-binding cassette sub-family A member 12 polypeptide, a 1-acylglycerol-3-phosphate O-acyltransferase ABHD5 polypeptide, an Aldehyde dehydrogenase family 3 member A2 polypeptide, an Arachidonate 12-lipoxygenase 12R-type polypeptide, a Hydroperoxide isomerase ALOXE3 polypeptide, an AP-1 complex subunit sigma-1A polypeptide, an Arylsulfatase E polypeptide, a Caspase-14 polypeptide, a Corneodesmosin polypeptide, a Ceramide synthase 3 polypeptide, a Carbohydrate sulfotransferase 8 polypeptide, a Claudin-1 polypeptide, a Cystatin-A polypeptide, a Cytochrome P450 4F22 polypeptide, a 3-beta-hydroxysteroid-Delta(8), Delta(7)-isomerase polypeptide, an Elongation of very long chain fatty acids protein 4 polypeptide, a Filaggrin polypeptide, a Filaggrin 2 polypeptide, a Gap junction beta-2 polypeptide, a Gap junction beta-3 polypeptide, a Gap junction beta-4 polypeptide, a Gap junction beta-6 polypeptide, a 3-ketodihydrosphingosine reductase polypeptide, a Keratin, type II cytoskeletal 1 polypeptide, a Keratin, type II cytoskeletal 2 epidermal polypeptide, a Keratin, type I cytoskeletal 9 polypeptide, a Keratin, type I cytoskeletal 10 polypeptide, a Lipase member N polypeptide, a Loricrin polypeptide, a Membrane-bound transcription factor site-2 protease polypeptide, a Magnesium transporter NIPA4 polypeptide, a Sterol-4-alpha-carboxylate 3-dehydrogenase, decarboxylating polypeptide, a Peroxisomal targeting signal 2 receptor polypeptide, a D-3-phosphoglycerate dehydrogenase polypeptide, a Phytanoyl-CoA dioxygenase, peroxisomal polypeptide, Patatin-like phospholipase domain-containing protein 1 polypeptide, a Proteasome maturation protein polypeptide, a Phosphoserine aminotransferase polypeptide, a Short-chain dehydrogenase/reductase family 9C member 7 polypeptide, a Serpin B8 polypeptide, a Long-chain fatty acid transport protein 4 polypeptide, a Synaptosomal-associated protein 29 polypeptide, a Suppressor of tumorigenicity 14 protein polypeptide, a Steryl-sulfatase polypeptide, a Vacuolar protein sorting-associated protein 33B polypeptide, and a CAAX prenyl protease 1 homolog polypeptide).

In some embodiments, a recombinant nucleic of the present disclosure does not comprise a polynucleotide encoding a Collagen alpha-1 (VII) chain polypeptide, a Lysyl hydroxylase 3 polypeptide, a Keratin type I cytoskeletal 17 polypeptide, and/or any chimeric polypeptides thereof. In some embodiments, a recombinant nucleic of the present disclosure does not comprise a polynucleotide encoding a Collagen alpha-1 (VII) chain polypeptide, a Lysyl hydroxylase 3 polypeptide, a Keratin type I cytoskeletal 17 polypeptide, a transglutaminase (TGM) polypeptide, a filaggrin polypeptide, a cosmetic protein, an antibody, a SPINK polypeptide, a CFTR polypeptide, an ichthyosis-associated polypeptide, an Alpha-1-antitrypsin polypeptide, a Sodium-dependent phosphate transport protein 2B polypeptide, a Dynein heavy chain 5 axonemal polypeptide, a Dynein heavy chain 11 axonemal polypeptide, a Coiled-coil domain-containing protein 39 polypeptide, a Dynein intermediate chain 1 axonemal polypeptide, a Coiled-coil domain-containing protein 40 polypeptide, a Coiled-coil domain containing protein 103 polypeptide, a Sperm-associated antigen 1 polypeptide, a Zinc finger MYND domain-containing protein 10 polypeptide, an Armadillo repeat containing protein 4 polypeptide, a Coiled-coil domain-containing protein 151 polypeptide, a Dynein intermediate chain 2 axonemal polypeptide, a Radial spoke head 1 homolog polypeptide, a Coiled-coil domain-containing protein 114 polypeptide, a Radial spoke head protein 4 homolog A polypeptide, a Dynein assembly factor 1 axonemal polypeptide, a Dynein assembly factor 2 axonemal polypeptide, a Leucine-rich repeat-containing protein 6 polypeptide, a Pulmonary surfactant-associated protein B polypeptide, a Pulmonary surfactant-associated protein C polypeptide, a Homeobox protein Nkx-2.1 polypeptide, an ATP-binding cassette sub-family A member 3 polypeptide, a Cytokine receptor common subunit beta polypeptide, a Granulocyte-macrophage colony-stimulating factor receptor subunit alpha polypeptide, a Bone morphogenetic protein receptor type-2 polypeptide, a Sarcoplasmic/endoplasmic reticulum calcium ATPase 2 polypeptide, a serine/threonine-protein kinase receptor R3 polypeptide, an Endoglin polypeptide, a Mothers against decapentaplegic homolog 9 polypeptide, a Caveolin-1 polypeptide, a Potassium channel subfamily K member 3 polypeptide, an eIF-2-alpha kinase GCN2 polypeptide, a Pulmonary surfactant-associated protein A2 polypeptide, a Telomerase reverse transcriptase polypeptide, a Dyskerin polypeptide, a Regulator of telomere elongation helicase 1 polypeptide, a Poly (A)-specific ribonuclease PARN polypeptide, a TERF1-interacting nuclear factor 2 polypeptide, an H/ACA ribonucleoprotein complex non-core subunit NAF1 polypeptide, a Mucin-5B polypeptide, a Desmoplakin polypeptide, a CST complex subunit STN1 polypeptide, a Dipeptidyl peptidase 9 polypeptide, and/or any chimeric polypeptides thereof.

IV. Viruses

Certain aspects of the present disclosure relate to viruses comprising any of the polynucleotides and/or recombinant nucleic acids described herein. In some embodiments, the virus is capable of infecting one or more target cells of a subject (e.g., a human). In some embodiments, the virus is suitable for delivering the polynucleotides and/or recombinant nucleic acids into one or more target cells of a subject (e.g., a human). In some embodiments, the one or more target cells are human cells. In some embodiments, the one or more target cells are one or more airway epithelial cells. In some embodiments, the one or more target cells are one or more cells of the respiratory tract (e.g., airway epithelial cells (such as goblet cells, ciliated cells, Clara cells, neuroendocrine cells, basal cells, intermediate or parabasal cells, Serous cells, brush cells, oncocytes, non-ciliated columnar cells, and/or metaplastic cells); alveolar cells (such as type 1 pneumocytes, type 2 pneumocytes, and/or cuboidal non-ciliated cells); salivary gland cells in bronchi (such as Serous cells, mucous cells, and/or ductal cells); etc.). In some embodiments, the one or more target cells are one or more cells of the lung.

Any suitable virus known in the art may be used, including, for example, adenovirus, adeno-associated virus, retrovirus, lentivirus, sendai virus, papillomavirus, herpes virus (e.g., a herpes simplex virus), vaccinia virus, and/or any hybrid or derivative viruses thereof. In some embodiments, the virus is attenuated. In some embodiments, the virus is replication competent. In some embodiments, the virus is replication defective. In some embodiments, the virus is not oncolytic. In some embodiments, the virus has been modified to alter its tissue tropism relative to the tissue tropism of a corresponding unmodified, wild-type virus. In some embodiments, the virus has reduced cytotoxicity (e.g., in a target cell) as compared to a corresponding wild-type virus. Methods of producing a virus comprising recombinant nucleic acids are well known to one of ordinary skill in the art.

In some embodiments, the virus is a member of the Herpesviridae family of DNA viruses, including, for example, a herpes simplex virus, a varicella zoster virus, a human cytomegalovirus, a herpesvirus 6A, a herpesvirus 6B, a herpesvirus 7, an Epstein-Barr virus, and a Kaposi's sarcoma-associated herpesvirus, etc. In some embodiments, the herpes virus is attenuated. In some embodiments, the herpes virus is replication defective. In some embodiments, the herpes virus is replication competent. In some embodiments, the herpes virus has been engineered to reduce or eliminate expression of one or more herpes virus genes (e.g., one or more toxic herpes virus genes). In some embodiments, the herpes virus has reduced cytotoxicity as compared to a corresponding wild-type herpes virus. In some embodiments, the herpes virus is not oncolytic.

In some embodiments, the virus is a herpes simplex virus. Herpes simplex viruses comprising recombinant nucleic acids may be produced by a process disclosed, for example, in U.S. Pat. No. 10,174,341, US 2019/0276845, U.S. Pat. Nos. 9,877,990, 10,155,016, 10,441,614, 11,185,564, US 2020/0093874, U.S. Pat. No. 10,525,090, US 2020/0197456, US 2021/0261649, US 2021/0395775, U.S. Pat. No. 10,829,529, US 2021/0087245, US 2021/0189427, U.S. Pat. No. 10,786,438, US 2021/0045988, and/or WO2021/046131, all of which are incorporated by reference herein in their entirety. In some embodiments, the herpes simplex virus is attenuated. In some embodiments, the herpes simplex virus is replication defective. In some embodiments, the herpes simplex virus is replication competent. In some embodiments, the herpes simplex virus has been engineered to reduce or eliminate expression of one or more herpes simplex virus genes (e.g., one or more toxic herpes simplex virus genes). In some embodiments, the herpes simplex virus has reduced cytotoxicity as compared to a corresponding wild-type herpes simplex virus. In some embodiments, the herpes simplex virus is not oncolytic. In some embodiments, the herpes simplex virus is an HSV-1, an HSV-2, or any derivatives thereof. In some embodiments, the herpes simplex virus is an HSV-1 virus. In some embodiments, the HSV-1 is attenuated. In some embodiments, the HSV-1 is replication defective. In some embodiments, the HSV-1 is replication competent. In some embodiments, the HSV-1 has been engineered to reduce or eliminate expression of one or more HSV-1 genes (e.g., one or more toxic HSV-1 genes). In some embodiments, the HSV-1 has reduced cytotoxicity as compared to a corresponding wild-type HSV-1. In some embodiments, the HSV-1 is not oncolytic.

In some embodiments, the herpes simplex virus has been modified to alter its tissue tropism relative to the tissue tropism of an unmodified, wild-type herpes simplex virus. In some embodiments, the herpes simplex virus comprises a modified envelope. In some embodiments, the modified envelope comprises one or more (e.g., one or more, two or more, three or more, four or more, etc.) mutant herpes simplex virus glycoproteins. Examples of herpes simplex virus glycoproteins may include, but are not limited to, the glycoproteins gB, gC, gD, gH, and gL. In some embodiments, the modified envelope alters the herpes simplex virus tissue tropism relative to a wild-type herpes simplex virus.

In some embodiments, the transduction efficiency (in vitro and/or in vivo) of a virus of the present disclosure (e.g., a herpes virus such as a herpes simplex virus) for one or more target cells (e.g., one or more cells of the respiratory tract) is at least about 25%. For example, the transduction efficiency of the virus for one or more target cells may be at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, at least about 99.5%, or more. In some embodiments, the virus is a herpes simplex virus and the transduction efficiency of the virus for one or more target cells (e.g., one or more cells of the respiratory tract) is about 85% to about 100%. In some embodiments, the virus is a herpes simplex virus and the transduction efficiency of the virus for one or more target cells (e.g., one or more cells of the respiratory tract) is at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100%. Methods of measuring viral transduction efficiency in vitro or in vivo are well known to one of ordinary skill in the art, including, for example, qPCR analysis, deep sequencing, western blotting, fluorometric analysis (such as fluorescent in situ hybridization (FISH), fluorescent reporter gene expression, immunofluorescence, FACS), etc.

In some embodiments, provided herein are recombinant viruses, which may or may not be pseudotyped, that produce one or more therapeutic polypeptides for the treatment of cancer including solid tumors (e.g., advanced solid tumors) and hematologic malignancies. In some embodiments, the recombinant virus is non-oncolytic. In some embodiments, the one or more therapeutic polypeptides produced by the recombinant viruses described herein mediate or enhance an anti-tumor effect, such as by effector-cell mediated lysis of tumor cells. The present disclosure further provides therapeutic compositions comprising the recombinant viruses and methods of use in the treatment of solid tumors and hematologic malignancies.

In some embodiments, the therapeutic polypeptide is an immunomodulatory polypeptide. In some embodiments, the immunomodulatory polypeptide modulates the activity of one or more cell types, such as regulatory T cells (Tregs), myeloid-derived suppressor cells (MDSCs), dendritic cells, T cells, macrophages, neutrophils, and/or NK cells.

V. Pharmaceutical Compositions and Formulations

Certain aspects of the present disclosure relate to pharmaceutical compositions or formulations comprising any of the recombinant nucleic acids (e.g., a recombinant herpes virus genome) and/or viruses (e.g., a herpes virus comprising a recombinant genome) described herein (such as a herpes simplex virus comprising a recombinant herpes simplex virus genome), and a pharmaceutically acceptable excipient or carrier.

In some embodiments, the pharmaceutical composition or formulation comprises any one or more of the viruses (e.g., herpes viruses) described herein. In some embodiments, the pharmaceutical composition or formulation comprises from about $10^4$ to about $10^{12}$ plaque forming units (PFU)/mL of the virus. For example, the pharmaceutical composition or formulation may comprise from about $10^4$ to about $10^{12}$, about $10^5$ to about $10^{12}$, about $10^6$ to about $10^{12}$, about $10^7$ to about $10^{12}$, about $10^8$ to about $10^{12}$, about $10^9$ to about $10^{12}$, about $10^{10}$ to about $10^{12}$, about $10^{11}$ to about $10^{12}$, about $10^4$ to about $10^{11}$, about $10^5$ to about $10^{11}$, about $10^6$ to about $10^{11}$, about $10^7$ to about $10^{11}$, about $10^8$ to about $10^{11}$, about $10^9$ to about $10^{11}$, about $10^{10}$ to about $10^{11}$, about $10^4$ to about $10^{10}$, about $10^5$ to about $10^{10}$, about $10^6$ to about $10^{10}$, about $10^7$ to about $10^{10}$, about $10^8$ to about $10^{10}$, about $10^9$ to about $10^{10}$, about $10^4$ to about $10^9$, about $10^5$ to about $10^9$, about $10^6$ to about $10^9$, about $10^7$ to about $10^9$, about $10^8$ to about $10^9$, about $10^4$ to about $10^8$, about $10^5$ to about $10^8$, about $10^6$ to about $10^8$, about $10^7$ to about $10^8$, about $10^4$ to about $10^7$, about $10^5$ to about $10^7$, about $10^6$ to about $10^7$, about $10^4$ to about $10^6$, about $10^5$ to about $10^6$, or about $10^4$ to about $10^5$ PFU/mL of the virus. In some embodiments, the pharmaceutical composition or formulation comprises about $10^4$, about $10^5$, about $10^6$, about $10^7$, about $10^8$, about $10^9$, about $10^{10}$, about $10^{11}$, or about $10^{12}$ PFU/mL of the virus.

Pharmaceutical compositions and formulations can be prepared by mixing the active ingredient(s) (such as a recombinant nucleic acid and/or a virus) having the desired degree of purity with one or more pharmaceutically acceptable carriers or excipients. Pharmaceutically acceptable carriers or excipients are generally nontoxic to recipients at the dosages and concentrations employed, and may include, but are not limited to: buffers (such as phosphate, citrate, acetate, and other organic acids); antioxidants (such as ascorbic acid and methionine); preservatives (such as octadecyldimethylbenzyl ammonium chloride, benzalkonium chloride, benzethonium chloride, phenol, butyl or benzyl alcohol, alkyl parabens, catechol, resorcinol, cyclohexanol, 3-pentanol, and m-cresol); amino acids (such as glycine, glutamine, asparagine, histidine, arginine, or lysine); low molecular weight (less than about 10 residues) polypeptides; proteins (such as serum albumin, gelatin, or immunoglobulins); polyols (such as glycerol, e.g., formulations including 1%, 2%, 3%, 4%, 5%, 6%, 7%, 8%, 9%, 10%, 11%, 12%, 13%, 14%, 15%, etc. glycerol); hydrophilic polymers (such as polyvinylpyrrolidone); monosaccharides, disaccharides, and other carbohydrates (including glucose, mannose, or dextrins); chelating agents (such as EDTA); sugars (such as sucrose, mannitol, trehalose, or sorbitol); salt-forming counter-ions (such as sodium); metal complexes (such as Zn-protein complexes); and/or non-ionic surfactants (such as polyethylene glycol (PEG)). A thorough discussion of pharmaceutically acceptable carriers is available in REMINGTON'S PHARMACEUTICAL SCIENCES (Mack Pub. Co., N.J. 1991).

In some embodiments, the pharmaceutical composition or formulation comprises one or more lipid (e.g., cationic lipid) carriers. In some embodiments, the pharmaceutical composition or formulation comprises one or more nanoparticle carriers. Nanoparticles are submicron (less than about 1000 nm) sized drug delivery vehicles that can carry encapsulated drugs (such as synthetic small molecules, proteins, peptides, cells, viruses, and nucleic acid-based biotherapeutics) for rapid or controlled release. A variety of molecules (e.g., proteins, peptides, recombinant nucleic acids, etc.) can be efficiently encapsulated in nanoparticles using processes well known in the art. In some embodiments, a molecule "encapsulated" in a nanoparticle may refer to a molecule (such as a virus) that is contained within the nanoparticle or attached to and/or associated with the surface of the nanoparticle, or any combination thereof. Nanoparticles for use in the compositions or formulations described herein may be any type of biocompatible nanoparticle known in the art, including, for example, nanoparticles comprising poly(lactic acid), poly(glycolic acid), PLGA, PLA, PGA, and any combinations thereof (see e.g., Vauthier et al. Adv Drug Del Rev. (2003) 55: 519-48; US 2007/0148074; US 2007/0092575; US 2006/0246139; U.S. Pat. Nos. 5,753,234; 7,081,483; and US 2008/0260851, all of which are incorporated by reference herein in their entirety).

In some embodiments, the pharmaceutically acceptable carrier or excipient may be adapted for or suitable for any administration route known in the art, including, for example, intravenous, intramuscular, subcutaneous, cutaneous, oral, intranasal, intratracheal, sublingual, buccal, topical, transdermal, intradermal, intraperitoneal, intraorbital, intravitreal, subretinal, transmucosal, intraarticular, by implantation, by inhalation, intrathecal, intraventricular, and/or intranasal administration. In some embodiments, the pharmaceutically acceptable carrier or excipient is adapted for or suitable for oral, intranasal, intratracheal, and/or inhaled administration. In some embodiments, the pharmaceutically acceptable carrier or excipient is adapted for or suitable for intranasal and/or inhaled administration. In some embodiments, the pharmaceutically acceptable carrier or excipient is adapted for or suitable for inhaled administration.

In some embodiments, the pharmaceutical composition or formulation is adapted for or suitable for any administration route known in the art, including, for example, intravenous, intramuscular, subcutaneous, cutaneous, oral, intranasal, intratracheal, sublingual, buccal, topical, transdermal, intradermal, intraperitoneal, intraorbital, intravitreal, subretinal, transmucosal, intraarticular, by implantation, by inhalation, intrathecal, intraventricular, or intranasal administration. In some embodiments, the pharmaceutical composition or formulation is adapted for or suitable for oral, intranasal, intratracheal, and/or inhaled administration. In some embodiments, the pharmaceutical composition or formulation is adapted for or suitable for intranasal and/or inhaled administration. In some embodiments, the pharmaceutical composition or formulation is adapted for or suitable for inhaled administration.

In some embodiments, the pharmaceutical composition or formulation further comprises one or more additional components. Examples of additional components may include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); wetting agents (e.g., sodium lauryl sulphate, etc.); salt solutions; alcohols; polyethylene glycols; gelatin; lactose; amylase; magnesium stearate; talc; silicic acid; viscous paraffin; hydroxymethylcellulose; polyvinylpyrrolidone; sweetenings; flavorings; perfuming agents; colorants; moisturizers; sunscreens; antibacterial agents; agents able to stabilize polynucleotides or prevent their degradation, and the like. In some embodiments, the pharmaceutical composition or formulation comprises a methylcellulose gel (e.g., hydroxypropyl methylcellulose, carboxy methylcellulose, etc.). In some embodiments, the pharmaceutical composition or formulation comprises a phosphate buffer. In some embodiments, the pharmaceutical composition or formulation comprises glycerol (e.g., at about 1%, about 2%, about 3%, about 4%, about 5%, about 6%, about 7%, about 8%, about 9%, about 10%, about 11%, about 12%, about 13%, about 14%, about 15%, etc.). In some embodiments, the pharmaceutical composition or formulation comprises a phosphate buffer and glycerol.

Pharmaceutical compositions and formulations to be used for in vivo administration are generally sterile. Sterility may be readily accomplished, e.g., by filtration through sterile filtration membranes.

In some embodiments, any of the recombinant nucleic acids, viruses, and/or pharmaceutical compositions or formulations described herein may be used to deliver one or more polynucleotides encoding a polypeptide (e.g., an immunomodulatory polypeptide such as an IL-2 or IL-12 polypeptide) into one or more cells of a subject (e.g., one or more cells of the respiratory tract of the subject). In some embodiments, the subject suffers from cancer. In some embodiments, any of the recombinant nucleic acids, viruses, and/or pharmaceutical compositions or formulations described herein may be used in the treatment of cancer. In some embodiments, any of the recombinant nucleic acids, viruses, and/or pharmaceutical compositions or formulations described herein may be used in the treatment of carcinoma. In some embodiments, any of the recombinant nucleic acids, viruses, and/or pharmaceutical compositions or formulations described herein may be used in the treatment of lymphoma. In some embodiments, any of the recombinant nucleic acids, viruses, and/or pharmaceutical compositions or formulations described herein may be used in the treatment of blastoma. In some embodiments, any of the recombinant nucleic acids, viruses, and/or pharmaceutical compositions or formulations described herein may be used in the treatment of sarcoma. In some embodiments, any of the recombinant nucleic acids, viruses, and/or pharmaceutical compositions or formulations described herein may be used in the treatment of a neuroendocrine tumor. In some embodiments, any of the recombinant nucleic acids, viruses, and/or pharmaceutical compositions or formulations described herein may be used in the treatment of mesothelioma. In some embodiments, any of the recombinant nucleic acids, viruses, and/or pharmaceutical compositions or formulations described herein may be used in the treatment of schwannoma. In some embodiments, any of the recombinant nucleic acids, viruses, and/or pharmaceutical compositions or formulations described herein may be used in the treatment of meningioma. In some embodiments, any of the recombinant nucleic acids, viruses, and/or pharmaceutical compositions or formulations described herein may be used in the treatment of adenocarcinoma. In some embodiments, any of the recombinant nucleic acids, viruses, and/or pharmaceutical compositions or formulations described herein may be used in the treatment of melanoma. In some embodiments, any of the recombinant nucleic acids, viruses, and/or pharmaceutical compositions or formulations described herein may be used in the treatment of leukemia. In some embodiments, any of the recombinant nucleic acids, viruses, and/or pharmaceutical compositions or formulations described herein may be used in the treatment of lymphoid malignancy.

In some embodiments, any of the recombinant nucleic acids, viruses, and/or pharmaceutical compositions or formulations described herein may be used to deliver one or more polynucleotides encoding a polypeptide (e.g., an immunomodulatory polypeptide such as an IL-2 or IL-12 polypeptide) into one or more cells of a subject (e.g., one or more cells of the respiratory tract of the subject). In some embodiments, the subject suffers from cancer. In some embodiments, any of the recombinant nucleic acids, viruses, and/or pharmaceutical compositions or formulations described herein may be used in the treatment of a solid tumor. In some embodiments, any of the recombinant nucleic acids, viruses, and/or pharmaceutical compositions or formulations described herein may be used in the treatment of a hematologic cancer. In some embodiments, any of the recombinant nucleic acids, viruses, and/or pharmaceutical compositions or formulations described herein may be used in the treatment of bladder cancer. In some embodiments, any of the recombinant nucleic acids, viruses, and/or pharmaceutical compositions or formulations described herein may be used in the treatment of brain cancer. In some embodiments, any of the recombinant nucleic acids, viruses, and/or pharmaceutical compositions or formulations described herein may be used in the treatment of breast cancer. In some embodiments, any of the recombinant nucleic acids, viruses, and/or pharmaceutical compositions or formulations described herein may be used in the treatment of colon cancer. In some embodiments, any of the recombinant nucleic acids, viruses, and/or pharmaceutical compositions or formulations described herein may be used in the treatment of gastric cancer. In some embodiments, any of the recombinant nucleic acids, viruses, and/or pharmaceutical compositions or formulations described herein may be used in the treatment of glioma. In some embodiments, any of the recombinant nucleic acids, viruses, and/or pharmaceutical compositions or formulations described herein may be used in the treatment of head cancer. In some embodiments, any of the recombinant nucleic acids, viruses, and/or pharmaceutical compositions or formulations described herein may be used in the treatment of leukemia. In some embodiments, any of the recombinant nucleic acids, viruses, and/or pharmaceutical compositions or formulations described herein may be used in the treatment of liver cancer. In some embodiments, any of the recombinant nucleic acids, viruses, and/or pharmaceutical compositions or formulations described herein may be used in the treatment of lung cancer. In some embodiments, any of the recombinant nucleic acids, viruses, and/or pharmaceutical compositions or formulations described herein may be used in the treatment of lymphoma. In some embodiments, any of the recombinant nucleic acids, viruses, and/or pharmaceutical compositions or formulations described herein may be used in the treatment of myeloma. In some embodiments, any of the recombinant nucleic acids, viruses, and/or pharmaceutical compositions or formulations described herein may be used in the treatment of neck cancer. In some embodiments, any of the recombinant nucleic acids, viruses, and/or pharmaceutical compositions or formulations described herein may be used in the treatment of ovarian cancer. In some embodiments, any of the recombinant nucleic acids, viruses, and/or pharmaceutical compositions or formulations described herein may be used in the treatment of melanoma. In some embodiments, any of the recombinant nucleic acids, viruses, and/or pharmaceutical compositions or formulations described herein may be used in the treatment of pancreatic cancer. In some embodiments, any of the recombinant nucleic acids, viruses, and/or pharmaceutical compositions or formulations described herein may be used in the treatment of renal cancer. In some embodiments, any of the recombinant nucleic acids, viruses, and/or pharmaceutical compositions or formulations described herein may be used in the treatment of salivary cancer. In some embodiments, any of the recombinant nucleic acids, viruses, and/or pharmaceutical compositions or formulations described herein may be used in the treatment of skin cancer (e.g., melanoma, basal cell carcinoma, squamous cell carcinoma, actinic keratosis, an atypical mole, and/or Merkel cell carcinoma). In some embodiments, any of the recombinant nucleic acids, viruses, and/or pharmaceutical compositions or formulations described herein may be used in the treatment of stomach cancer. In some embodiments, any of the recombinant nucleic acids, viruses, and/or pharmaceutical compositions or formulations described herein may be used in the treatment of thymic epithelial cancer. In some embodiments, any of the recombinant nucleic acids, viruses, and/or pharmaceutical compositions or formulations described herein may be used in the treatment of thyroid cancer. In some embodiments, any of the recombinant nucleic acids, viruses, and/or pharmaceutical compositions or formulations described herein may be used in the treatment of osteosarcoma.

In some embodiments, any of the recombinant nucleic acids, viruses, and/or pharmaceutical compositions or formulations described herein may be used to deliver one or more polynucleotides encoding a polypeptide (e.g., an immunomodulatory polypeptide such as an IL-2 or IL-12 polypeptide) into one or more cells of a subject (e.g., one or more cells of the respiratory tract of the subject). In some embodiments, the subject suffers from lung cancer. Lung cancers are often divided into the broad categories of small-cell lung cancer (SCLC), also called oat cell cancer, and non-small-cell lung cancer (NSCLC). NSCLC is further divided into three major types, squamous, cell carcinoma (SCC), adenocarcinoma and large cell carcinomas. In some embodiments, any of the recombinant nucleic acids, viruses, and/or pharmaceutical compositions or formulations described herein may be used in the treatment of small-cell lung cancer. In some embodiments, any of the recombinant nucleic acids, viruses, and/or pharmaceutical compositions or formulations described herein may be used in the treatment of adenocarcinoma of the lung. In some embodiments, any of the recombinant nucleic acids, viruses, and/or pharmaceutical compositions or formulations described herein may be used in the treatment of squamous carcinoma of the lung. In some embodiments, any of the recombinant nucleic acids, viruses, and/or pharmaceutical compositions or formulations described herein may be used in the treatment of non-small cell lung cancer.

VI. Methods

Certain aspects of the present disclosure relate to a method of delivering an immunomodulatory polypeptide to one or more cells of a subject (e.g., one or more cells of the respiratory tract, such as airway epithelial cells (goblet cells, ciliated cells, Clara cells, neuroendocrine cells, basal cells, intermediate or parabasal cells, Serous cells, brush cells, oncocytes, non-ciliated columnar cells, and/or metaplastic cells); alveolar cells (type 1 pneumocytes, type 2 pneumocytes, and/or cuboidal non-ciliated cells); salivary gland cells in bronchi (Serous cells, mucous cells, and/or ductal cells); etc.) comprising administering to the subject a pharmaceutical composition comprising any of the viruses described herein (e.g., a herpes simplex virus, such as an HSV-1) comprising any of the recombinant nucleic acids described herein (e.g., a recombinant herpes simplex virus genome, such as a recombinant HSV-1 genome) comprising one or more polynucleotides encoding the immunomodulatory polypeptide, and a pharmaceutically acceptable carrier. In some embodiments, the pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, periarticularly, intratumorally, locally, or via inhalation to the subject. In some embodiments, the pharmaceutical composition is administered orally, intranasally, intratracheally, or via inhalation to the subject. In some embodiments, the pharmaceutical composition is administered intranasally or via inhalation to the subject. In some embodiments, the pharmaceutical composition is administered via inhalation to the subject. In some embodiments, the herpes virus or pharmaceutical composition is administered using a dry powder inhaler, a pressurized metered dose inhaler, a soft mist inhaler, a nebulizer, or an electrohydrodynamic aerosol device. In some embodiments, the herpes virus or pharmaceutical composition is administered using a nebulizer. In some embodiments, the nebulizer is a vibrating mesh nebulizer. In some embodiments, the herpes virus (e.g., the herpes simplex virus) is replication competent. In some embodiments, the herpes virus (e.g., the herpes simplex virus) is not conditionally replication competent. In some embodiments, the herpes virus (e.g., the herpes simplex virus) does not replicate in cancerous cells. In some embodiments, the herpes virus (e.g., the herpes simplex virus) is replication defective. In some embodiments, the herpes virus (e.g., the herpes simplex virus) is not oncolytic.

In some embodiments, the subject is a human. In some embodiments, the subject suffers from a cancer. In some embodiments, the cancer is selected from acute myeloid leukemia (LAML or AML), acute lymphoblastic leukemia (ALL), adrenocortical carcinoma (ACC), bladder urothelial cancer (BLCA), brain stem glioma, brain lower grade glioma (LGG), brain tumor, breast cancer (BRCA), bronchial tumors, Burkitt lymphoma, cancer of unknown primary site, carcinoid tumor, carcinoma of unknown primary site, central nervous system atypical teratoid/rhabdoid tumor, central nervous system embryonal tumors, cervical squamous cell carcinoma, endocervical adenocarcinoma (CESC) cancer, childhood cancers, cholangiocarcinoma (CHOL), chordoma, chronic lymphocytic leukemia, chronic myelogenous leukemia, chronic myeloproliferative disorders, colon (adenocarcinoma) cancer (COAD), colorectal cancer, craniopharyngioma, cutaneous T-cell lymphoma, endocrine pancreas islet cell tumors, endometrial cancer, ependymoblastoma, ependymoma, esophageal cancer (ESCA), esthesioneuroblastoma, Ewing sarcoma, extracranial germ cell tumor, extragonadal germ cell tumor, extrahepatic bile duct cancer, gallbladder cancer, gastric (stomach) cancer, gastrointestinal carcinoid tumor, gastrointestinal stromal cell tumor, gastrointestinal stromal tumor (GIST), gestational trophoblastic tumor, glioblastoma multiforme glioma GBM), hairy cell leukemia, head and neck cancer (HNSD), heart cancer, Hodgkin lymphoma, hypopharyngeal cancer, intraocular melanoma, islet cell tumors, Kaposi sarcoma, kidney cancer, Langerhans cell histiocytosis, laryngeal cancer, lip cancer, liver cancer, Lymphoid Neoplasm Diffuse Large B-cell Lymphoma [DLBCL], malignant fibrous histiocytoma bone cancer, medulloblastoma, medulloepithelioma, melanoma, Merkel cell carcinoma, Merkel cell skin carcinoma, mesothelioma (MESO), metastatic squamous neck cancer with occult primary, mouth cancer, multiple endocrine neoplasia syndromes, multiple myeloma, multiple myeloma/plasma cell neoplasm, mycosis fungoides, myelodysplastic syndromes, myeloproliferative neoplasms, nasal cavity cancer, nasopharyngeal cancer, neuroblastoma, Non-Hodgkin lymphoma, nonmelanoma skin cancer, non-small cell lung cancer, oral cancer, oral cavity cancer, oropharyngeal cancer, osteosarcoma, other brain and spinal cord tumors, ovarian cancer, ovarian epithelial cancer, ovarian germ cell tumor, ovarian low malignant potential tumor, pancreatic cancer, papillomatosis, paranasal sinus cancer, parathyroid cancer, pelvic cancer, penile cancer, pharyngeal cancer, pheochromocytoma and paraganglioma (PCPG), pineal parenchymal tumors of intermediate differentiation, pineoblastoma, pituitary tumor, plasma cell neoplasm/multiple myeloma, pleuropulmonary blastoma, primary central nervous system (CNS) lymphoma, primary hepatocellular liver cancer, prostate cancer such as prostate adenocarcinoma (PRAD), rectal cancer, renal cancer, renal cell (kidney) cancer, renal cell cancer, respiratory tract cancer, retinoblastoma, rhabdomyosarcoma, salivary gland cancer, sarcoma (SARC), Sezary syndrome, skin cutaneous melanoma (SKCM), small cell lung cancer, small intestine cancer, soft tissue sarcoma, squamous cell carcinoma, squamous neck cancer, stomach (gastric) cancer, supratentorial primitive neuroectodermal tumors, T-cell lymphoma, testicular cancer testicular germ cell tumors (TGCT), throat cancer, thymic carcinoma, thymoma (THYM), thyroid cancer (THCA), transitional cell cancer, transitional cell cancer of the renal pelvis and ureter, trophoblastic tumor, ureter cancer, urethral cancer, uterine cancer, uterine cancer, uveal melanoma (UVM), vaginal cancer, vulvar cancer, Waldenstrom macroglobulinemia, and/or Wilms' tumor. In some embodiments, the cancer is a virus-associated cancer. In some embodiments, the cancer is a human papilloma virus (HPV)-associated cancer (e.g., an HPV-associated cancer of the back of the throat, cervix, anus, vulva, penis, and/or vagina). In some embodiments, the cancer is not skin cancer (e.g., melanoma, basal cell carcinoma, squamous cell carcinoma, actinic keratosis, an atypical mole, and/or Merkel cell carcinoma). In some embodiments, the cancer is not melanoma. In some embodiments, the subject suffers from one or more of carcinoma, lymphoma, blastoma, sarcoma, a neuroendocrine tumor, mesothelioma, schwannoma, meningioma, adenocarcinoma, melanoma, leukemia, and lymphoid malignancy. In some embodiments, the subject suffers from one or more of a solid tumor, a hematologic cancer, bladder cancer, brain cancer, breast cancer, colon cancer, gastric cancer, glioma, head cancer, leukemia, liver cancer, lung cancer, lymphoma, myeloma, neck cancer, ovarian cancer, melanoma, pancreatic cancer, renal cancer, salivary cancer, skin cancer, stomach cancer, thymic epithelial cancer, and thyroid cancer. In some embodiments, the subject suffers from one or more of small-cell lung cancer, non-small cell lung cancer, adenocarcinoma of the lung, or squamous carcinoma of the lung. In some embodiments, the subject suffers from osteosarcoma.

In some embodiments, administration of the recombinant nucleic acid, virus, medicament, and/or pharmaceutical composition or formulation to the subject increases the immunomodulatory polypeptide levels (transcript or protein levels) by at least about 2-fold in one or more contacted or treated cells of the subject, as compared to the endogenous levels of the polypeptide in one or more corresponding untreated cells in the subject. For example, administration of the recombinant nucleic acid, virus, medicament, and/or pharmaceutical composition or formulation may increase the immunomodulatory polypeptide levels (transcript or protein levels) by at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, at least about 1000-fold, or more in one or more contacted or treated cells of the subject, as compared to the endogenous levels of the polypeptide in one or more corresponding untreated cells in the subject. In some embodiments, the one or more contacted or treated cells are one or more cells of the respiratory tract (e.g., one or more cells of the airway epithelia). Methods of measuring transcript or protein levels from a sample are well known to one of ordinary skill in the art, including, for example, qPCR, western blot, mass spectrometry, etc.

Other aspects of the present disclosure relate to a method of providing prophylactic, palliative, or therapeutic relief to one or more signs or symptoms of cancer in a subject in need thereof comprising administering to the subject an effective amount of any of the recombinant nucleic acids, viruses, medicaments, and/or pharmaceutical compositions or formulations described herein. In some embodiments, the subject is a human. In some embodiments, the subject suffers from a cancer. In some embodiments, the cancer is selected from acute myeloid leukemia (LAML or AML), acute lymphoblastic leukemia (ALL), adrenocortical carcinoma (ACC), bladder urothelial cancer (BLCA), brain stem glioma, brain lower grade glioma (LGG), brain tumor, breast cancer (BRCA), bronchial tumors, Burkitt lymphoma, cancer of unknown primary site, carcinoid tumor, carcinoma of unknown primary site, central nervous system atypical teratoid/rhabdoid tumor, central nervous system embryonal tumors, cervical squamous cell carcinoma, endocervical adenocarcinoma (CESC) cancer, childhood cancers, cholangiocarcinoma (CHOL), chordoma, chronic lymphocytic leukemia, chronic myelogenous leukemia, chronic myeloproliferative disorders, colon (adenocarcinoma) cancer (COAD), colorectal cancer, craniopharyngioma, cutaneous T-cell lymphoma, endocrine pancreas islet cell tumors, endometrial cancer, ependymoblastoma, ependymoma, esophageal cancer (ESCA), esthesioneuroblastoma, Ewing sarcoma, extracranial germ cell tumor, extragonadal germ cell tumor, extrahepatic bile duct cancer, gallbladder cancer, gastric (stomach) cancer, gastrointestinal carcinoid tumor, gastrointestinal stromal cell tumor, gastrointestinal stromal tumor (GIST), gestational trophoblastic tumor, glioblastoma multiforme glioma GBM), hairy cell leukemia, head and neck cancer (HNSD), heart cancer, Hodgkin lymphoma, hypopharyngeal cancer, intraocular melanoma, islet cell tumors, Kaposi sarcoma, kidney cancer, Langerhans cell histiocytosis, laryngeal cancer, lip cancer, liver cancer, Lymphoid Neoplasm Diffuse Large B-cell Lymphoma [DLBCL], malignant fibrous histiocytoma bone cancer, medulloblastoma, medulloepithelioma, melanoma, Merkel cell carcinoma, Merkel cell skin carcinoma, mesothelioma (MESO), metastatic squamous neck cancer with occult primary, mouth cancer, multiple endocrine neoplasia syndromes, multiple myeloma, multiple myeloma/plasma cell neoplasm, mycosis fungoides, myelodysplastic syndromes, myeloproliferative neoplasms, nasal cavity cancer, nasopharyngeal cancer, neuroblastoma, Non-Hodgkin lymphoma, nonmelanoma skin cancer, non-small cell lung cancer, oral cancer, oral cavity cancer, oropharyngeal cancer, osteosarcoma, other brain and spinal cord tumors, ovarian cancer, ovarian epithelial cancer, ovarian germ cell tumor, ovarian low malignant potential tumor, pancreatic cancer, papillomatosis, paranasal sinus cancer, parathyroid cancer, pelvic cancer, penile cancer, pharyngeal cancer, pheochromocytoma and paraganglioma (PCPG), pineal parenchymal tumors of intermediate differentiation, pineoblastoma, pituitary tumor, plasma cell neoplasm/multiple myeloma, pleuropulmonary blastoma, primary central nervous system (CNS) lymphoma, primary hepatocellular liver cancer, prostate cancer such as prostate adenocarcinoma (PRAD), rectal cancer, renal cancer, renal cell (kidney) cancer, renal cell cancer, respiratory tract cancer, retinoblastoma, rhabdomyosarcoma, salivary gland cancer, sarcoma (SARC), Sezary syndrome, skin cutaneous melanoma (SKCM), small cell lung cancer, small intestine cancer, soft tissue sarcoma, squamous cell carcinoma, squamous neck cancer, stomach (gastric) cancer, supratentorial primitive neuroectodermal tumors, T-cell lymphoma, testicular cancer testicular germ cell tumors (TGCT), throat cancer, thymic carcinoma, thymoma (THYM), thyroid cancer (THCA), transitional cell cancer, transitional cell cancer of the renal pelvis and ureter, trophoblastic tumor, ureter cancer, urethral cancer, uterine cancer, uterine cancer, uveal melanoma (UVM), vaginal cancer, vulvar cancer, Waldenstrom macroglobulinemia, and/or Wilms' tumor. In some embodiments, the cancer is a virus-associated cancer. In some embodiments, the cancer is a human papilloma virus (HPV)-associated cancer (e.g., an HPV-associated cancer of the back of the throat, cervix, anus, vulva, penis, and/or vagina). In some embodiments, the cancer is not skin cancer (e.g., melanoma, basal cell carcinoma, squamous cell carcinoma, actinic keratosis, an atypical mole, and/or Merkel cell carcinoma). In some embodiments, the cancer is not melanoma. In some embodiments, the subject suffers from one or more of carcinoma, lymphoma, blastoma, sarcoma, a neuroendocrine tumor, mesothelioma, schwannoma, meningioma, adenocarcinoma, melanoma, leukemia, and lymphoid malignancy. In some embodiments, the subject suffers from one or more of a solid tumor, a hematologic cancer, bladder cancer, brain cancer, breast cancer, colon cancer, gastric cancer, glioma, head cancer, leukemia, liver cancer, lung cancer, lymphoma, myeloma, neck cancer, ovarian cancer, melanoma, pancreatic cancer, renal cancer, salivary cancer, stomach cancer, thymic epithelial cancer, and thyroid cancer. In some embodiments, the subject suffers from one or more of small-cell lung cancer, non-small cell lung cancer, adenocarcinoma of the lung, or squamous carcinoma of the lung. In some embodiments, the subject suffers from osteosarcoma.

The recombinant nucleic acids, viruses, medicaments, and/or pharmaceutical compositions or formulations described herein may be administered by any suitable method or route known in the art, including, without limitation, orally, intranasally, intratracheally, sublingually, buccally, topically, rectally, via inhalation, transdermally, subcutaneously, intradermally, intravenously, intraarterially, intramuscularly, intracardially, intraosseously, intraperitoneally, transmucosally, vaginally, intravitreally, intraorbitally, subretinally, intraarticularly, peri-articularly, locally, epicutaneously, or any combinations thereof. The present disclosure thus encompasses methods of delivering any of the recombinant nucleic acids, viruses, medicaments, or pharmaceutical compositions or formulations described herein to an individual (e.g., an individual having cancer). In some embodiments, the recombinant nucleic acids, viruses, medicaments, and/or pharmaceutical compositions or formulations described herein are administered orally, intranasally, intratracheally, and/or via inhalation. In some embodiments, the recombinant nucleic acids, viruses, medicaments, and/or pharmaceutical compositions or formulations described herein are administered intranasally or via inhalation. In some embodiments, the recombinant nucleic acids, viruses, medicaments, and/or pharmaceutical compositions or formulations described herein are administered via inhalation. In some embodiments, the recombinant nucleic acids, viruses, medicaments, and/or pharmaceutical compositions or formulations described herein are administered using a dry powder inhaler, a pressurized metered dose inhaler, a soft mist inhaler, a nebulizer, or an electrohydrodynamic aerosol device. In some embodiments, the recombinant nucleic acids, viruses, medicaments, and/or pharmaceutical compositions or formulations described herein are administered using a nebulizer. In some embodiments, the nebulizer is a vibrating mesh nebulizer.

Methods of delivering drugs to the airways and/or lungs via oral, intranasal, intratracheal, and or inhaled routes of administration are generally known to one of ordinary skill in the art (see e.g., Gardenhire et al. A Guide to Aerosol Delivery Devices for Respiratory Therapists, 4$^{th}$ Edition, American Association for Respiratory care, 2017; Patil et al. Pulmonary Drug Delivery Strategies: A Concise, Systematic Review, Lung India. 2012. 29(1):44-9; Marx et al. Intranasal Drug Administration—An Attractive Delivery Route for Some Drugs, 2015).

In some embodiments, the recombinant nucleic acids, viruses, medicaments, and/or compositions or formulations are delivered to the lungs by inhalation of an aerosolized formulation. In some embodiments, the recombinant nucleic acids, viruses, medicaments, and/or compositions or formulations are delivered to the lungs by inhalation of an aerosolized formulation after lung tumor resection. Inhalation may occur through the nose and/or the mouth of the subject. Exemplary devices for delivering the recombinant nucleic acids, viruses, medicaments, and/or pharmaceutical compositions or formulations to the lung may include, without limitation, dry powder inhalers, pressurized metered dose inhalers, soft mist inhalers, nebulizers, (e.g., jet nebulizers, ultrasonic nebulizers, vibrating mesh nebulizers), colliding jets, extrudedjets, surface wave microfluidic atomization, capillary aerosol generation, electrohydrodynamic aerosol devices, etc. (see e.g., Carvalho and McConville. The function and performance of aqueous devices for inhalation therapy. (2016) Journal of Pharmacy and Pharmacology).

Liquid formulations may be administered to the lungs of a subject, e.g., using a pressurized metered dose inhaler (pMDI). pMDIs generally include at least two components: a canister in which the liquid formulation is held under pressure in combination with one or more propellants, and a receptacle used to hold and actuate the canister. The canister may contain a single dose or multiple doses of the formulation. The canister may include a valve, typically a metering valve, from which the contents of the canister may be discharged. Aerosolized drug is dispensed from the pMDI by applying a force on the canister to push it into the receptacle, thereby opening the valve and causing the drug particles to be conveyed from the valve through the receptacle outlet. Upon discharge from the canister, the liquid formulation is atomized, forming an aerosol. pMDIs typically employ one or more propellants to pressurize the contents of the canister and to propel the liquid formulation out of the receptacle outlet, forming an aerosol. Any suitable propellants may be utilized, and may take a variety of forms, including, for example, a compressed gas or a liquified gas.

Liquid formulations may be administered to the lungs of a subject, e.g., using a nebulizer. Nebulizers are liquid aerosol generators that convert the liquid formulation into mists or clouds of small droplets, often having diameters less than about 5 microns mass median aerodynamic diameter, which can be inhaled into the lower respiratory tract. The droplets carry the active agent(s) into the nose, upper airways, and/or deep lungs when the aerosol cloud is inhaled. Any type of nebulizer known in the art may be used to administer the formulation to a patient, including, without limitation, pneumatic (jet) nebulizers, electromechanical nebulizers (e.g., ultrasonic nebulizers, vibrating mesh nebulizers), etc. Pneumatic (jet) nebulizers use a pressurized gas supply as a driving force for atomization of the liquid formulation. Compressed gas is delivered through a nozzle or jet to create a low-pressure field which entrains a surrounding liquid formulation and shears it into a thin film or filaments. The film or filaments are unstable and break up into small droplets that are carried by the compressed gas flow into the inspiratory breath. Baffles inserted into the droplet plume screen out the larger droplets and return them to the bulk liquid reservoir. Electromechanical nebulizers use electrically generated mechanical force to atomize liquid formulations. The electromechanical driving force can be applied, for example, by vibrating the liquid formulation at ultrasonic frequencies, or by forcing the bulk liquid through small holes in a thin film. The forces generate thin liquid films or filament streams which break up into small droplets to form a slow-moving aerosol stream which can be entrained in an inspiratory flow. In some embodiments, the nebulizer is a vibrating mesh nebulizer. Examples of vibrating mesh nebulizers include, for example, the Phillips Inno-Spire, the Aerogen Solo, the PARI eFlow, etc.

Liquid formulations may be administered to the lungs of a subject, e.g., using an electrohydrodynamic (EHD) aerosol device. EHD aerosol devices use electrical energy to aerosolize liquid drug solutions or suspensions.

Dry powder formulations may be administered to the lungs of a subject, e.g., using a dry powder inhaler (DPI). DPIs typically use a mechanism such as a burst of gas to create a cloud of dry powder inside a container, which can then be inhaled by the subject. In a DPI, the dose to be administered is stored in the form of a non-pressurized dry powder and, upon actuation of the inhaler, the particles of the powder are inhaled by the subject. In some cases, a compressed gas may be used to dispense the powder, similar to pMDIs. In some cases, the DPI may be breath actuated (an aerosol is created in precise response to inspiration). Typically, dry powder inhalers administer a dose of less than a few tens of milligrams per inhalation to avoid provocation of cough. Examples of DPIs include, for example, the Turbohaler® inhaler (AstraZeneca), the Clickhaler® inhaler (Innovata), the Diskus® inhaler (Glaxo), the EasyHaler® (Orion), the Exubera® inhaler (Pfizer), etc.

In some embodiments, the recombinant nucleic acids, viruses, medicaments, and/or pharmaceutical compositions or formulations are administered once to the subject. In some embodiments, the recombinant nucleic acids, viruses, medicaments, and/or pharmaceutical compositions are administered at least twice (e.g., at least 2 times, at least 3 times, at least 4 times, at least 5 times, at least 10 times, etc.) to the subject. In some embodiments, at least about 1 hour (e.g., at least about 1 hour, at least about 6 hours, at least about 12 hours, at least about 18 hours, at least about 1 day, at least about 2 days, at least about 3 days, at least about 4 days, at least about 5 days, at least about 6 days, at least about 7 days, at least about 15 days, at least about 20 days, at least about 30 days, at least about 40 days, at least about 50 days, at least about 60 days, at least about 70 days, at least about 80 days, at least about 90 days, at least about 100 days, at least about 120 days, etc.) pass between administrations (e.g., between the first and second administrations, between the second and third administrations, etc.). In some embodiments, the recombinant nucleic acids, viruses, medicaments, and/or pharmaceutical compositions or formulations are administered one, two, three, four, five or more times per day to the subject. In some embodiments, the recombinant nucleic acids, viruses, medicaments, and/or pharmaceutical compositions or formulations are administered one, two, three, four, five or more times per month to the subject.

VI. Host Cells

Certain aspects of the present disclosure relate to one or more host cells comprising any of the recombinant nucleic acids described herein. Any suitable host cell (prokaryotic or eukaryotic) known in the art may be used, including, for example: prokaryotic cells including eubacteria, such as Gram-negative or Gram-positive organisms, for example Enterobacteriaceae such as *Escherichia* (e.g., *E. coli*), *Enterobacter, Erminia, Klebsiella, Proteus, Salmonella* (e.g., *S. typhimurium*), *Serratia* (e.g., *S. marcescans*), and *Shigella*, as well as Bacilli such as *B. subtilis* and *B. licheniformis*; fungal cells (e.g., *S. cerevisiae*); insect cells (e.g., S2 cells, etc.); and mammalian cells, including monkey kidney CV1 line transformed by SV40 (COS-7, ATCC CRL 1651), human embryonic kidney line (293 or 293 cells subcloned for growth in suspension culture), baby hamster kidney cells (BHK, ATCC CCL 10), mouse Sertoli cells (TM4), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TRI cells, MRC 5 cells, FS4 cells, human hepatoma line (Hep G2), Chinese hamster ovary (CHO) cells, including DHFR" CHO cells, and myeloma cell lines such as NSO and Sp2/0. In some embodiments, the host cell is a human or non-human primate cell. In some embodiments, the host cells are cells from a cell line. Examples of suitable host cells or cell lines may include, but are not limited to, 293, HeLa, SH-Sy5y, Hep G2, CACO-2, A549, L929, 3T3, K562, CHO-KI, MDCK, HUVEC, Vero, N20, COS-7, PSN1, VCaP, CHO cells, and the like.

In some embodiments, the recombinant nucleic acid is a herpes simplex viral vector. In some embodiments, the recombinant nucleic acid is a herpes simplex virus amplicon. In some embodiments, the recombinant nucleic acid is an HSV-1 amplicon or HSV-1 hybrid amplicon. In some embodiments, a host cell comprising a helper virus is contacted with an HSV-1 amplicon or HSV-1 hybrid amplicon described herein, resulting in the production of a virus comprising one or more recombinant nucleic acids described herein. In some embodiments, the virus is collected from the supernatant of the contacted host cell. Methods of generating virus by contacting host cells comprising a helper virus with an HSV-1 amplicon or HSV-1 hybrid amplicon are known in the art.

In some embodiments, the host cell is a complementing host cell. In some embodiments, the complementing host cell expresses one or more genes that are inactivated in any of the viral vectors described herein. In some embodiments, the complementing host cell is contacted with a recombinant herpes virus genome (e.g., a recombinant herpes simplex virus genome) described herein. In some embodiments, contacting a complementing host cell with a recombinant herpes virus genome results in the production of a herpes virus comprising one or more recombinant nucleic acids described herein. In some embodiments, the virus is collected from the supernatant of the contacted host cell. Methods of generating virus by contacting complementing host cells with a recombinant herpes simplex virus are generally described in U.S. Pat. No. 10,174,341, US 2019/ 0276845, U.S. Pat. Nos. 9,877,990, 10,155,016, 10,441,614, 11,185,564, US 2020/0093874, U.S. Pat. No. 10,525,090, US 2020/0197456, US 2021/0261649, US 2021/0395775, U.S. Pat. No. 10,829,529, US 2021/0087245, US 2021/0189427, U.S. Pat. No. 10,786,438, US 2021/0045988, and/or WO2021/046131, all of which are incorporated by reference herein in their entirety.

VIII. Articles of Manufacture or Kits

Certain aspects of the present disclosure relate to an article of manufacture or a kit comprising any of the recombinant nucleic acids, viruses, medicaments, and/or pharmaceutical compositions or formulations described herein. In some embodiments, the article of manufacture or kit comprises a package insert comprising instructions for administering the recombinant nucleic acid, virus, medicament, and/or pharmaceutical composition or formulation.

Suitable containers for the recombinant nucleic acids, viruses, medicaments, and/or pharmaceutical compositions or formulations may include, for example, bottles, vials, bags, tubes, and syringes. The container may be formed from a variety of materials such as glass, plastic (such as polyvinyl chloride or polyolefin), or metal alloy (such as stainless steel or hastelloy). In some embodiments, the container comprises a label on, or associated with the container, wherein the label indicates directions for use. The article of manufacture or kit may further include other materials desirable from a commercial and user standpoint, including other buffers, diluents, filters, inhalers, nebulizers, intranasal administration devices, a package insert, and the like.

IX. Enumerated Embodiments

Embodiment 1: a recombinant herpes virus genome comprising one or more polynucleotides encoding an immunomodulatory polypeptide.

Embodiment 2: the recombinant herpes virus genome of embodiment 1, wherein the recombinant herpes virus genome is replication competent.

Embodiment 3: the recombinant herpes virus genome of any of embodiments 1 or 2, wherein the recombinant herpes virus genome is replication defective.

Embodiment 4: the recombinant herpes virus genome of any of embodiments 1-3, wherein the recombinant herpes virus genome is selected from the group consisting of a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Epstein-Barr virus genome, a recombinant Kaposi's sarcoma-associated herpesvirus genome, and any derivatives thereof.

Embodiment 5: the recombinant herpes virus genome of any of embodiments 1-4, wherein the recombinant herpes virus genome is a recombinant herpes simplex virus genome.

Embodiment 6: the recombinant herpes virus genome of any of embodiments 1-5, wherein the recombinant herpes simplex virus genome is a recombinant herpes simplex virus type 1 (HSV-1) genome, a recombinant herpes simplex virus type 2 (HSV-2) genome, or any derivatives thereof.

Embodiment 7: the recombinant herpes virus genome of any of embodiments 1-6, wherein the recombinant herpes simplex virus genome is a recombinant herpes simplex virus type 1 (HSV-1) genome.

Embodiment 8: the recombinant herpes virus genome of any of embodiments 1-7, wherein the recombinant herpes simplex virus genome is a recombinant herpes simplex virus type 2 (HSV-2) genome.

Embodiment 9: the recombinant herpes virus genome of any of embodiments 1-8, wherein the recombinant herpes simplex virus genome has been engineered to reduce or eliminate expression of one or more toxic herpes simplex virus genes.

Embodiment 10: the recombinant herpes virus genome of any of embodiments 1-9, wherein the recombinant herpes simplex virus genome has been engineered to reduce and eliminate expression of one or more toxic herpes simplex virus genes.

Embodiment 11: the recombinant herpes virus genome of any of embodiments 1-10, wherein the recombinant herpes simplex virus genome comprises an inactivating mutation.

Embodiment 12: the recombinant herpes virus genome of any of embodiments 1-11, wherein the inactivating mutation is in a herpes simplex virus gene.

Embodiment 13: the recombinant herpes virus genome of any of embodiments 1-12, wherein the inactivating mutation is a deletion of the coding sequence of the herpes simplex virus gene.

Embodiment 14: the recombinant herpes virus genome of any of embodiments 1-13, wherein the herpes simplex virus gene is selected from the group consisting of Infected Cell Protein (ICP) 0, ICP4, ICP22, ICP27, ICP47, thymidine kinase (tk), Long Unique Region (UL) 41, and UL55.

Embodiment 15: the recombinant herpes virus genome of any of embodiments 1-14, wherein the herpes simplex virus gene is ICP4.

Embodiment 16: the recombinant herpes virus genome of any of embodiments 1-15, wherein the herpes simplex virus gene is ICP22.

Embodiment 17: the recombinant herpes virus genome of any of embodiments 1-16, wherein the recombinant herpes simplex virus genome comprises an inactivating mutation in one or both copies of the ICP4 gene.

Embodiment 18: the recombinant herpes virus genome of any of embodiments 1-17, wherein the recombinant herpes simplex virus genome comprises an inactivating mutation in one or both copies of the ICP4 gene.

Embodiment 19: the recombinant herpes virus genome of any of embodiments 1-18, wherein the recombinant herpes simplex virus genome comprises an inactivating mutation in the UL41 gene.

Embodiment 20: the recombinant herpes virus genome of any of embodiments 1-19, wherein the recombinant herpes simplex virus genome comprises an inactivating mutation in one or both copies of the ICP0 gene.

Embodiment 21: the recombinant herpes virus genome of any of embodiments 1-20, wherein the recombinant herpes simplex virus genome comprises an inactivating mutation in one copy of the ICP0 gene.

Embodiment 22: the recombinant herpes virus genome of any of embodiments 1-21: wherein the recombinant herpes simplex virus genome comprises an inactivating mutation in both copies of the ICP0 gene.

Embodiment 23: the recombinant herpes virus genome of any of embodiments 1-22, wherein the recombinant herpes simplex virus genome comprises an inactivating mutation in the ICP27 gene.

Embodiment 24: the recombinant herpes virus genome of any of embodiments 1-23, wherein the recombinant herpes simplex virus genome comprises an inactivating mutation in the UL55 gene.

Embodiment 25: the recombinant herpes virus genome of any of embodiments 1-24, wherein the recombinant herpes simplex virus genome does not comprise an inactivating mutation in the ICP47 gene.

Embodiment 26: the recombinant herpes virus genome of any of embodiments 1-25, wherein the recombinant herpes simplex virus does not comprise an inactivating mutation in one or both copies of the ICP34.5 gene.

Embodiment 27: the recombinant herpes virus genome of any of embodiments 1-26, wherein the recombinant herpes simplex virus does not comprise an inactivating mutation in one copy of the ICP34.5 gene.

Embodiment 28: the recombinant herpes virus genome of any of embodiments 1-27, wherein the recombinant herpes simplex virus does not comprise an inactivating mutation in both copies of the ICP34.5 gene.

Embodiment 29: the recombinant herpes virus genome of any of embodiments 1-28, wherein the recombinant herpes simplex virus genome comprises the one or more polynucleotides encoding the immunomodulatory polypeptide within one or both of the ICP4 viral gene loci.

Embodiment 30: the recombinant herpes virus genome of any of embodiments 1-29, wherein the recombinant herpes simplex virus genome comprises the one or more polynucleotides encoding the immunomodulatory polypeptide within one of the ICP4 viral gene loci.

Embodiment 31: the recombinant herpes virus genome of any of embodiments 1-30, wherein the recombinant herpes simplex virus genome comprises the one or more polynucleotides encoding the immunomodulatory polypeptide within both of the ICP4 viral gene loci.

Embodiment 32: the recombinant herpes virus genome of any of embodiments 1-31: wherein the recombinant herpes simplex virus genome comprises the one or more polynucleotides encoding the immunomodulatory polypeptide within the ICP22 viral gene locus.

Embodiment 33: the recombinant herpes virus genome of any of embodiments 1-32, wherein the recombinant herpes simplex virus genome comprises the one or more polynucleotides encoding the immunomodulatory polypeptide within the UL41 viral gene locus.

Embodiment 34: the recombinant herpes virus genome of any of embodiments 1-33, wherein the recombinant herpes simplex virus genome comprises the one or more polynucleotides encoding the immunomodulatory polypeptide within one or both of the ICP0 viral gene loci.

Embodiment 35: the recombinant herpes virus genome of any of embodiments 1-34, wherein the recombinant herpes simplex virus genome comprises the one or more polynucleotides encoding the immunomodulatory polypeptide within one of the ICP0 viral gene loci.

Embodiment 36: the recombinant herpes virus genome of any of embodiments 1-35, wherein the recombinant herpes simplex virus genome comprises the one or more polynucleotides encoding the immunomodulatory polypeptide within both of the ICP0 viral gene loci.

Embodiment 37: the recombinant herpes virus genome of any of embodiments 1-36, wherein the recombinant herpes simplex virus genome comprises the one or more polynucleotides encoding the immunomodulatory polypeptide within the ICP27 viral gene locus.

Embodiment 38: the recombinant herpes virus genome of any of embodiments 1-37, wherein the recombinant herpes simplex virus genome comprises the one or more polynucleotides encoding the immunomodulatory polypeptide within the UL55 viral gene locus.

Embodiment 39: the recombinant herpes virus genome of any of embodiments 1-38, wherein the immunomodulatory polypeptide is a human immunomodulatory polypeptide.

Embodiment 40: the recombinant herpes virus genome of any of embodiments 1-39, wherein the immunomodulatory polypeptide is a cytokine or chemokine.

Embodiment 41: the recombinant herpes virus genome of any of embodiments 1-40, wherein the cytokine is a pro-inflammatory cytokine.

Embodiment 42: the recombinant herpes virus genome of any of embodiments 1-42, wherein the cytokine is selected from the group consisting of Interleukin (IL)-1, IL-2, IL-7, IL-12, IL-13, IL-15, IL-17, IL-18, IL-28, IL-32, IL-33, IL-34, Tumor Necrosis Factor alpha (TNFα), Interferon gamma (IFNγ), Granulocyte Colony-Stimulating Factor (G-CSF), and Granulocyte-Macrophage Colony-Stimulating Factor (GM-CSF).

Embodiment 43: the recombinant herpes virus genome of any of embodiments 1-42, wherein the cytokine is IL-2.

Embodiment 44: the recombinant herpes virus genome of any of embodiments 1-43, wherein the cytokine is IL-12.

Embodiment 45: the recombinant herpes virus genome of any of embodiments 1-44, wherein the cytokine is G-CSF.

Embodiment 46: the recombinant herpes virus genome of any of embodiments 1-45, wherein the cytokine is GM-CSF.

Embodiment 47: the recombinant herpes virus genome of any of embodiments 1-46, wherein the cytokine is not GM-CSF.

Embodiment 48: the recombinant herpes virus genome of any of embodiments 1-47, wherein the IL-2 comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 3.

Embodiment 49: the recombinant herpes virus genome of any of embodiments 1-48, wherein the IL-12 comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NO: 5, SEQ ID NO: 6, and SEQ ID NO: 85.

Embodiment 50: the recombinant herpes virus genome of any of embodiments 1-49, wherein the chemokine is a pro-inflammatory chemokine.

Embodiment 51: the recombinant herpes virus genome of any of embodiments 1-50, wherein the chemokine is selected from the group consisting of Chemokine (C—X—C motif) Ligand 1 (CXCL1), CXCL2, CXCL8, CXCL9, CXCL11, CXCL16, C—C Motif Chemokine Ligand 2 (CCL2), CCL3, CCL4, CCL5, and CCL11.

Embodiment 52: the recombinant herpes virus genome of any of embodiments 1-51, wherein the immunomodulatory polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOs: 1-30.

Embodiment 53: the recombinant herpes virus genome of any of embodiments 1-52, wherein the immunomodulatory polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOs: 1-19.

Embodiment 54: the recombinant herpes virus genome of any of embodiments 1-53, wherein the immunomodulatory polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOs: 20-30.

Embodiment 55: the recombinant herpes virus genome of any of embodiments 1-54, wherein the recombinant herpes virus genome has reduced cytotoxicity when introduced into a target cell as compared to a corresponding wild-type herpes virus genome.

Embodiment 56: the recombinant herpes virus genome of any of embodiments 1-55, wherein the target cell is a human cell.

Embodiment 57: the recombinant herpes virus genome of any of embodiments 1-56, wherein the target cell is a cell of the respiratory tract.

Embodiment 58: the recombinant herpes virus genome of any of embodiments 1-57, wherein the target cell is an airway epithelial cell.

Embodiment 59: a herpes virus comprising the recombinant herpes virus genome of any of embodiments 1-58.

Embodiment 60: the herpes virus of embodiment 59, wherein the herpes virus is replication competent.

Embodiment 61: the herpes virus of embodiment 59 or 60, wherein the herpes virus is replication defective.

Embodiment 62: the herpes virus of any of embodiments 59-61, wherein the herpes virus is not oncolytic.

Embodiment 63: the herpes virus of any of embodiments 59-62, wherein the herpes virus has reduced cytotoxicity as compared to a corresponding wild-type herpes virus.

Embodiment 64: the herpes virus of any of embodiments 59-63, wherein the herpes virus is selected from the group consisting of a herpes simplex virus, a varicella zoster virus, a human cytomegalovirus, a herpesvirus 6A, a herpesvirus 6B, a herpesvirus 7, an Epstein-Barr virus, and a Kaposi's sarcoma-associated herpesvirus.

Embodiment 65: the herpes virus of any of embodiments 59-64, wherein the herpes virus is a herpes simplex virus.

Embodiment 66: the herpes virus of any of embodiments 59-65, wherein the herpes simplex virus is a herpes simplex virus type 1 (HSV-1), a herpes simplex virus type 2 (HSV-2), or any derivatives thereof.

Embodiment 67: the herpes virus of any of embodiments 59-66, wherein the herpes simplex virus is a herpes simplex virus type 1 (HSV-1).

Embodiment 68: the herpes virus of any of embodiments 59-67, wherein the herpes simplex virus is a herpes simplex virus type 2 (HSV-2).

Embodiment 69; the herpes virus of any of embodiments 59-68, wherein the herpes simplex virus is not oncolytic.

Embodiment 70: a pharmaceutical composition comprising the recombinant herpes virus genome of any of embodiments 1-58 or the herpes virus of any of embodiments 59-69 and a pharmaceutically acceptable excipient.

Embodiment 71: the pharmaceutical composition of embodiment 70, wherein the pharmaceutical composition is suitable for topical, transdermal, subcutaneous, intradermal, oral, intranasal, intratracheal, sublingual, buccal, rectal, vaginal, inhaled, intravenous, intraarterial, intramuscular, intracardiac, intraosseous, intraperitoneal, transmucosal, intravitreal, subretinal, intraarticular, peri-articular, local, or epicutaneous administration.

Embodiment 72: the pharmaceutical composition of embodiment 70 or 71, wherein the pharmaceutical composition is suitable for oral, intranasal, intratracheal, or inhaled administration.

Embodiment 73: the pharmaceutical composition of any of embodiments 70-72, wherein the pharmaceutical composition is suitable for intranasal or inhaled administration.

Embodiment 74: the pharmaceutical composition of any of embodiments 70-73, wherein the pharmaceutical composition is suitable for inhaled administration.

Embodiment 75: the pharmaceutical composition of any of embodiments 70-74, wherein the pharmaceutical composition is suitable for intranasal administration.

Embodiment 76: the pharmaceutical composition of any of embodiments 70-75, wherein the pharmaceutical composition is suitable for use in a dry powder inhaler, a pressurized metered dose inhaler, a soft mist inhaler, a nebulizer, an electrohydrodynamic aerosol device, or any combinations thereof.

Embodiment 77: the pharmaceutical composition of any of embodiments 70-76, wherein the pharmaceutical composition is suitable for use in a nebulizer.

Embodiment 78: the pharmaceutical composition of any of embodiments 70-77, wherein the nebulizer is a vibrating mesh nebulizer.

Embodiment 79: the herpes virus of any one of embodiments 59-69 or the pharmaceutical composition of any of embodiments 70-78 for use as a medicament.

Embodiment 80: the herpes virus of any of embodiments 59-69 or the pharmaceutical composition of any of embodiments 70-78 for use in a therapy.

Embodiment 81: use of the herpes virus of any of embodiments 59-69 or the pharmaceutical composition of any of embodiments 70-78 in the manufacture of a medicament for treating cancer.

Embodiment 82: the use of embodiment 81, wherein the cancer is selected from the group consisting of acute myeloid leukemia, acute lymphoblastic leukemia, adrenocortical carcinoma, bladder urothelial cancer, brain stem glioma, brain lower grade glioma, brain tumor, breast cancer, bronchial tumors, Burkitt lymphoma, cancer of unknown primary site, carcinoid tumor, carcinoma of unknown primary site, central nervous system atypical teratoid/rhabdoid tumor, central nervous system embryonal tumors, cervical squamous cell carcinoma, endocervical adenocarcinoma cancer, childhood cancers, cholangiocarcinoma, chordoma, chronic lymphocytic leukemia, chronic myelogenous leukemia, chronic myeloproliferative disorders, colon cancer, colorectal cancer, craniopharyngioma, cutaneous T-cell lymphoma, endocrine pancreas islet cell tumors, endometrial cancer, ependymoblastoma, ependymoma, esophageal cancer, esthesioneuroblastoma, Ewing sarcoma, extracranial germ cell tumor, extragonadal germ cell tumor, extrahepatic bile duct cancer, gallbladder cancer, gastric cancer, gastrointestinal carcinoid tumor, gastrointestinal stromal cell tumor, gastrointestinal stromal tumor, gestational trophoblastic tumor, glioblastoma multiforme glioma, hairy cell leukemia, head and neck cancer, heart cancer, Hodgkin lymphoma, hypopharyngeal cancer, intraocular melanoma, islet cell tumors, Kaposi sarcoma, kidney cancer, Langerhans cell histiocytosis, laryngeal cancer, lip cancer, liver cancer, Lymphoid Neoplasm Diffuse Large B-cell Lymphoma, malignant fibrous histiocytoma bone cancer, medulloblastoma, medulloepithelioma, melanoma, Merkel cell carcinoma, Merkel cell skin carcinoma, mesothelioma, metastatic squamous neck cancer with occult primary, mouth cancer, multiple endocrine neoplasia syndromes, multiple myeloma, multiple myeloma/plasma cell neoplasm, mycosis fungoides, myelodysplastic syndromes, myeloproliferative neoplasms, nasal cavity cancer, nasopharyngeal cancer, neuroblastoma, Non-Hodgkin lymphoma, nonmelanoma skin cancer, non-small cell lung cancer, oral cancer, oral cavity cancer, oropharyngeal cancer, osteosarcoma, other brain and spinal cord tumors, ovarian cancer, ovarian epithelial cancer, ovarian germ cell tumor, ovarian low malignant potential tumor, pancreatic cancer, papillomatosis, paranasal sinus cancer, parathyroid cancer, pelvic cancer, penile cancer, pharyngeal cancer, pheochromocytoma and paraganglioma, pineal parenchymal tumors of intermediate differentiation, pineoblastoma, pituitary tumor, plasma cell neoplasm/multiple myeloma, pleuropulmonary blastoma, primary central nervous system lymphoma, primary hepatocellular liver cancer, prostate cancer such as prostate adenocarcinoma, rectal cancer, renal cancer, renal cell cancer, renal cell cancer, respiratory tract cancer, retinoblastoma, rhabdomyosarcoma, salivary gland cancer, sarcoma, Sezary syndrome, skin cutaneous melanoma, small cell lung cancer, small intestine cancer, soft tissue sarcoma, squamous cell carcinoma, squamous neck cancer, stomach cancer, supratentorial primitive neuroectodermal tumors, T-cell lymphoma, testicular cancer testicular germ cell tumors, throat cancer, thymic carcinoma, thymoma, thyroid cancer, transitional cell cancer, transitional cell cancer of the renal pelvis and ureter, trophoblastic tumor, ureter cancer, urethral cancer, uterine cancer, uterine cancer, uveal melanoma, vaginal cancer, vulvar cancer, Waldenstrom macroglobulinemia, and Wilms' tumor.

Embodiment 83: a method of expressing, enhancing, increasing, augmenting, and/or supplementing the levels of an immunomodulatory polypeptide in one or more cells of a subject, the method comprising administering to the subject an effective amount of the herpes virus of any of embodiments 59-69 or the pharmaceutical composition of any of embodiments 70-78.

Embodiment 84: the method of embodiment 83, wherein the one or more cells are one or more cells of the respiratory tract, airway epithelial, and/or lung.

Embodiment 85: the method of any of embodiments 83 or 84, wherein the one or more cells are one or more cells of the respiratory tract.

Embodiment 86: the method of any of embodiments 83-85, wherein the one or more cells are one or more cells of the airway epithelial.

Embodiment 87: the method of any of embodiments 83-86, wherein the one or more cells are one or more cells of the lung.

Embodiment 88: a method of providing prophylactic, palliative, or therapeutic relief of one or more signs or symptoms of cancer in a subject in need thereof, the method comprising administering to the subject an effective amount of the herpes virus of any of embodiments 59-69 or the pharmaceutical composition of any of embodiments 70-78.

Embodiment 89: a method of treating cancer in a subject in need thereof, the method comprising administering to the subject an effective amount of the herpes virus of any of embodiments 59-69 or the pharmaceutical composition of any of embodiments 70-78.

Embodiment 90: the method of any of embodiments 88 or 89, wherein the cancer is selected from the group consisting of carcinoma, lymphoma, blastoma, sarcoma, a neuroendocrine tumor, mesothelioma, schwannoma, meningioma, adenocarcinoma, melanoma, leukemia, and lymphoid malignancy.

Embodiment 91: the method of any of embodiments 88-90, wherein the cancer is selected from the group consisting of a solid tumor, a hematologic cancer, bladder cancer, brain cancer, breast cancer, colon cancer, gastric cancer, glioma, head cancer, leukemia, liver cancer, lung cancer, lymphoma, myeloma, neck cancer, ovarian cancer, melanoma, pancreatic cancer, renal cancer, salivary cancer, stomach cancer, thymic epithelial cancer, and thyroid cancer.

Embodiment 92: the method of any of embodiments 88-91, wherein the cancer is small-cell lung cancer, non-small cell lung cancer, adenocarcinoma of the lung, or squamous carcinoma of the lung.

Embodiment 93: the method of any of embodiments 88-92, wherein the cancer is small-cell lung cancer.

Embodiment 94: the method of any of embodiments 88-93, wherein the cancer is non-small cell lung cancer.

Embodiment 95: the method of any of embodiments 88-94, wherein the cancer is adenocarcinoma of the lung.

Embodiment 96: the method of any of embodiments 88-95, wherein the cancer is squamous carcinoma of the lung.

Embodiment 97: the method of any of embodiments 88-96, wherein the cancer is osteosarcoma.

Embodiment 98: the method of any of embodiments 88-97, wherein the subject is a human.

Embodiment 99: the method of any of embodiments 88-98, wherein the herpes virus or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, peri-articularly, intratumorally, locally, or via inhalation to the subject.

Embodiment 100: the method of any of embodiments 88-99, wherein the herpes virus or pharmaceutical composition is administered orally, intranasally, intratracheally, or via inhalation to the subject.

Embodiment 101: the method of any of embodiments 88-100, wherein the herpes virus or pharmaceutical composition is administered intranasally or via inhalation to the subject.

Embodiment 102: the method of any of embodiments 88-101, wherein the herpes virus or pharmaceutical composition is administered intranasally to the subject.

Embodiment 103: the method of any of embodiments 88-102, wherein the herpes virus or pharmaceutical composition is administered via inhalation to the subject.

Embodiment 104: the method of any of embodiments 88-103, wherein the herpes virus or pharmaceutical composition is administered using a dry powder inhaler, a pressurized metered dose inhaler, a soft mist inhaler, a nebulizer, or an electrohydrodynamic aerosol device.

Embodiment 105: the method of any of embodiments 88-104, wherein the herpes virus or pharmaceutical composition is administered using a nebulizer.

Embodiment 106: the method of any of embodiments 88-105, wherein the nebulizer is a vibrating mesh nebulizer.

The specification is considered to be sufficient to enable one skilled in the art to practice the present disclosure. Various modifications of the present disclosure in addition to those shown and described herein will become apparent to those skilled in the art from the foregoing description and fall within the scope of the appended claims.

EXAMPLES

The present disclosure will be more fully understood by reference to the following examples. It should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1: Modified Herpes Simplex Virus Vectors Encoding an Immunomodulatory Polypeptide To make modified herpes simplex virus genome vectors capable of expressing immunomodulatory polypeptides in a target mammalian cell (such as cells of the respiratory tract), a herpes simplex virus genome (FIG. 1A) is first modified to inactivate one or more herpes simplex virus genes. Such modifications may decrease the toxicity of the genome in mammalian cells. Next, variants of these modified/attenuated recombinant viral constructs are generated such that they carry one or more polynucleotides encoding the desired immunomodulatory polypeptide. These variants include: a recombinant ΔICP4-modified HSV-1 genome comprising expression cassettes containing the coding sequence of an immunomodulatory polypeptide (e.g., SEQ ID NO: 3) under the control of a heterologous promoter integrated at each ICP4 locus (FIG. 1B); a recombinant ΔICP4/ΔUL41-modified HSV-1 genome comprising expression cassettes containing the coding sequence of an immunomodulatory polypeptide (e.g., SEQ ID NO: 3) under the control of a heterologous promoter integrated at each ICP4 locus (FIG. 1C); a recombinant ΔICP4/ΔUL41-modified HSV-1 genome comprising an expression cassette containing the coding sequence of an immunomodulatory polypeptide (e.g., SEQ ID NO: 3) under the control of a heterologous promoter integrated at the UL41 locus (FIG. 1D); a recombinant ΔICP4/ΔICP22-modified HSV-1 genome comprising expression cassettes containing the coding sequence of an immunomodulatory polypeptide (e.g., SEQ ID NO: 3) under the control of a heterologous promoter integrated at each ICP4 locus (FIG. 1E); a recombinant ΔICP4/ΔICP22-modified HSV-1 genome comprising an expression cassette containing the coding sequence of an immunomodulatory polypeptide (e.g., SEQ ID NO: 3) under the control of a heterologous promoter integrated at the ICP22 locus (FIG. 1F); a recombinant ΔICP4/ΔUL41/ΔICP22-modified HSV-1 genome comprising expression cassettes containing the coding sequence of an immunomodulatory polypeptide (e.g., SEQ ID NO: 3) under the control of a heterologous promoter integrated at each ICP4 locus (FIG. 1G); a recombinant ΔICP4/ΔUL41/ΔICP22-modified HSV-1 genome comprising an expression cassette containing the coding sequence of an immunomodulatory polypeptide (e.g., SEQ ID NO: 3) under the control of a heterologous promoter integrated at the UL41 locus (FIG. 1H); and a recombinant ΔICP4/ΔUL41/ΔICP22-modified HSV-1 genome comprising an expression cassette containing the coding sequence of an immunomodulatory polypeptide (e.g., SEQ ID NO: 3) under the control of a heterologous promoter integrated at the ICP22 locus (FIG. 1I).

These modified herpes simplex virus genome vectors are transfected into engineered cells that are modified to express one or more herpes simplex virus genes. These engineered cells secrete into the supernatant of the cell culture a replication-defective herpes simplex virus with the modified genomes packaged therein. The supernatant is then collected, concentrated, and sterile filtered.

Modified herpes simplex virus genome vectors described herein can express any one or more of the exemplary immunomodulatory polypeptides in Table 1 below, in any suitable combination.

Complementing cells were mock infected with vehicle control or were infected with HSV-IL12, HSV-IL2, or HSV-GMCSF at a multiplicity of infection (MOI) of 1 in serum free cell culture medium. 24- or 48-hours post-infection, cell pellets were harvested, lysed in RIPA buffer containing protease inhibitors, and protein content was quantified via a BCA assay. 30-40 µg of each sample was loaded and run on

TABLE 1

Representative Immunomodulatory Polypeptides

| Amine acid SEQ ID NO. | Protein Name | UniProt Accession No. | Nucleic acid SEQ ID NO. | Gene Name | NCBI Gene ID No. |
|---|---|---|---|---|---|
| 1 | IL-1α | P01583 | 31 | IL1A | 3552 |
| 2 | IL-1β | P01584 | 32 | IL1B | 3553 |
| 3 | IL-2 | P60568 | 33 | IL2 | 3558 |
| 4 | IL-7 | P13232 | 34 | IL7 | 3574 |
| 5 | IL-12 subunit α | P29459 | 35 | IL12A | 3592 |
| 6 | IL-12 subunit β | P29460 | 36 | IL12B | 3593 |
| 7 | IL-13 | P35225 | 37 | IL13 | 3596 |
| 8 | IL-15 | P40933 | 38 | IL15 | 3600 |
| 9 | IL-17A | Q16552 | 39 | IL17A | 3605 |
| 10 | IL-18 | Q14116 | 40 | IL18 | 3606 |
| 11 | IL-28A Interferon lambda-2 | Q8IZJ0 | 41 | IFNL2 | 282616 |
| 12 | IL-28B Interferon lambda-3 | Q8IZI9 | 42 | IFNL3 | 282617 |
| 13 | IL-32 | P24001 | 43 | IL32 | 9235 |
| 14 | IL-33 | O95760 | 44 | IL33 | 90865 |
| 15 | IL-34 | Q6ZMJ4 | 45 | IL34 | 146433 |
| 16 | TNFα | P01375 | 46 | TNF | 7124 |
| 17 | IFNγ | P01579 | 47 | IFNG | 3458 |
| 18 | Granulocyte Colony-Stimulating Factor (G-CSF) | P09919 | 48 | CSF3 | 1440 |
| 19 | Granulocyte-Macrophage Colony-Stimulating Factor (GM-CSF) | P04141 | 49 | CSF2 | 1437 |
| 20 | Chrmokine (C-X-C motif) Ligand 1 (CXCL1) | P09341 | 50 | CXCL1 | 2919 |
| 21 | CXCL2 | P19875 | 51 | CXCL2 | 2920 |
| 22 | CXCL8 | P10145 | 52 | CXCL8 | 3576 |
| 23 | CXCL9 | Q07325 | 53 | CXCL9 | 4283 |
| 24 | CSCL11 | O14625 | 54 | CXCL11 | 6373 |
| 25 | CXCL16 | Q9H2A7 | 55 | CXCL16 | 58191 |
| 26 | C-C Motif Chemokine Ligand 2 (CCL2) | P13500 | 56 | CCL2 | 6347 |
| 27 | CCL3 | P10147 | 57 | CCL3 | 6348 |
| 28 | CCL4 | P13236 | 58 | CCL4 | 3883726351 |
| 29 | CCL5 | P13501 | 59 | CCL5 | 6352 |
| 30 | CCL11 | P51671 | 60 | CCL11 | 6356 |

Example 2: Construction of a Modified Herpes Simplex Virus Vector Encoding Human IL-12, IL-2, and GM-CSF The following example describes the engineering of a recombinant herpes simplex virus type 1 (HSV-1) that successfully encoded human IL-12 (see e.g. SEQ ID Nos: 35 and 36; HSV-IL12), IL-2 (see e.g. SEQ ID NO: 33; HSV-IL2), or GM-CSF (see e.g. SEQ ID NO: 49; HSV-GMCSF) and expressed full-length human IL-12 (see e.g. SEQ ID Nos: 5 and 6), IL-2 (see e.g. SEQ ID NO: 3), or GM-CSF (see e.g. SEQ ID NO: 19) protein.

Figure 2A:
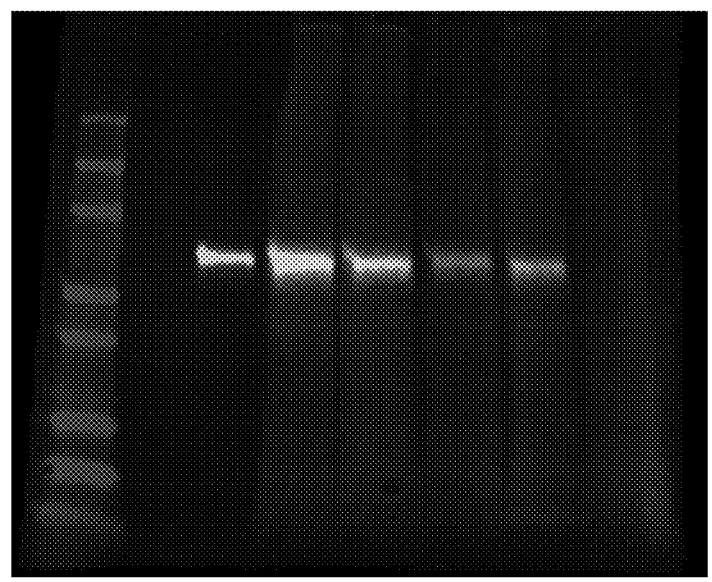
FIGS. 2A-2B depict western blot detection of human IL-12 and IL-2 in uninfected control cells (mock) or cells infected with a modified herpes simplex virus encoding human IL-12 (FIG. 2A) or IL-2 (FIG. 2B) transgene at a multiplicity of infection (MOI) of 1. Recombinant human IL-12 (FIG. 2A) or IL-2 (FIG. 2B) was used as a positive control.
Figure 2B:
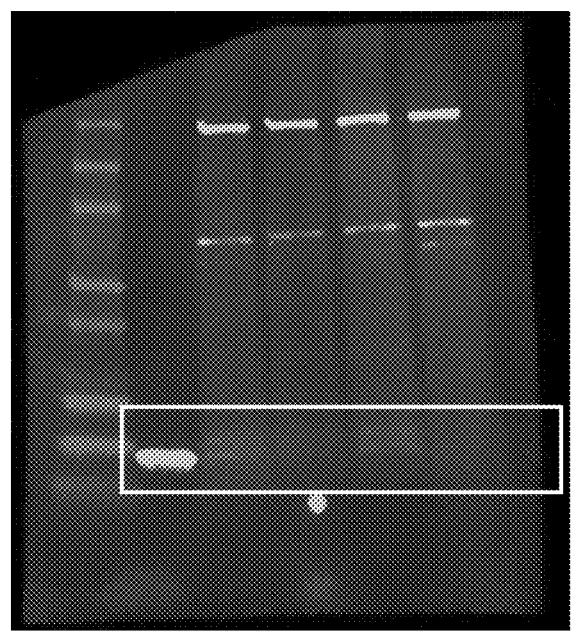

A recombinant HSV-1 was engineered to incorporate a human IL-12, IL-2, or GM-CSF expression cassette containing a heterologous promoter and polyA sequence (see Example 1). Viral plaques putatively containing the human IL-12, IL-2, or GM-CSF cassette were picked and screened by infection in a complementing cell line to test for human IL-12, IL-2, and GM-CSF protein expression via western blot analysis (data not shown). High expressing clones, termed HSV-IL12, HSV-IL2, and HSV-GMCSF, were subsequently selected for additional in vitro analysis.

a 4-20% acrylamide gel, and expression of the HSV-encoded human protein was assessed via western blot analysis (FIGS. 2A-2B). Recombinant human IL-12 or IL-2 was loaded on the gel as a positive control. While no human IL-12 or IL-2 was detected in the uninfected control cells, robust expression of human IL-12 (FIG. 2A) and IL-2 (FIG. 2B) was observed after infection with HSV-IL12 and HSV-IL2, respectively, in cells.

Because IL-12, IL-2, and GM-CSF are naturally secreted proteins, cell culture supernatants were also harvested and tested for the presence of the human protein by ELISA. In line with the western blot data, human IL-12 (2.01 µg/ml and 2.58 µg/ml), IL-2 (0.531 µg/ml, 0.850 µg/ml, and 1.200 µg/ml), and GM-CSF (643.427 ng/ml, 513.56 ng/ml, and 200.167 ng/ml) were detected in the supernatants of cells infected with HSV-IL12, HSV-IL2, and HSV-GMCSF, respectively, at the MOIs tested, suggesting that the full-length human protein was being properly processed/secreted after expression from the recombinant vector.

Taken together, the data presented in this example indicated that the recombinant HSV-1 vectors HSV-IL12, HSV- IL2, and HSV-GMCSF efficiently infected multiple cell types and were capable of expressing the human transgene encoded therein. Furthermore, the data indicated that the exogenous human protein was subsequently (properly) secreted from infected cells. Without wishing to be bound by theory, it is believed that this data further supports the use of engineered herpes simplex viruses as novel, targeted, broadly applicable gene therapy vectors for the treatment of various cancers (e.g. osteosarcoma).

Example 3: In Vitro Human and Mouse IL-12 Bioactivity Assay

The objective of this study was, in part, to determine if the recombinant human and/or murine IL-12 protein made from a recombinant herpes simplex virus type 1 (HSV-1) was as bioactive as commercially available recombinant IL-12 protein.

Figure 3A:
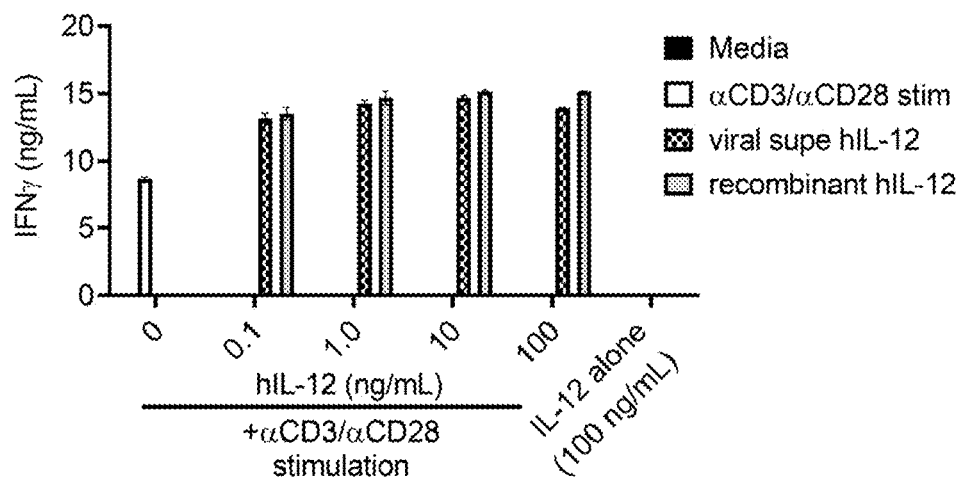
FIGS. 3A-3B depict an in vitro bioactivity assay of human (FIG. 3A) and mouse (FIG. 3B) HSV-IL12 as a function of IFNγ release from human PBMCs (FIG. 3A) or mouse splenocytes (FIG. 3B). Data indicative of cells assayed in triplicate, and data are presented as mean±standard deviation (SD), n=1.
Figure 3B:
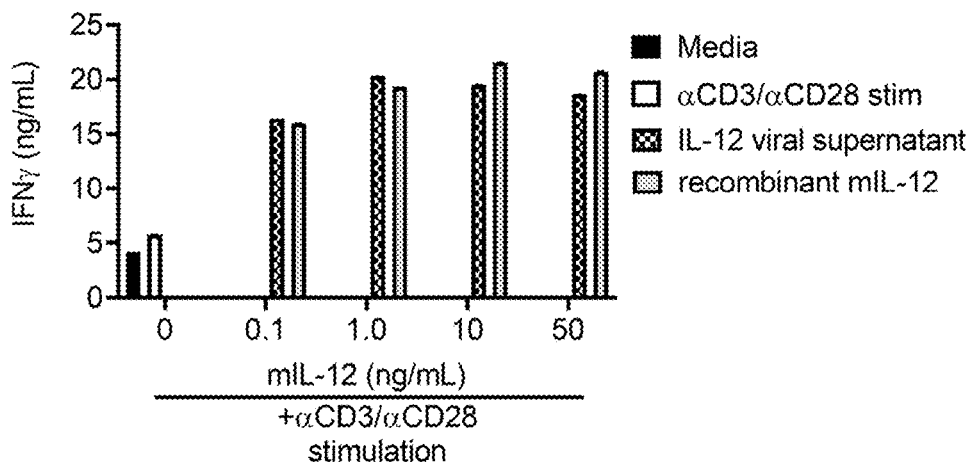

Human embryonic kidney 293 (HEK293) cells were infected at an MOI=1 with HSV-IL12 for 48 hours. IL-12 concentrations in supernatants from HEK293 infections were determined by ELISA. Human PBMCs and murine splenocytes were cultured in complete RPMI or DMEM, respectively, and maintained at 37° C. at 5% $CO_2$ in a humid environment. Commercially available human or murine αCD3/αCD28 coated beads were washed and added to PBMC or splenocyte cultures, respectively, at an amount of 2 µL per well. As indicated in FIGS. 3A-3B, serial dilutions of supernatants from HEK293 infections with human or murine HSV-IL12 were added to PBMC or splenocyte cultures in conjunction with αCD3/αCD28 coated beads. Commercially available recombinant IL-12 protein was added to some cultures at similar concentrations as a comparison. 24 hours post-stimulation, PBMC or murine splenocyte culture supernatants were harvested and assayed by ELISA for IFNγ production.

As shown in FIGS. 3A-3B, the addition of αCD3/αCD28 coated beads resulted in the release of IFNγ from both human PBMCs (FIG. 3A) and murine splenocytes (FIG. 3B). In comparison, the addition of viral supernatant from both human HSV-IL12 and murine HSV-IL12 to the αCD3/αCD28 stimulated human PBMCs (FIG. 3A) and murine splenocytes (FIG. 2B) induced greater levels of IFNγ secretion when compared to αCD3/αCD28 stimulation alone. Further, the HSV-IL12 dependent release of IFNγ was comparable to that of recombinant IL-12 (FIGS. 3A-3B).

Taken together, these results suggested the recombinant human and murine IL-12 protein made from the recombinant herpes simplex virus was as bioactive as commercially available recombinant IL-12 protein.

Example 4: Intratracheal Administration and In Vivo Evaluation of HSV-IL12 in Healthy Mice More recently in cancer treatment, immunotherapy or targeting the immune system, has shown great promise at reducing tumor burden. Specifically, administration of recombinant Interleukin(IL)-12 protein, a potent proinflammatory cytokine, has been assessed. IL-12 is a heterodimeric cytokine comprised of the p35 and p40 subunits linked by three disulfide bridges. As a proinflammatory cytokine, IL-12 is primarily produced by activated antigen presenting cells (e.g., macrophages and dendritic cells), stimulating increased Interferon-γ (IFNγ) production by T cells and Natural Killer (NK) cells. In turn, IFNγ is then capable of initiating tumor cell apoptosis, upregulating tumor cell antigen presentation, and inducing macrophage tumoricidal activity, among other effects. Research over the past few decades has indicated that IL-12 is a potent stimulator of anti-tumor immune responses, supporting its use as a cancer therapy. However, previous clinical trials have shown that systemic IL-12 treatments in cancer patients result in high levels of toxicity.

We have utilized a non-replicating HSV-1-based gene therapy vector to develop a modified vector that encodes the il12a and il12b genes (HSV-IL12) for the p35 and p40 subunits, respectively. Infection with HSV-IL12 resulted in expression of the IL-12 p70 heterodimer, with the subunits covalently linked by a G4S linker. In vitro studies comparing virally produced and recombinant IL-12 protein indicated similar efficacy at inducing IFNγ expression (see Example 3 above) during activation of murine splenic T cells.

As these studies confirmed transgene bioactivity, the next step was to test HSV-IL12 in vivo. The present study evaluated IL-12 expression, in conjunction with toxicity, following a single dose of HSV-IL12 administered intratracheally (i.t.) to young (8-10 weeks) BALB/c animals. Three different doses of HSV-IL12 were assessed for IL-12 expression by nucleic acid and protein analysis in the lung tissue, bronchoalveolar lavage fluid (BALF), and serum. Toxicity was measured by reductions in overall body weight over the course of the study (24- and 48-hours post-administration). Additionally, a group of animals received recombinant IL-12 protein systemically (subcutaneous; s.c.) as a means of comparing local HSV-IL12 delivery to previously studied administration routes.

All procedures conducted were in compliance with applicable animal welfare acts and were approved by the local Institutional Animal Care and Use Committee (IACUC). 22-28 healthy, 8-week-old female BALB/c mice were used in this study.

Mice were sedated with an intraperitoneal mix of Telazol and Dexdomitor. Sedation was determined by using the toe pinch reflex test. Eye ointment (Puralube Vet) was applied on the eyes to prevent dryness. The animals were placed on a metal tray on a supportive table for dosing.

Intratracheal (i.t.) administration was performed by thawing the viral vector on wet ice, diluting in vehicle to achieve the appropriate titers, and administering in 50 µL doses. The lower jaw and tongue were gently moved away with tweezers to expose the epiglottis and larynx. A ~4.5 cm catheter tube was inserted halfway into the trachea, and a 23G needle connected to the syringe was attached at the top of the catheter to administer the dose. Negative control mice were injected it. with vehicle alone. Following administration, animals were monitored during recovering from anesthesia.

Additionally, a group of animals received a subcutaneous (s.c.) injection of recombinant IL-12 protein (0.5 mg diluted in 1×PBS) as a systemic route of administration. This dose was chosen as it was demonstrated to be toxic in mice. For administration, awake animals were scruffed and the dose was administered behind the neck using a 1 mL syringe and 27G needle.

At the indicated timepoints after i.t. or s.c. administration of the above treatments, animals were euthanized by $CO_2$ asphyxiation, and a cardiac puncture was performed to collect blood in serum separator tubes (BD Biosciences). Tubes were centrifuged to pellet red blood cells and the serum was removed and snap frozen in Eppendorf tubes. Then, animals were perfused with 40 mL cold 1×PBS at a rate of 20 mL per minute. Brochoalveolar lavage (BAL) was performed using 2 mL of 1×PBS. Recovery volumes were recorded for each animal. BAL samples were centrifuged to remove cells and the BAL fluid (BALF) was collected to be assayed. 100× protease inhibitors (Fisher Scientific) were added to all BALF samples at a final concentration of 1×. Left and right lungs were then excised and snap frozen in liquid nitrogen for protein and nucleic acid analysis.

Resuspended BAL cell pellets were centrifuged at 2000 rpm for 5 minutes and supernatants removed and discarded. Residual red blood cells were lysed using 1× Red Blood Cell lysis buffer (Sigma) (incubated at room temperature for 2 minutes). 500 µL of 1× PBS was added to stop the lysis reaction and cells were centrifuged as described above. Supernatants were removed and cells were resuspended in 100-500 µL 1×PBS depending on the size of the cell pellet. An aliquot of each sample was diluted in Trypan Blue (Fisher Scientific) and cell number and viability were assessed using a hemocytometer.

Snap-frozen lungs were stored at −80° C. until processing. On the day of processing, frozen lungs were biopsied using a razor blade, quickly weighed, and returned to dry ice. Two biopsies were cut, one for RNA/DNA work and one for making homogenates for ELISA. Biopsies for nucleic acid analysis were immediately resuspended in 350 µL RLT buffer prepared with fresh DTT according to the manufacturer's protocol (Qiagen). Biopsies for protein analysis were resuspended in 300 µL of Pierce's TPER reagent (Fisher Scientific) supplemented with 1× protease inhibitors (Fisher Scientific). A 5 mm metal bead was added to each tube, and samples were homogenized with a Tissue Lyser (Qiagen) at 25 Hz for 3 minutes. Nucleic acids were immediately extracted and protein homogenates were processed as follows: samples were centrifuged for 5 minutes at 10,000×g to pellet debris; supernatants were collected and aliquoted into Eppendorf tubes. Homogenates were stored at −20° C. until ELISA and BCA assay.

DNA and RNA extractions were performed using the Qiagen AllPrep DNA/RNA extraction kit according to the manufacturer's protocol. Both DNA and RNA samples were eluted in distilled deionized RNase free water. Residual genomic DNA was eliminated from RNA samples using the TURBO DNA kit (Invitrogen) using the manufacturer's instructions. All nucleic acids were quantified spectrophotometrically on a Nanodrop (BioTek). Absolute quantification of il12 DNA genomes and RNA transcripts was performed by TaqMan Real Time PCR analysis using custom, transgene-specific primer/probe pairs. A 20× il12 primer/probe mix containing 45 nmoles each of the forward and reverse primers and 12.5 nmoles of the probe were diluted to 1× in each reaction to achieve the final primer and probe concentrations. RNA was reverse transcribed into cDNA using MultiScribe Reverse Transcriptase (Applied Biosystems) prior to qRT-PCR analysis.

Taqman® Fast Advanced Master Mix (Applied Biosystems) was used for DNA (qPCR) and RNA quantification (qRT-PCR). 50 ng of DNA or cDNA were used for the qPCR and qRT-PCR assays, respectively. All samples were run in duplicate, and copy number was determined using a standard curve derived from a dilution series of gBlock standard containing a known copy number of the il12 transgene.

Prior to ELISA, protein concentration of lung homogenates was determined by BCA assay (Pierce). For ELISA, all reagents used were obtained from R&D Systems. Lung homogenates, BALF, and serum were then assayed on ELISA plates that were coated overnight with αIL-12 capture antibody according to the manufacturer's instructions. After blocking the plates with 1× reagent diluent for 1 hour at room temperature, samples and standards were diluted accordingly in reagent diluent and assayed in duplicate (50 µL per well). Samples were incubated on plates for 2 hours at room temperature with shaking. After incubation, plates were washed with 1× wash buffer 3 times with blotting between each wash.

Biotinylated detection antibody was diluted in reagent diluent to the working concentration specified in the protocol and 100 µL added to each well. Samples were incubated at room temperature for 2 hours with shaking. Following incubation, plates were washed as described above, and 40× streptavidin was diluted in reagent diluent to 1×. 100 µL was added to each well and plates were incubated at room temperature in the dark for 20 minutes. Plates were washed again and then developed using TMB substrate for 20 minutes in the dark. Reactions were quenched with 2N $H_2SO_4$. Plates were read on a SpectraMax spectrophotometer using SoftMax Pro software. All ODs had background subtracted based on the plate blank, and concentrations were determined using a 4-point standard curve.

For lung homogenates, IL-12 concentrations determined by ELISA were normalized to total protein concentrations obtained from the BCA assay and calculated as pg of IL-12 per µg of protein.

Example 4a: HSV-IL12 Single Dose

The objectives of this study were: (1) to evaluate the kinetics of HSV-IL12-mediated expression of murine IL-12 at the transcript and protein levels locally and systemically, upon intratracheal administration, to healthy BALB/c mice; (2) to assess toxicity of HSV-IL12 at various doses; and (3) to compare toxicity and IL-12 localization between HSV-IL12 administered intratracheally versus recombinant IL-12 protein administered systemically.

An in vivo study was conducted to evaluate HSV-IL12-mediated expression of murine IL-12 in healthy, immuno-competent mice upon i.t. delivery of the viral vector. A total of twenty-eight BALB/c mice were used for this study. Table 2 provides a synopsis of the experimental design. At the indicated timepoints after i.t. or s.c. administration of active or control test articles, animals were sacrificed, and lungs were snap frozen for downstream analysis.

TABLE 2

Study Design and Test Article (TA) Administration

| Grp # | Tot. Animal number | Animal # | TA name | PFU or dose | TA total volume/ animal | Route | Dosing Day | Termination |
|---|---|---|---|---|---|---|---|---|
| 1 | 2 | 1, 2 | Vehicle | — | 50 mL | i.t. | Day 0 | 24 hr post-IT |
| 2 | 2 | 3, 4 | | | | | | 48 hr post-IT |
| 3 | 3 | 5, 6, 7 | High dose | 9.5E8 pfu | 50 mL | i.t. | Day 0 | 24 hr post-IT |
| 4 | 3 | 8, 9, 10 | | | | | | 48 hr post-IT |
| 5 | 3 | 11, 12, 13 | Mid dose | 1.9E8 pfu | 50 mL | i.t. | Day 0 | 24 hr post-IT |
| 6 | 3 | 14, 15, 16 | | | | | | 48 hr post-IT |

TABLE 2-continued

Study Design and Test Article (TA) Administration

| Grp # | Tot. Animal number | Animal # | TA name | PFU or dose | TA total volume/ animal | Route | Dosing Day | Termination |
|---|---|---|---|---|---|---|---|---|
| 7 | 3 | 17, 18, 19 | Low | 3.8E7 | 50 mL | i.t. | Day 0 | 24 hr post-IT |
| 8 | 3 | 20, 21, 22 | dose | pfu | | | | 48 hr post-IT |
| 9 | 3 | 23, 24, 25 | Recombinant | 0.5 mg | 50 mL | s.c. | Day 0 | 24 hr post-IT |
| 10 | 3 | 26, 27, 28 | mIL-12 | | | | | 48 hr post-IT | hr—hour;
i.t.—intratracheal administration;
s.c.—subcutaneous administration

Prior to administration and also sacrifice, all animals were weighed to evaluate testing agent toxicity. Data indicated that the animals in the High dose group (9.5E8 pfu) demonstrated dramatic weight loss at 48 hours post-treatment (~16%), suggesting toxicity either to the virus, IL-12, or both (FIG. 4A). Animals in the other groups demonstrated no change in weight following treatment, indicating no toxic effect from dosing.

Figure 4D:
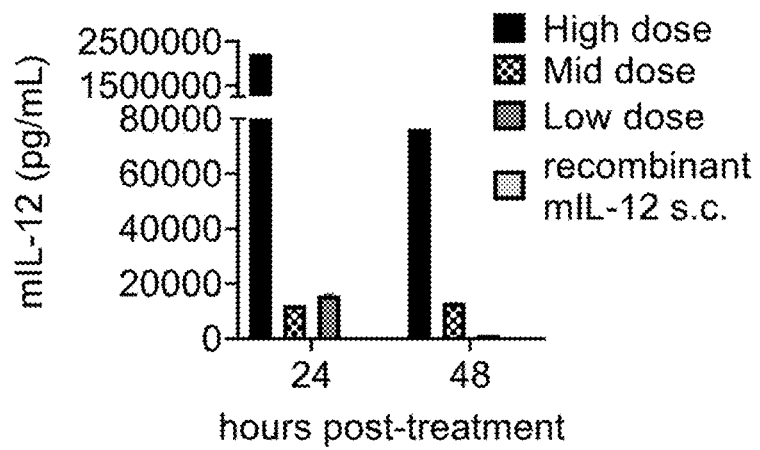
Figure 4E:
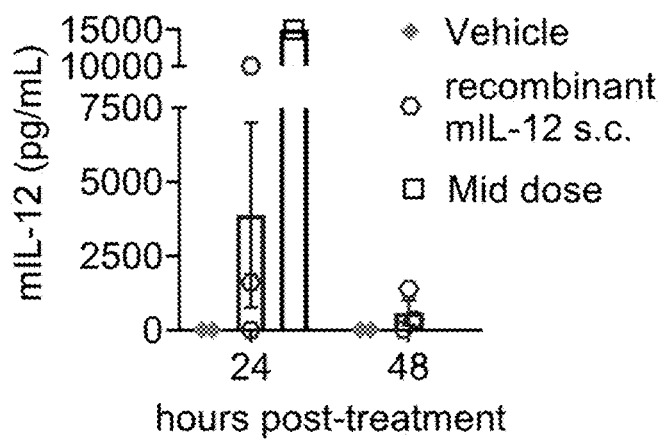

Post-sacrifice qPCR analyses of lung tissue indicated that il12 genomes demonstrated a direct relationship with administration dose at both 24- and 48-hours post-treatment (FIG. 4B). Additionally, DNA levels were relatively stable between the two time points within each dosing group. While il12 genomes differed between treatment groups, il12 transcript levels were comparable regardless of dose (FIG. 4C). These data suggest that transcript levels may plateau at a certain level of genomes in which, the presence of more genomes does not result in an increase in transcripts. This would indicate that the highest level of transgene expression (undiluted, High dose) is attainable even at a 1:25 dilution of the virus (Low dose). rIL-12 s.c. administration did not result in appreciable levels of il12 genomes or transcripts (FIGS. 4B-4C), which was expected as they received IL-12 protein, not DNA and/or RNA. Also as expected, vehicle control recipients demonstrated il12 genome/transcript levels near the limit of detection of the assays (FIGS. 4B-4C). The High dose group demonstrated >0.08 μg/mL of IL-12 protein in the serum (FIG. 4D), which was most likely a contributor to toxicity (FIG. 4A). Yet, this dramatically decreased in the mid and low dose groups (ng/mL range) (FIG. 4D). IL-12 was also detected in the BALF (FIG. 4E) in the Mid dose group. Further, considerably more IL-12 was observed in the BALF of the HSV-IL12 treated compared to the recombinant IL-12 treated group suggesting efficient local delivery of HSV-IL12.

Figure 4F:
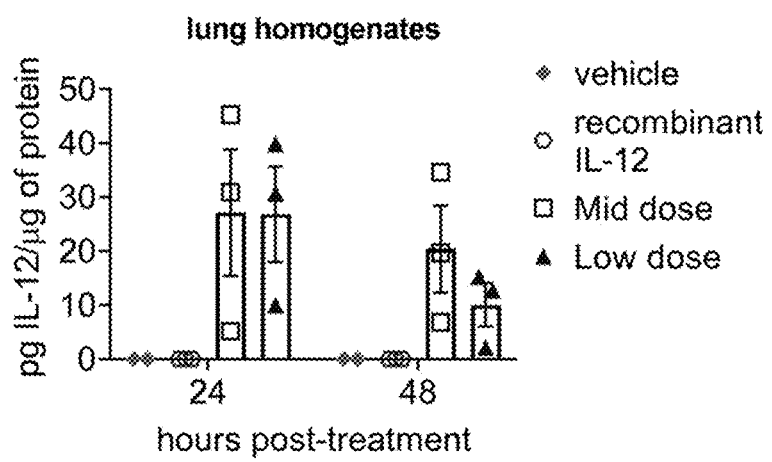

In addition to serum and BALF, lung biopsies were homogenized for IL-12 ELISA analysis. After normalizing for total protein, the results indicated that there was no significant difference in IL-12 protein concentration between vehicle and s.c. recombinant protein (FIG. 4F). Additionally, homogenates from the mid and low dose groups did contain detectable levels of IL-12 protein.

The present study evaluated: (1) the kinetics of HSV-IL12-mediated expression of murine IL-12 upon intratracheal administration to healthy BALB/c mice; (2) the toxicity of HSV-IL12 at various doses; and (3) the tolerability between HSV-IL12 compared to recombinant IL-12 protein administered systemically. Weight measurements of the mice at sacrifice indicated that the High dose (9.5E8 pfu) in this study was not tolerated well, as animals lost close to 20% of their body weight 48 hours post-administration (FIG. 4A). However, upon further investigation, it was determined that a high level of recombinant IL-12 protein was co-purified and administered i.t. with HSV-IL12, potentially contributing to the toxicity. Significant weight loss was not observed in any of the other treatment groups, indicating tolerability. While the s.c. administered rIL-12 dose was hypothesized to be somewhat toxic, animals in this study only received one dose; this is in contrast to previous studies where toxicity was observed following consecutive daily doses.

The qRT-PCR data indicated that il12 transcript levels were comparable between dosing groups at 24- and 48 hours post-treatment (FIG. 4C), even though il12 genomes decreased with test agent dosing (FIG. 4B). These results would indicate that il12 transcription may be more efficient at lower test agent doses and should be further investigated. It would also suggest lower doses of virus could be administered but would still result in high levels of transgene expression. This would be advantageous in a patient setting where HSV-IL12 is administered through nebulization.

It was observed that IL-12 protein levels in serum (FIG. 4D) and BALF (FIG. 4E) did somewhat trend with the dose of HSV-IL12 administered. IL-12 protein concentrations were quite variable in lung homogenates (FIG. 4F), indicating that further studies are necessary for understanding protein expression due to HSV-IL12 treatment.

Example 4b: HSV-IL12 Weekly Dose

The objective of this study was to, in part, evaluate HSV-IL12-mediated expression of murine IL-12 and its toxicity in healthy, immunocompetent mice. Vehicle and doses of intratracheal administered HSV-IL12, along with s.c. rIL-12, were performed once weekly for three consecutive weeks. A total of twenty-two BALB/c mice were used for this study. Table 3 provides a synopsis of the experimental design.

TABLE 3

Study Design and Test Article (TA) Administration

| Grp # | Total animals | Animal # | TA Name | PFU or dose | TA total volume/animal | Route | Day dosing | Termination |
|---|---|---|---|---|---|---|---|---|
| 1 | 2 | 1, 2 | Vehicle | — | 50 mL | i.t. | Day 0 | Day 15 |
| 2 | 2 | 3, 4 | | | | | Day 7 | |
| 3 | 3 | 5, 6, 7 | Dose #1 | 1.9E8 | 50 mL | i.t. | Day 14 | |
| 4 | 3 | 8, 9, 10 | | | | | | |
| 5 | 3 | 11, 12, 13 | Dose #2 | 3.8E7 | 50 mL | i.t. | | |
| 6 | 3 | 14, 15, 16 | | | | | | |
| 7 | 3 | 17, 18, 19 | Dose #3 | 7.6E6 | 50 mL | i.t. | | |
| 8 | 3 | 20, 21, 22 | | | | | | |
| 9 | 3 | 23, 24, 25 | rIL-12 | 0.5 mg | 50 mL | s.c. | | |
| 10 | 3 | 26, 27, 28 | | | | | | | i.t.—Intratracheal;
s.c.—subcutaneous

Prior to each administration and terminal sacrifice, animal weights were recorded. Terminal sacrifice occurred 24 hours following the last dose (day 15). BALF and associated cells, serum, and lungs were collected for downstream analysis.

Figure 4G:
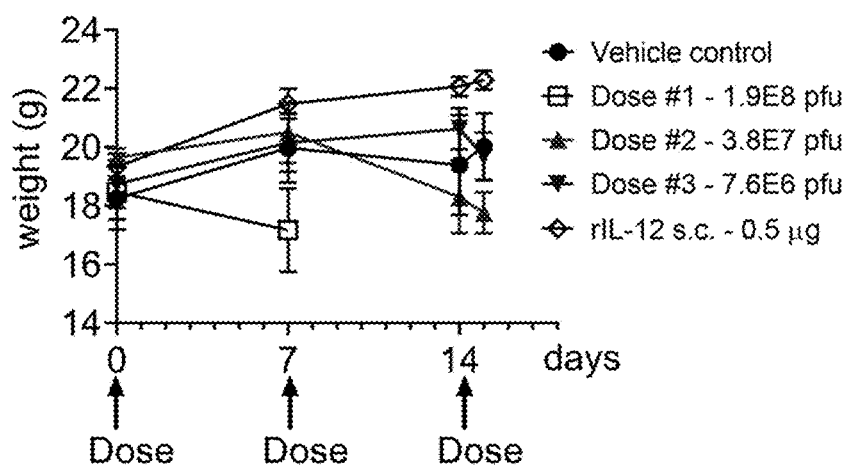
Figure 4H:
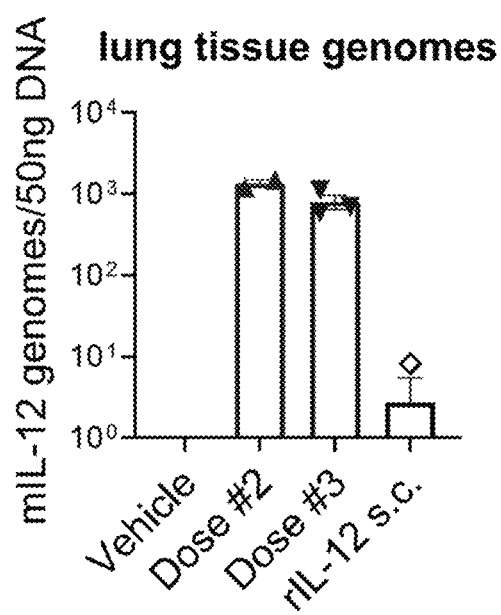
Figure 4I:
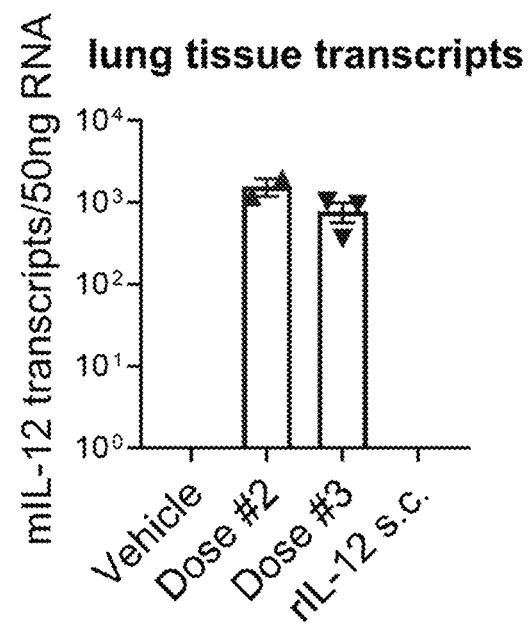

Prior to each weekly dose administration and terminal sacrifice, all animals were weighed to evaluate test agent toxicity. Following the second weekly dose administration, all animals in the highest HSV-IL12 dose group (Dose #1) died, indicating strong toxicity at this dose (FIG. 4G). Alternatively, animals in all other groups stayed relatively the same weight through the second dose. From the second to third dose however, animals in the Dose #2 group (3.8E7 pfu) lost an average of 10% of their body weight, suggesting toxicity over multiple doses. One animal from this group also died following the second administration. Animals in the Dose #3 group showed no marked signs of toxicity (weights were similar to vehicle and rIL-12 recipient groups), demonstrating that 7.6E6 pfu once weekly was the highest tolerable dose in this model.

qPCR analyses of lung tissue indicated that differences in il12 genomes between HSV-IL12 dosing groups were not statistically significant (FIG. 4H). Similar trends were observed with il12 transcripts in that animals from the Dose #2 group had slightly increased transcript copy numbers (FIG. 4I). Yet, this difference was not statistically significant from total copies in Dose #3 animals. Together, these results suggest that while there was a 5-fold decrease in administered pfu between animals in Dose #2 (3.8E7 pfu) and Dose #3 (7.6E6 pfu) groups, it did not result in higher il12 genome or transcript copies, suggesting efficient transgene expression even at lower viral doses.

Figure 4J:
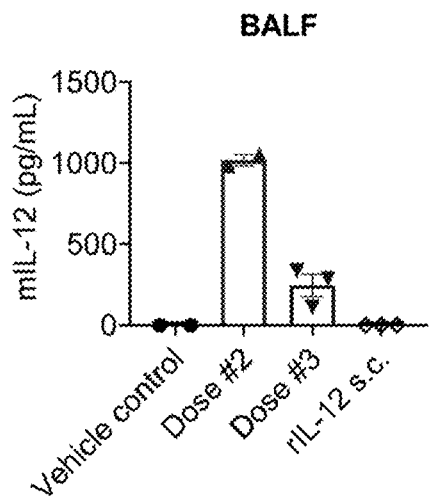
Figure 4K:
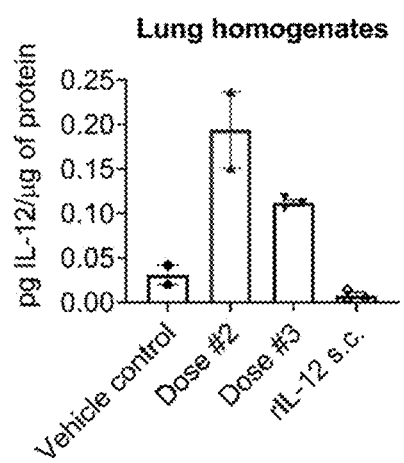
Figure 4L:
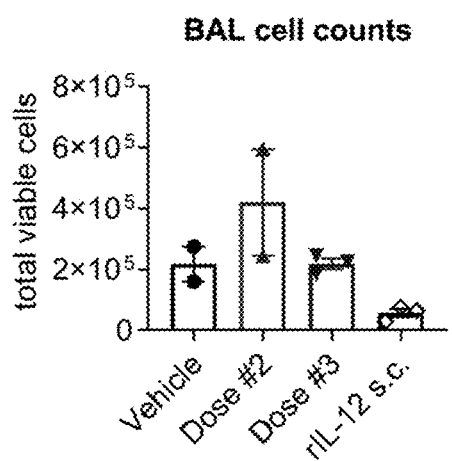
Figure 4M:
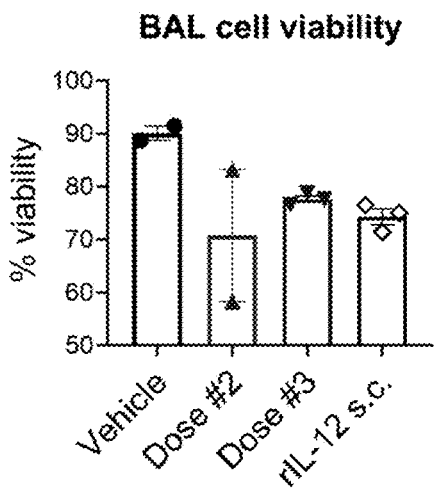

Further, and as shown in FIGS. 4J-4K, IL-12 protein levels in BALF and lung homogenates showed a direct relationship with dosing. In addition to serum and BALF, lung biopsies were homogenized for IL-12 ELISA analysis. After normalizing for total protein, the results indicated that there was no significant difference in IL-12 protein concentration between vehicle and s.c. recombinant protein (FIGS. 4L-4M). Additionally, homogenates from the mid and low dose groups did contain detectable levels of IL-12 protein.

Taken together, these data indicated intratracheal administration of low dose (7.6E6 pfu) HSV-IL12 given once weekly for three consecutive weeks was well tolerated in healthy mice.

Example 5: Intratracheal Administration and In Vivo Evaluation of HSV-IL2 in Healthy Mice Interleukin-2 (IL-2) is a monomeric cytokine that is predominantly produced by activated T cells and NK cells. For these cells, IL-2 signals, often in a paracrine manner, to stimulate cell growth and division. Specifically for T cells, IL-2 stimulation following activation is necessary for optimal clonal expansion and upregulation of anti-apoptotic signals. Research has supported the use of IL-2 as an immunotherapeutic in cancer. However, the one significant drawback to IL-2 monotherapy is its toxicity. Additionally, IL-2 has a very short serum half-life (several minutes), and therefore, must be administered systemically at extremely high doses (upwards of 600,000 IU/kg) and at high frequency (multiple times per day) to exhibit efficacy. At these doses and dose frequencies, IL-2 treatment can lead to, e.g., but not limited to, vascular leak syndrome, hypotension, and heart toxicities.

Example 5a: HSV-IL2 Single Dose

The objective of this study was, in part, to evaluate transgene expression in the lungs and serum 24-hours post intratracheal administration of HSV-IL2 compared to recombinant protein administration. Young (8-10 weeks) BALB/c animals were administered a single dose of HSV-IL2 intratracheally (i.t.). Three different doses of HSV-IL2 were assessed for IL-2 expression by nucleic acid and protein analysis in the lung tissue, bronchoalveolar lavage fluid (BALF), and serum. Additionally, a group of animals received recombinant IL-2 protein as a means of comparing local HSV-IL2 delivery to previously studied administration routes. All procedures have been described above (e.g. see Example 4 above). Table 4 provides a synopsis of the experimental design.

TABLE 4

Study Design and Test Article (TA) Administration

| Grp # | Tot. Animal No. | Animal # | TA name | PFU or dose | TA total volume/animal | Route | Dosing Day | Termination | Readout |
|---|---|---|---|---|---|---|---|---|---|
| 1 | 3 | 1, 2, 3 | Vehicle | — | 50 mL | IT | Day 0 | Day 1 (24 hours | qPCR, qRT-PCR, |
| 2 | 3 | 4, 5, 6 | High dose | 2.1E8 pfu | 50 mL | IT | | | |

TABLE 4-continued

Study Design and Test Article (TA) Administration

| Grp # | Tot. Animal No. | Animal # | TA name | PFU or dose | TA total volume/animal | Route | Dosing Day | Termination | Readout |
|---|---|---|---|---|---|---|---|---|---|
| 3 | 3 | 7, 8, 9 | Mid dose | 4.2E7 pfu | 50 mL | IT | | post-treatment) | ELISA |
| 4 | 3 | 10, 11, 12 | Low dose | 8.4E6 pfu | 50 mL | IT | | | |
| 5 | 3 | 13, 14, 15 | IT rIL-2 | 48 ng | 50 mL | IT | | | |
| 6 | 3 | 16, 17, 18 | IV rIL-2 | 48 ng | 100 mL | IV | | | |

IT—Intratracheal administration;
IV—Intravenous administration

Figure 5D:
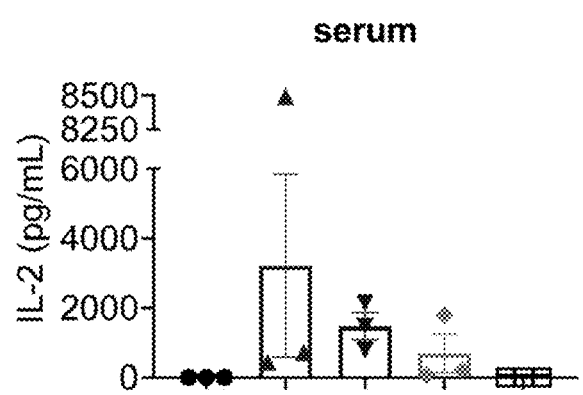
Figure 5E:
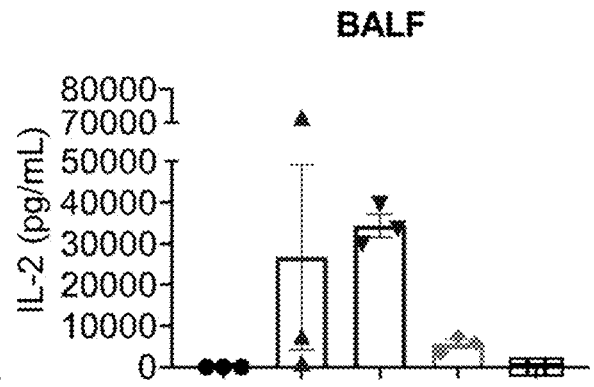
Figure 5F:
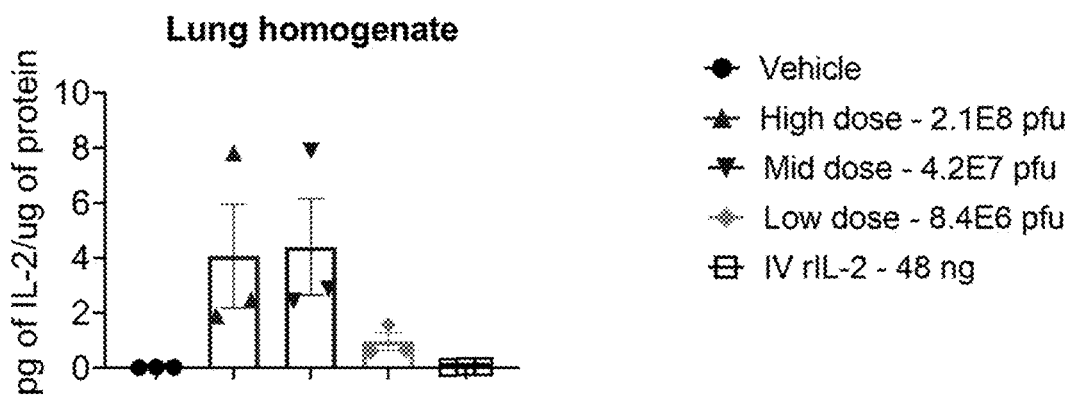

Results from this study suggest no differences in bodyweights were noted between groups (FIG. 5A). Post-sacrifice qPCR analyses of lung tissue indicated that il2 genomes demonstrated a direct relationship with administration dose at 24-hours post-treatment (FIG. 5B). While il2 genomes differed between treatment groups, il2 transcript levels were comparable regardless of dose (FIG. 5C). These results were similar to what was observed with single dose HSV-IL12 in healthy mice (FIG. 4B-4C), demonstrating consistency of the vector independent of the inserted transgene. With regards to protein levels, while IL-2 was detected in the serum (FIG. 5D), the levels in the lung as measured in the BALF (FIG. 5E) were more than 10-fold higher, indicating more significant expression in the target tissue, with limited systemic exposure. While IL-2 protein levels in lung homogenates demonstrated some variability between animals, levels were detectable and relatively high compared to recombinant protein treated animals (FIG. 5F). Further, IL-2 protein levels were undetectable in lung homogenates at 24 hours post IV injection of recombinant IL-2, most likely due to its short half-life. These data suggest prolonged effector exposure from HSV-IL2 compared to recombinant protein therapy.

Taken together, these data indicated that infection with HSV-IL2 resulted in expression of full-length, functional murine IL-2. Moreover, i.t. administration of HSV-IL2 resulted in high levels of IL-2 protein in the target organ (lung), with limited systemic exposure (as measured in the serum).

Example 5b: HSV-IL2 Pharmacokinetics

The objective of this study was, in part, to quantitatively measure the kinetics of vector transduction and IL-2 expression in lung tissues and fluids harvested from healthy mice following a single dose of HSV-IL2 administered intratracheally (i.t.).

All procedures have been described above (e.g. see Example 4 above). Table 5 provides a synopsis of the experimental design.

TABLE 5

Study Design and Test Article (TA) Administration

Figure 5G:
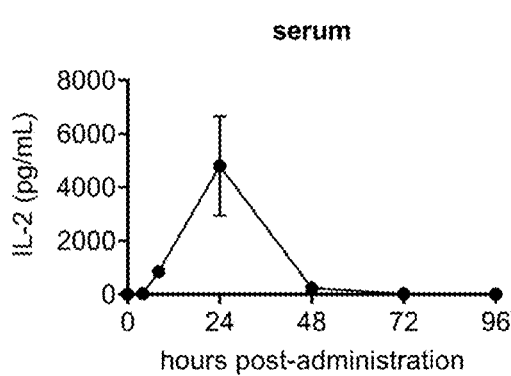
Figure 5H:
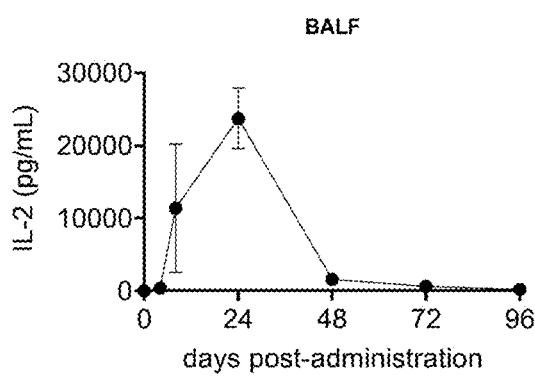
Figure 5I:
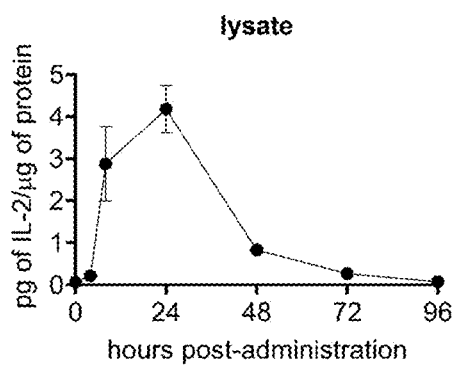

| Grp # | Tot. Animal number | Animal # | TA name | pfu | TA total volume/animal | Route | Dosing Day | Termination | Readout |
|---|---|---|---|---|---|---|---|---|---|
| 1 | 3 | 1, 2, 3 | Vehicle | — | 50 µL | i.t. | Day 0 | 48 h.p. i.t. (Day 2) | qPCR/RT-qPCR, ELISA |
| 2 | 3 | 4, 5, 6 | HSV-IL2 | 4.2E7 pfu | 50 µL | i.t. | Day 0 | 4 h.p. i.t. (Day 0) | qPCR/RT-qPCR, ELISA |
| 3 | 3 | 7, 8, 9 | | | | | | 8 h.p. i.t. (Day 0) | |
| 4 | 3 | 10, 11, 12 | | | | | | 24 h.p. i.t. (Day 1) | |
| 5 | 3 | 13, 14, 15 | | | | | | 48 h.p. i.t. (Day 2) | |
| 6 | 3 | 16, 17, 18 | | | | | | 72 h.p. i.t. (Day 3) | |
| 7 | 3 | 19, 20, 21 | | | | | | 96 h.p. i.t. (Day 4) | | i.t.: intratracheal administration;
h.p. i.t.: hours post-intratracheal administration Results from this study are shown in FIGS. 5G-5I and demonstrate the pharmacokinetics of IL-2 expression in the serum (FIG. 5G), BALF (FIG. 5H), and lysate (FIG. 5I) following the single-dose intratracheal administration of HSV-IL2. Overall, these results indicated that IL-2 protein levels peak at 24-hours post-i.t. administration of HSV-IL2, and decrease between 24- and 48-hours post-administration, which could be due to reductions in transgene translation, the short half-life of IL-2, or a combination thereof. However, IL2 protein exposure in these animals was significantly prolonged when expressed from the vector as compared to recombinant protein therapy.

Example 6: Intratracheal Administration and In Vivo Evaluation of HSV-GMCSF in Healthy Mice Granulocyte-macrophage colony-stimulating factor (GM-CSF) is a monomeric cytokine that plays a critical role in the activation and migration of myeloid cells to sites of inflammation. With respect to cancer therapy, GM-CSF has been shown to effectively activate anti-tumor immune responses, especially in instances of chemotherapy resistance, in addition to enhancing neutrophil recovery following chemotherapy. With regards to OS lung metastasis, a clinical trial examining inhaled GM-CSF therapy determined that multiple daily doses in patients were feasible with limited toxicity.

Example 6a: HSV-GMCSF Single Dose

The objective of this study was, in part, to evaluate transgene expression of GM-CSF at 24- and 48-hours post HSV-GMCSF intratracheal administration compared to recombinant protein to determine the optimal dose for limited toxicity and robust GM-CSF expression.

Young (8-10 weeks) BALB/c animals were administered a single dose of HSV-GMCSF intratracheally (i.t.). Three different doses of HSV-GMCSF were assessed for GM-CSF expression by nucleic acid and protein analysis in the lung tissue, bronchoalveolar lavage fluid (BALF), and serum. Additionally, a group of animals received recombinant GM-CSF protein as a means of comparing local HSV-GMCSF delivery to previously studied administration routes.

Figure 6A:
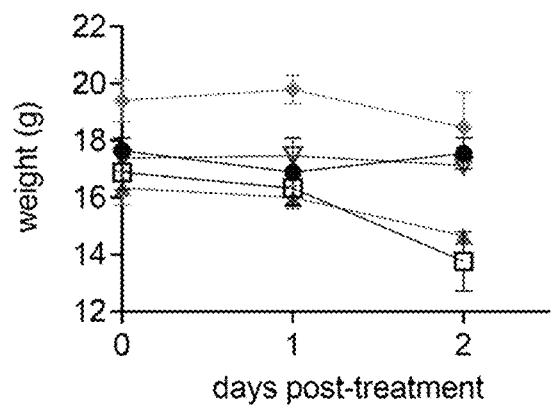
FIGS. 6A-6N show the in vivo evaluation of HSV-GMCSF in healthy mice.
Figure 6B:
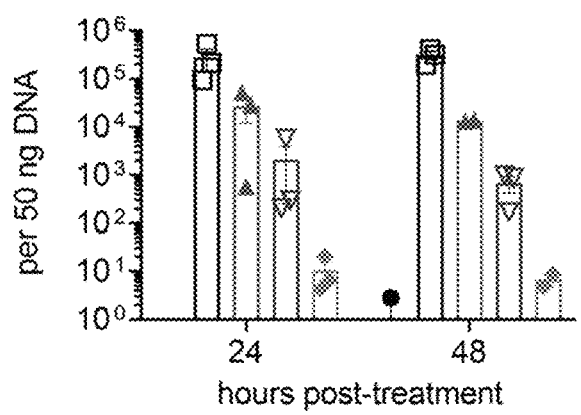
FIGS. 6B-6C show gmcsf genome (FIG. 6B) and transcript (FIG. 6C) levels in lungs of BALB/c animals post-intratracheal administration of HSV-GMCSF. qPCR (FIG. 6B) and qRT-PCR (FIG. 6C) was performed to measure gmcsf genomes and transcripts; respectively. Data are indicative of samples run in duplicate and displayed as mean±SEM of n=2-3 animals per group.
Figure 6C:
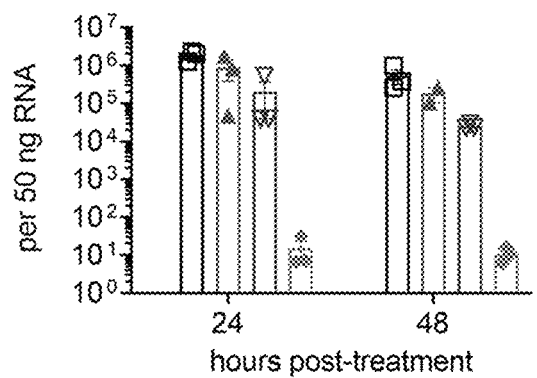
Figure 6D:
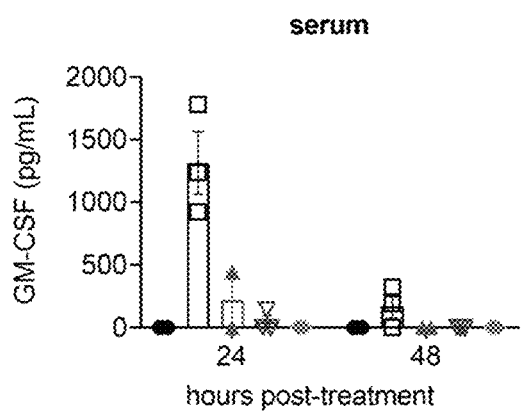
FIGS. 6D-6E show GM-CSF protein concentrations in serum (FIG. 6D) and bronchoalveolar lavage fluid (BALF.
Figure 6E:
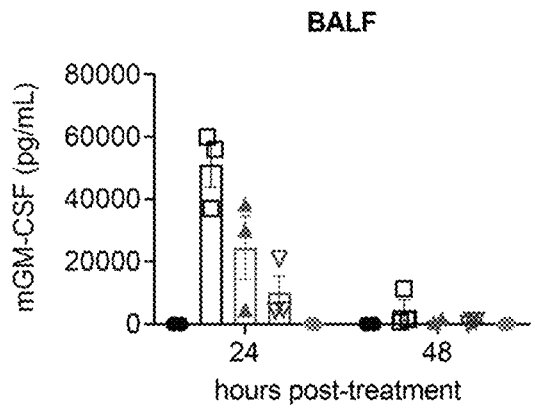
Figure 6F:
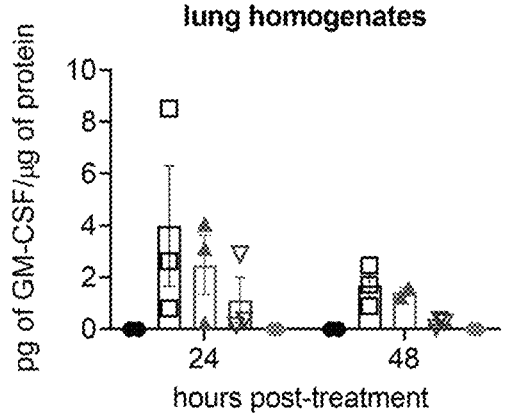
FIG. 6F depicts GM-CSF concentration in lung homogenates following HSV-GMCSF intratracheal administration.

All procedures have been described above (e.g. see Example 4 above). Table 6 provides a synopsis of the experimental design.

strated no change in weight following treatment, indicating no toxic effect from dosing. Post-sacrifice qPCR analyses of lung tissue indicated that gmcsf genomes demonstrated a direct relationship with administration dose at both 24- and 48-hours post-treatment (FIG. 6B). While gmcsf genomes differed between treatment groups, gmcsf transcript levels were comparable regardless of dose (FIG. 6C). Further, low levels of GM-CSF were detected in the serum (FIG. 6D) of HSV-GMCSF treated animals; however, these levels were approximately 40-fold lower than those in the BALF (FIG. 6E), again demonstrating limited systemic exposure. Lung homogenate analysis revealed detectable GM-CSF levels at both 24- and 48-hours post-administration, with a reduction between the two time points (FIG. 6F).

Taken together, these data indicated that infection with HSV-GMCSF resulted in expression of full-length murine GM-CSF.

Example 6b: HSV-GMCSF Weekly Dose

The objective of this study was, in part, to evaluate the toxicity of once weekly intratracheal administration of HSV-GMCSF compared to recombinant GM-CSF protein over the course of three weeks. All procedures have been described above (e.g. see Example 4 above). Table 7 provides a synopsis of the experimental design.

TABLE 6

Study Design and Test Article (TA) Administration

| Grp # | Tot. Animal number | Animal # | TA name | PFU or dose | TA total volume/animal | Route | Dosing Day | Termination | Readout |
|---|---|---|---|---|---|---|---|---|---|
| 1 | 2 | 1, 2 | Vehicle | — | 50 µL | IT | Day 0 | 24 hr post-IT | qPCR, |
| 2 | 2 | 3, 4 | | | | | | 48 hr post-IT | qRT-PCR, |
| 3 | 3 | 5, 6, 7 | High dose | 4.88E8 pfu | 50 µL | IT | Day 0 | 24 hr post-IT | ELISA |
| 4 | 3 | 8, 9, 10 | | | | | | 48 hr post-IT | |
| 5 | 3 | 11, 12, 13 | Mid dose | 9.75E7 pfu | 50 µL | IT | Day 0 | 24 hr post-IT | |
| 6 | 3 | 14, 15, 16 | | | | | | 48 hr post-IT | |
| 7 | 3 | 17, 18, 19 | Low dose | 1.95E7 pfu | 50 µL | IT | Day 0 | 24 hr post-IT | |
| 8 | 3 | 20, 21, 22 | | | | | | 48 hr post-IT | |
| 9 | 3 | 23, 24, 25 | rGM-CSF | 0.6 mg | 50 µL | IT | Day 0 | 24 hr post-IT | |
| 10 | 3 | 26, 27, 28 | | | | | | 48 hr post-IT | | hr—hours;
IT—Intratracheal administration

Results from this study indicated that the animals in the high (4.88E8 pfu) and mid (9.75E7 pfu) dose groups demonstrated weight loss at 48 hours post-treatment (FIG. 6A), suggesting toxicity. Animals in the other groups demon- Prior to each administration and terminal sacrifice, animal weights were recorded. Terminal sacrifice occurred 24 hours following the last dose (day 15). BALF and associated cells, serum, and lungs were collected for downstream analysis.

TABLE 7

Study Design and Test Article (TA) Administration

| Grp # | Total animals | Animal # | TA Name | PFU or dose | TA total volume/animal | Route | Day dosing | Termination | Readout |
|---|---|---|---|---|---|---|---|---|---|
| 1 | 2 | 1, 2 | Vehicle | — | 50 mL | IT | Day 0 Day 7 Day 14 | Day 15 | BAL, ELISA, qPCR/qRT-PCR |

TABLE 7-continued

Study Design and Test Article (TA) Administration

| Grp # | Total animals | Animal # | TA Name | PFU or dose | TA total volume/ animal | Route | Day dosing | Termination | Readout |
|---|---|---|---|---|---|---|---|---|---|
| 2 | 2 | 3, 4 | | | | | | | histology |
| 3 | 3 | 5, 6, 7 | Dose #1 | 1.95E7 | 50 mL | IT | | | BAL, ELISA, qPCR/qRT-PCR |
| 4 | 3 | 8, 9, 10 | | | | | | | histology |
| 5 | 3 | 11, 12, 13 | Dose #2 | 3.9E6 | 50 mL | IT | | | BAL, ELISA, qPCR/qRT-PCR |
| 6 | 3 | 14, 15, 16 | | | | | | | histology |
| 7 | 3 | 17, 18, 19 | rGM-CSF suspension | 0.6 mg | 50 mL | IT | | | BAL, ELISA, qPCR/qRT-PCR |
| 8 | 3 | 20, 21, 22 | | | | | | | histology |

IT—Intratracheal

Figure 6G:
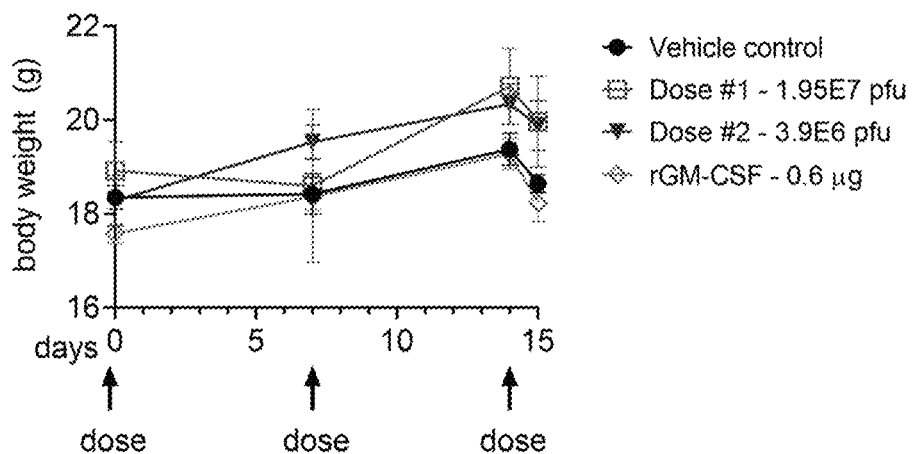
FIG. 6G depicts animal weights following once weekly HSV-GMCSF intratracheal administration. Animals were weighed prior to HSV-GMCSF administration at the indicated time points. Data are presented as mean±SEM; n=2-3 animals per group.
Figure 6H:
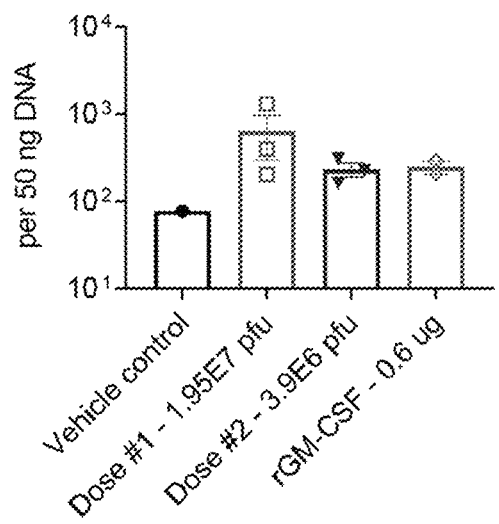
FIGS. 6H-6I depict gmcsf genome (FIG. 6H) and transcript (FIG. 6I) levels in lungs of BALB/c animals following once weekly treatment for three consecutive weeks. Data are indicative of samples run in duplicate. Values from individual animals are displayed in conjunction with the mean±SEM of n=2-3 animals per group.
Figure 6I:
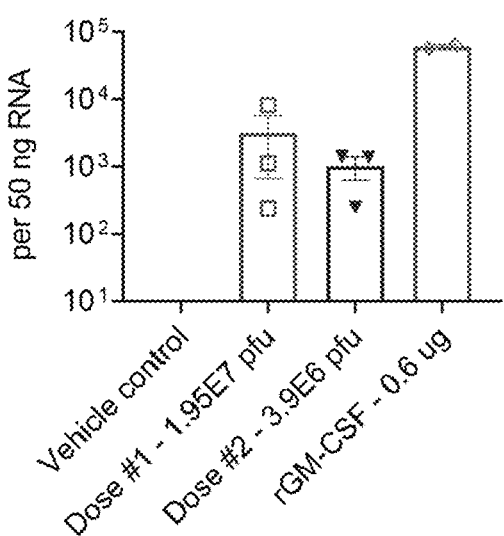

As shown in FIG. 6G, animals in either the Dose #1 or Dose #2 stayed relatively the same weight throughout the course of the study indicating both Dose #1 and Dose #2 were well tolerated. qPCR analyses of lung tissue indicated that differences in gmcsf genomes and transcripts between HSV-GMCSF dosing groups were not statistically significant (FIGS. 6H-6I). Together, these results suggest efficient transgene expression at both of the administered doses.

Figure 6J:
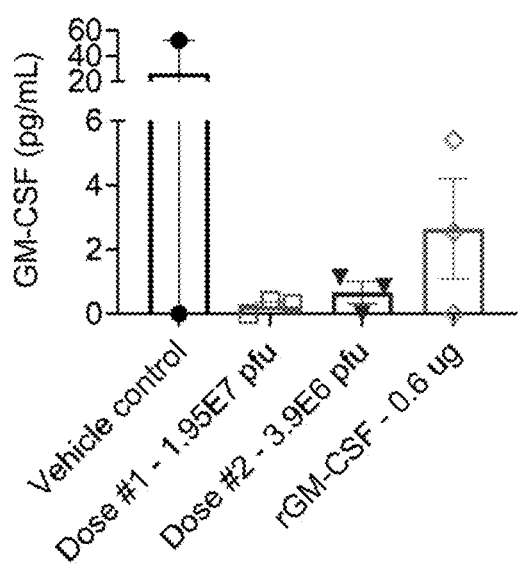
FIGS. 6J-6L depict GMCSF protein concentrations in serum (FIG. 6J), BALF (FIG. 6K), and lung homogenates (FIG. 6L). All samples were assayed in duplicate. Values from individual animals are shown in conjunction with the mean±SEM of n=2-3 animals per group.
Figure 6K:
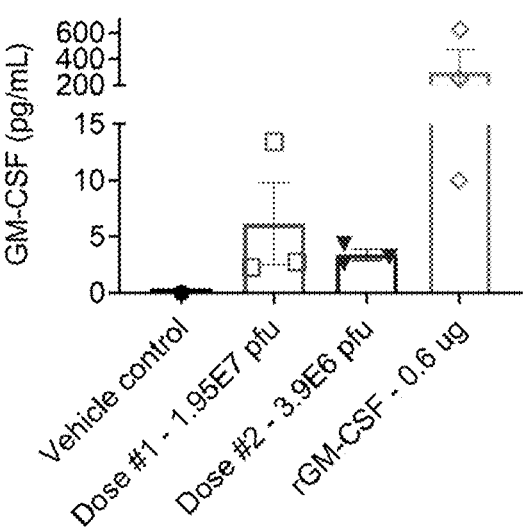
Figure 6L:
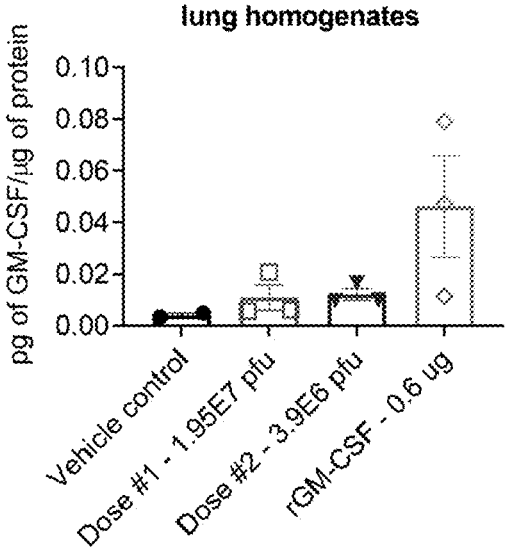
Figure 6M:
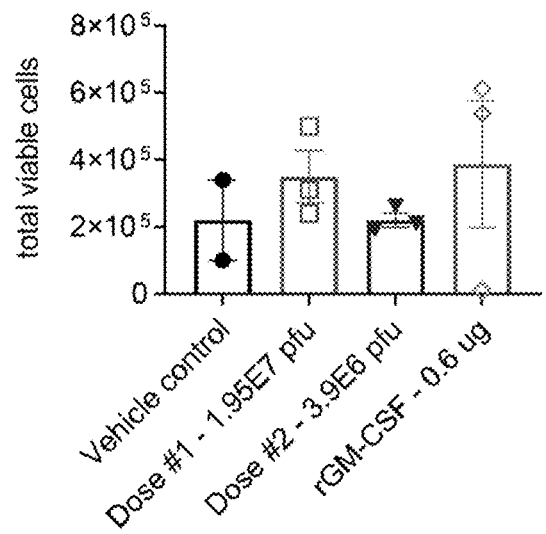
Figure 6N:
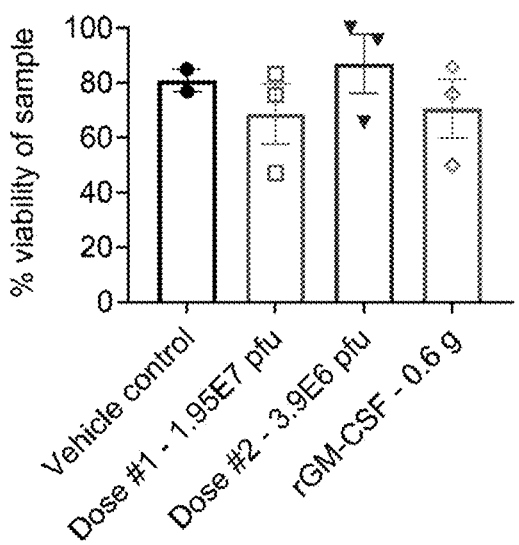

In assessing GM-CSF protein levels, it was again determined that while there was some systemic exposure to GM-CSF from the HSV-GMCSF treatment (serum levels; FIG. 6J), it was minimal compared to local expression/exposure (BALF; FIG. 6K).

Taken together, these data suggested HSV-GMCSF was well tolerated following once weekly intratracheal administration at the indicated doses.

Example 7: Establishment of In Vivo Murine Model of Osteosarcoma

Osteosarcoma (OS) is the most common type of bone cancer diagnosed in the clinic, primarily occurring in children and young adults. In terms of incidence, 3.4 cases per million people are diagnosed each year, making OS a relatively rare malignancy. Yet, with an incidence of 5.6 cases per million children (<15 years of age), it is the third most common cancer in adolescents.

OS is derived from malignant spindle-shaped stromal cells, capable of producing bone-like tissues. It is usually subdivided into one of three groups, osteoblastic, chondroblastic, or fibroblastic, based on the characteristics of the predominant cell type of the tumor. 80% of cases originate in the metaphysis (location of the growth plate) of long bones including the proximal tibia, proximal humerus and the distal femur. Although rare, cases have also been observed in the spine and pelvis.

The main site of OS metastasis is the lung, which it is estimated that 20% of OS patients have metastatic disease at the time of diagnosis. Unfortunately, the presence of lung metastases dramatically impacts the 5-year survival rate of patients, reducing it from 70% in non-metastatic patients to 30%. The standard treatment for OS pulmonary metastasis is lung resection; however, clinical trials are investigating the use of other singular and combinatorial therapies.

Several preclinical animal models have been developed to study OS tumor progression and treatment efficacy, including the K7M2 tumor-BALB/c murine model. K7M2 cells are a derivative of a BALB/c spontaneously occurring murine osteosarcoma; however, it differs from its parent line in that inoculation results in lethal lung metastasis in >90% of inoculated animals. Being a syngeneic tumor, its inoculation into immunocompetent BALB/c animals also allows for studying tumor growth and regression in the presence of a fully intact immune system. Together, these characteristics make it a suitable model for human osteosarcoma lung metastasis and preliminary studies of drug developing in this indication.

The goal of this study was to establish the previously described K7M2 BALB/c model of osteosarcoma lung metastasis following intravenous administration of K7M2 cells, and to elucidate the kinetics of tumor metastasis. All procedures have been described above (e.g. see Example 4 above). Table 8 provides a synopsis of the experimental design.

TABLE 8

Study Design and Test Article (TA) Administration

| Grp # | Total # of animals | Animal # | TA name | TA dosing | TA total volume per animal | Route | Dosing Day | Termination | Readouts |
|---|---|---|---|---|---|---|---|---|---|
| 1 | 2 | 1, 2 | Vehicle | — | 100 µL | IV | Day 0 | 3 weeks | Lung weight histology |
| 2 | 2 | 3, 4 | | | | | | | |

TABLE 8-continued

Study Design and Test Article (TA) Administration

| Grp # | Total # of animals | Animal # | TA name | TA dosing | TA total volume per animal | Route | Dosing Day | Termination | Readouts |
|---|---|---|---|---|---|---|---|---|---|
| 3 | 2 | 5, 6 | | | | | | 6 weeks | Lung weight |
| 4 | 2 | 7, 8 | | | | | | | histology |
| 5 | 5 | 9, 10, 11, 12, 13 | K7M2 | 1E6 total cells | 100 µL | IV | Day 0 | 3 weeks | Lung weight |
| 6 | 2 | 14, 15 | | | | | | | histology |
| 7 | 5 | 16, 17, 18, 19, 20 | | | | | | 6 weeks | Lung weight |
| 8 | 2 | 21, 22 | | | | | | | histology |

Figure 7A:
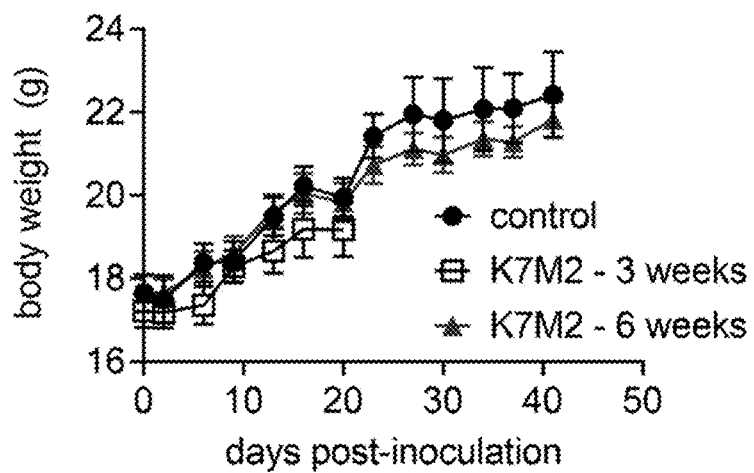
FIGS. 7A-7G depict the establishment of an in vivo osteosarcoma lung metastasis model in immunocompetent mice.
Figure 7B:
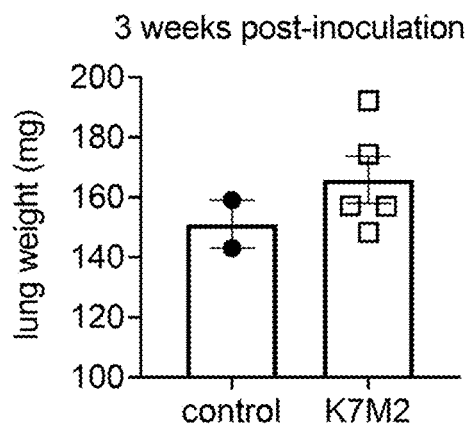
Figure 7C:
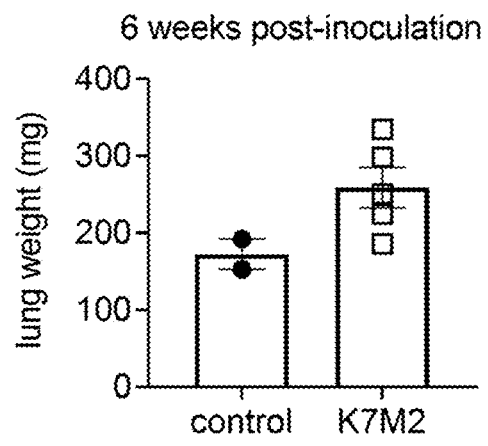
Figure 7D:
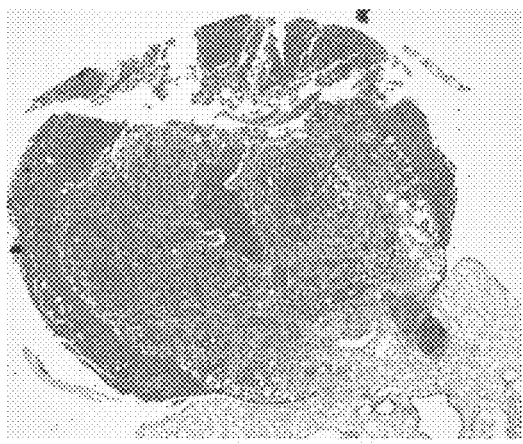
Figure 7E:
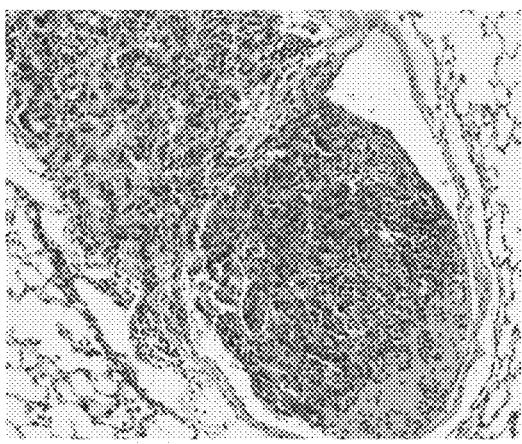
Figure 7F:
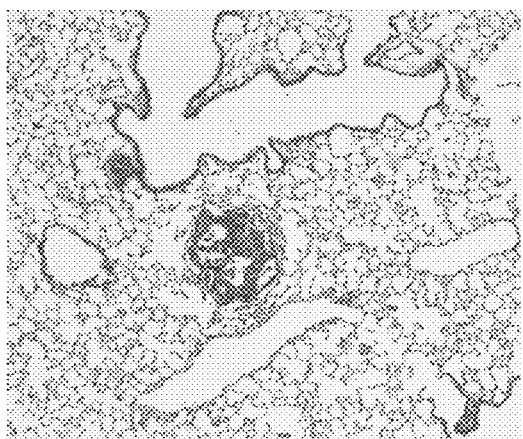
Figure 7G:

As shown in FIGS. 7A-7C, while body weight (FIG. 7A) remained relatively unchanged between the groups throughout the duration of the study, lung weights were increased in tumor recipient mice at both 3-weeks (FIG. 7B) and 6-weeks (FIG. 7C) post-inoculation of K7M2 cells. Further, histological analysis in the lungs of a K7M2 recipient 6-weeks post inoculation revealed tumor burden with signs of tumor metastasis in more than 90% of blood vessels, along with partial thrombus formation (FIGS. 7D-7G).

Taken together, these data established the K7M2 BALB/c model of osteosarcoma lung metastasis following intravenous administration of K7M2 cells with increased lung weight and positive tumor formation in the lung.

Example 8: HSV-IL12 Efficacy in an In Vivo Murine Model of Osteosarcoma

The objective of this study was, in part, to evaluate the efficacy of intratracheal administration of HSV-IL12 at inhibiting established metastatic osteosarcoma lung tumor growth. All procedures have been described above (e.g. see Example 4 above). Table 9 provides a synopsis of the experimental design.

TABLE 9

Study Design

| Grp # | Total animals | Animal # | Inoculating agent/Route | Inoculating day | TA Name/ dose | TA total volume/Route | TA Dosing Days | Termination | Readout |
|---|---|---|---|---|---|---|---|---|---|
| 1 | 5 | 1, 2, 3, 4, 5 | 1X PBS, IV | Day 0 | — | — | Day 21 Day 28 Day 35 | Day 42 | Lung weight qPCR qRT-PCR |
| 2 | 5 | 6, 7, 8, 9, 10 | K7M2, 1.0E6 cells, IV | | Vehicle | 50 mL IT | | | Lung weight qPCR qRT-PCR |
| 3 | 5 | 11, 12, 13, 14, 15 | K7M2, 1.0E6 cells, IV | | HSV-IL12 3.73E7 pfu | | | | Lung weight qPCR qRT-PCR |
| 4 | 5 | 16, 17, 18, 19, 20 | K7M2, 1.0E6 cells, IV | | rmIL-12 0.5 mg | 50 mL, IV | | | Lung weight qPCR qRT-PCR |
| 5 | 5 | 21, 22, 23, 24, 25 | K7M2, 1.0E6 cells, IV | | IL-12 suspension 48 ng | 50 mL, IT | | | Lung weight qPCR qRT-PCR |

IT—Intratracheal;
IV—Intravenous

Figure 8A:
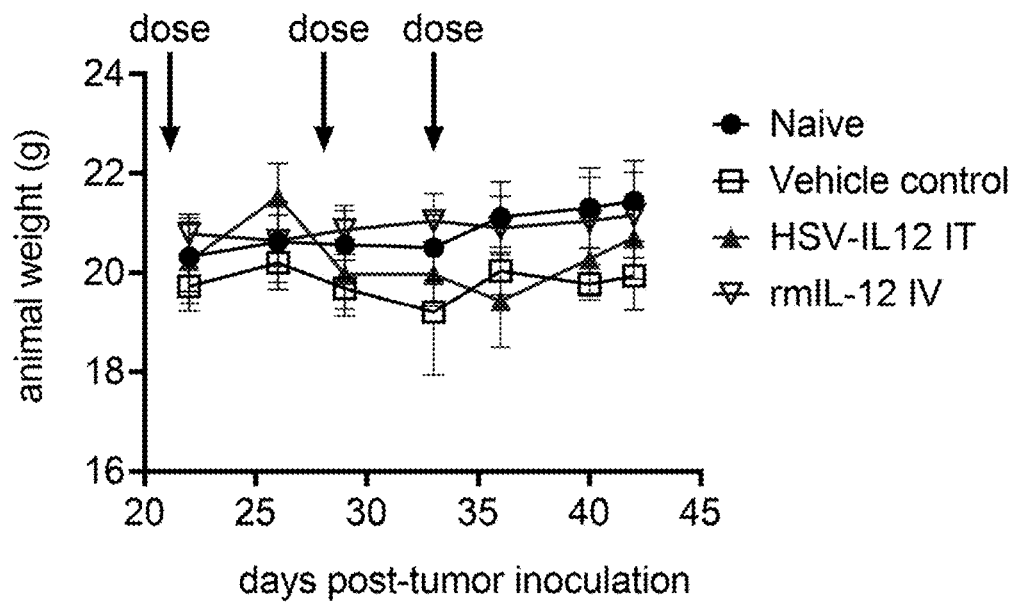
FIGS. 8A-8B depict HSV-IL12 efficacy in an in vivo murine model of osteosarcoma.
Figure 8B:
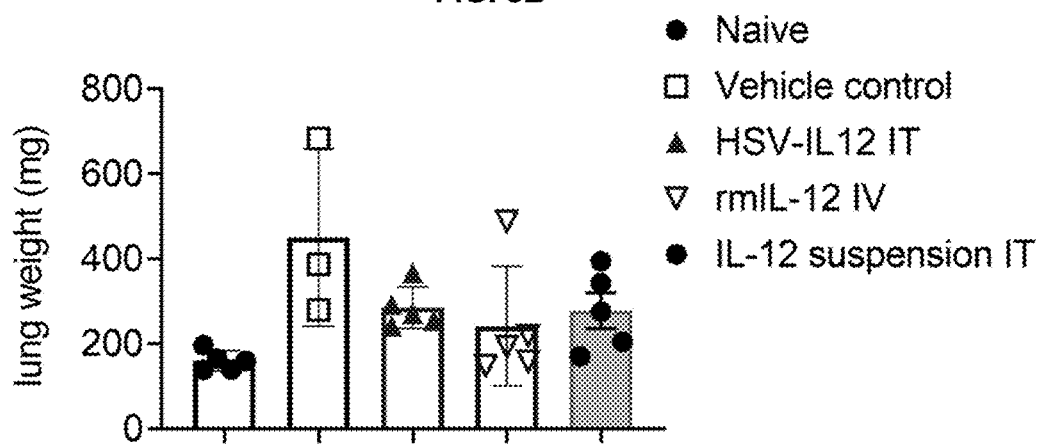

As shown in FIGS. 8A-8B, while body weight (FIG. 8A) remained relatively unchanged between the groups throughout the duration of the study, lung weights were increased in mice at 6-weeks post-inoculation of K7M2 cells (FIG. 8B). Notably, intratracheal administration of HSV-IL12 attenuated the K7M2-mediated increase in lung weights (FIG. 8B).

Additionally, while all five HSV-IL12 treated animals survived to the scheduled sacrifice timepoint, two vehicle treated animals died early in the study. HSV-IL12 appeared to have comparable efficacy as recombinant protein therapy.

Taken together, these data may suggest HSV-IL12 was efficacious at inhibiting established metastatic osteosarcoma lung tumor growth.

Example 9: Intratracheal Administration and In Vivo Evaluation of Once Weekly Combinatorial HSV-IL12+HSV-GMCSF in Healthy Mice The objective of this study was, in part, to assess the toxicity of once weekly dosing with intratracheally administered, combinatorial cytokine-expressing (IL-12 and GM-CSF), non-replicating HSV-1 vectors in healthy mice. All procedures have been described above (e.g. see Example 4 above). Table 10 provides a synopsis of the experimental design.

TABLE 10

Study Design

| Grp # | Tot. Animal # | Animal # | Dose group | TA | Dose (pfu) | Volume & Route | Dosing Day | Termination | Readout |
|---|---|---|---|---|---|---|---|---|---|
| 1 | 2 | 1, 2 | Vehicle | — | — | 50 μL i.t. | Day 0 Day 7 | Day 9 | qPCR/qRT-PCR ELISA |
| 2 | 3 | 3, 4 | | | | | | | histology |
| 3 | 3 | 5, 6, 7 | High Dose | HSV-IL12 + HSV-GMCSF | 3.73E7 1.95E7 | | | | qPCR/qRT-PCR ELISA |
| 4 | 2 | 8, 9 | | | | | | | histology |
| 5 | 3 | 10, 11, 12 | Mid Dose | | 7.46E6 3.9E6 | | | | qPCR/qRT-PCR ELISA |
| 6 | 2 | 13, 14 | | | | | | | histology |
| 7 | 3 | 15, 16, 17 | Recombinant protein | rIL-12 + rGM-CSF | 48 ng + 2.5 ng | | | | qPCR/qRT-PCR ELISA |
| 8 | 2 | 18, 19 | | | | | | | histology | i.t.: intratracheal administration

Figure 9A:
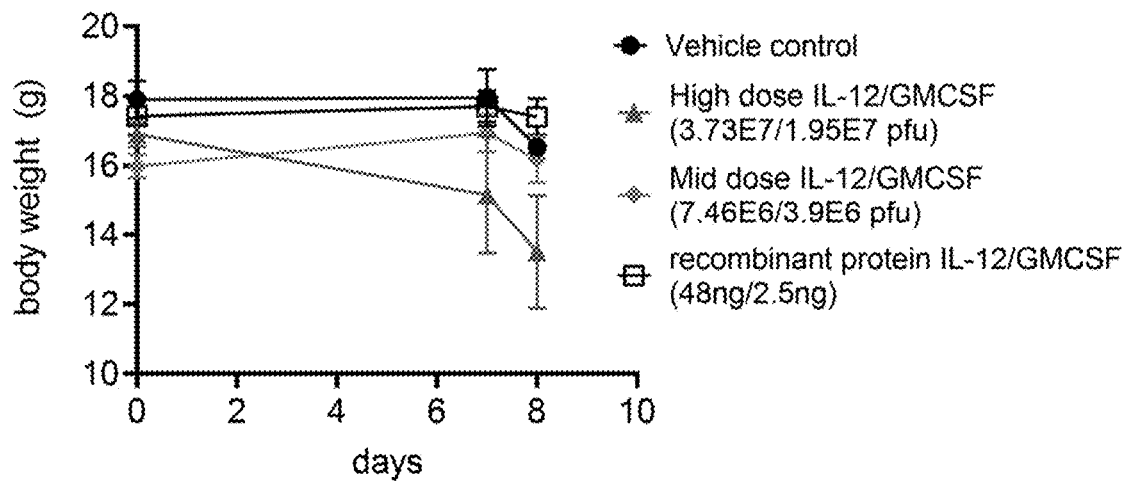
FIGS. 9A-9F show the in vivo evaluation of once weekly combinatorial HSV-IL12/GMCSF intratracheal administration in healthy mice.
Figure 9B:
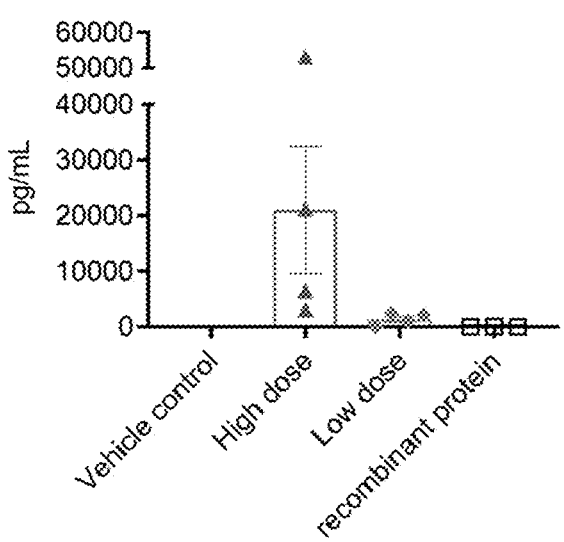
Figure 9C:
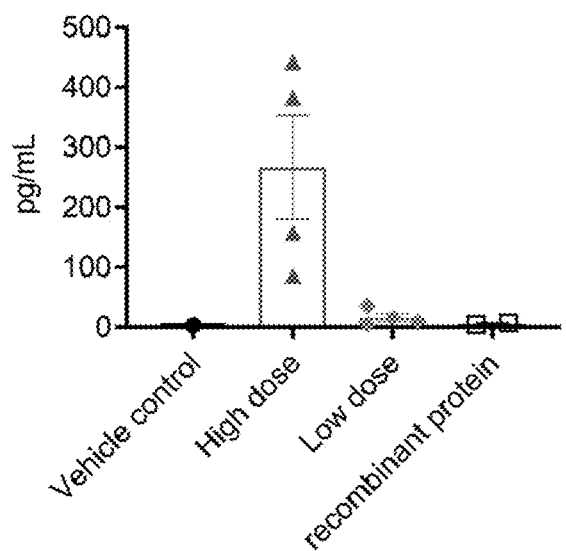
Figure 9D:
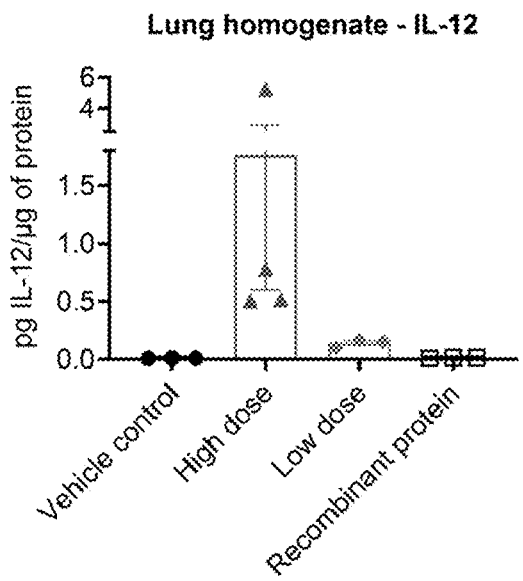
Figure 9E:
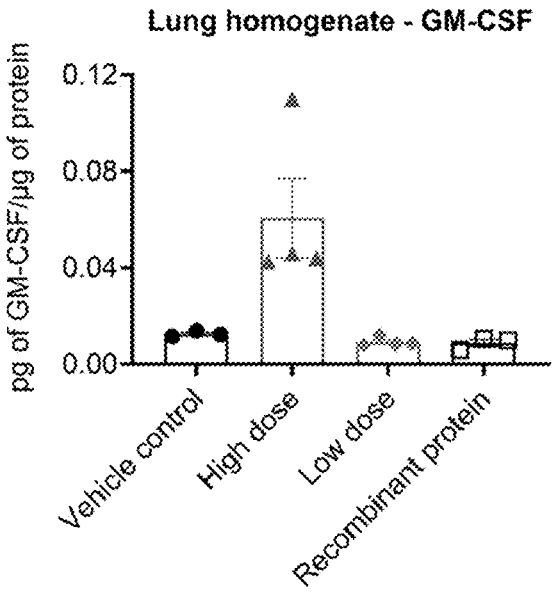
Figure 9F:
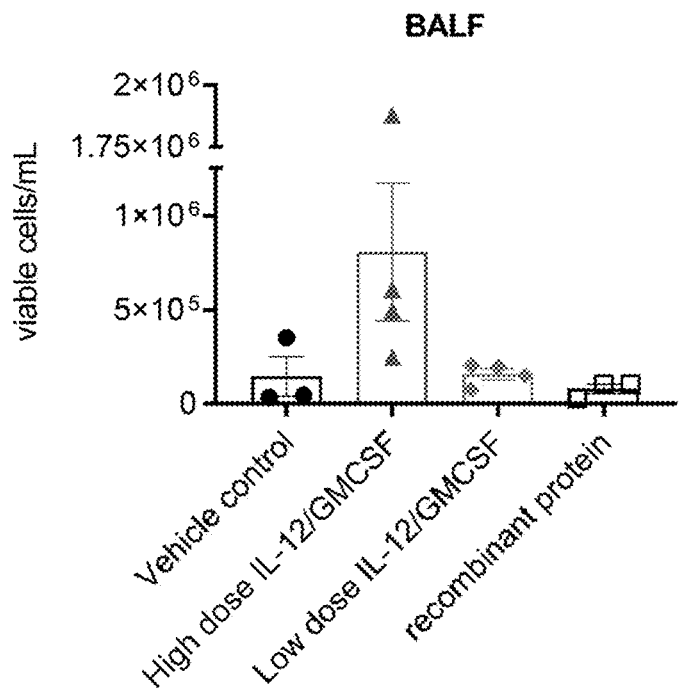

Results from this study suggested that the animals in the high dose group demonstrated somewhat dramatic weight loss following each of the weekly doses administered at 0 and 7 days (FIG. 9A). This was somewhat surprising given that each of the high doses of HSV-GMCSF and HSV-IL12 were not toxic following weekly administrations when given individually. Alternatively, animals in the mid dose group demonstrated no change in weight following treatment, indicating no toxic effect from the indicated dose. Protein analysis of IL-12 and GM-CSF expression following combinatorial treatment revealed high levels of both cytokines in the BALF (FIGS. 9B-9C) and lung homogenates (FIGS. 9D-9E) of animals treated with the high dose of both viruses. There was a reduction in both cytokine concentrations in each of the lung specimens from animals treated with the mid dose compared to the high dose group (FIGS. 9B-9E), indicating a dose effect on transgene expression. Finally, enumeration of cellular infiltrate in the BALF indicated that the high dose treatment resulted in greater immune cell influx into the tissue (FIG. 9F), potentially contributing to the toxicity exemplified by weight loss in these animals (FIG. 9G).

Taken together, these data suggested once weekly dosing with intratracheally administered HSV-IL12+HSV-GMCSF non-replicating HSV-1 vectors resulted in expression of full-length murine IL-12 and GM-CSF which at doses of 7.46E6 and 3.9E6, respectively, are well tolerated in healthy animals.

Example 10: Combinatorial HSV-IL12 and HSV-GMCSF Efficacy in an In Vivo Murine Model of Osteosarcoma The objective of this study was, in part, to evaluate the efficacy of intratracheal administration of combinatorial HSV-IL12 and HSV-GMCSF therapy at inhibiting established metastatic osteosarcoma lung tumor growth. All procedures have been described above (e.g. see Example 4 above). Table 11 provides a synopsis of the experimental design.

TABLE 11

Study Design

| Grp # | Tot. Animal # | Animal # | Inoculation | TA | Dose | Volume & Route | Dosing Day | Termination | Readout |
|---|---|---|---|---|---|---|---|---|---|
| 1 | 5 | 1, 2, 3, 4, 5 | — | — | — | — | — | Day 42 | Body weight |
| 2 | 5 | 6, 7, 8, 9, 10 | K7M2 tumors 100 mL | Vehicle | — | 50 mL i.t. | Day 21 Day 28 Day 35 | | Lung weight |
| 3 | 5 | 11, 12, 13, 14, 15 | 1.0E6 cells i.v. day 0 | Recombinant protein | 48 ng IL-12 2.5 ng GM-CSF | | | | |
| 4 | 5 | 16, 17, 18, 19, 20 | | HSV-IL12 | 7.46E6 pfu | | Day 22 Day 29 | | |
| 5 | 5 | 21, 22, 23, 24, 25 | | HSV-GMCSF | 3.9E6 pfu | | Day 36 | | |
| 6 | 5 | 26, 27, 28, 29, 30 | | HSV-IL12 + HSV-GMCSF | 7.46E6 pfu 3.9E6 pfu | | | | | it.: intratracheal administration;
iv.: intravenous administration

Figure 10A:
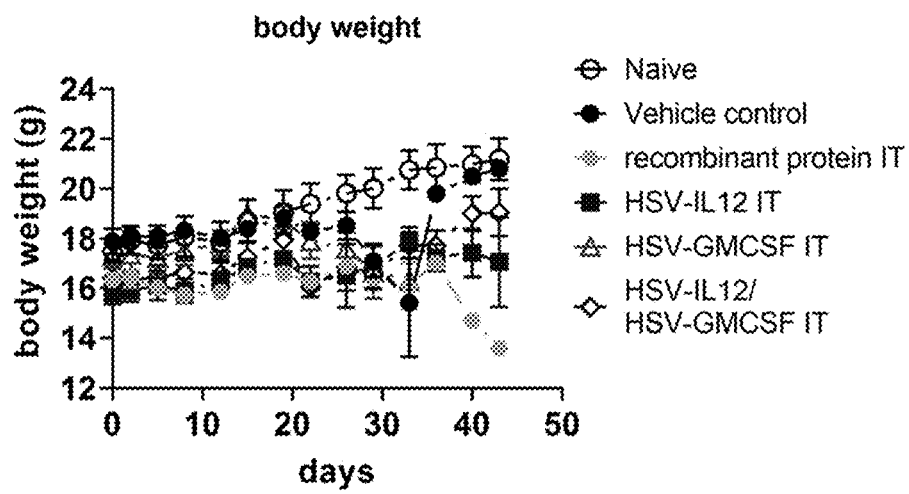
FIGS. 10A-10B depict combinatorial HSV-IL12 and HSV-GMCSF efficacy in an in vivo murine model of osteosarcoma.
Figure 10B:
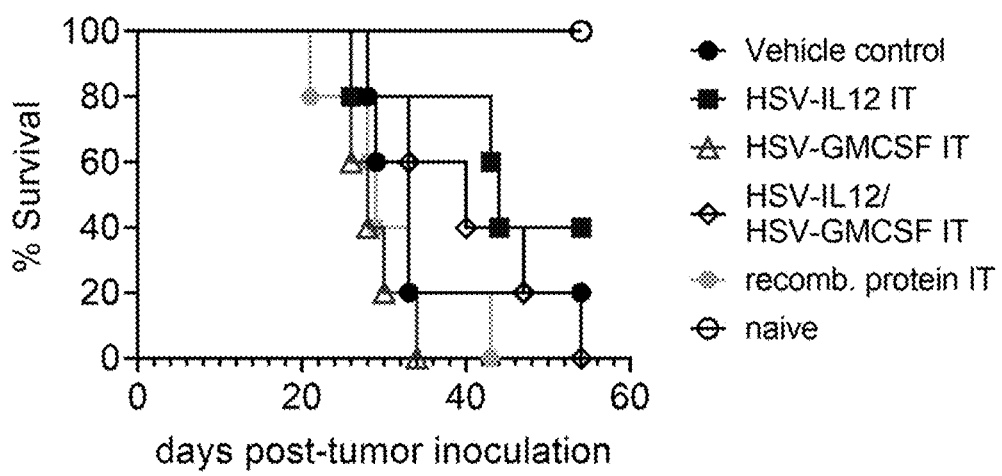

As shown in FIG. 10A, animal body weights did show some fluctuation during PP1T the course of the study, which was indicative of animals succumbing to disease (FIG. 10A). With respect to survival, HSV-GMCSF administration to tumor-bearing mice resulted in a significant decline in the survival rate compared to all other therapies given to K17M2-inoculated animals, including vehicle alone (FIG. 10B). The results shown in FIG. 10B were surprising given the approval for human use of a replicating viral vector encoding GM-CSF for the treatment of metastatic melanoma. Further, while HSV-GMCSF therapy may not have been effective, treatment with HSV-IL12 to tumor-bearing mice enhanced survival compared to vehicle control animals, and prolonged survival of animals exposed to exogenous GM-CSF (FIG. 10B). Importantly, one animal in the HSV-IL12 treatment group was euthanized on a compassionate basis due to tumors interfering with mobility; however, when the animal was necropsied, no visible tumors were present in the lungs.

These data suggest HSV-IL12 may hold promise at limiting established metastatic lung tumor growth.

What is claimed is:

1. A pharmaceutical composition comprising:
   (a) a herpes simplex virus comprising a recombinant herpes simplex virus genome, wherein the recombinant herpes simplex virus genome comprises a polynucleotide encoding an Interleukin (IL)-2 polypeptide and a polynucleotide encoding an IL-12 polypeptide; and
   (b) a pharmaceutically acceptable excipient,
   wherein the recombinant herpes simplex virus genome does not comprise a polynucleotide encoding a Granulocyte-Macrophage Colony-Stimulating Factor (GM-CSF) polypeptide; and
   wherein the recombinant herpes simplex virus genome comprises an inactivating mutation in an Infected Cell Polypeptide (ICP) 22 herpes simplex virus gene.

2. The pharmaceutical composition of claim 1, wherein the herpes simplex virus is replication defective.

3. The pharmaceutical composition of claim 1, wherein the recombinant herpes simplex virus genome is a recombinant herpes simplex virus type 1 (HSV-1) genome or a recombinant herpes simplex virus type 2 (HSV-2) genome.

4. The pharmaceutical composition of claim 1, wherein the recombinant herpes simplex virus genome is a recombinant HSV-1 genome.

5. The pharmaceutical composition of claim 1, wherein the recombinant herpes simplex virus genome further comprises an inactivating mutation in a herpes simplex virus gene selected from the group consisting of ICP0, ICP4, ICP27, ICP47, thymidine kinase (tk), Long Unique Region (UL) 41, and UL55.

6. The pharmaceutical composition of claim 1, wherein the recombinant herpes simplex virus genome comprises an inactivating mutation in one or both copies of the ICP4 gene.

7. The pharmaceutical composition of claim 1, wherein the herpes simplex virus is not oncolytic.

8. The pharmaceutical composition of claim 1, wherein the herpes simplex virus has reduced cytotoxicity as compared to a corresponding wild-type herpes simplex virus.

9. The pharmaceutical composition of claim 1, wherein the IL-2 polypeptide comprises an amino acid sequence having at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 3.

10. The pharmaceutical composition of claim 1, wherein the IL-12 polypeptide comprises an amino acid sequence having at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 5, SEQ ID NO: 6, or SEQ ID NO: 85.

11. The pharmaceutical composition of claim 1, wherein the pharmaceutical composition is suitable for topical, transdermal, subcutaneous, epicutaneous, intradermal, oral, intranasal, intratracheal, sublingual, buccal, rectal, vaginal, intravenous, intraarterial, intramuscular, intraosseous, intracardial, intraperitoneal, transmucosal, intravitreal, subretinal, intraarticular, peri-articular, intratumoral, local, or inhaled administration.

12. The pharmaceutical composition of claim 1, wherein the pharmaceutical composition is suitable for intratumoral administration.

13. The pharmaceutical composition of claim 1, wherein the recombinant herpes simplex virus genome comprises the polynucleotide encoding the IL-12 polypeptide and the polynucleotide encoding the IL-2 polypeptide within the same viral gene locus.

14. The pharmaceutical composition of claim 13, wherein the viral gene locus is an ICP4 viral gene locus.

15. The pharmaceutical composition of claim 1, wherein the recombinant herpes simplex virus genome comprises the polynucleotide encoding the IL-12 polypeptide and the polynucleotide encoding the IL-2 polypeptide within different viral gene loci.

16. The pharmaceutical composition of claim 1, wherein the IL-2 polypeptide and the IL-12 polypeptide are human polypeptides.

17. A pharmaceutical composition consisting essentially of:
(a) a population of herpes simplex viruses, wherein the population of herpes simplex viruses is either all replication defective or all replication competent, and wherein the population of herpes simplex viruses comprises recombinant herpes simplex virus genomes comprising a polynucleotide encoding an IL-2 polypeptide and a polynucleotide encoding an IL-12 polypeptide; and
(b) a pharmaceutically acceptable excipient;
wherein the recombinant herpes simplex virus genome comprises an inactivating mutation in an ICP22 herpes simplex virus gene.

18. The pharmaceutical composition of claim 17, wherein the polynucleotide encoding the IL-2 polypeptide and the polynucleotide encoding the IL-12 polypeptide are comprised within the same recombinant herpes simplex virus genome.

19. The pharmaceutical composition of claim 17, wherein the population of herpes simplex viruses is replication defective.

20. The pharmaceutical composition of claim 17, wherein the recombinant herpes simplex virus genomes are recombinant HSV-1 genomes or recombinant HSV-2 genomes.

21. The pharmaceutical composition of claim 17, wherein the recombinant herpes simplex genomes are recombinant HSV-1 genomes.

22. The pharmaceutical composition of claim 17, wherein the recombinant herpes simplex virus genomes further comprise an inactivating mutation in a herpes simplex virus gene selected from the group consisting of ICP0, ICP4, ICP27, ICP47, tk, UL41, and UL55.

23. The pharmaceutical composition of claim 17, wherein the recombinant herpes simplex virus genomes comprise an inactivating mutation in one or both copies of the ICP4 gene.

24. The pharmaceutical composition of claim 17, wherein the population of herpes simplex viruses is not oncolytic.

25. The pharmaceutical composition of claim 17, wherein the population of herpes simplex viruses has reduced cytotoxicity as compared to a corresponding population of wild-type herpes simplex viruses.

26. The pharmaceutical composition of claim 17, wherein the IL-2 polypeptide comprises an amino acid sequence having at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 3.

27. The pharmaceutical composition of claim 17, wherein the IL-12 polypeptide comprises an amino acid sequence having at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 5, SEQ ID NO: 6, or SEQ ID NO: 85.

28. The pharmaceutical composition of claim 17, wherein the pharmaceutical composition is suitable for topical, transdermal, subcutaneous, epicutaneous, intradermal, oral, intranasal, intratracheal, sublingual, buccal, rectal, vaginal, intravenous, intraarterial, intramuscular, intraosseous, intracardial, intraperitoneal, transmucosal, intravitreal, subretinal, intraarticular, peri-articular, intratumoral, local, or inhaled administration.

29. The pharmaceutical composition of claim 17, wherein the pharmaceutical composition is suitable for intratumoral administration.

30. The pharmaceutical composition of claim 17, wherein the recombinant herpes simplex virus genomes comprise the polynucleotide encoding the IL-12 polypeptide and the polynucleotide encoding the IL-2 polypeptide within the same viral gene locus.

31. The pharmaceutical composition of claim 30, wherein the viral gene locus is an ICP4 viral gene locus.

32. The pharmaceutical composition of claim 17, wherein the recombinant herpes simplex virus genomes comprise the polynucleotide encoding the IL-12 polypeptide and the polynucleotide encoding the IL-2 polypeptide within different viral gene loci.

* * * * *